(12) United States Patent
Jacobsen et al.

(10) Patent No.: US 8,192,937 B2
(45) Date of Patent: Jun. 5, 2012

(54) METHODS FOR QUANTIFICATION OF MICRORNAS AND SMALL INTERFERING RNAS

(75) Inventors: Nana Jacobsen, Gentofte (DK); Lars Kongsbak, Holte (DK); Sakari Kauppinen, Smørum (DK); Søren Morgenthaler Echwald, Humlebaek (DK); Peter Mouritzen, Jyllinge (DK); Peter Stein Nielsen, Birkerød (DK); Mikkel Nørholm, København V (DK)

(73) Assignee: Exiqon A/S, Vedbaek (DK)

( * ) Notice: Subject to any disclaimer, the term of this patent is extended or adjusted under 35 U.S.C. 154(b) by 748 days.

(21) Appl. No.: 11/100,897

(22) Filed: Apr. 7, 2005

(65) Prior Publication Data

US 2005/0272075 A1    Dec. 8, 2005

Related U.S. Application Data

(60) Provisional application No. 60/560,148, filed on Apr. 7, 2004, provisional application No. 60/590,856, filed on Jul. 23, 2004, provisional application No. 60/600,961, filed on Aug. 12, 2004, provisional application No. 60/619,291, filed on Oct. 15, 2004, provisional application No. 60/648,221, filed on Jan. 28, 2005.

(51) Int. Cl.
 *C12Q 1/68* (2006.01)
 *C07H 21/04* (2006.01)
(52) U.S. Cl. ............... 435/6.12; 536/24.2; 536/24.3
(58) Field of Classification Search .............. None
 See application file for complete search history.

(56) References Cited

U.S. PATENT DOCUMENTS

| 3,687,808 A | 8/1972 | Merigan, Jr. et al. |
| 4,889,818 A | 12/1989 | Gelfand et al. |
| 5,525,470 A * | 6/1996 | Cohen et al. ............. 435/6 |
| 5,643,766 A * | 7/1997 | Scheele et al. ............. 435/91.2 |
| 6,043,060 A | 3/2000 | Imanishi |
| 6,045,994 A * | 4/2000 | Zabeau et al. ............. 435/6 |
| 6,117,635 A * | 9/2000 | Nazarenko et al. ............. 435/6 |
| 6,268,490 B1 | 7/2001 | Imanishi et al. |
| 6,706,476 B1 * | 3/2004 | Thirstrup et al. ............. 506/17 |
| 2002/0068708 A1 * | 6/2002 | Wengel et al. ............. 514/44 |

(Continued)

FOREIGN PATENT DOCUMENTS

EP    1072679    7/2000

(Continued)

OTHER PUBLICATIONS

Schmittgen et al. A high-throughput method to monitor the expression of microRNA precursors. Nucleic Acids Research, vol. 32, No. 4, e43, published online Feb. 25, 2004 (10 pages).*

(Continued)

*Primary Examiner* — Samuel Woolwine
(74) *Attorney, Agent, or Firm* — Clark & Elbing LLP; Kristina Bieker-Brady

(57) ABSTRACT

The invention relates to ribonucleic acids, probes and methods for detection, quantification as well as monitoring the expression of mature microRNAs and small interfering RNAs (siRNAs). The invention furthermore relates to methods for monitoring the expression of other non-coding RNAs, mRNA splice variants, as well as detecting and quantifying RNA editing, allelic variants of single transcripts, mutations, deletions, or duplications of particular exons in transcripts, e.g., alterations associated with human disease such as cancer. The invention furthermore relates to methods for detection, quantification as well as monitoring the expression of deoxy nucleic acids.

28 Claims, 45 Drawing Sheets

U.S. PATENT DOCUMENTS

| | | | |
|---|---|---|---|
| 2002/0187485 | A1* | 12/2002 | Jakobsen et al. ............... 435/6 |
| 2004/0235005 | A1 | 11/2004 | Friedlander et al. |
| 2005/0196782 | A1 | 9/2005 | Kiefer et al. |
| 2005/0266418 | A1* | 12/2005 | Chen et al. ............... 435/6 |
| 2007/0292878 | A1 | 12/2007 | Raymond |
| 2009/0123912 | A1 | 5/2009 | Raymond |

FOREIGN PATENT DOCUMENTS

| | | |
|---|---|---|
| EP | 1851336 | 11/2007 |
| WO | WO 97/12896 | 4/1997 |
| WO | WO 98/39352 | 11/1998 |
| WO | WO 99/14226 | 3/1999 |
| WO | WO 00/56746 | 9/2000 |
| WO | WO 00/56748 | 9/2000 |
| WO | WO 00/66604 | 11/2000 |
| WO | WO 01/06004 | 1/2001 |
| WO | WO 01/07455 | 1/2001 |
| WO | WO 01/00641 | 4/2001 |
| WO | WO 02/057479 | 7/2002 |
| WO | WO 03/020739 | 3/2003 |
| WO | WO 2004/048511 | 6/2004 |
| WO | WO 2004/057017 | 7/2004 |
| WO | WO 2005/003318 | 1/2005 |
| WO | WO 2005/040419 | 5/2005 |
| WO | WO 2005/098029 | 10/2005 |
| WO | WO 2006/081284 | 8/2006 |

OTHER PUBLICATIONS

Schmittgen et al Supplementary Material [online], published online Feb. 25, 2004 [retrieved on Jan. 30, 2008], retrieved from the Internet: http://nar.oxfordjournals.org/cgi/data/32/4/e43/DC1/1 (2 pages).*
Lau et al. Supplementary Material [online] Oct. 26, 2001 [retrieved on Nov. 7, 2008] retrieved from http://www.sciencemag.org/feature/data/lau1065062_SupMat.htm (6 pages).*
Lau et al. An abundant class of tiny RNAs with probable regulatory roles in Caenorhabditis elegans. Science 294:858-862 (2001).*
Heid et al. Real time quantitative PCR. Genome Research 6:986-994 (1996).*
Elbashir et al. RNA interference is mediated by 21- and 22-nucleotide RNAs. Genes & Development 15:188-200 (2001).*
Pfeffer, S., Lagos-Quintana, M., and Tuschl, T. 2003. Cloning of small RNA molecules. In Current Protocols in Molecular Biology, vol. 4 (F.M. Ausubel, R. Brent, R.E. Kingston, D.D. Moore, J.G. Seidman, J.A. Smith, and K. Struhl, eds.) pp. 26.4.1-26.4.18. John Wiley & Sons, Hoboken, N.J.*
Brownie et al. The elimination of primer-dimer accumulation in PCR. Nucleic Acids Research 25(16):3235-41 (1997).*
Shuldiner et al. RNA template-specific polymerase chain reaction (RS-PCR): a novel strategy to reduce dramatically false positives. Gene 91:139-142 (1990).*
Loewen et al. Template secondary structure can increase the error frequency of the DNA polymerase from *Thermus aquaticus*. Gene 164:59-63 (1995).*
Adams et al., "Hindered Dialkylamino Nucleoside Phosphite Reagents in the Synthesis of Two DNA 51-Mers", *J. Am. Chem. Soc.* 105(3): 661-663, 1983.
Caruthers et al., "Chemical Synthesis and Biological Studies on Mutated Gene-Control Regions", *Cold Spring Harbor Symp. Quant. Biol.* 47: 411-418, 1982.
Concise Encyclopedia of Polymer Science and Engineering, J. I. Kroschwitz Ed., John Wiley & Sons, pp. 858-859, 1990.
Cook, "Medicinal Chemistry of Antisense Oligonucleotides—Future Opportunities", *Anti-Cancer Drug Design* 6: 585-607, 1991.
Croft et al., "ISIS, the Intron Information System, Reveals the High Frequency of Alternative Splicing in the Human Genome", *Nature Genetics* 24(4): 340-341, 2000.
De Mesmaeker et. al., "Backbone Modifications in Oligonucleotides and Peptide Nucleic Acid Systems", *Current Opinion in Structural Biology* 5: 343-355, 1995.
Englisch et al., "Chemically Modified Oligonucleotides as Probes and Inhibitors", *Angewandte Chemie*, International Edition, 30: 613-629, 1991.

Freier and Altmann, "The Ups and Downs of Nucleic Acid Duplex Stability: Structure-Stability Studies on Chemically-Modified DNA: RNA Duplexes", *Nucleic Acid Research* 25(22): 4429-4443, 1997.
Gall and Pardue, "Formation and Detection of RNA-DNA Hybrid Molecules in Cytological Preparations", *Proc. Natl. Acad. Sci.*, USA 63(2): 378-383, 1969.
Gott, "Expanding Genome Capacity Via RNA Editing", *C.R. Biologies*, 326: 901-908. 2003.
Grad et al., "Computational and Experimental Identification of C. Elegans microRNAs", *Molecular Cell* (11): 1253-1263, 2003.
Hakansson et al., "Convenient Synthesis of 7-Hydroxy-1-(hydroxymethyl)-3-(thymin-1-yl)-2, 5-dioxabicycl[2.2.1] heptanes:α-$_L$-Ribo-and α-$_L$-Xylo-Configured LNA Nucleosides", *J. Org. Chem.* 65(17): 5161-5166, 2000.
Hakansson et al., "The Adenine Derivative of α-$_L$-LNA (α-$_L$-*ribo* Configured Locked Nucleic Acid): Synthesis and High-Affinity Hybridization Towards DNA, RNA, LNA, and α-$_L$-LNA Complementary Sequences", *Bioorg. Med. Chem. Lett.* 11(7): 935-938, 2001.
Hermanson, "Immobolization of Ligands", Academic Press, San Diego, California: Chapter 3, pp. 137-ff, 1992.
John et al., "RNA-DNA Hybrids at the Cytological Level", *Nature* 223(206): 582-587, 1969.
Juarez et al., "microRNA-Mediated Repression of *Rolled Leaf1* Species Maize Leaf Polarity", *Nature* 428(6978): 84-88, 2004.
Kampa et al., "Novel RNAs Identified From an In-Depth Analysis of the Transcriptome of Human Chromosomes 21 and 22", *Genome Research* 14(3): 331-342, 2004.
Kidner and Martienssen, "Spatially Restricted microRNA Directs Leaf Polarity Through Argonaute1", *Nature* 428(6978): 81-84, 2004.
Koshkin et al., "A Simplified and Efficient Route to 2'-O, 4'-C-Methylene-Linked Bicyclic Ribonucleosides (Locked Nucleic Acid)", *J. Org. Chem.* 66(25): 8504-8512, 2001.
Koshkin et al., "LNA (Locked Nucleic Acids): Synthesis of Adenine, Cytosine, Guanine, 5-Methylcytosine, Thymine, and Uracil Bicyclonucleoside Monomers, Oligmerisation, and Unprecedented Nucleic Acid Recognition", *Tetrahedron* 54: 3607-30, 1998.
Krichevsky et al., "A microRNA Array Reveals Extensive Regulation of microRNAs During Brain Development", *RNA* 9(10): 1274-1281, 2003.
Kumar et al., "The First Analogues of LNA (Locked Nucleic Acids): Phosphorothioate-LNA and 2'-Thio-LNA", *Bioorg. Med. Chem. Lett.* 8(16): 2219-2222, 1998.
Kvaerno et al., "Novel Bicyclic Nucleoside Analogue (1S, 5S, 6S)-6-Hydroxy-5-hydroxymethyl-1-(uracil-1-yl)-3, 8-dioxabicyclo[3.2.1] octane: Synthesis and Incorporation into Oligodeoxynucleotides", *J. Org. Chem.* 66(16): 5498-5503, 2001.
Kvaerno et al., "Synthesis of Abasic Locked Nucleic Acid and Two *seco*-LNA Derivatives and Evaluation of Their Hybridization Properties Compared with Their More Flexible DNA Counterparts", *J. Org. Chem.* 65(17): 5167-5176, 2000.
Lagos-Quintana et al., "Identification of Novel Genes Coding for Small Expressed RNAs", *Science* 294(5543): 853-858, 2001.
Lee and Ambros, "An Extensive Class of Small RNAs in *Caenorhabditis elegans*", *Science* 294(5543): 862-864, 2001.
Mattick, "Non-Coding RNAs: The Architects of Eukaryotic Complexity", *EMBO Reports* 2(11): 986-991, 2001.
Michael et al., "Reduced Accumulation of Specific MicroRNAs in Colorectal Neoplasia", *Molecular Cancer Research* 1: 882-891, 2003.
Morita et al., "2'-O, 4'-C- Ethylene-Bridged Nucleic Acids (ENA): Highly Nuclease-Resistant and Thermodynamically Stable Oligonucleotides for Antisense Drug," *Bioorg. Med. Chem. Lett.* 12(1):73-76, 2002.
Moss, "MicroRNAs: Hidden in the Genome", *Current Biology* 12: R138-140, 2002.
Okazaki et al., "Analysis of Mouse Transcriptome Based on Functional Annotation of 60,770 Full-Length cDNAs", *Nature* 420(6915): 563-573, 2002.
Pfundheller et al., "Evaluation of Oligonucleotides Containing Two Novel 2'O-Methyl Modified Nucleotides Monomers: A 3'-C-Allyl and a 2'-O, 3-C-Linked Bicyclic Derivative," *Nucleosides & Nucleotides* 18(9): 2017-2030, 1999.

Reinhart et al., "The 21-Nucleotide *Let-7* RNA Regulates Developmental Timing in *Caenorhabditis elegans*", *Nature* 403(6772): 901-906, 2000.

Saiki et al., (1988), "Primer-Directed Enzymatic Amplification of DNA with a Thermostable DNA Polymerase", *Science* 239(4839): 487-491, 1988.

Sanghvi, "Heterocyclic Base Modifications in Nucleic Acids and Their Applications in Antisense Oligonucleotides", *Antisense Research and Application*, Chapter 15, pp. 273-288, Ed. S. T. Cooke and B. Lebleu, *CRC* Press, 1993.

Schmittgen et al., "A High-Throughput Method to Monitor the Expression of microRNA Precursors", *Nucleic Acids Research* 32(4): e43, 2004.

Venkatesan et al., "Novel Phosphoramidite Building Blocks in Synthesis and Applications Toward Modified Oligonucleotides", *Current Medical Chemistry* 10(19): 1973-1991, 2003.

Yelin et al., "Widespread Occurance of Antisense Transcription in the Human Genome", *Nature Biotechnology* 21(4): 379-386, 2003. Epub Mar. 17, 2003.

Zeng and Cullen, "Sequence Requirements for micro RNA Processing and Function in Human Cells", *RNA* 9(1): 112-123, 2003.

Raymond et al., "Simple, Quantitative Primer-Extension PCR Assay for Direct Monitoring of MicroRNAs and Short-Interfering RNAs," *RNA* 11:1737-1744, 2005.

Johnson et al., "Locked nucleic acid (LNA) single nucleotide polymorphism (SNP) genotype analysis and validation using real-time PCR," *Nucleic Acids Res.* 32:1-9, 2004.

Latorra et al., "Enhanced allele-specific PCR discrimination in SNP genotyping using 3' locked nucleic acid (LNA) primers," *Hum Mutat.* 22:79-85, 2003.

Latorra et al., "Design considerations and effects of LNA in PCR primers," *Mol Cell Probes.* 17:253-259, 2003.

\* cited by examiner

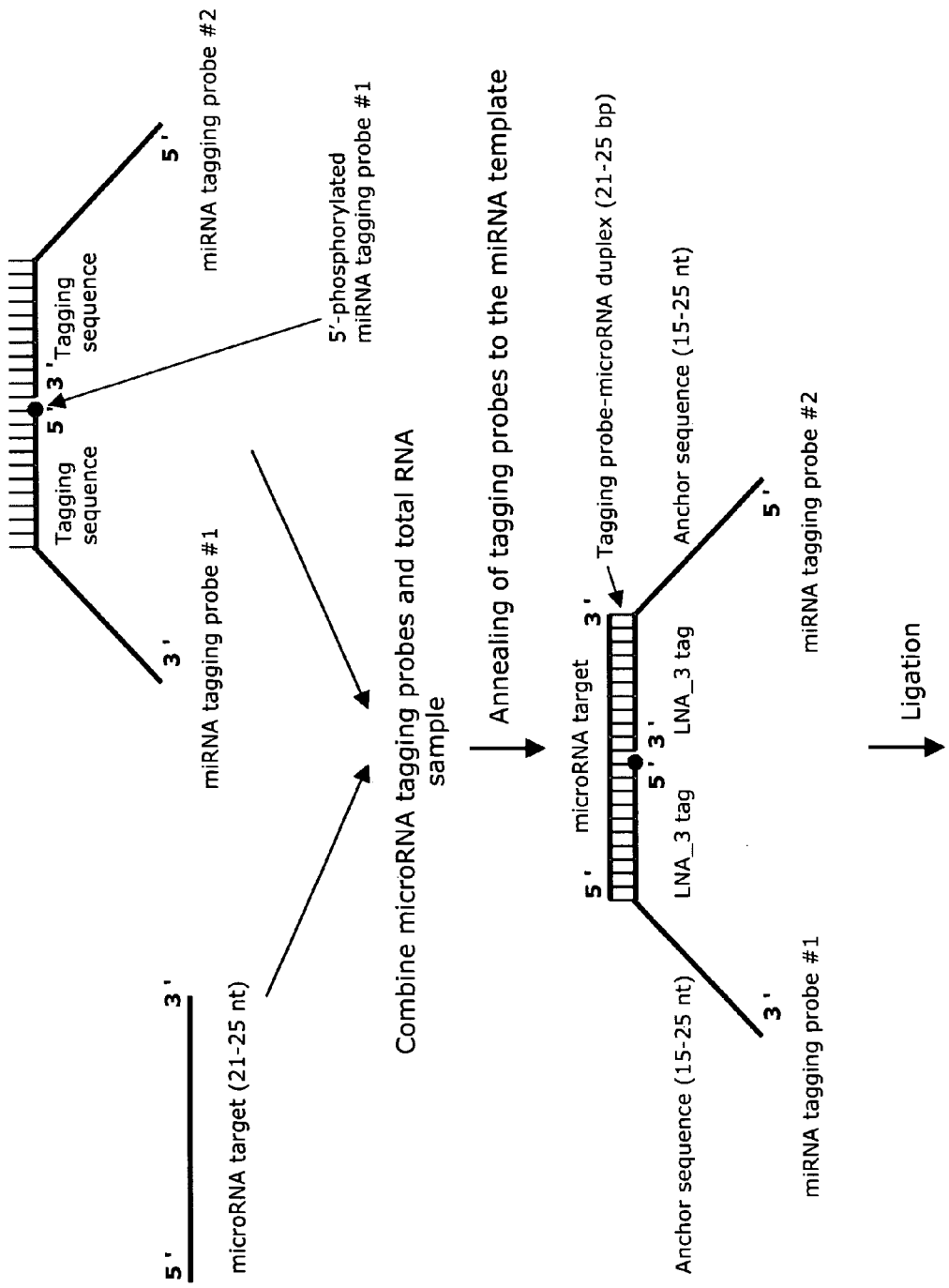
Fig. 1 (1/2)

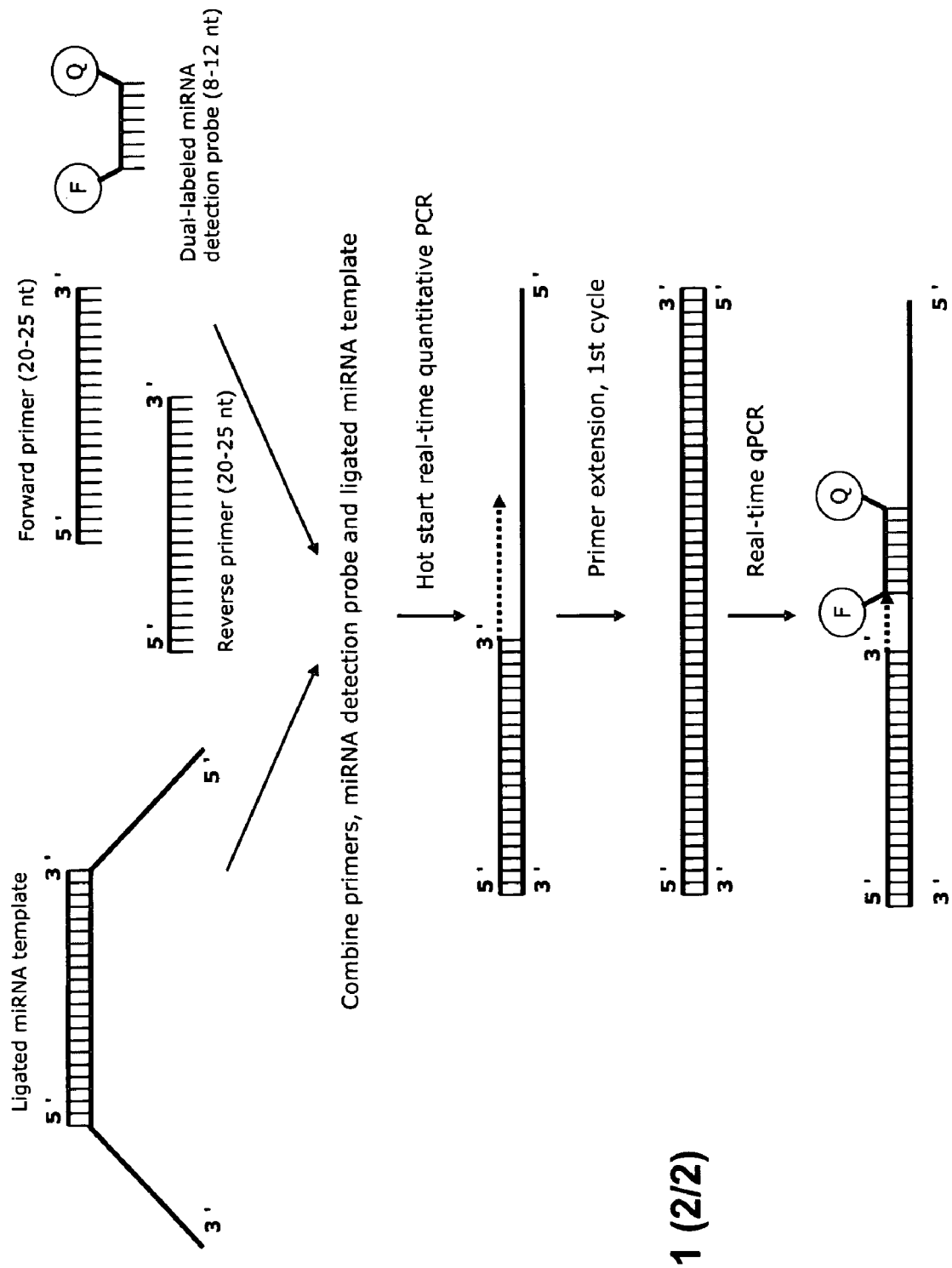
Fig. 1 (2/2)

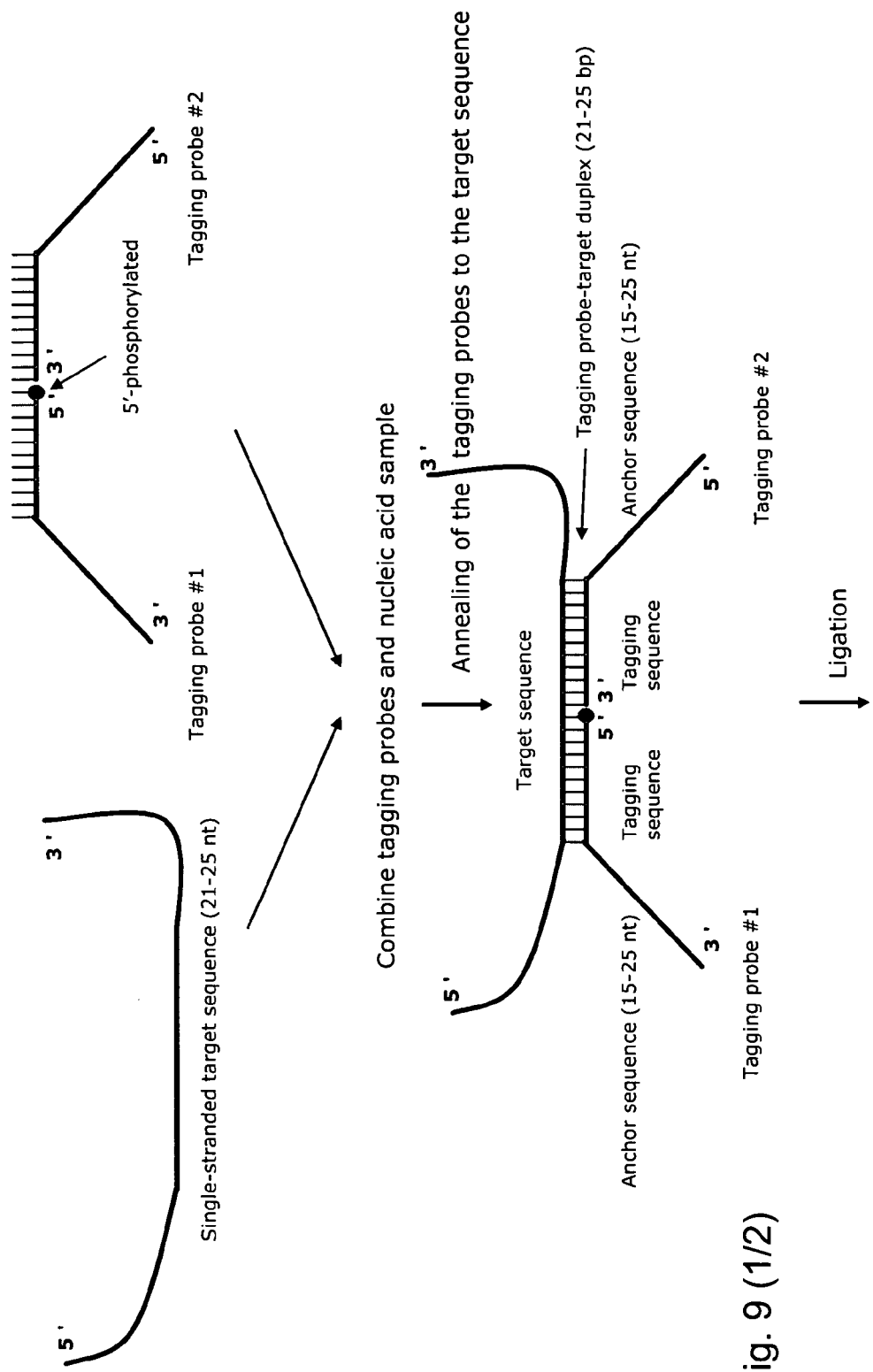
Fig. 9 (1/2)

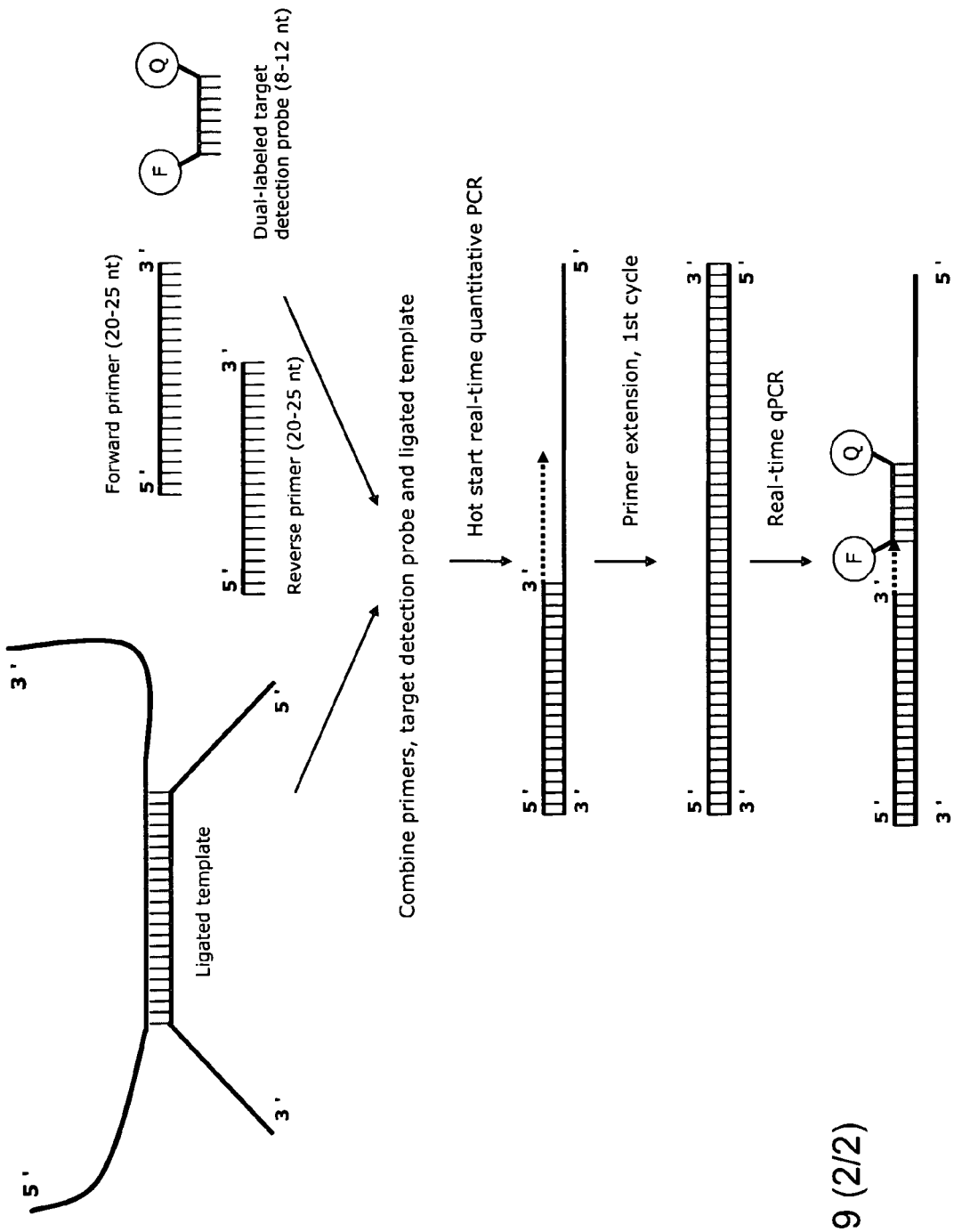
Fig. 9 (2/2)

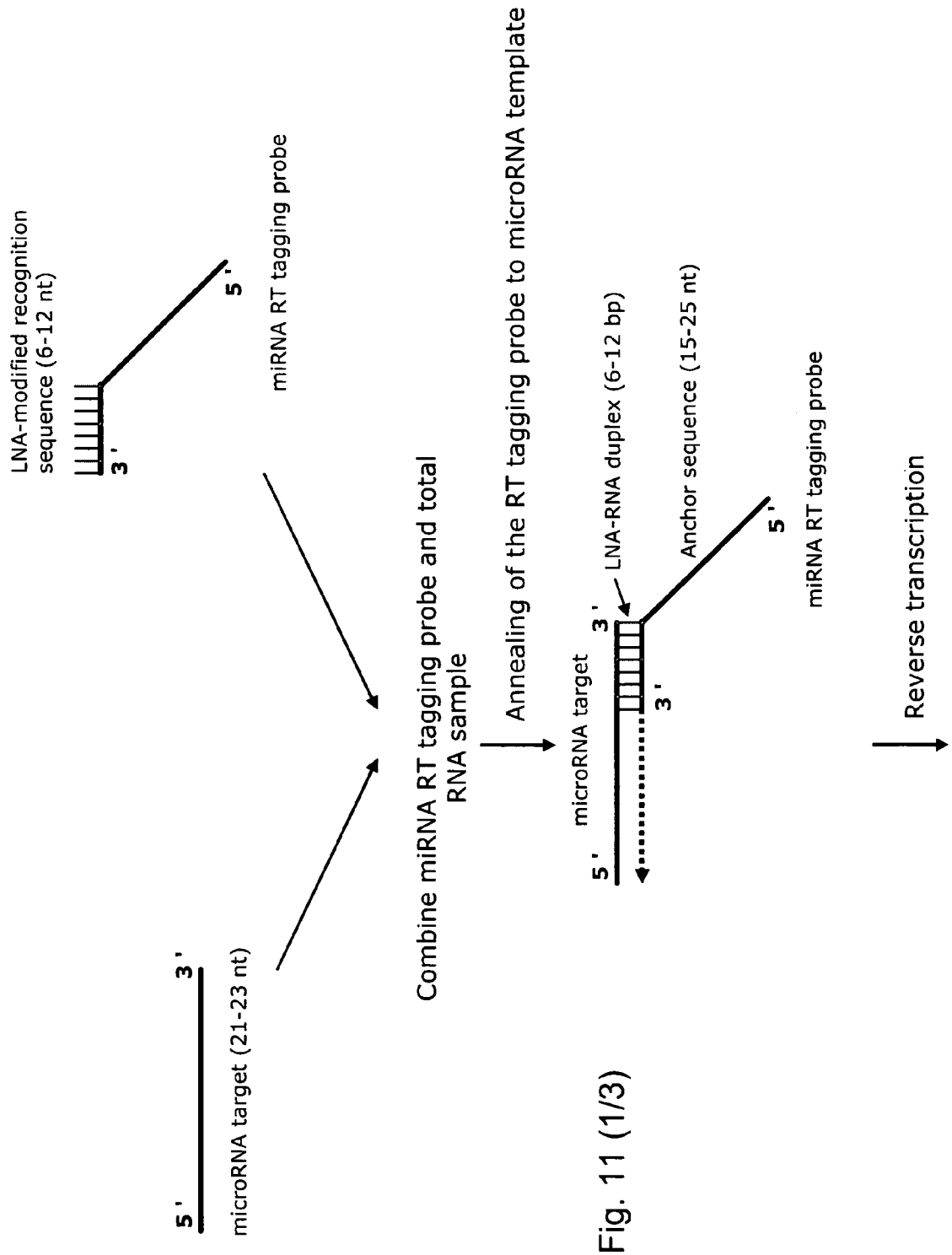
Fig. 11 (1/3)

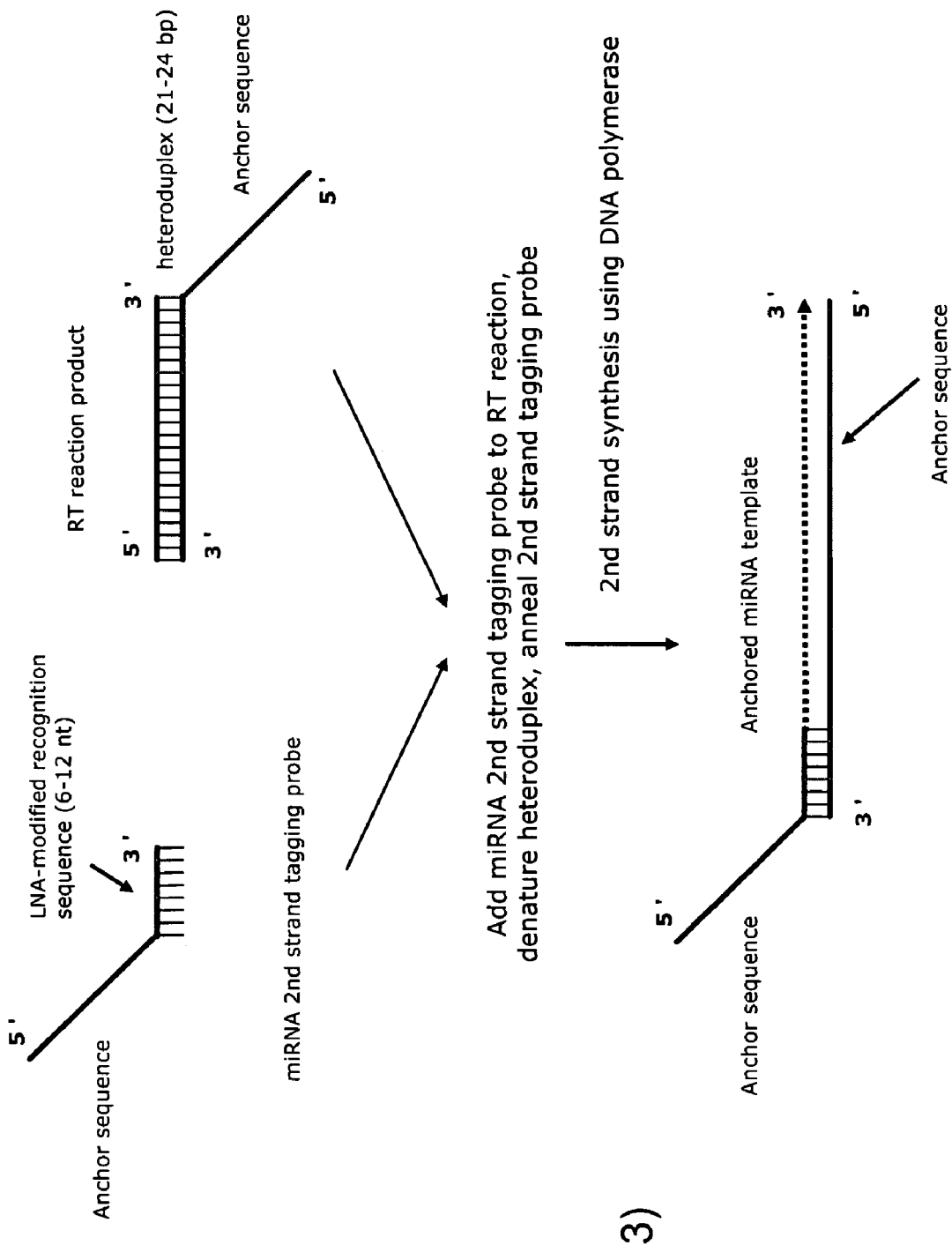
Fig. 11 (2/3)

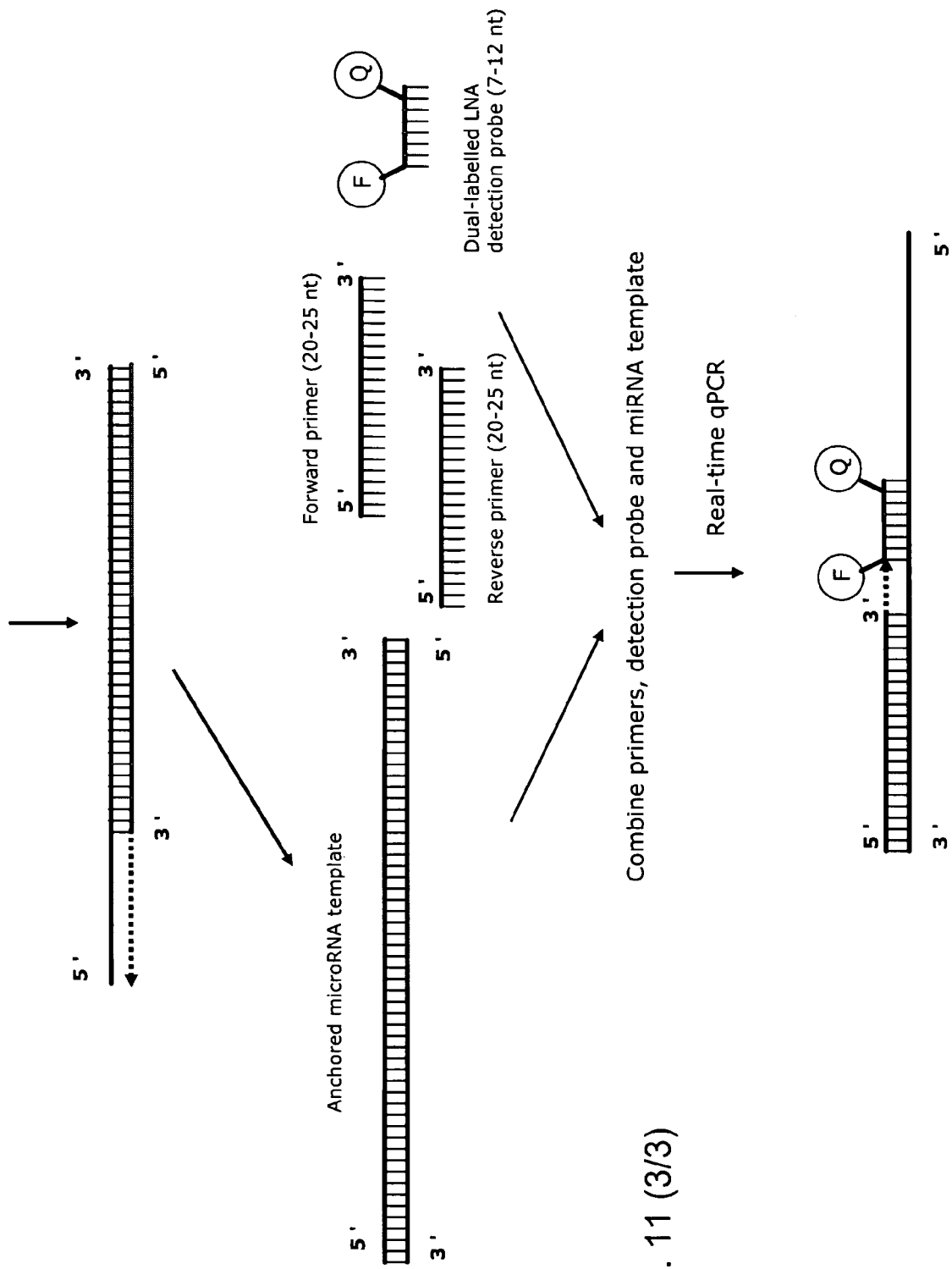
Fig. 11 (3/3)

A. LNA-2,6-diaminopurine (LNA-D)
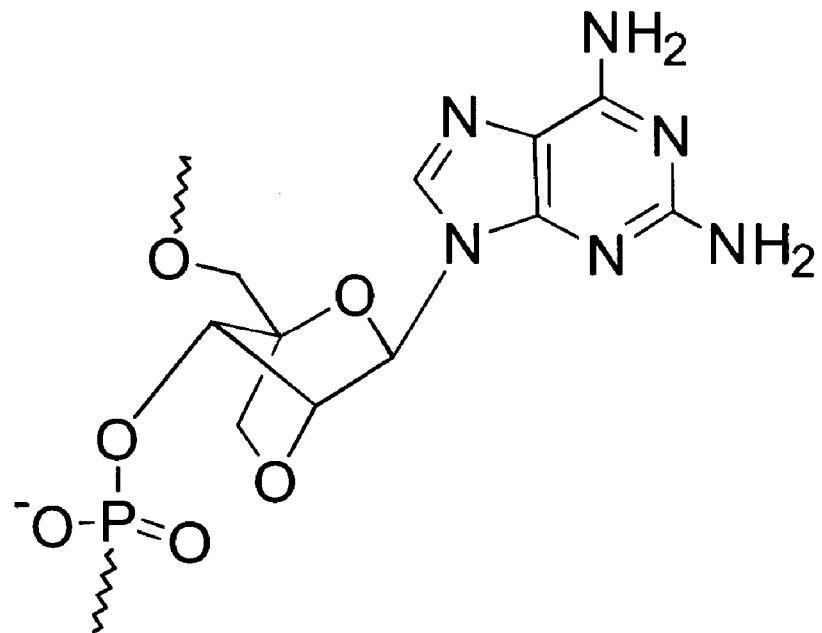
B. LNA-2-thiothymidine (2-thio-T)
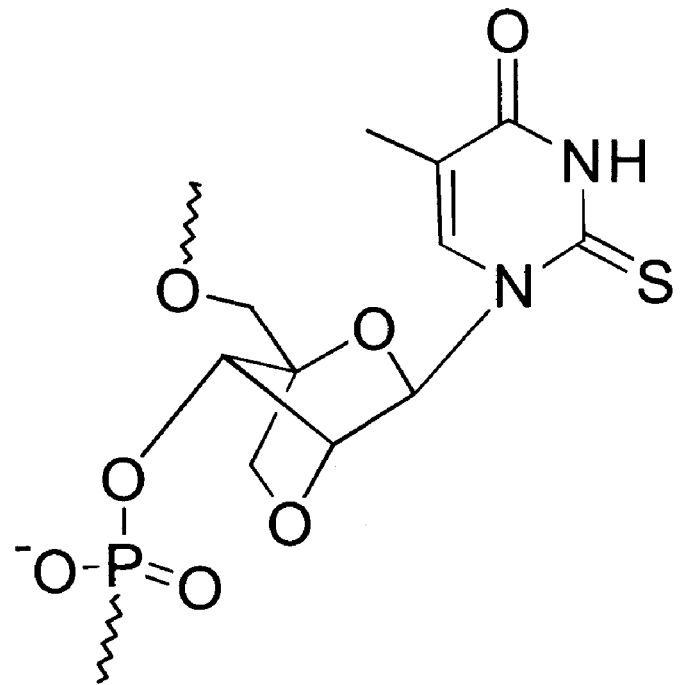
Fig. 12

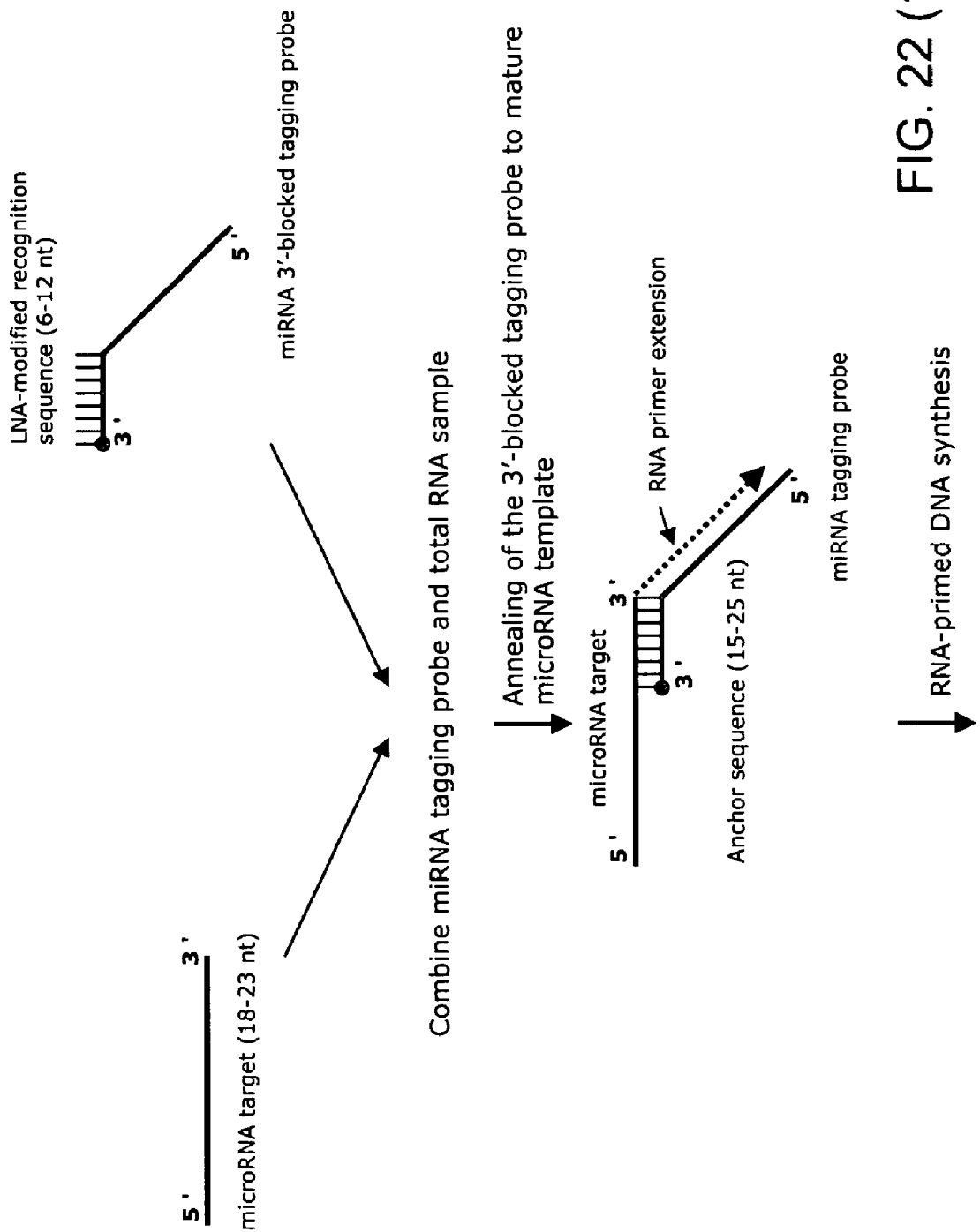
FIG. 22 (1/4)

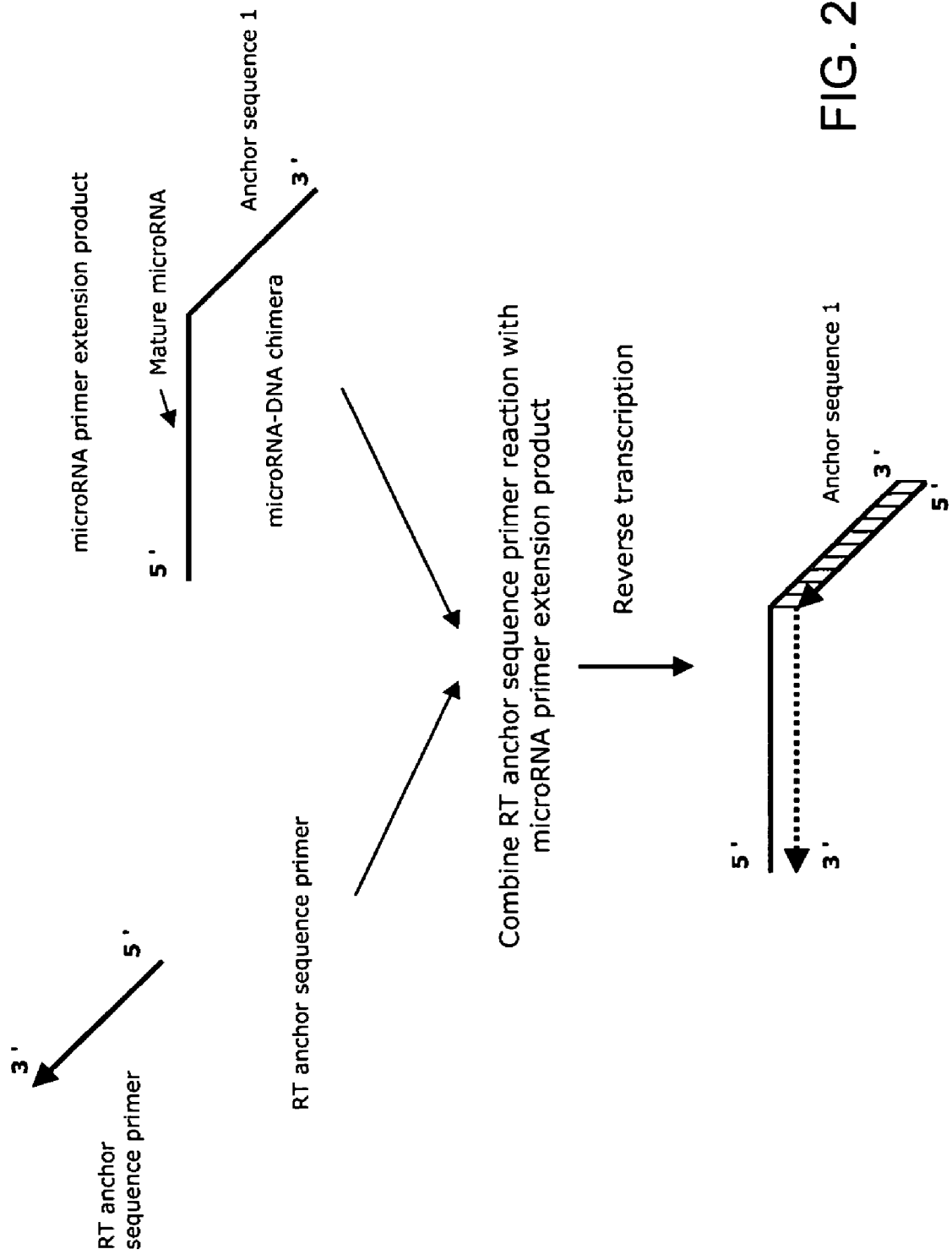
FIG. 22 (2/4)

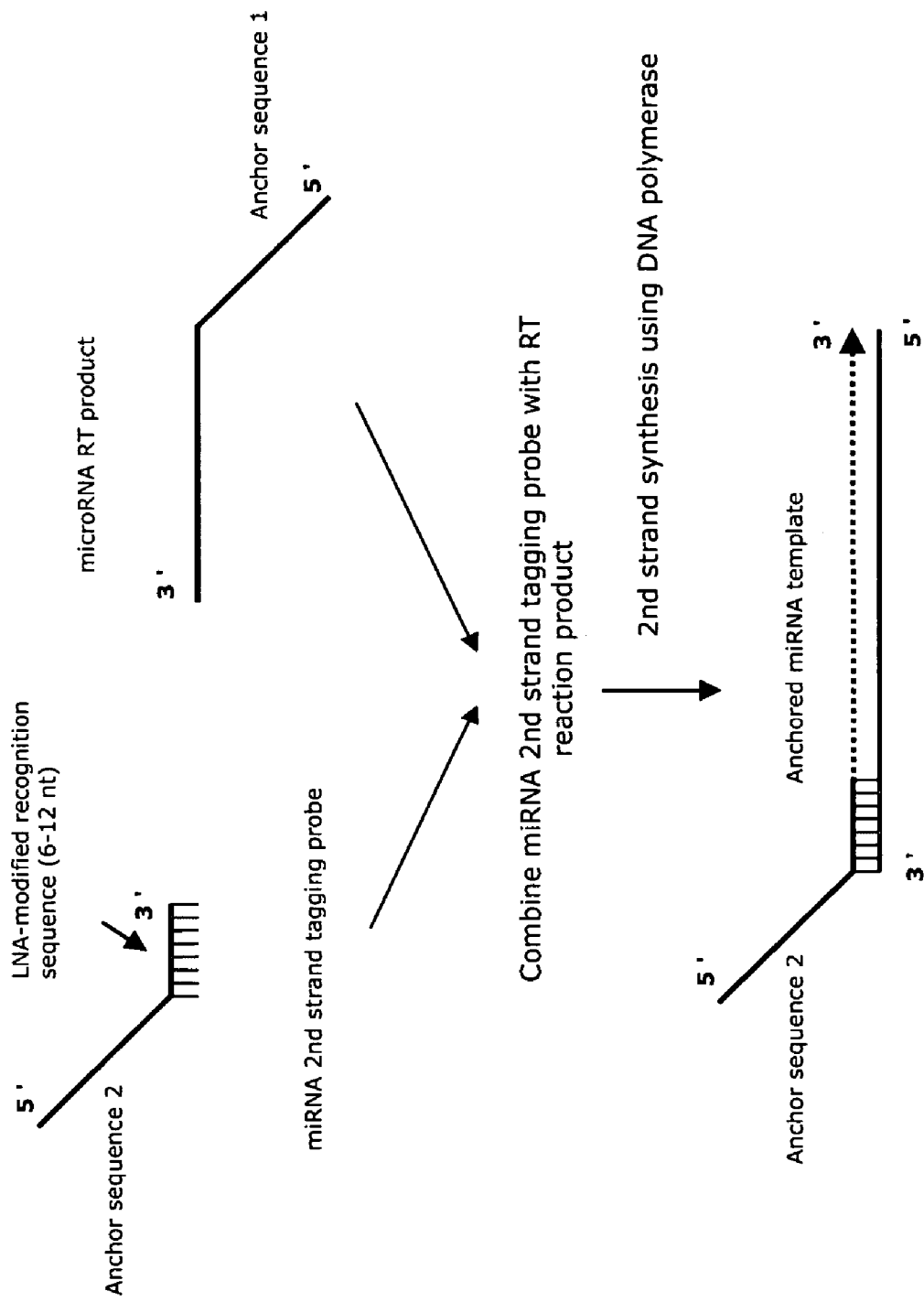
FIG. 22 (3/4)

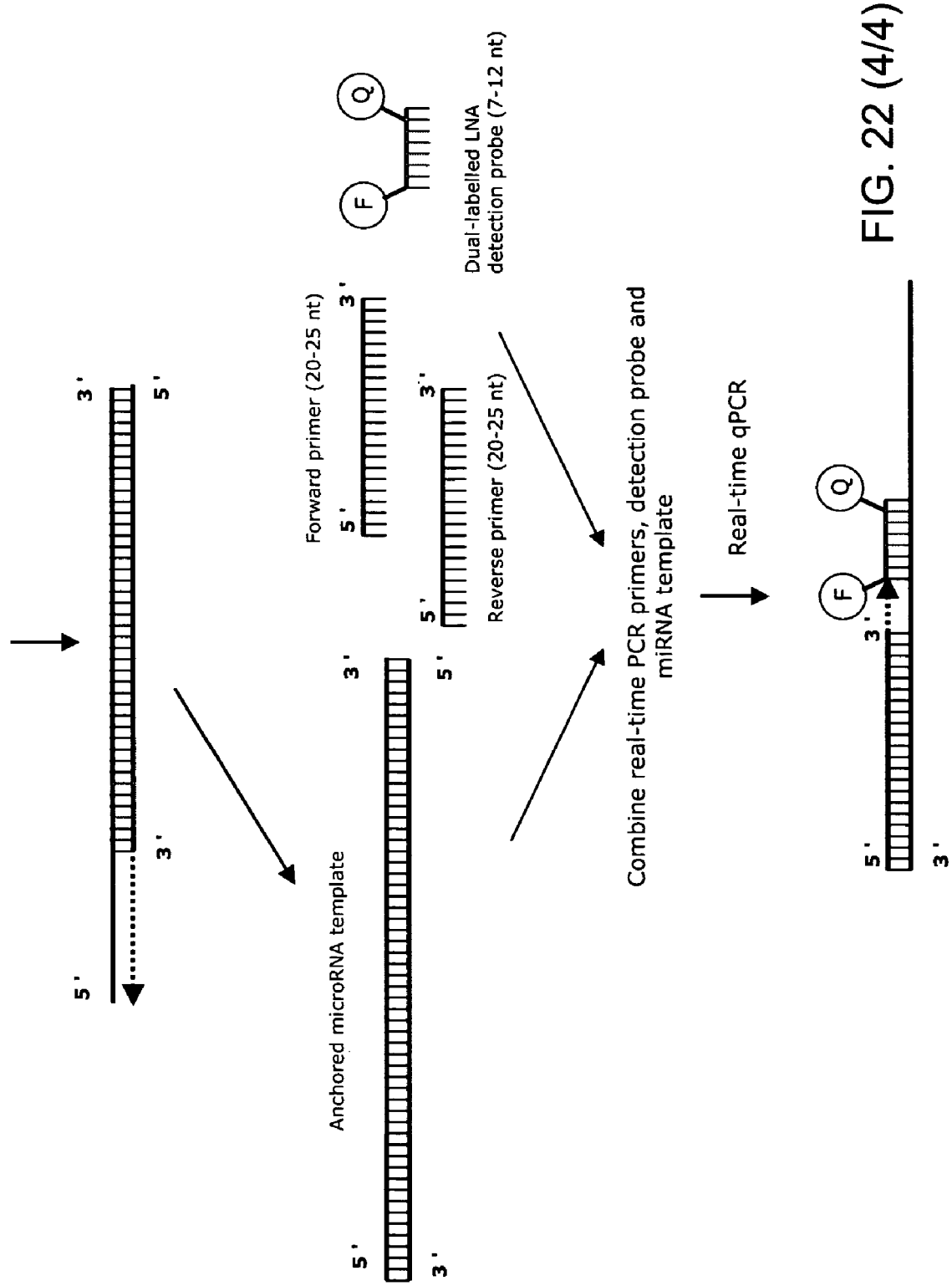
FIG. 22 (4/4)

Hsa miR-15a sequences

Stem-loop:

Fig. 29

```
5'
        gaguaaa ua           ua            ga  u
ccuug        g  gcagcaca  augguuugug    uu  u
|||||        |  ||||||||  |||||||||     ||  g    SEQ ID NO:72
ggaac        c  cgucgugu  uaccggacgu    aa  a
        auaaaaa uc           ua            gg  a
3'
```

When the miRNA is located on the upper strand of the stem-loop molecule, processing by the Dicer enzyme results in a unique 3'- end of the mature miR.

Mature:

```
14                    35
  uagcagcacauaaugguuugug        SEQ ID NO:73
```

Annealing a small LNA-modified oligo onto the RT primer prior to the cDNA synthesis reaction will introduce a local double helical structure in the RT-primer

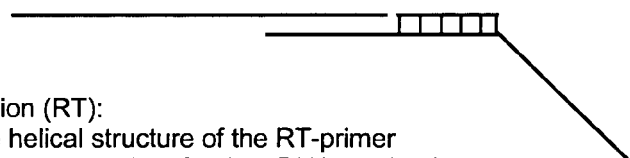

Reverse transcriptase reaction (RT):
Because of the local double helical structure of the RT-primer
only the mature miR will serve as template for the cDNA synthesis

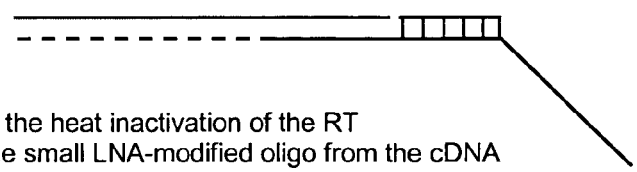

Following cDNA synthesis, the heat inactivation of the RT
enzyme also will melt off the small LNA-modified oligo from the cDNA

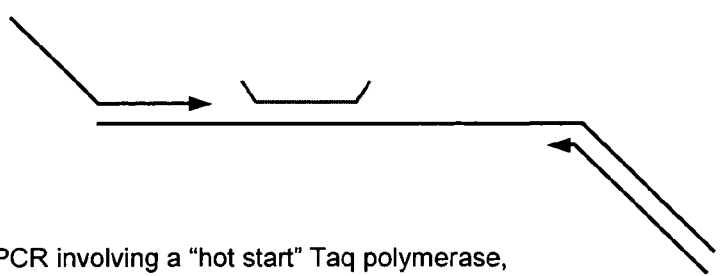

Real-time PCR:
Standard real-time PCR involving a "hot start" Taq polymerase,
if desired. The first cycle of PCR should use reduced annealing
temperature compared to the standard 60 °C, the remaining PCR
cycles can be performed at standard real-time PCR conditions.

Hsa-miR-143 sequences

Stem-loop:

```
-gc    c  ccug    c  ag      g             g          u  -  ag
   gcag gc    ucuc c    ccugag ugcagugcu caucuc gg uc u
   |||| ||    |||| |    |||||| ||||||||| |||||| || ||       SEQ ID NO:74
   cguc ug    agag g    ggacuc augucacga guagag cu ag u
cga    u  uuga    a  aa      g             a          u  g  gg
```

3'

When the miRNA is located on the lower strand of the stem-loop molecule, processing by the Dicer enzyme results in a unique 5'- end of the mature miR, whereas the 3'- end is identical for the pre-miR and the mature miR.

Mature:

61                              82
   ugagaugaagcacuguagcuca         SEQ ID NO:75

Reverse transcriptase reaction (RT):
The RT-primer will anneal to both
the mature miR and the pre-miR
(if present in the sample) and the reverse
transcriptase enzyme will make a cDNA copy of both molecules

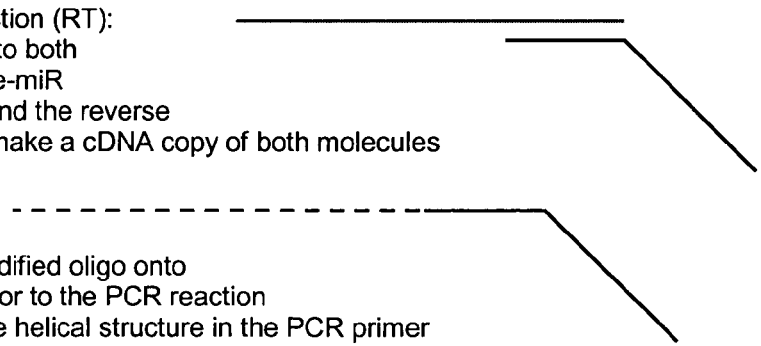

Annealing a small LNA-modified oligo onto
the forward PCR primer prior to the PCR reaction
will introduce a local double helical structure in the PCR primer Real-time PCR:
Because of the local
double helical structure
of the forward PCR primer,
the primer will preferably anneal
to the cDNA derived from the mature miR
The initial PCR cycle, which is actually a primer
extension reaction should be performed with a non "hot start"
Taq polymerase or a Klenow enzyme. The annealing temperature
should be around 45 °C or low enough to ensure that the local double
helical structure of the forward PCR primer is stable. The standard extension
temperature of 60 °C should work fine. The remaining PCR cycles can be performed
at standard real-time PCR conditions.

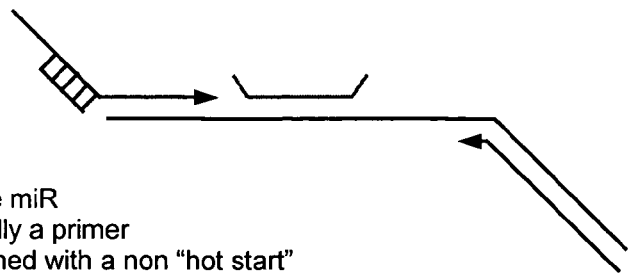

Open squares represent reaction with purification in step 2, closed squares represent reaction without purification in step 2. The curves that do not rise from the baseline represents the corresponding "No miR"-controls.

Hsa-miR-143 sequences
Stem-loop:

```
-gc    c  ccug    c  ag      g           g         u  -  ag
  gcag gc   ucuc c  ccugag ugcagugcu caucuc gg uc  u
  |||| ||   |||| |  |||||| ||||||||| |||||| || ||          SEQ ID NO:76
  cguc ug   agag g  ggacuc augucacga guagag cu ag  u
cga    u  uuga    a  aa      g           a         u  g   gg
```

3'

When the miRNA is located on the lower strand of the stem-loop molecule, processing by the Dicer enzyme results in a unique 5'- end of the mature miRNA, whereas the 3'- end is identical for the pre-miR and the mature miR.

Mature:

```
61                         82
   ugagaugaagcacuguagcuca        SEQ ID NO:77
```

Reverse transcriptase reaction (RT):
The RT-primer will anneal to both the mature miR and the pre-miR (if present in the sample) and the reverse transcriptase enzyme will make a cDNA copy of both molecules

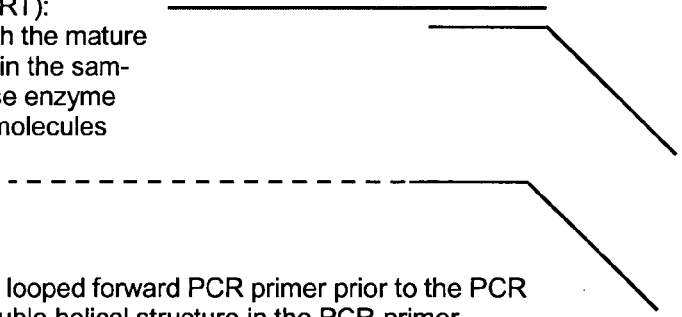

Annealing a small LNA-modified looped forward PCR primer prior to the PCR reaction will introduce a local double helical structure in the PCR primer

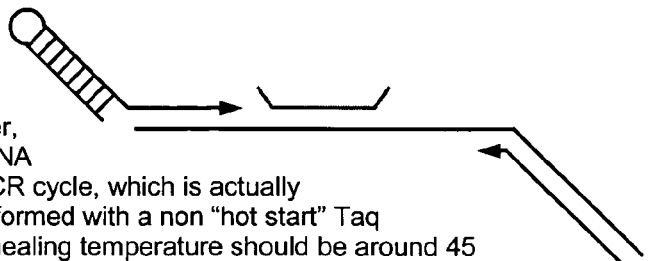

Real-time PCR:
Because of the looped forward PCR primer, the primer will preferably anneal to the cDNA derived from the mature miR The initial PCR cycle, which is actually a primer extension reaction should be performed with a non "hot start" Taq polymerase or a Klenow enzyme. The annealing temperature should be around 45 °C or low enough to ensure that the local double helical structure of the forward PCR primer is stable. The standard extension temperature of 60 °C should work fine. The remaining PCR cycles can be performed at standard real-time PCR conditions

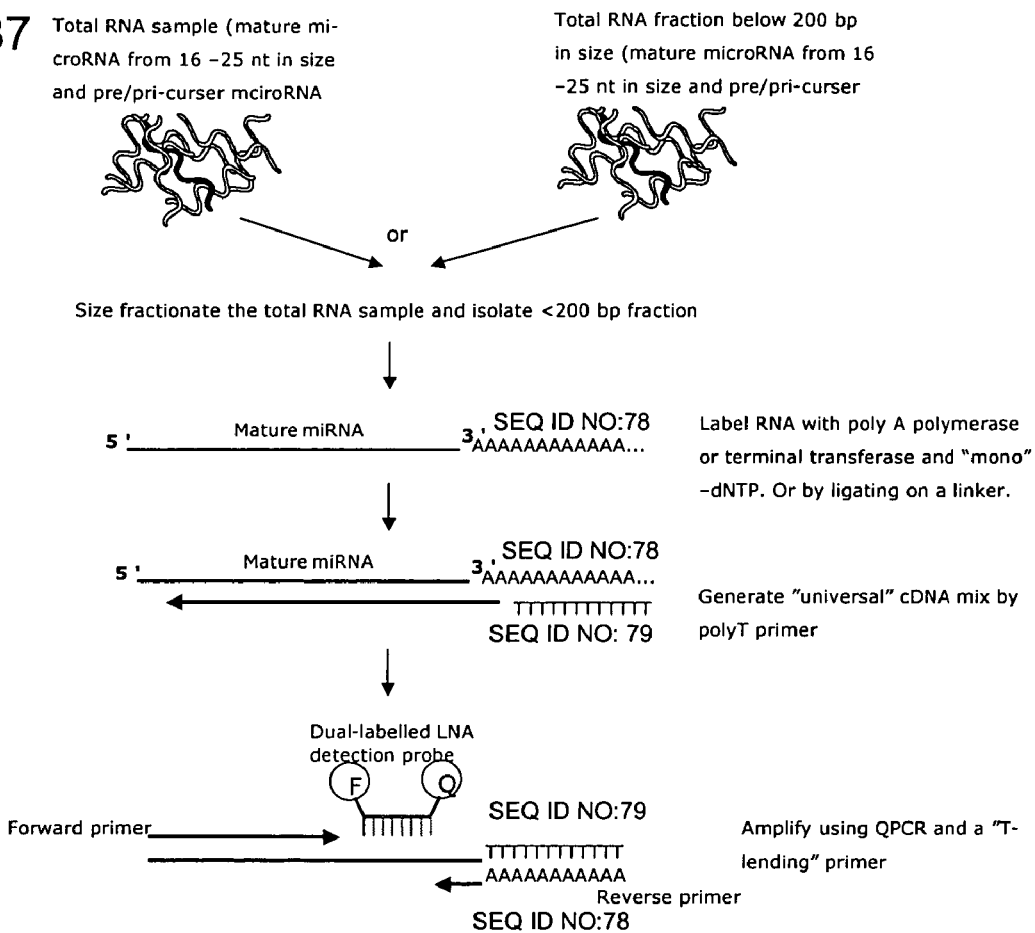

SEQUENCE LISTING

```
<160> NUMBER OF SEQ ID NOS: 79

<210> SEQ ID NO 1
<211> LENGTH: 17
<212> TYPE: DNA
<213> ORGANISM: artificial sequence
<220> FEATURE:
<223> OTHER INFORMATION: Synthetic sequence

<400> SEQUENCE: 1
gtaaaacgac ggccagt                                                    17

<210> SEQ ID NO 2
<211> LENGTH: 17
<212> TYPE: DNA
<213> ORGANISM: artificial sequence
<220> FEATURE:
<223> OTHER INFORMATION: Synthetic sequence

<400> SEQUENCE: 2
gaaacagcta tgacatg                                                    17

<210> SEQ ID NO 3
<211> LENGTH: 28
<212> TYPE: DNA
<213> ORGANISM: artificial sequence
<220> FEATURE:
<223> OTHER INFORMATION: Synthetic sequence

<400> SEQUENCE: 3
atgtgctgct aactggccgt cgttttac                                        28

<210> SEQ ID NO 4
<211> LENGTH: 28
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (24)..(24)
<223> OTHER INFORMATION: n is a, c, g, or t

<400> SEQUENCE: 4
gaaacagcta tgacatgcac aaancatt                                        28

<210> SEQ ID NO 5
<211> LENGTH: 22
<212> TYPE: DNA
<213> ORGANISM: artificial sequence
<220> FEATURE:
```

<223> OTHER INFORMATION: Synthetic sequence

<400> SEQUENCE: 5
tagcagcaca taatggtttg tg                                    22

<210> SEQ ID NO 6
<211> LENGTH: 22
<212> TYPE: DNA
<213> ORGANISM: artificial sequence
<220> FEATURE:
<223> OTHER INFORMATION: Synthetic sequence

<400> SEQUENCE: 6
tagcagcacg taaatattgg cg                                    22

<210> SEQ ID NO 7
<211> LENGTH: 22
<212> TYPE: RNA
<213> ORGANISM: artificial sequence
<220> FEATURE:
<223> OTHER INFORMATION: Synthetic sequence

<400> SEQUENCE: 7
uagcagcaca uaaugguuug ug                                    22

<210> SEQ ID NO 8
<211> LENGTH: 22
<212> TYPE: RNA
<213> ORGANISM: artificial sequence
<220> FEATURE:
<223> OTHER INFORMATION: Synthetic sequence

<400> SEQUENCE: 8
uagcagcacg uaaauauugg cg                                    22

<210> SEQ ID NO 9
<211> LENGTH: 18
<212> TYPE: DNA
<213> ORGANISM: artificial sequence
<220> FEATURE:
<223> OTHER INFORMATION: Synthetic sequence

<400> SEQUENCE: 9
cgtaaaacga cggccagt                                         18

<210> SEQ ID NO 10
<211> LENGTH: 25
<212> TYPE: DNA
<213> ORGANISM: artificial sequence
<220> FEATURE:
<223> OTHER INFORMATION: Synthetic sequence

<400> SEQUENCE: 10
caagtcttga aacagctatg acatg                                 25

<210> SEQ ID NO 11
<211> LENGTH: 20
<212> TYPE: DNA
<213> ORGANISM: artificial sequence
<220> FEATURE:
<223> OTHER INFORMATION: Synthetic sequence

<400> SEQUENCE: 11
gtaaaacgac ggccagttag                                       20

<210> SEQ ID NO 12

```
<211> LENGTH: 20
<212> TYPE: DNA
<213> ORGANISM: artificial sequence
<220> FEATURE:
<223> OTHER INFORMATION: Synthetic sequence

<400> SEQUENCE: 12
ccgaaacagc tatgacatgc                                              20

<210> SEQ ID NO 13
<211> LENGTH: 28
<212> TYPE: DNA
<213> ORGANISM: artificial sequence
<220> FEATURE:
<223> OTHER INFORMATION: Synthetic sequence

<400> SEQUENCE: 13
atgtgctgct aactggccgt cgttttac                                     28

<210> SEQ ID NO 14
<211> LENGTH: 28
<212> TYPE: DNA
<213> ORGANISM: artificial sequence
<220> FEATURE:
<223> OTHER INFORMATION: Synthetic sequence

<400> SEQUENCE: 14
gaaacagcta tgacatgcac aaaccatt                                     28

<210> SEQ ID NO 15
<211> LENGTH: 28
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 15
gaaacagcta tgacatgnan aaaccatt                                     28

<210> SEQ ID NO 16
<211> LENGTH: 28
<212> TYPE: DNA
<213> ORGANISM: artificial sequence
<220> FEATURE:
<223> OTHER INFORMATION: Synthetic sequence

<400> SEQUENCE: 16
gaaacagcta tgacatgcac aaaccatt                                     28

<210> SEQ ID NO 17
<211> LENGTH: 28
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (6)..(6)
<223> OTHER INFORMATION: n is a, c, g, or t

<400> SEQUENCE: 17
```

```
atgtgntgct aactggccgt cgttttac                                    28
```

<210> SEQ ID NO 18
<211> LENGTH: 28
<212> TYPE: DNA
<213> ORGANISM: artificial sequence
<220> FEATURE:
<223> OTHER INFORMATION: Synthetic sequence

<400> SEQUENCE: 18

```
gaaacagcta tgacatgcac aaaccatt                                    28
```

<210> SEQ ID NO 19
<211> LENGTH: 10
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 19

```
agnanataat                                                        10
```

<210> SEQ ID NO 20
<211> LENGTH: 10
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (6)..(6)
<223> OTHER INFORMATION: LNA-2,6-diaminopurine

<400> SEQUENCE: 20

```
agnanntaat                                                        10
```

<210> SEQ ID NO 21
<211> LENGTH: 10
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (4)..(4)
<223> OTHER INFORMATION: LNA-2,6-diaminopurine
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (6)..(6)

```
<223> OTHER INFORMATION: LNA-2,6-diaminopurine

<400> SEQUENCE: 21 agnnnntaat                                                                 10

<210> SEQ ID NO 22
<211> LENGTH: 10
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (4)..(4)
<223> OTHER INFORMATION: LNA-2,6-diaminopurine
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (6)..(6)
<223> OTHER INFORMATION: LNA-2,6-diaminopurine
<220> FEATURE:
<221> NAME/KEY: misc_feature
<222> LOCATION: (8)..(8)
<223> OTHER INFORMATION: LNA-2,6-diaminopurine

<400> SEQUENCE: 22 agnnnntnat                                                                 10

<210> SEQ ID NO 23
<211> LENGTH: 28
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (26)..(26)
<223> OTHER INFORMATION: n is a, c, g, or t

<400> SEQUENCE: 23
gtaaaacgac ggccagttag cagcanat                                             28

<210> SEQ ID NO 24
<211> LENGTH: 28
<212> TYPE: DNA
<213> ORGANISM: artificial sequence
<220> FEATURE:
<223> OTHER INFORMATION: Synthetic sequence

<400> SEQUENCE: 24
gtaaaacgac ggccagttag cagcacat                                             28

<210> SEQ ID NO 25
<211> LENGTH: 25
<212> TYPE: DNA
<213> ORGANISM: artificial sequence
<220> FEATURE:
<223> OTHER INFORMATION: Synthetic sequence

<400> SEQUENCE: 25
gaaacagcta tgacatgcac aaacc                                                25

<210> SEQ ID NO 26
```

```
<211> LENGTH: 25
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 26
gaaacagcta tgacatgnac aaanc                                              25

<210> SEQ ID NO 27
<211> LENGTH: 27
<212> TYPE: DNA
<213> ORGANISM: artificial sequence
<220> FEATURE:
<223> OTHER INFORMATION: Synthetic sequence

<400> SEQUENCE: 27
gtaaaacgac ggccagttag cagcaca                                            27

<210> SEQ ID NO 28
<211> LENGTH: 27
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 28
gtaaaacgac ggccagttag nagnaca                                            27

<210> SEQ ID NO 29
<211> LENGTH: 25
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 29
gaaacagcta tgacatgnac aaanc                                              25

<210> SEQ ID NO 30
<211> LENGTH: 24
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
```

```
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 30
gaaacagcta tgacatgnac aaan                                            24

<210> SEQ ID NO 31
<211> LENGTH: 24
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 31
gaaacagcta tgacatgnac aaan                                            24

<210> SEQ ID NO 32
<211> LENGTH: 24
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 32
gaaacagcta tgacatgnac aaan                                            24

<210> SEQ ID NO 33
<211> LENGTH: 24
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 33
gaaacagcta tgacatgnac aaan                                            24

<210> SEQ ID NO 34
<211> LENGTH: 25
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
```

```
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 34
gaaacagcta tgacatgnac aaanc                                            25

<210> SEQ ID NO 35
<211> LENGTH: 24
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 35
gaaacagcta tgacatgnac aaan                                             24

<210> SEQ ID NO 36
<211> LENGTH: 24
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 36
gaaacagcta tgacatgnac aaan                                             24

<210> SEQ ID NO 37
<211> LENGTH: 24
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 37
gaaacagcta tgacatgnac aaan                                             24

<210> SEQ ID NO 38
<211> LENGTH: 24
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
```

```
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 38
gaaacagcta tgacatgnac aaan                                           24

<210> SEQ ID NO 39
<211> LENGTH: 24
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 39
gaaacagcta tgacatgnac aaan                                           24

<210> SEQ ID NO 40
<211> LENGTH: 23
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 40
gaaacagcta tgacatgnan aaa                                            23

<210> SEQ ID NO 41
<211> LENGTH: 22
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 41
gaaacagcta tgacatgnan aa                                             22

<210> SEQ ID NO 42
<211> LENGTH: 28
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
```

```
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t

<400> SEQUENCE: 42
gaaacagcta tgacatgnan aaannatt                                         28

<210> SEQ ID NO 43
<211> LENGTH: 27
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t

<400> SEQUENCE: 43
gaaacagcta tgacatgnan aaannat                                          27

<210> SEQ ID NO 44
<211> LENGTH: 26
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t

<400> SEQUENCE: 44
gaaacagcta tgacatgnan aaanna                                           26

<210> SEQ ID NO 45
<211> LENGTH: 25
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(25)
```

<223> OTHER INFORMATION: n is a, c, g, or t

<400> SEQUENCE: 45
gaaacagcta tgacatgnan aaann    25

<210> SEQ ID NO 46
<211> LENGTH: 24
<212> TYPE: DNA
<213> ORGANISM: artificial sequence
<220> FEATURE:
<223> OTHER INFORMATION: Synthetic sequence

<400> SEQUENCE: 46
tatggaacgc ttcacgaatt tgcg    24

<210> SEQ ID NO 47
<211> LENGTH: 20
<212> TYPE: DNA
<213> ORGANISM: artificial sequence
<220> FEATURE:
<223> OTHER INFORMATION: Synthetic sequence

<400> SEQUENCE: 47
cgcttcggca gcacatatac    20

<210> SEQ ID NO 48
<211> LENGTH: 27
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 48
tactgagtaa tcgatatcna caaanca    27

<210> SEQ ID NO 49
<211> LENGTH: 23
<212> TYPE: DNA
<213> ORGANISM: artificial sequence
<220> FEATURE:
<223> OTHER INFORMATION: Synthetic sequence

<400> SEQUENCE: 49
caatttcaca caggatactg agt    23

<210> SEQ ID NO 50
<211> LENGTH: 22
<212> TYPE: DNA
<213> ORGANISM: artificial sequence
<220> FEATURE:
<223> OTHER INFORMATION: Synthetic sequence

<400> SEQUENCE: 50
agcggataac tagcagcaca ta    22

<210> SEQ ID NO 51
<211> LENGTH: 10
<212> TYPE: DNA
<213> ORGANISM: artificial sequence
<220> FEATURE:

-continued

<223> OTHER INFORMATION: Synthetic sequence

<400> SEQUENCE: 51
ttgtggatat                                                          10

<210> SEQ ID NO 52
<211> LENGTH: 28
<212> TYPE: DNA
<213> ORGANISM: artificial sequence
<220> FEATURE:
<223> OTHER INFORMATION: Synthetic sequence

<400> SEQUENCE: 52
caatttcaca caggatactg agtaatcg                                      28

<210> SEQ ID NO 53
<211> LENGTH: 22
<212> TYPE: RNA
<213> ORGANISM: artificial sequence
<220> FEATURE:
<223> OTHER INFORMATION: Synthetic sequence

<400> SEQUENCE: 53
ugagguagua gguuguauag uu                                            22

<210> SEQ ID NO 54
<211> LENGTH: 22
<212> TYPE: RNA
<213> ORGANISM: artificial sequence
<220> FEATURE:
<223> OTHER INFORMATION: Synthetic sequence

<400> SEQUENCE: 54
ugagguagua gauuguauag uu                                            22

<210> SEQ ID NO 55
<211> LENGTH: 21
<212> TYPE: RNA
<213> ORGANISM: artificial sequence
<220> FEATURE:
<223> OTHER INFORMATION: Synthetic sequence

<400> SEQUENCE: 55
ugagguagua guuuguacag u                                             21

<210> SEQ ID NO 56
<211> LENGTH: 35
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (33)..(33)
<223> OTHER INFORMATION: n is a, c, g, or t

<400> SEQUENCE: 56
gttgaggatg gatggtagga tgagtaacta tanaa                              35

<210> SEQ ID NO 57
<211> LENGTH: 23
<212> TYPE: DNA
<213> ORGANISM: artificial sequence
<220> FEATURE:
<223> OTHER INFORMATION: Synthetic sequence

<400> SEQUENCE: 57

-continued agaatggatg gatctgaggt agt                                           23

<210> SEQ ID NO 58
<211> LENGTH: 21
<212> TYPE: DNA
<213> ORGANISM: artificial sequence
<220> FEATURE:
<223> OTHER INFORMATION: Synthetic sequence

<400> SEQUENCE: 58
aggatggatg gtaggatgag t                                             21

<210> SEQ ID NO 59
<211> LENGTH: 21
<212> TYPE: DNA
<213> ORGANISM: artificial sequence
<220> FEATURE:
<223> OTHER INFORMATION: Synthetic sequence

<400> SEQUENCE: 59
gttgaggatg gatggtagga t                                             21

<210> SEQ ID NO 60
<211> LENGTH: 12
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t

<400> SEQUENCE: 60
actatanaan nt                                                       12

<210> SEQ ID NO 61
<211> LENGTH: 12
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t

<400> SEQUENCE: 61
actatanaan nt                                                       12

<210> SEQ ID NO 62
<211> LENGTH: 97
<212> TYPE: DNA
<213> ORGANISM: artificial sequence
<220> FEATURE:
<223> OTHER INFORMATION: Synthetic sequence

<400> SEQUENCE: 62
aagacagtag attgtatagt tatctcccag tggtgggtgt gaccctaaaa ctatacaacc   60
tactacctca tctccctata gtgagtcgta ttaaatt                            97

<210> SEQ ID NO 63
<211> LENGTH: 27
<212> TYPE: DNA
<213> ORGANISM: artificial sequence
<220> FEATURE:
<223> OTHER INFORMATION: Synthetic sequence

<400> SEQUENCE: 63
aatttaatac gactcactat agggaga                                           27

<210> SEQ ID NO 64
<211> LENGTH: 22
<212> TYPE: RNA
<213> ORGANISM: artificial sequence
<220> FEATURE:
<223> OTHER INFORMATION: Synthetic sequence

<400> SEQUENCE: 64
ugagaugaag cacuguagcu ca                                                22

<210> SEQ ID NO 65
<211> LENGTH: 36
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 65
ctgatagagc tttgcgtcca ctgattgagn tanagt                                 36

<210> SEQ ID NO 66
<211> LENGTH: 41
<212> TYPE: DNA
<213> ORGANISM: artificial sequence
<220> FEATURE:
<223> OTHER INFORMATION: Synthetic sequence

<400> SEQUENCE: 66
tgaatccgaa tctaacgttg cctaggctga gatgaagcac t                           41

<210> SEQ ID NO 67
<211> LENGTH: 21
<212> TYPE: DNA
<213> ORGANISM: artificial sequence
<220> FEATURE:
<223> OTHER INFORMATION: Synthetic sequence

<400> SEQUENCE: 67
tgaatccgaa tctaacgttg c                                                 21

<210> SEQ ID NO 68
<211> LENGTH: 20
<212> TYPE: DNA
<213> ORGANISM: artificial sequence
<220> FEATURE:
<223> OTHER INFORMATION: Synthetic sequence

<400> SEQUENCE: 68
ctgatagagc tttgcgtcca                                                   20

<210> SEQ ID NO 69
<211> LENGTH: 21
<212> TYPE: RNA
<213> ORGANISM: artificial sequence
<220> FEATURE:
<223> OTHER INFORMATION: Synthetic sequence

<400> SEQUENCE: 69
acucauccua ccauccaucc u                                              21

<210> SEQ ID NO 70
<211> LENGTH: 20
<212> TYPE: RNA
<213> ORGANISM: artificial sequence
<220> FEATURE:
<223> OTHER INFORMATION: Synthetic sequence

<400> SEQUENCE: 70
acucauccua ccauccaucc                                                20

<210> SEQ ID NO 71
<211> LENGTH: 16
<212> TYPE: DNA
<213> ORGANISM: artificial sequence
<220> FEATURE:
<223> OTHER INFORMATION: Synthetic sequence

<400> SEQUENCE: 71
ggatgagtaa ctatac                                                    16

<210> SEQ ID NO 72
<211> LENGTH: 83
<212> TYPE: RNA
<213> ORGANISM: Homo sapiens

<400> SEQUENCE: 72
ccuuggagua aaguagcagc acauaauggu uuguggauuu ugaaaaggug caggccauau     60
ugugcugccu caaaaauaca agg                                            83

<210> SEQ ID NO 73
<211> LENGTH: 22
<212> TYPE: RNA
<213> ORGANISM: Homo sapiens

<400> SEQUENCE: 73
uagcagcaca uaaugguuug ug                                             22

<210> SEQ ID NO 74
<211> LENGTH: 106
<212> TYPE: RNA
<213> ORGANISM: Homo sapiens

<400> SEQUENCE: 74
gcgcagcgcc cugucuccca gccugaggug cagcgcugca ucucuggucu guugggaguc     60
ugagaugaag cacuguagcu caggaagaga gaaguuguuc ugcagc                   106

<210> SEQ ID NO 75
<211> LENGTH: 22
<212> TYPE: RNA
<213> ORGANISM: Homo sapiens

<400> SEQUENCE: 75
ugagaugaag cacuguagcu ca                                             22

```
<210> SEQ ID NO 76
<211> LENGTH: 106
<212> TYPE: RNA
<213> ORGANISM: Homo sapiens

<400> SEQUENCE: 76
gcgcagcgcc cugucuccca gccugaggug cagugcugca ucucugguca guugggaguc      60
ugagaugaag cacuguagcu caggaagaga gaaguuguuc ugcagc                    106

<210> SEQ ID NO 77
<211> LENGTH: 22
<212> TYPE: RNA
<213> ORGANISM: Homo sapiens

<400> SEQUENCE: 77
ugagaugaag cacuguagcu ca                                               22

<210> SEQ ID NO 78
<211> LENGTH: 12
<212> TYPE: DNA
<213> ORGANISM: artificial sequence
<220> FEATURE:
<223> OTHER INFORMATION: Synthetic sequence

<400> SEQUENCE: 78
aaaaaaaaaa aa                                                          12

<210> SEQ ID NO 79
<211> LENGTH: 12
<212> TYPE: DNA
<213> ORGANISM: artificial sequence
<220> FEATURE:
<223> OTHER INFORMATION: Synthetic sequence

<400> SEQUENCE: 79
tttttttttt tt                                                          12
```

METHODS FOR QUANTIFICATION OF MICRORNAS AND SMALL INTERFERING RNAS

CROSS-REFERENCE TO RELATED APPLICATIONS

This application claims benefit from U.S. Provisional Application Nos. 60/560,148, filed Apr. 7, 2004; 60/590,856, filed Jul. 23, 2004; 60/600,961, filed Aug. 12, 2004; 60/619, 291, filed Oct. 15, 2004; and 60/648,221, filed Jan. 28, 2005, each of which is hereby incorporated by reference.

The present invention relates to nucleic acids, probes and methods for detection, quantification as well as monitoring the expression of mature microRNAs and small interfering RNAs (siRNAs). The invention furthermore relates to methods for monitoring the expression of other non-coding RNAs, mRNA splice variants, as well as detecting and quantifying RNA editing, allelic variants of single transcripts, mutations, deletions, or duplications of particular exons in transcripts, e.g. alterations associated with human disease, such as cancer. The invention furthermore relates to methods for detection and quantification of a target DNA sequence.

BACKGROUND OF THE INVENTION

The present invention relates to the quantification of target nucleotide sequences in a wide variety of nucleic acid samples and more specifically to the methods employing the design and use of oligonucleotide probes that are useful for detecting and quantifying target nucleotide sequences, especially RNA target sequences, such as microRNA and siRNA target sequences of interest and for detecting differences between nucleic acid samples (e.g., such as samples from a cancer patient and a healthy patient).

MicroRNAs

The expanding inventory of international sequence databases and the concomitant sequencing of nearly 200 genomes representing all three domains of life—bacteria, archea and eukaryota—have been the primary drivers in the process of deconstructing living organisms into comprehensive molecular catalogs of genes, transcripts and proteins. The importance of the genetic variation within a single species has become apparent, extending beyond the completion of genetic blueprints of several important genomes, culminating in the publication of the working draft of the human genome sequence in 2001 (Lander, Linton, Birren et al., 2001 Nature 409: 860-921; Venter, Adams, Myers et al., 2001 Science 291: 1304-1351; Sachidanandam, Weissman, Schmidt et al., 2001 Nature 409: 928-933). On the other hand, the increasing number of detailed, large-scale molecular analyses of transcription originating from the human and mouse genomes along with the recent identification of several types of non-protein-coding RNAs, such as small nucleolar RNAs, siRNAs, microRNAs and antisense RNAs, indicate that the transcriptomes of higher eukaryotes are much more complex than originally anticipated (Wong et al. 2001, Genome Research 11: 1975-1977; Kampa et al. 2004, Genome Research 14: 331-342).

As a result of the Central Dogma: 'DNA makes RNA, and RNA makes protein', RNAs have been considered as simple molecules that just translate the genetic information into protein. Recently, it has been estimated that although most of the genome is transcribed, almost 97% of the genome does not encode proteins in higher eukaryotes, but putative, non-coding RNAs (Wong et al. 2001, Genome Research 11: 1975-1977). The non-coding RNAs (ncRNAs) appear to be particularly well suited for regulatory roles that require highly specific nucleic acid recognition. Therefore, the view of RNA is rapidly changing from the merely informational molecule to comprise a wide variety of structural, informational and catalytic molecules in the cell.

Recently, a large number of small non-coding RNA genes have been identified and designated as microRNAs (miRNAs) (for review, see Ke et al. 2003, Curr. Opin. Chem. Biol. 7:516-523). The first miRNAs to be discovered were the lin-4 and let-7 that are heterochronic switching genes essential for the normal temporal control of diverse developmental events (Lee et al. 1993, Cell 75:843-854; Reinhart et al. 2000, Nature 403: 901-906) in the roundworm *C. elegans*. miRNAs have been evolutionarily conserved over a wide range of species and exhibit diversity in expression profiles, suggesting that they occupy a wide variety of regulatory functions and exert significant effects on cell growth and development (Ke et al. 2003, Curr. Opin. Chem. Biol. 7:516-523). Recent work has shown that miRNAs can regulate gene expression at many levels, representing a novel gene regulatory mechanism and supporting the idea that RNA is capable of performing similar regulatory roles as proteins. Understanding this RNA-based regulation will help us to understand the complexity of the genome in higher eukaryotes as well as understand the complex gene regulatory networks.

miRNAs are 21-25 nucleotide (nt) RNAs that are processed from longer endogenous hairpin transcripts (Ambros et al. 2003, RNA 9: 277-279). To date more than 719 microRNAs have been identified in humans, worms, fruit flies and plants according to the miRNA registry database hosted by Sanger Institute, UK, and many miRNAs that correspond to putative genes have also been identified. Some miRNAs have multiple loci in the genome (Reinhart et al. 2002, Genes Dev. 16: 1616-1626) and occasionally, several miRNA genes are arranged in tandem clusters (Lagos-Quintana et al. 2001, Science 294: 853-858). The fact that many of the miRNAs reported to date have been isolated just once suggests that many new miRNAs will be discovered in the future. A recent in-depth transcriptional analysis of the human chromosomes 21 and 22 found that 49% of the observed transcription was outside of any known annotation, and furthermore, that these novel transcripts were both coding and non-coding RNAs (Kampa et al. 2004, Genome Research 14: 331-342). The identified miRNAs to date represent most likely the tip of the iceberg, and the number of miRNAs might turn out to be very large.

The combined characteristics of microRNAs characterized to date (Ke et al. 2003, Curr. Opin. Chem. Biol. 7:516-523; Lee et al. 1993, Cell 75:843-854; Reinhart et al. 2000, Nature 403: 901-906) can be summarized as:

1. miRNAs are single-stranded RNAs of about 21-25 nt.
2. They are cleaved from a longer endogenous double-stranded hairpin precursor by the enzyme Dicer.
3. miRNAs match precisely the genomic regions that can potentially encode precursor RNAs in the form of double-stranded hairpins.
4. miRNAs and their predicted precursor secondary structures are phylogenetically conserved.

Several lines of evidence suggest that the enzymes Dicer and Argonaute are crucial participants in miRNA biosynthesis, maturation and function (Grishok et al. 2001, Cell 106: 23-24). Mutations in genes required for miRNA biosynthesis lead to genetic developmental defects, which are, at least in part, derived from the role of generating miRNAs. The current view is that miRNAs are cleaved by Dicer from the hairpin precursor in the form of duplex, initially with 2 or 3 nt overhangs in the 3' ends, and are termed pre-miRNAs. Cofactors join the pre-miRNP and unwind the pre-miRNAs into single-stranded miRNAs, and pre-miRNP is then transformed to miRNP. miRNAs can recognize regulatory targets while part of the miRNP complex. There are several similarities between miRNP and the RNA-induced silencing complex, RISC, including similar sizes and both containing RNA helicase and the PPD proteins. It has therefore been proposed that miRNP and RISC are the same RNP with multiple functions (Ke et al. 2003, Curr. Opin. Chem. Biol. 7:516-523). Different effectors direct miRNAs into diverse pathways. The structure of pre-miRNAs is consistent with the observation that 22 nt RNA duplexes with 2 or 3 nt overhangs at the 3' ends are beneficial for reconstitution of the protein complex and might be required for high affinity binding of the short RNA duplex to the protein components (for review, see Ke et al. 2003, Curr. Opin. Chem. Biol. 7:516-523).

Growing evidence suggests that miRNAs play crucial roles in eukaryotic gene regulation. The first miRNAs genes to be discovered, lin-4 and let-7, base-pair incompletely to repeated elements in the 3' untranslated regions (UTRs) of other heterochronic genes, and regulate the translation directly and negatively by antisense RNA-RNA interaction (Lee et al. 1993, Cell 75:843-854; Reinhart et al. 2000, Nature 403: 901-906). Other miRNAs are thought to interact with target mRNAs by limited complementary and suppressed translation as well (Lagos-Quintana et al. 2001, Science 294: 853-858; Lee and Ambros 2001, Science 294: 858-862). Many studies have shown, however, that given a perfect complementarity between miRNAs and their target RNA, could lead to target RNA degradation rather than inhibit translation (Hut-vanger and Zamore 2002, Science 297: 2056-2060), suggesting that the degree of complementarity determines their functions. By identifying sequences with near complementarity, several targets have been predicted, most of which appear to be potential transcriptional factors that are crucial in cell growth and development. The high percentage of predicted miRNA targets acting as developmental regulators and the conservation of target sites suggest that miRNAs are involved in a wide range of organism development and behaviour and cell fate decisions (for review, see Ke et al. 2003, Curr. Opin. Chem. Biol. 7:516-523).

MicroRNAs and Human Disease

Analysis of the genomic location of miRNAs indicates that they play important roles in human development and disease. Several human diseases have already been pinpointed in which miRNAs or their processing machinery might be implicated. One of them is spinal muscular atrophy (SMA), a paediatric neurodegenerative disease caused by reduced protein levels or loss-of-function mutations of the survival of motor neurons (SMN) gene (Paushkin et al. 2002, Curr. Opin. Cell Biol. 14: 305-312). Two proteins (Gemin3 and Gemin4) that are part of the SMN complex are also components of miRNPs, whereas it remains to be seen whether miRNA biogenesis or function is dysregulated in SMA and what effect this has on pathogenesis. Another neurological disease linked to mi/siRNAs is fragile X mental retardation (FXMR) caused by absence or mutations of the fragile X mental retardation protein (FMRP)(Nelson et al. 2003, TIBS 28: 534-540), and there are additional clues that miRNAs might play a role in other neurological diseases. Yet another interesting finding is that the miR-224 gene locus lies within the minimal candidate region of two different neurological diseases: early-onset Parkinsonism and X-linked mental retardation (Dostie et al. 2003, RNA: 9: 180-186). Links between cancer and miRNAs have also been recently described. The most frequent single genetic abnormality in chronic lymphocytic leukaemia (CLL) is a deletion localized to chromosome 13q14 (50% of the cases). A recent study determined that two different miRNA (miR15 and miR16) genes are clustered and located within the intron of LEU2, which lies within the deleted minimal region of the B-cell chronic lymphocytic leukaemia (B-CLL) tumour suppressor locus, and both genes are deleted or down-regulated in the majority of CLL cases (Calin et al. 2002, Proc. Natl. Acad. Sci. U.S.A. 99: 15524-15529). It has been anticipated that connections between miRNAs and human diseases will only strengthen in parallel with the knowledge of miRNAs and the gene networks that they control. Moreover, the understanding of the regulation of RNA-mediated gene expression is leading to the development of novel therapeutic approaches that will be likely to revolutionize the practice of medicine (Nelson et al. 2003, TIBS 28: 534-540).

Small Interfering RNAs and RNAi

Some of the recent attention paid to small RNAs in the size range of 21 to 25 nt is due to the phenomenon RNA interference (RNAi), in which double-stranded RNA leads to the degradation of any RNA that is homologous (Fire et al. 1998, Nature 391: 806-811). RNAi relies on a complex and ancient cellular mechanism that has probably evolved for protection against viral attack and mobile genetic elements. A crucial step in the RNAi mechanism is the generation of short interfering RNAs (siRNAs), double-stranded RNAs that are about 22 nt long each. The siRNAs lead to the degradation of homologous target RNA and the production of more siRNAs against the same target RNA (Lipardi et al. 2001, Cell 107: 297-307). The present view for the mRNA degradation pathway of RNAi is that antiparallel Dicer dimers cleave long double-stranded dsRNAs to form siRNAs in an ATP-dependent manner. The siRNAs are then incorporated in the RNA-induced silencing complex (RISC) and ATP-dependent unwinding of the siRNAs activates RISC (Zhang et al. 2002, EMBO J. 21: 5875-5885; Nykänen et al. 2001, Cell 107: 309-321). The active RISC complex is thus guided to degrade the specific target mRNAs.

Detection and Analysis of MicroRNAs and siRNAs

The current view that miRNAs may represent a newly discovered, hidden layer of gene regulation has resulted in high interest among researchers around the world in the discovery of miRNAs, their targets and mechanism of action. Detection and analysis of these small RNAs is, however not trivial. Thus, the discovery of more than 700 miRNAs to date has required taking advantage of their special features. First, the research groups have used the small size of the miRNAs as a primary criterion for isolation and detection. Consequently, standard cDNA libraries would lack miRNAs, primarily because RNAs that small are normally excluded by sixe selection in the cDNA library construction procedure. Total RNA from fly embryos, worms or HeLa cells have been size fractionated so that only molecules 25 nucleotides or smaller would be captured (Moss 2002, Curr. Biology 12: R138-R140). Synthetic oligomers have then been ligated directly to the RNA pools using T4 RNA ligase. Then the sequences have been reverse-transcribed, amplified by PCR, cloned and sequenced (Moss 2002, Curr. Biology 12: R138-R140). The genome databases have subsequently been queried with the sequences, confirming the origin of the miRNAs from these organisms as well as placing the miRNA genes physically in the context of other genes in the genome. The vast majority of the cloned sequences have been located in intronic regions or between genes, occasionally in clusters, suggesting that the tandemly arranged miRNAs are processed from a single transcript to allow coordinate regulation. Furthermore, the genomic sequences have revealed the fold-back structures of the miRNA precursors (Moss 2002, Curr. Biology 12: R138-R140).

The size and sometimes low level of expression of different miRNAs require the use of sensitive and quantitative analysis tools. Due to their small size of 21-25 nt, the use of quantitative real-time PCR for monitoring expression of mature miRNAs is excluded. Therefore, most miRNA researchers currently use Northern blot analysis combined with polyacrylamide gels to examine expression of both the mature and pre-miRNAs (Reinhart et al. 2000, Nature 403: 901-906; Lagos-Quintana et al. 2001, Science 294: 853-858; Lee and Ambros 2001, Science 294: 862-864). Primer extension has also been used to detect the mature miRNA (Zeng and Cullen 2003, RNA 9:112-123). The disadvantage of all the gel-based assays (Northern blotting, primer extension, RNase protection assays etc.) as tools for monitoring miRNA expression includes low throughput and poor sensitivity. DNA microarrays would appear to be a good alternative to Northern blot analysis to quantify miRNAs since microarrays have excellent throughput. However, the drawbacks of microarrays are the requirement of high concentrations of input target for efficient hybridization and signal generation, poor sensitivity for rare targets, and the necessity for post-array validation using more sensitive assays such as real-time quantitative PCR, which is not feasible. A recent report used cDNA microarrays to monitor the expression of miRNAs during neuronal development with 5 to 10 µg aliquot of input total RNA as target, but the mature miRNAs had to be separated from the miRNA precursors using micro concentrators prior to microarray hybridizations (Krichevsky et al. 2003, RNA 9: 1274-1281). A PCR approach has also been used to determine the expression levels of mature miRNAs (Grad et al. 2003, Mol. Cell 11: 1253-1263). This method is useful to clone miRNAs, but highly impractical for routine miRNA expression profiling, since it involves gel isolation of small RNAs and ligation to linker oligonucleotides. Schmittgen et al. (2004, Nucleic Acids Res. 32: e43) describe an alternative method to Northern blot analysis, in which they use real-time PCR assays to quantify the expression of miRNA precursors. The disadvantage of this method is that it only allows quantification of the precursor miRNAs, which does not necessarily reflect the expression levels of mature miRNAs. In order to fully characterize the expression of large numbers of miRNAs, it is necessary to quantify the mature miRNAs, such as those expressed in human disease, where alterations in miRNA biogenesis produce levels of mature miRNAs that are very different from those of the precursor miRNA. For example, the precursors of 26 miRNAs were equally expressed in non-cancerous and cancerous colorectal tissues from patients, whereas the expression of mature human miR143 and miR145 was greatly reduced in cancer tissues compared with non-cancer tissues, suggesting altered processing for specific miRNAs in human disease (Michael et al. 2003, Mol. Cancer Res. 1: 882-891). On the other hand, recent findings in maize with miR166 and miR165 in *Arabidopsis thaliana*, indicate that microRNAs act as signals to specify leaf polarity in plants and may even form movable signals that emanate from a signalling centre below the incipient leaf (Juarez et al. 2004, Nature 428: 84-88; Kidner and Martienssen 2004, Nature 428: 81-84).

In conclusion, the biggest challenge in measuring the mature miRNAs as well as siRNAs using real-time quantitative PCR is their small size of the of 21-25 nt. The described method of invention addresses the aforementioned practical problems in detection and quantification of small RNA molecules, miRNAs as well as siRNAs, and aims at ensuring the development of flexible, convenient and inexpensive assays for accurate and specific quantification of miRNA and siRNA transcripts.

RNA Editing and Alternative Splicing

RNA editing is used to describe any specific change in the primary sequence of an RNA molecule, excluding other mechanistically defined processes such as alternative splicing or polyadenylation. RNA alterations due to editing fall into two broad categories, depending on whether the change happens at the base or nucleotide level (Gott 2003, C. R. Biologies 326 901-908). RNA editing is quite widespread, occurring in mammals, viruses, marsupials, plants, flies, frogs, worms, squid, fungi, slime molds, dinoflagellates, kinetoplastid protozoa, and other unicellular eukaryotes. The current list most likely represents only the tip of the iceberg; based on the distribution of homologues of known editing enzymes, as RNA editing almost certainly occurs in many other species, including all metazoa. Since RNA editing can be regulated in a developmental or tissue-specific manner, it is likely to play a significant role in the etiology of human disease (Gott 2003, C. R. Biologies 326 901-908).

A common feature for eukaryotic genes is that they are composed of protein-encoding exons and introns. Introns are characterized by being excised from the pre-mRNA molecule in RNA splicing, as the sequences on each side of the intron are spliced together. RNA splicing not only provides functional mRNA, but is also responsible for generating additional diversity. This phenomenon is called alternative splicing, which results in the production of different mRNAs from the same gene. The mRNAs that represent isoforms arising from a single gene can differ by the use of alternative exons or retention of an intron that disrupts two exons. This process often leads to different protein products that may have related or drastically different, even antagonistic, cellular functions. There is increasing evidence indicating that alternative splicing is very widespread (Croft et al. Nature Genetics, 2000). Recent studies have revealed that at least 80% of the roughly 35,000 genes in the human genome are alternatively spliced (Kampa et al. 2004, Genome Research 14: 331-342). Clearly, by combining different types of modifications and thus generating different possible combinations of transcripts of different genes, alternative splicing together with RNA editing are potent mechanisms for generating protein diversity.

Analysis of the alternative splice variants and RNA editing, in turn, represents a novel approach to functional genomics, disease diagnostics and pharmacogenomics.

Misplaced Control of Alternative Splicing as a Causative Agent for Human Disease The detection of the detailed structure of the transcriptional output is an important goal for molecular characterization of a cell or tissue. Without the ability to detect and quantify the splice variants present in one tissue, the transcript content or the protein content cannot be described accurately. Molecular medical research shows that many cancers result in altered levels of splice variants, so an accurate method to detect and quantify these transcripts is required. Mutations that produce an aberrant splice form can also be the primary cause of such severe diseases such as spinal muscular dystrophy and cystic fibrosis.

Much of the study of human disease, indeed much of genetics is based upon the study of a few model organisms. The evolutionary stability of alternative splicing patterns and the degree to which splicing changes according to mutations and environmental and cellular conditions influence the relevance of these model systems. At present, there is little understanding of the rates at which alternative splicing patterns or RNA editing change, and the factors influencing these rates.

Previously, other analysis methods have been performed with the aim of detecting either splicing of RNA transcripts per se in yeast, or of detecting putative exon skipping splicing events in rat tissues, but neither of these approaches had sufficient resolution to estimate quantities of splice variants, a factor that could be essential to an understanding of the changes in cell life cycle and disease. Thus, improved methods are needed for nucleic acid amplification, hybridization, and quantification. The present method of invention enables to distinguish between mRNA splice variants as well as RNA-edited transcripts and quantify the amount of each variant in a nucleic acid sample, such as a sample derived from a patient.

Antisense Transcription in Eukaryotes

RNA-mediated gene regulation is widespread in higher eukaryotes and complex genetic phenomena like RNA interference, co-suppression, transgene silencing, imprinting, methylation, and possibly position-effect variegation and transvection, all involve intersecting pathways based on or connected to RNA signalling (Mattick 2001; EMBO reports 2, 11: 986-991). Recent studies indicate that antisense transcription is a very common phenomenon in the mouse and human genomes (Okazaki et al. 2002; Nature 420: 563-573; Yelin et al. 2003, Nature Biotechnol.). Thus, antisense modulation of gene expression in eukaryotic cells, e.g. human cells appear to be a common regulatory mechanism. In light of this, the present invention provides a method for quantification of non-coding antisense RNAs, as well as a method for highly accurate mapping of the overlapping regions between sense-antisense transcriptional units.

SUMMARY OF THE INVENTION

The challenges of establishing genome function and understanding the layers of information hidden in the complex transcriptomes of higher eukaryotes call for novel, improved technologies for detection, analysis and quantification of RNA molecules in complex nucleic acid samples. Thus, it would be highly desirable to be able to detect and quantify the expression of mature microRNAs, siRNAs, RNA-edited transcripts as well as highly homologous splice variants in the transcriptomes of eukaryotes using methods based on specific and sensitive oligonucleotide detection probes in a homogeneous assay system.

The present invention solves the current problems faced by conventional approaches to homogeneous assays outlined above by providing a method for the design, synthesis and combined use of novel oligonucleotide tagging probes and detection probes with sufficient sequence specificity and high affinity to short nucleic acid targets, e.g. RNA target sequences—so that they are unlikely to detect a random RNA target molecule and also unlikely to detect pre-mature RNA molecules. Such tagging probes contain a sequence, anchored to the tagging probes, essential as priming sites for subsequent amplification of the nucleic acids by polymerase chain reaction in real-time quantitative PCR assays. The method of invention utilizes two anchored tagging probes, each designed in combination to detect a complementary target sequence, e.g. a short RNA sequence, where the first tagging probe hybridizes to a first region within a target sequence and the second tagging probe hybridizes to a second region within the same complementary target sequence, e.g. a short RNA target sequence that is adjacent to the first region. In the preferred mode, one of the tagging probes is 5' phosphorylated enabling covalent coupling of the two contiguous tagging oligonucleotide probes hybridized to the complementary target sequence by a ligase to form a single oligonucleotide sequence. The background in the hybridization to the target RNA sequence in complex nucleic acid samples is eliminated by the use of two tagging probes, where the hybridization of both probes to the complementary target sequence, e.g. short RNA target sequence is required for the covalent joining of the two probes. The method furthermore takes the advantage of substitution of the recognition sequences with high-affinity nucleotide analogues, e.g. LNA, for sensitive and specific hybridization to short target sequences, e.g. miRNAs or siRNAs. The ligation reaction is followed by quantitative real-time PCR of the target sequence, e.g. ribonucleic acid-templated, covalently joined oligonucleotide molecules using the anchor sequences attached to the tagging probes as priming sites for the PCR primers and a short detection probe with sufficient duplex stability to allow binding to the amplicon, and employing any of a variety of detection principles used in homogeneous assays. In the preferred mode, the detection probe is substituted with duplex-stabilizing, high-affinity nucleotide analogues, e.g. LNA, and preferably oxy-LNA, to allow use of short detection probes in the real-time quantitative PCR assay.

In another approach the covalent joining of the tagging probes hybridized to the target ribonucleic acid in the nucleic acid sample is carried out using a thermostable ligase, which allows repetitive cycles of denaturation, annealing and ligation at elevated temperatures to be carried out in the target sequence tagging reaction, thus generating a plurality of covalently joined template molecules for the subsequent real-time quantitative PCR assay. In the preferred mode the annealing temperature is adjusted so as to allow discrimination between highly homologous target ribonucleic acids in complex nucleic acid samples. In another aspect the annealing temperature is adjusted to allow single mismatch discrimination between highly homologous target sequences.

In yet another approach the recognition sequence of the first tagging probe is complementary to a sequence in the target ribonucleic acid sequence, e.g. to the 3'-end of the mature microRNA or siRNA or to a sequence located 3' to the RNA edited nucleotide, splice junction, single nucleotide polymorphism or point mutation in the target ribonucleic acid sequence. The said first tagging probe, designated as RT tagging probe, is used as an anchored primer in a reverse transcription reaction to generate a primer extension product, complementary to the target RNA sequence using a reverse transcriptase enzyme. The second tagging probe, designated as $2^{nd}$ strand tagging probe, is designed so that its recognition sequence is complementary to the reverse transcriptase-extended nucleotide sequence corresponding to the 5'-end of the mature microRNA or siRNA or located 5' to the RNA edited nucleotide, splice junction, single nucleotide polymorphism or point mutation in the ribonucleic acid target sequence The $2^{nd}$ strand tagging probe is used as anchored primer to generate the second strand complementary to the primer extension product. The specificity of the reaction is based on the sequential use of the two anchored tagging probes, hybridising to complementary 3'-end and 5'-end regions of the target RNA and complementary DNA sequences, respectively. In a preferred mode the recognition sequence of the RT tagging probe is modified with duplex-stabilizing, high-affinity nucleotide analogues e.g. LNA, and preferably oxy-LNA, to allow use of high-stringency primer annealing conditions. In yet another preferred mode the recognition sequences of both tagging probes are modified with duplex-stabilizing, high-affinity nucleotide analogues e.g. LNA, and preferably oxy- LNA, to allow use of high-stringency primer annealing conditions in both the reverse transcription and second strand synthesis reactions, respectively. The second strand reaction is followed by quantitative real-time PCR of the resulting double-stranded target sequence, corresponding to an anchored target ribonucleic acid sequence, e.g. a microRNA sequence, using the anchor sequences attached to the tagging probes as priming sites for the PCR primers and a short detection probe with sufficient duplex stability to allow binding to the amplicon, and employing any of a variety of detection principles used in homogeneous assays. In the preferred mode, the detection probe is substituted with duplex-stabilizing, high-affinity nucleotide analogues, e.g. LNA, and preferably oxy-LNA, to allow use of short detection probes in the real-time quantitative PCR assay. In yet another preferred mode, the detection probe is furthermore substituted with duplex-stabilizing LNA diaminopurine or LNA 2-thio-T high-affinity analogues in combination with LNA monomers.

The present methods of invention are highly useful and applicable for detection and quantification of individual small RNA molecules in complex mixtures composed of hundreds of thousands of different nucleic acids, such as detecting mature miRNAs or siRNAs, when combined with a miRNA or siRNA target specific tagging probe set and a miRNA or a siRNA detection probe. The recognition sequences in the tagging probe set as well as the detection probe are synthesized by substitution of high affinity nucleotide analogues, e.g. LNA, and preferably oxy-LNA, allowing highly sensitive and specific hybridization and ligation to occur at elevated temperatures. By the use of short detection probes of the invention, substituted with high affinity nucleotide analogues, e.g. LNA, LNA diaminopurine and LNA 2-thio-thymidine, short amplicons corresponding to mature miRNAs or siRNAs, including the anchor primer sites from the tagging probe set can be monitored directly in standard real-time quantitative PCR assays. The present method is furthermore highly useful in the detection and quantification of non-coding RNAs other than miRNAs or siRNAs, antisense RNA transcripts, RNA-edited transcripts or highly homologous, alternatively spliced transcripts in complex nucleic acid samples, such as the human, mouse, rat, *C. elegans, Drosophila melanogaster, Arabidopsis thaliana*, rice and maize transcriptomes composed of hundreds of thousands of different ribonucleic acids in their respective transcriptomes. The method is also directly applicable to detecting, testing, diagnosing or quantifying miRNAs, siRNAs, other non-coding RNAs, RNA-edited transcripts or alternative mRNA splice variants implicated in or connected to human disease in complex human nucleic acid samples, e.g. from cancer patients.

BRIEF DESCRIPTION OF THE DRAWINGS

FIG. 1 is a schematic presentation of one method of the invention for quantification of microRNAs by sequence-specific real-time quantitative RT-PCR.

FIG. 9 is a schematic presentation of one method of the invention for quantification of microRNAs by sequence-specific real-time quantitative RT-PCR.

FIG. 11 is a schematic presentation of one method of the invention for quantification of microRNAs by sequence-specific real-time quantitative RT-PCR.

FIG. 12 shows the structures of LNA 2,6-diaminopurine and LNA 2-thiothymidine nucleosides.

FIG. 22 is a schematic presentation of one method of the invention for quantification of microRNAs by sequence-specific real-time quantitative RT-PCR.

FIG. 34 shows part of the Hsa miR-143 precursor sequence, the mature Hsa miR-143 sequence and a schematic presentation of one method of the invention for quantification of microRNAs by sequence-specific real-time quantitative RT-PCR.

FIG. 37 shows a schematic presentation of one method of the invention for quantification of microRNAs by sequence-specific real-time quantitative RT-PCR.

DEFINITIONS

Figure 2A:
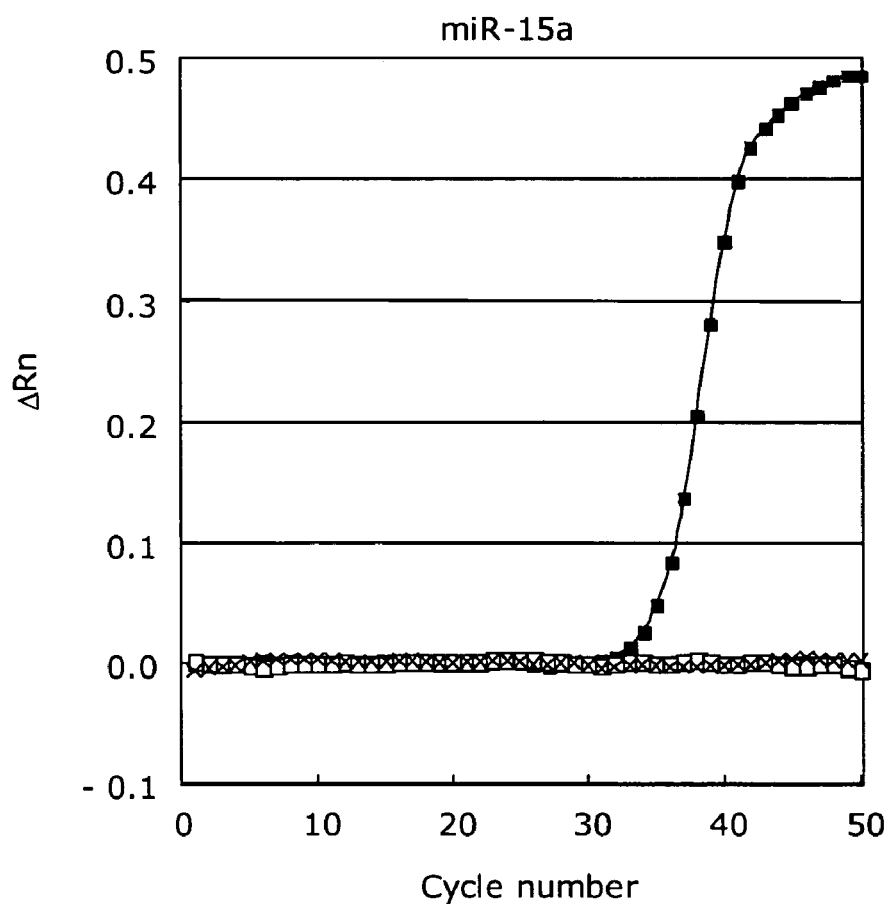
FIG. 2A shows the real-time quantitative PCR amplification plot for the human miR-15a microRNA target sequence. The sequence-specific LNA-modified microRNA tagging probes were annealed, ligated and the ligated tagging probes were subsequently detected using real-time PCR, anchor PCR primers and an LNA-modified dual-labelled detection probe for the miR-15a microRNA (solid squares) using a minus template as a negative control (crosses). The specificity of the reaction was tested using a reaction without ligase (open squares). The threshold cycle (Ct) for the ligated microRNA probes using the miR-15a microRNA template was 35.0 whereas no Ct values were detectable for the negative control experiments (minus template and minus ligase). The ΔRn is the baseline corrected normalized reporter signal (Rn) and represents the Rn minus the baseline signal established in the first few cycles of PCR.

For the purposes of the subsequent detailed description of the invention the following definitions are provided for specific terms, which are used in the disclosure of the present invention:

In the following, "Blocker probe" or "blocker probes" refer to a probe or probes, comprising a recognition sequence, complementary to the target sequence, e.g. a short RNA target sequence, an oligonucleotide, a primer. The said blocker probe is used to prevent hybridization of sequence identical molecules towards the complementary target sequence. Generally, the blocker probe contains one, two or more LNA monomers and the 3'- terminus of the blocker probe is modified to prohibit incorporation of the blocker probe into a primer extension product. This "blocking" may be achieved by using non-complementary bases or by adding a chemical moiety such as biotin or a phosphate group to the 3' -hydroxyl group of the last nucleotide.

In the following, "dNTP" means a mixture of 2'-deoxyadenosine-5'-triphosphate, 2'-deoxycytidine-5'-triphosphate, 2'-deoxyguanosine-5'-triphosphate, and 2'-deoxythymidine-5'-triphosphate "RT-primer" refers to a primer, comprising a recognition sequence, complementary to a sequence in the target deoxyribonucleic and/or ribonucleic acid sequence, e.g. to the 3'-end of the mature microRNA or siRNA, or to an RNA-DNA chimerical moiety, or to a sequence located 3' to a RNA-edited nucleotide, splice junction, single nucleotide polymorphism or point mutation in the target ribonucleic acid sequence, and an anchor sequence essential for subsequent capture or amplification by PCR. The said RT-primer is used as an anchored primer in a reverse transcription reaction to generate a primer extension product, complementary to the target RNA sequence using a reverse transcriptase enzyme.

The term "Capture probes" or "capture probe" refer to a probe(s), comprising a recognition sequence, complementary to the target sequence, e.g. a short RNA target sequence, and an anchor sequence essential for subsequent capture, reverse transcription reaction, or amplification by PCR. The anchor sequence function as priming sites for the RT- or PCR primers in subsequent reverse transcription reaction, real-time PCR, or as tags for capture assays.

In the present context, the term "linker" means a thermochemically and photochemically non-active distance-making group that is used to join two or more different nucleotide moieties of the types defined above. Linkers are selected on the basis of a variety of characteristics including their hydrophobicity, hydrophilicity, molecular flexibility and length (e.g. see Hermanson et. al., "Immobilized Affinity Ligand Techniques", Academic Press, San Diego, Calif. (1992), p. 137-ff). Generally, the length of the linkers is less than or about 400 angstroms, in some applications preferably less than 100 angstroms. The linker, thus, comprises a chain of carbon atoms optionally interrupted or terminated with one or more heteroatoms, such as oxygen atoms, nitrogen atoms, and/or sulphur atoms. Thus, the linker may comprise one or more amide, ester, amino, ether, and/or thioether functionalities, and optionally aromatic or mono/polyunsaturated hydrocarbons, polyoxyethylene such as polyethylene glycol, oligo/polyamides such as poly-(3-alanine, polyglycine, polylysine, and peptides in general, oligosaccharides, oligo/polyphosphates. Moreover the linker may consist of combined units thereof. The length of the linker may vary, taking into consideration the desired or necessary positioning and spatial orientation of the "active/functional" part of the group in question in relation to the 5- or 6-membered ring. In particularly interesting embodiments, the linker includes a chemically cleavable group. Examples of such chemically cleavable groups include disulphide groups cleavable under reductive conditions, peptide fragments cleavable by peptidases, etc.

In the present context a "solid support" may be chosen from a wide range of polymer materials e.g. CPG (controlled pore glass), polypropylene, polystyrene, polycarbonate or polyethylene and is may take a variety of forms such as a tube, a microtiter well plate, a stick, a bead, a particle, a filter etc. The oligonucleotide may be immobilized to the solid support via its 5'- or 3'-end (or via the terminus of a linker attached to the 5'- or 3'-end) by a variety of chemical or photochemical methods usually employed in the immobilization of oligonucleotides or by non-covalent coupling e.g. via binding of a biotinylated oligonucleotide to immobilized streptavidin.

A "looped primer" refers to a probe, comprising a recognition sequence, complementary to a sequence in the target deoxyribonucleic acid sequence which recognition sequence is complementary to the reverse transcriptase-extended nucleotide sequence corresponding to the 5'-end of the mature microRNA or siRNA or located 5' to the RNA edited nucleotide, splice junction, single nucleotide polymorphism or point mutation in the initial ribonucleic acid target sequence, and an anchor sequence essential for subsequent capture or amplification by PCR. The said looped primer is used as an anchored primer to generate the second nucleic acid strand, which is complementary to the primer extension product. Another aspect of the looped primer is that the anchor sequence forms an intramolecular hairpin structure at the chosen assay temperature mediated by complementary sequences at the 5'- and the 3'-end of the oligonucleotide. The specificity of the reaction is based on the sequential use of the two anchored tagging probes with non-overlapping recognition sequences, hybridising to complementary 3'-end and 5'-end regions of the target RNA and complementary DNA sequences, respectively.

A "hairpin structure" refers to an intramolecular structure of an oligonucleotide at the chosen assay temperature mediated by hybridization of complementary sequences at the 5'- and the 3'-end of the oligonucleotide.

"U" refers to a enzyme unit defined as the amount of enzyme required to convert a given amount reactants to a product using a defined time and temperature.

In the present context "ligand" means something, which binds. Ligands comprise biotin and functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$-$C_{20}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

The singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

"Transcriptome" refers to the complete collection of transcriptional units of the genome of any species. In addition to protein-coding mRNAs, it also represents noncoding RNAs, such as small nucleolar RNAs, siRNAs, microRNAs and antisense RNAs, which comprise important structural and regulatory roles in the cell.

The term "amplicon" refers to small, replicating DNA fragments.

"Sample" refers to a sample of cells, or tissue or fluid isolated from an organism or organisms, including but not limited to, for example, skin, plasma, serum, spinal fluid, lymph fluid, synovial fluid, urine, tears, blood cells, organs, tumours, and also to samples of in vitro cell culture constituents (including but not limited to conditioned medium resulting from the growth of cells in cell culture medium, recombinant cells and cell components).

An "organism" refers to a living entity, including but not limited to, for example, human, mouse, rat, *Drosophila, C. elegans*, yeast, *Arabidopsis thaliana*, maize, rice, zebra fish, primates, domestic animals, etc.

"Tagging probes" or "tagging probe" refer to a probe(s), comprising a recognition sequence, complementary to the target sequence, e.g. a short RNA target sequence, and an anchor sequence essential for subsequent capture or amplification by PCR. "Two tagging probes" or a "Pair of tagging probes" refer to two anchored tagging probes, each designed to detect in combination a short complementary target sequence, e.g. a short RNA sequence, where the recognition sequence of the first tagging probe hybridizes to a first region within a target sequence and the recognition sequence of the second tagging probe hybridizes to a second region within the same complementary target sequence, e.g. a short RNA target sequence that is adjacent to the first region. In the method of invention, one of the tagging probes is 5' phosphorylated enabling covalent coupling of the two contiguous, non-overlapping tagging oligonucleotide probes hybridized to the complementary target sequence by a ligase to form a single oligonucleotide sequence. The anchor sequences attached to the tagging probes are designed so that they do not cross-hybridize to any target nucleic acid in a given transcriptome or to each other under the hybridization conditions used in the method of invention. The anchor sequences function as priming sites for the PCR primers in subsequent real-time quantitative PCR or as tags for capture assays.

"RT tagging probe" refers to a probe, comprising a recognition sequence, complementary to a sequence in the target ribonucleic acid sequence, e.g. to the 3'-end of the mature microRNA or siRNA or to a sequence located 3' to a RNA-edited nucleotide, splice junction, single nucleotide polymorphism or point mutation in the target ribonucleic acid sequence, and an anchor sequence essential for subsequent capture or amplification by PCR. The said RT tagging probe is used as an anchored primer in a reverse transcription reaction to generate a primer extension product, complementary to the target RNA sequence using a reverse transcriptase enzyme. "$2^{nd}$ strand tagging probe" refers to an anchored tagging probe, which recognition sequence is complementary to the reverse transcriptase-extended nucleotide sequence corresponding to the 5'-end of the mature microRNA or siRNA or located 5' to the RNA edited nucleotide, splice junction, single nucleotide polymorphism or point mutation in the initial ribonucleic acid target sequence. The $2^{nd}$ strand tagging probe is used as anchored primer to generate the second nucleic acid strand, which is complementary to the primer extension product. The specificity of the reaction is based on the sequential use of the two anchored tagging probes with non-overlapping recognition sequences, hybridising to complementary 3'-end and 5'-end regions of the target RNA and complementary DNA sequences, respectively.

"Two tagging probes" or a "Pair of tagging probes" refer to two anchored tagging probes, each designed to detect in combination a short complementary target sequence, e.g. a short RNA sequence, where the recognition sequence of the first tagging probe hybridizes to a first region within a target sequence and the recognition sequence of the $2^{nd}$ strand tagging probe recognizing a sequence is complementary to the reverse transcriptase-extended nucleotide sequence corresponding to the 5'-end of the mature microRNA or siRNA or located 5' to the RNA edited nucleotide, splice junction, single nucleotide polymorphism or point mutation in the initial ribonucleic acid target sequence. The $2^{nd}$ strand tagging probe is used as anchored primer to generate the second nucleic acid strand, which is complementary to the primer extension product.

The anchor sequences attached to each of the two tagging probes are designed so that they do not cross-hybridize to any target nucleic acid in a given transcriptome or to each other under the hybridization conditions used in the method of invention. The anchor sequences function as priming sites for the PCR primers in subsequent real-time quantitative PCR or as tags for capture assays.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification by a polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The terms "Detection probes" or "detection probe" refer to labelled oligonucleotide, which forms a duplex structure with a sequence within the amplified target nucleic acid, e.g. short RNA target sequence, due to complementarity of the probe with a sequence in the target region. The detection probe, preferably, does not contain a sequence complementary to sequence(s) used to prime the polymerase chain reaction.

Generally the 3' terminus of the probe will be "blocked" to prohibit incorporation of the probe into a primer extension product. "Blocking" may be achieved by using non-complementary bases or by adding a chemical moiety such as biotin or a phosphate group to the 3' hydroxyl of the last nucleotide, which may, depending upon the selected moiety, serve a dual purpose by also acting as a label.

The terms "miRNA" and "microRNA" refer to 21-25 nt non-coding RNAs derived from endogenous genes. They are processed from longer (ca 75 nt) hairpin-like precursors termed pre-miRNAs. MicroRNAs assemble in complexes termed miRNPs and recognize their targets by antisense complementarity. If the microRNAs match 100% their target, i.e. the complementarity is complete, the target mRNA is cleaved, and the miRNA acts like a siRNA. If the match is incomplete, i.e. the complementarity is partial, then the translation of the target mRNA is blocked.

The terms "Small interfering RNAs" or "siRNAs" refer to 21-25 nt RNAs derived from processing of linear double-stranded RNA. siRNAs assemble in complexes termed RISC (RNA-induced silencing complex) and target homologous RNA sequences for endonucleolytic cleavage. Synthetic siRNAs also recruit RISCs and are capable of cleaving homologous RNA sequences The term "RNA interference" (RNAi) refers to a phenomenon where double-stranded RNA homologous to a target mRNA leads to degradation of the targeted mRNA. More broadly defined as degradation of target mRNAs by homologous siRNAs.

The term "Recognition sequence" refers to a nucleotide sequence that is complementary to a region within the target nucleotide sequence essential for sequence-specific hybridization between the target nucleotide sequence and the recognition sequence. The tagging probes as well as the detection probes of invention contain a target sequence-specific recognition sequence.

The term "Anchor sequences" refer to two nucleotide sequences contiguously attached to the pair of tagging probes, which anchor sequences are designed so that they do not cross-hybridize with each other or with a target nucleotide sequence or any nucleotide sequence in the nucleic acid sample, containing the target nucleotide sequence.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetric, X-ray diffraction or absorption, magnetism, enzymatic activity, and the like.

A label is a reporter group detectable either by itself or as a part of a detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are DANSYL (5-dimethylamino )-1-naphthalenesulfonyl),DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (trademarks for Biological Detection Systems, Inc.), erythrosine, coumaric acid, umbelliferone, Texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radio isotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy). Especially interesting examples are biotin, fluorescein, Texas Red, rhodamine, dinitrophenyl, digoxigenin, Ruthenium, Europium, Cy5, Cy3, etc.

"Ligation" or "covalent coupling" refers to covalent coupling of two adjacent nucleotide sequences, e.g. the tagging oligonucleotide probe sequences of the invention, to form a single nucleotide sequence. The reaction is catalyzed by the enzyme ligase, which forms a phosphodiester bond between the 5'-end of one nucleotide sequence and the 3'-end of the adjacent nucleotide sequence, e.g. between the two adjacent tagging probes of invention, annealed to their complementary, target nucleic acid sequence.

"RNA-templated oligonucleotide ligation" refers to covalent coupling of two adjacent oligonucleotide probe sequences annealed to a complementary RNA target sequence, to form a single nucleotide sequence. The reaction is catalyzed by the enzyme ligase, which forms a phosphodiester bond between the 5'-end of one nucleotide sequence and the 3'-end of the adjacent nucleotide sequence, e.g. between the two adjacent tagging probes of invention.

The terms "PCR reaction", "PCR amplification", "PCR", "pre-PCR" and "real-time quantitative PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence based amplification (NASBA™, Cangene, Mississauga, Ontario) and Q Beta Replicase systems. The products formed by said amplification reaction may or may not be monitored in real time or only after the reaction as an end point measurement.

As used herein, the terms "nucleic acid", "polynucleotide" and "oligonucleotide" refer to primers, probes, oligomer fragments to be detected, oligomer controls and unlabelled blocking oligomers and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA. The oligonucleotide is comprised of a sequence of approximately at least 3 nucleotides, preferably at least about 6 nucleotides, and more preferably at least about 8-30 nucleotides corresponding to a region of the designated target nucleotide sequence. "Corresponding" means identical to or complementary to the designated sequence. The oligonucleotide is not necessarily physically derived from any existing or natural sequence but may be generated in any manner, including chemical synthesis, DNA replication, reverse transcription or a combination thereof.

The terms "oligonucleotide" or "nucleic acid" intend a polynucleotide of genomic DNA or RNA, cDNA, semi synthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature. Because mononucleotides are reacted to make oligonucleotides in a manner such that the 5'-phosphate of one mononucleotide pentose ring is attached to the 3' oxygen of its neighbour in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have a 5' and 3' ends. When two different, non-overlapping oligonucleotides anneal to different regions of the same linear complementary nucleic acid sequence, the 3' end of one oligonucleotide points toward the 5' end of the other; the former may be called the "upstream" oligonucleotide and the latter the "downstream" oligonucleotide.

Figure 4:
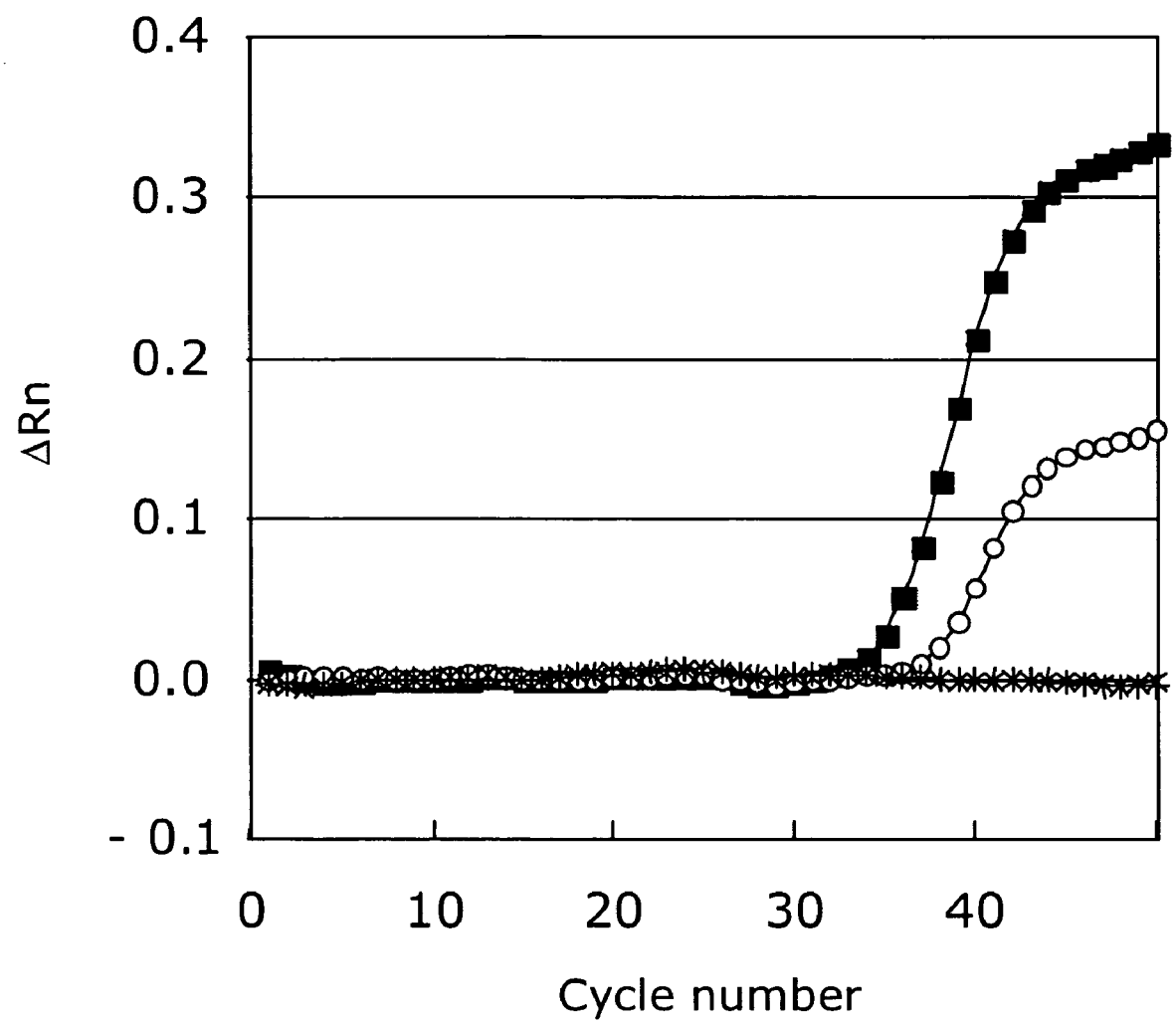
FIG. 4 shows the real-time quantitative PCR amplification plots for the human miR-15a and human miR-16 microRNA target sequences. Sequence-specific microRNA target sequence recognition of the method of invention was assessed by using the miR-15a microRNA target (solid squares) in comparison with the miR-16 target (open circles) that has 72% sequence identity with the miR-15a target sequence. Neither the minus template control (crosses) nor the NTC in the real-time PCR reaction (black vertical line) were shown to give any signals. The hybridization conditions for the annealing of the LNA-modified miR-15a target sequence-specific tagging probes towards the miR-15a target resulted in a Ct value of 36.2, whereas the use of the same tagging probes for the highly homologous miR-16 resulted in a Ct value of 39.9, corresponding to a 13-fold discriminative difference.

By the term "SBC nucleobases" is meant "Selective Binding Complementary" nucleobases, i.e. modified nucleobases that can make stable hydrogen bonds to their complementary nucleobases, but are unable to make stable hydrogen bonds to other SBC nucleobases. As an example, the SBC nucleobase A', can make a stable hydrogen bonded pair with its complementary unmodified nucleobase, T. Likewise, the SBC nucleobase T' can make a stable hydrogen bonded pair with its complementary unmodified nucleobase, A. However, the SBC nucleobases A' and T' will form an unstable hydrogen bonded pair as compared to the base pairs A'-T and A-T'. Likewise, a SBC nucleobase of C is designated C' and can make a stable hydrogen bonded pair with its complementary unmodified nucleobase G, and a SBC nucleobase of G is designated G' and can make a stable hydrogen bonded pair with its complementary unmodified nucleobase C, yet C' and G' will form an unstable hydrogen bonded pair as compared to the base pairs C'-G and C-G'. A stable hydrogen bonded pair is obtained when 2 or more hydrogen bonds are formed e.g. the pair between A' and T, A and T', C and G', and C' and G. An unstable hydrogen bonded pair is obtained when 1 or no hydrogen bonds is formed e.g. the pair between A' and T', and C' and G'. Especially interesting SBC nucleobases are 2,6-diaminopurine (A', also called D) together with 2-thio-uracil (U', also called $^{2S}$U)(2-thio-4-oxo-pyrimidine) and 2-thio-thymine (T', also called $^{2S}$T)(2-thio-4-oxo-5-methyl-pyrimidine). FIG. 4 illustrates that the pairs A-$^{2S}$T and D-T have 2 or more than 2 hydrogen bonds whereas the D-$^{2S}$T pair forms a single (unstable) hydrogen bond. Likewise the SBC nucleobases pyrrolo-[2,3-d]pyrimidine-2(3H)-one (C', also called PyrroloPyr) and hypoxanthine (G', also called I)(6-oxo-purine) are shown in FIG. 9 where the pairs PyrroloPyr-G and C-I have 2 hydrogen bonds each whereas the PyrroloPyr-I pair forms a single hydrogen bond.

"SBC LNA oligomer" refers to a "LNA oligomer" containing at least one LNA monomer where the nucleobase is a "SBC nucleobase". By "LNA monomer with an SBC nucleobase" is meant a "SBC LNA monomer". Generally speaking SBC LNA oligomers include oligomers that besides the SBC LNA monomer(s) contain other modified or naturally occurring nucleotides or nucleosides. By "SBC monomer" is meant a non-LNA monomer with a SBC nucleobase. By "isosequential oligonucleotide" is meant an oligonucleotide with the same sequence in a Watson-Crick sense as the corresponding modified oligonucleotide e.g. the sequences agTtcATg is equal to agTscD$^{2S}$Ug where s is equal to the SBC DNA monomer 2-thio-t or 2-thio-u, D is equal to the SBC LNA monomer LNA-D and $^{2S}$U is equal to the SBC LNA monomer LNA $^{2S}$U The complement of a nucleic acid sequence as used herein refers to an oligonucleotide which, when aligned with the nucleic acid sequence such that the 5' end of one sequence is paired with the 3' end of the other, is in "antiparallel association." Bases not commonly found in natural nucleic acids may be included in the nucleic acids of the present invention include, for example, inosine and 7-deazaguanine. Complementarity may not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

The melting temperature, or "Tm" measures stability of a nucleic acid duplex. The $T_m$ of a particular nucleic acid duplex under specified conditions is the temperature at which half of the duplexes have disassociated.

As defined herein, "5'→3' nuclease activity" or "5' to 3' nuclease activity" refers to that activity of a template-specific nucleic acid polymerase including either a 5'→3' exonuclease activity traditionally associated with some DNA polymerases whereby nucleotides are removed from the 5' end of an oligonucleotide in a sequential manner, (i.e., *E. coli* DNA polymerase I has this activity whereas the Klenow fragment does not), or a 5'→3' endonuclease activity wherein cleavage occurs more than one nucleotide from the 5' end, or both.

"Thermostable nucleic acid polymerase" refers to an enzyme which is relatively stable to heat when compared, for example, to polymerases from *E. coli* and which catalyzes the polymerization of nucleosides. Generally, the enzyme will initiate synthesis at the 3'-end of the primer annealed to the target sequence, and will proceed in the 5'-direction along the template, and if possessing a 5' to 3' nuclease activity, hydrolyzing or displacing intervening, annealed probe to release both labelled and unlabelled probe fragments or intact probe, until synthesis terminates. A representative thermostable enzyme isolated from Thermus aquaticus (Taq) is described in U.S. Pat. No. 4,889,818 and a method for using it in conventional PCR is described in Saiki et al., (1988), Science 239:487.

"Thermostable Reverse transcriptase" refers to a reverse transcriptase enzyme, which is more heat-stable compared to, for example the Avian Myeloma Virus (AMV) reverse transcriptase or the Moloney Monkey Leukaemia Virus (MMLV) reverse transcriptase.

The term "nucleobase" covers the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, *Nucleic Acid Research*, 25: 4429-4443, 1997. The term "nucleobase" thus includes not only the known purine and pyrimidine heterocycles, but also heterocyclic analogues and tautomers thereof. Further naturally and non naturally occurring nucleobases include those disclosed in U.S. Pat. No. 3,687,808; in chapter 15 by Sanghvi, in *Antisense Research and Application*, Ed. S. T. Crooke and B. Lebleu, CRC Press, 1993; in Englisch, et al., *Angewandte Chemie, International Edition*, 30: 613-722, 1991 (see, especially pages 622 and 623, and in the *Concise Encyclopedia of Polymer Science and Engineering*, J. I. Kroschwitz Ed., John Wiley & Sons, pages 858-859, 1990, Cook, *Anti-Cancer Drug Design* 6: 585-607, 1991, each of which are hereby incorporated by reference in their entirety).

The term "nucleosidic base" or "nucleobase analogue" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole or a 5-nitroindole. Other preferred compounds include pyrene and pyridyloxazole derivatives, pyrenyl, pyrenylmethylglycerol derivatives and the like. Other preferred universal bases include, pyrrole, diazole or triazole derivatives, including those universal bases known in the art.

"Universal base" refers to a naturally-occurring or desirably a non-naturally occurring compound or moiety that can pair with at least one and preferably all natural bases (e.g., adenine, guanine, cytosine, uracil, and/or thymine), and that has a Tm differential of 15, 12, 10, 8, 6, 4, or 2oC or less as described herein.

By "oligonucleotide," "oligomer," or "oligo" is meant a successive chain of monomers (e.g., glycosides of heterocyclic bases) connected via internucleoside linkages. The linkage between two successive monomers in the oligo consist of 2 to 4, desirably 3, groups/atoms selected from —CH2-, —O—, —S—, —NRH—, >C=O, >C=NRH, >C=S, —Si (R")2-, —SO—, —S(O)2-, —P(O)2-, —PO(BH3)-, —P(O,S)—, —P(S)2-, —PO(R")—, —PO(OCH3)-, and —PO(NHRH)—, where RH is selected from hydrogen and C1-4-alkyl, and R" is selected from C1-6-alkyl and phenyl. Illustrative examples of such linkages are —CH2-CH2-CH2-, —CH2-CO—CH2-, —CH2-CHOH—CH2-, —O—CH2-O—, —O—CH2-CH2-, —O—CH2-CH= (including R5 when used as a linkage to a succeeding monomer), —CH2-CH2-O—, —NRH—CH2-CH2-, —CH2-CH2-NRH—, —CH2-NRH—CH2-, —O—CH2-CH2-NRH—, —NRH—CO—O—, —NRH—CO—NRH—, —NRH—CS—NRH—, —NRH—C(=NRH)—NRH—, —NRH—CO—CH2-NRH—, —O—CO—O—, —O—CO—CH2-O—, —O—CH2-CO—O—, —CH2-CO—NRH—, —O—CO—NRH—, —NRH—CO—CH2-, —O—CH2-CO—NRH—, —O—CH2-CH2-NRH—, —CH=N—O—, —CH2-NRH—O—, —CH2-O—N= (including R5 when used as a linkage to a succeeding monomer), —CH2-O—NRH—, —CO—NRH—CH2-, —CH2-NRH—O—, —CH2-NRH—CO—, —O—NRH—CH2-, —O—NRH—, —O—CH2-S—, —S—CH2-O—, —CH2-CH2-S—, —O—CH2-CH2-S—, —S—CH2-CH= (including R5 when used as a linkage to a succeeding monomer), —S—CH2-CH2-, —S—CH2-CH2-O—, —S—CH2-CH2-S—, —CH2-S—CH2-, —CH2-SO—CH2-, —CH2-SO2-CH2-, —O—SO—O—, —O—S(O)2-O—, —O—S(O)2-CH2-, —O—S(O)2-NRH—, —NRH—S(O)2-CH2-, —O—S(O)2-CH2-, —O—P(O)2-O—, —O—P(O,S)—O—, —O—P(S)2-O—, —S—P(O)2-O—, —S—P(O,S)—O—, —S—P(S)2-O—, —O—P(O)2-S—, —O—P(O,S)—S—, —O—P(S)2-S—, —S—P(O)2-S—, —S—P(O,S)—S—, —S—P(S)2-S—, —O—PO(R")—O—, —O—PO(OCH3)—O—, —O—PO—(OCH2CH3)—O—, —O—PO(OCH2CH2S—R)—O—, —O—PO(BH3)—O—, —O—PO(NHRN)—O—, —O—P(O)2-NRH—, —NRH—P(O)2-O—, —O—P(O,NRH)—O—, —CH2-P(O)2-O—, —O—P(O)2-CH2-, and —O—Si(R")2-O—; among which —CH2-CO—NRH—, —CH2-NRH—O—, —S—CH2-O—, —O—P(O)2-O—, —O—P(O,S)—O—, —O—P(S)2-O—, —NRH—P(O)2-O—, —O—P(O,NRH)—O—, —O—PO(R")—O—, —O—PO(CH3)—O—, and —O—PO(NHRN)—O—, where RH is selected form hydrogen and C1-4-alkyl, and R" is selected from C1-6-alkyl and phenyl, are especially desirable. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443. The left-hand side of the internucleoside linkage is bound to the 5-membered ring as substituent P* at the 3'-position, whereas the right-hand side is bound to the 5'-position of a preceding monomer.

By "LNA" or "LNA monomer" (e.g., an LNA nucleoside or LNA nucleotide) or an LNA oligomer (e.g., an oligonucleotide or nucleic acid) is meant a nucleoside or nucleotide analogue that includes at least one LNA monomer. LNA monomers as disclosed in PCT Publication WO 99/14226 are in general particularly desirable modified nucleic acids for incorporation into an oligonucleotide of the invention. Additionally, the nucleic acids may be modified at either the 3' and/or 5' end by any type of modification known in the art. For example, either or both ends may be capped with a protecting group, attached to a flexible linking group, attached to a reactive group to aid in attachment to the substrate surface, etc. Desirable LNA monomers and their method of synthesis also are disclosed in U.S. Pat. No. 6,043,060, U.S. Pat. No. 6,268,490, PCT Publications WO 01/07455, WO 01/00641, WO 98/39352, WO 00/56746, WO 00/56748 and WO 00/66604 as well as in the following papers: Morita et al., Bioorg. Med. Chem. Left. 12(1):73-76, 2002; Hakansson et al., Bioorg. Med. Chem. Lett. 11(7):935-938, 2001; Koshkin et al., J. Org. Chem. 66(25):8504-8512, 2001; Kvaerno et al., J. Org. Chem. 66(16):5498-5503, 2001; Hakansson et al., J. Org. Chem. 65(17):5161-5166, 2000; Kvaerno et al., J. Org. Chem. 65(17):5167-5176, 2000; Pfundheller et al., Nucleosides Nucleotides 18(9):2017-2030, 1999; and Kumar et al., Bioorg. Med. Chem. Lett. 8(16):2219-2222, 1998.

Preferred LNA monomers, also referred to as "oxy-LNA" are LNA monomers which include bicyclic compounds as disclosed in PCT Publication WO 03/020739 wherein the bridge between $R^{4'}$ and $R^{2'}$ as shown in formula (I) below together designate —$CH_2$—O— or —$CH_2$—$CH_2$-O—.

By "LNA modified oligonucleotide" or "LNA substituted oligonucleotide" is meant a oligonucleotide comprising at least one LNA monomer of formula (I), described infra, having the below described illustrative examples of modifications:

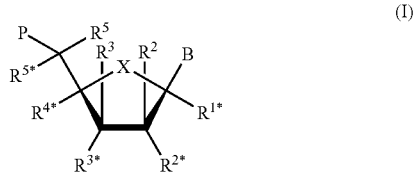

(I)

wherein X is selected from —O—, —S—, —N($R^N$)—, —C($R^6R^{6*}$)—, —O—C($R^7R^{7*}$)—, —C($R^6R^{6*}$)—O—, —S—C($R^7R^{7*}$)—, —($R^6R^{6*}$)—S—, —N($R^{N*}$)—C($R^7R^{7*}$)—, —C($R^6R^{6*}$)—N($R^{N*}$)—, and —C($R^6R^{6*}$)—C($R^7R^{7*}$).

B is selected from a modified base as discussed above e.g. an optionally substituted carbocyclic aryl such as optionally substituted pyrene or optionally substituted pyrenylmethylglycerol, or an optionally substituted heteroalicylic or optionally substituted heteroaromatic such as optionally substituted pyridyloxazole, optionally substituted pyrrole, optionally substituted diazole or optionally substituted triazole moieties; hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands.

P designates the radical position for an internucleoside linkage to a succeeding monomer, or a 5'-terminal group, such internucleoside linkage or 5'-terminal group optionally including the substituent $R^5$. One of the substituents $R^2$, $R^{2*}$, $R^3$, and $R^{3*}$ is a group P* which designates an internucleoside linkage to a preceding monomer, or a 2'/3'-terminal group. The substituents of $R^{1*}$, $R^{4*}$, $R^5$, $R^{5*}$, $R^6$, $R^{6*}$, $R^7$, $R^{7*}$, $R^N$, and the ones of $R^2$, $R^{2*}$, $R^3$, and $R^{3*}$ not designating P* each designates a biradical comprising about 1-8 groups/atoms selected from —C($R^aR^b$)—, —C($R^a$)=C($R^a$)—, —C($R^a$)=N—, —C($R^a$)—O—, —O—, —Si($R^a$)$_2$—, —C($R^a$)—S, —S—, —$SO_2$—, —C($R^a$)—N($R^b$)—, —N($R^a$)—, and >C=Q, wherein Q is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, hetero-aryloxycarbonyl, heteroaryloxy, heteroarylcarbonyl, amino, mono- and di($C_{1-6}$alkyl)amino, carbamoyl, mono- and di($C_{1-6}$-alkyl)-amino-carbonyl, amino-$C_{1-6}$alkyl-aminocarbonyl, mono- and di($C_{1-6}$-alkyl)amino-$C_{1-6}$alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents $R^a$ and $R^b$ together may designate optionally substituted methylene (=$CH_2$), and wherein two non-geminal or geminal substituents selected from $R^a$, $R^b$, and any of the substituents $R^{1*}$, $R^2$, $R^{2*}$, $R^3$, $R^{3*}$, $R^{4*}$, $R^5$, $R^{5*}$, $R^6$ and $R^{6*}$, $R^7$, and $R^{7*}$ which are present and not involved in P, P* or the biradical(s) together may form an associated biradical selected from biradicals of the same kind as defined before; the pair(s) of non-geminal substituents thereby forming a mono- or bicyclic entity together with (i) the atoms to which said non-geminal substituents are bound and (ii) any intervening atoms.

Each of the substituents $R^{1*}$, $R^2$, $R^{2*}$, $R^3$, $R^{4*}$, $R^5$, $R^{5*}$, $R^6$ and $R^{6*}$, $R^7$, and $R^{7*}$ which are present and not involved in P, P* or the biradical(s), is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di-($C_{1-6}$ alkyl)amino, carbamoyl, mono- and di($C_{1-6}$alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/ groups selected from —O—, —S—, and —(NR$^N$)— where R$^N$ is selected from hydrogen and C$_{1-4}$-alkyl, and where two adjacent (non-geminal) substituents may designate an additional bond resulting in a double bond; and R$^{N*}$, when present and not involved in a biradical, is selected from hydrogen and C$_{1-4}$-alkyl; and basic salts and acid addition salts thereof.

Exemplary 5', 3', and/or 2' terminal groups include —H, —OH, halo (e.g., chloro, fluoro, iodo, or bromo), optionally substituted aryl, (e.g., phenyl or benzyl), alkyl (e.g., methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

It is understood that references herein to a nucleic acid unit, nucleic acid residue, LNA monomer, or similar term are inclusive of both individual nucleoside units and nucleotide units and nucleoside units and nucleotide units within an oligonucleotide.

A "modified base" or other similar terms refer to a composition (e.g., a non-naturally occurring nucleobase or nucleosidic base), which can pair with a natural base (e.g., adenine, guanine, cytosine, uracil, and/or thymine) and/or can pair with a non-naturally occurring nucleobase or nucleosidic base. Desirably, the modified base provides a T$_m$ differential of 15, 12, 10, 8, 6, 4, or 2° C. or less as described herein. Exemplary modified bases are described in EP 1 072 679 and WO 97/12896.

The term "chemical moiety" refers to a part of a molecule. "Modified by a chemical moiety" thus refer to a modification of the standard molecular structure by inclusion of an unusual chemical structure. The attachment of said structure can be covalent or non-covalent.

The term "inclusion of a chemical moiety" in an oligonucleotide probe thus refers to attachment of a molecular structure. Such as chemical moiety include but are not limited to covalently and/or non-covalently bound minor groove binders (MGB) and/or intercalating nucleic acids (INA) selected from a group consisting of asymmetric cyanine dyes, DAPI, SYBR Green I, SYBR Green II, SYBR Gold, PicoGreen, thiazole orange, Hoechst 33342, Ethidium Bromide, 1-O-(1-pyrenylmethyl)glycerol and Hoechst 33258. Other chemical moieties include the modified nucleobases, nucleosidic bases or LNA modified oligonucleotides.

The term "Dual-labelled probe" refers to an oligonucleotide with two attached labels. In one aspect, one label is attached to the 5' end of the probe molecule, whereas the other label is attached to the 3' end of the molecule. A particular aspect of the invention contain a fluorescent molecule attached to one end and a molecule which is able to quench this fluorophore by Fluorescence Resonance Energy Transfer (FRET) attached to the other end. 5' nuclease assay probes and some Molecular Beacons are examples of Dual labelled probes.

"5' nuclease assay probe" refers to a dual labelled probe which may be hydrolyzed by the 5'-3' exonuclease activity of a DNA polymerase. A 5' nuclease assay probes is not necessarily hydrolyzed by the 5'-3' exonuclease activity of a DNA polymerase under the conditions employed in the particular PCR assay. The name "5' nuclease assay" is used regardless of the degree of hydrolysis observed and does not indicate any expectation on behalf of the experimenter. The term "5' nuclease assay probe" and "5' nuclease assay" merely refers to assays where no particular care has been taken to avoid hydrolysis of the involved probe. "5' nuclease assay probes" are often referred to as a "TaqMan assay probes", and the "5' nuclease assay" as "TaqMan assay". These names are used interchangeably in this application.

"Oligonucleotide analogue" refers to a nucleic acid binding molecule capable of recognizing a particular target nucleotide sequence. A particular oligonucleotide analogue is peptide nucleic acid (PNA) in which the sugar phosphate backbone of an oligonucleotide is replaced by a protein like backbone. In PNA, nucleobases are attached to the uncharged polyamide backbone yielding a chimeric pseudopeptide-nucleic acid structure, which is homomorphous to nucleic acid forms.

"Molecular Beacon" refers to a single or dual labelled probe which is not likely to be affected by the 5'-3' exonuclease activity of a DNA polymerase. Special modifications to the probe, polymerase or assay conditions have been made to avoid separation of the labels or constituent nucleotides by the 5'-3' exonuclease activity of a DNA polymerase. The detection principle thus rely on a detectable difference in label elicited signal upon binding of the molecular beacon to its target sequence. In one aspect of the invention the oligonucleotide probe forms an intramolecular hairpin structure at the chosen assay temperature mediated by complementary sequences at the 5'- and the 3'-end of the oligonucleotide. The oligonucleotide may have a fluorescent molecule attached to one end and a molecule attached to the other, which is able to quench the fluorophore when brought into close proximity of each other in the hairpin structure. In another aspect of the invention, a hairpin structure is not formed based on complementary structure at the ends of the probe sequence instead the detected signal change upon binding may result from interaction between one or both of the labels with the formed duplex structure or from a general change of spatial conformation of the probe upon binding—or from a reduced interaction between the labels after binding. A particular aspect of the molecular beacon contain a number of LNA residues to inhibit hydrolysis by the 5'-3' exonuclease activity of a DNA polymerase.

"High affinity nucleotide analogue" refers to a non-naturally occurring nucleotide analogue that increases the "binding affinity" of an oligonucleotide probe to its complementary recognition sequence when substituted with at least one such high-affinity nucleotide analogue.

As used herein, a probe with an increased "binding affinity" for a recognition sequence compared to a probe which comprises the same sequence but does not comprise a stabilizing nucleotide, refers to a probe for which the association constant (K$_a$) of the probe recognition segment is higher than the association constant of the complementary strands of a double-stranded molecule. In another preferred embodiment, the association constant of the probe recognition segment is higher than the dissociation constant (K$_d$) of the complementary strand of the recognition sequence in the target sequence in a double stranded molecule.

Monomers are referred to as being "complementary" if they contain nucleobases that can form hydrogen bonds according to Watson-Crick base-pairing rules (e.g. G with C, A with T or A with U) or other hydrogen bonding motifs such as for example diaminopurine with T, 5-methyl C with G, 2-thiothymidine with A, inosine with C, pseudoisocytosine with G, etc.

The term "succeeding monomer" relates to the neighbouring monomer in the 5'-terminal direction and the "preceding monomer" relates to the neighbouring monomer in the 3'-terminal direction.

The term "target nucleic acid" or "target ribonucleic acid" refers to any relevant nucleic acid of a single specific sequence, e.g., a biological nucleic acid, e.g., derived from a patient, an animal (a human or non-human animal), a plant, a bacteria, a fungi, an archae, a cell, a tissue, an organism, etc. For example, where the target ribonucleic acid or nucleic acid is derived from a bacteria, archae, plant, non-human animal, cell, fungi, or non-human organism, the method optionally further comprises selecting the bacteria, archae, plant, non-human animal, cell, fungi, or non-human organism based upon detection of the target nucleic acid. In one embodiment, the target nucleic acid is derived from a patient, e.g., a human patient. In this embodiment, the invention optionally further includes selecting a treatment, diagnosing a disease, or diagnosing a genetic predisposition to a disease, based upon detection of the target nucleic acid.

"Target sequence" refers to a specific nucleic acid sequence within any target nucleic acid.

The term "stringent conditions", as used herein, is the "stringency" which occurs within a range from about $T_m$-5° C. (5° C. below the melting temperature ($T_m$) of the probe) to about 20° C. to 25° C. below $T_m$. As will be understood by those skilled in the art, the stringency of hybridization may be altered in order to identify or detect identical or related polynucleotide sequences. Hybridization techniques are generally described in *Nucleic Acid Hybridization, A Practical Approach*, Ed. Hames, B. D. and Higgins, S. J., IRL Press, 1985; Gall and Pardue, *Proc. Natl. Acad. Sci., USA* 63: 378-383, 1969; and John, et al. *Nature* 223: 582-587, 1969.

The present invention also provides a kit for the isolation, purification, amplification, detection, identification, quantification, or capture of natural or synthetic nucleic acids, where the kit comprises a reaction body and one or more LNA modified oligonucleotides (oligomer) as defined herein. The LNA modified oligonucleotides are preferably immobilised onto said reactions body.

For the kits according to the invention, the reaction body is preferably a solid support material, e.g. selected from borosilicate glass, soda-lime glass, polystyrene, polycarbonate, polypropylene, polyethylene, polyethyleneglycol terephthalate, polyvinylacetate, polyvinylpyrrolidinone, polymethylmethacrylate and polyvinylchloride, preferably polystyrene and polycarbonate. The reaction body may be in the form of a specimen tube, a vial, a slide, a sheet, a film, a bead, a pellet, a disc, a plate, a ring, a rod, a net, a filter, a tray, a microtitre plate, a stick, or a multi-bladed stick.

A written instruction sheet stating the optimal conditions for use of the kit typically accompanies the kits.

DETAILED DESCRIPTION OF THE INVENTION

The present invention relates to the use of an oligonucleotide for the isolation, purification, amplification, detection, identification, quantification, or capture of microRNA or small interfering RNAs characterized in that the oligonucleotide contains a number of nucleoside analogues.

More particular the present invention provides methods for detection and quantification of microRNA or small interfering RNAs having a high sensitivity and good selectivity. According to the invention the quantification of microRNA and small interfering RNAs is detectable at levels of from 10 fmol to 10 amol RNA target or less (10 zmol) in the sample corresponding to RNA target concentration of from 100 pM to 10 fM or less (10 aM).

In a preferred embodiment the invention comprises the following steps as shown in FIG. 1 and FIG. 9:
1) Two tagging probes are designed and synthesized so that each consist of a high-affinity nucleotide sequence complementary to 10-12 nt of the target sequence, e.g. a mature miRNA, and an anchor DNA sequence without any complementarity to the target sequence or each other. The two recognition element-containing tagging probes are hybridized under stringent conditions in combination to the target sequence in a complex nucleic acid sample in solution, thereby bringing the two tagging probes to close proximity as defined by the target, in which the 5'-end of one tagging probe is adjacent to the 3'-end of the other tagging probe.
2) The target-specific tagging probes are joined by ligation as the 5'-end of one of the probes is phosphorylated, using a DNA ligase and the target sequence, e.g. a miRNA, as template. The ligation reaction can be carried out at elevated temperatures using thermo stable ligases, and thus cycled to increase the number of copies of the template molecules for subsequent amplification by PCR.
3) Following target sequence-templated ligation of the high-affinity tagging probes, the ligated probe molecules are used as templates for quantitative real-time PCR, using a short detection probe with sufficient duplex stability to allow binding to the amplicon, and employing any of a variety of detection principles used in homogeneous assays.

Figure 27:
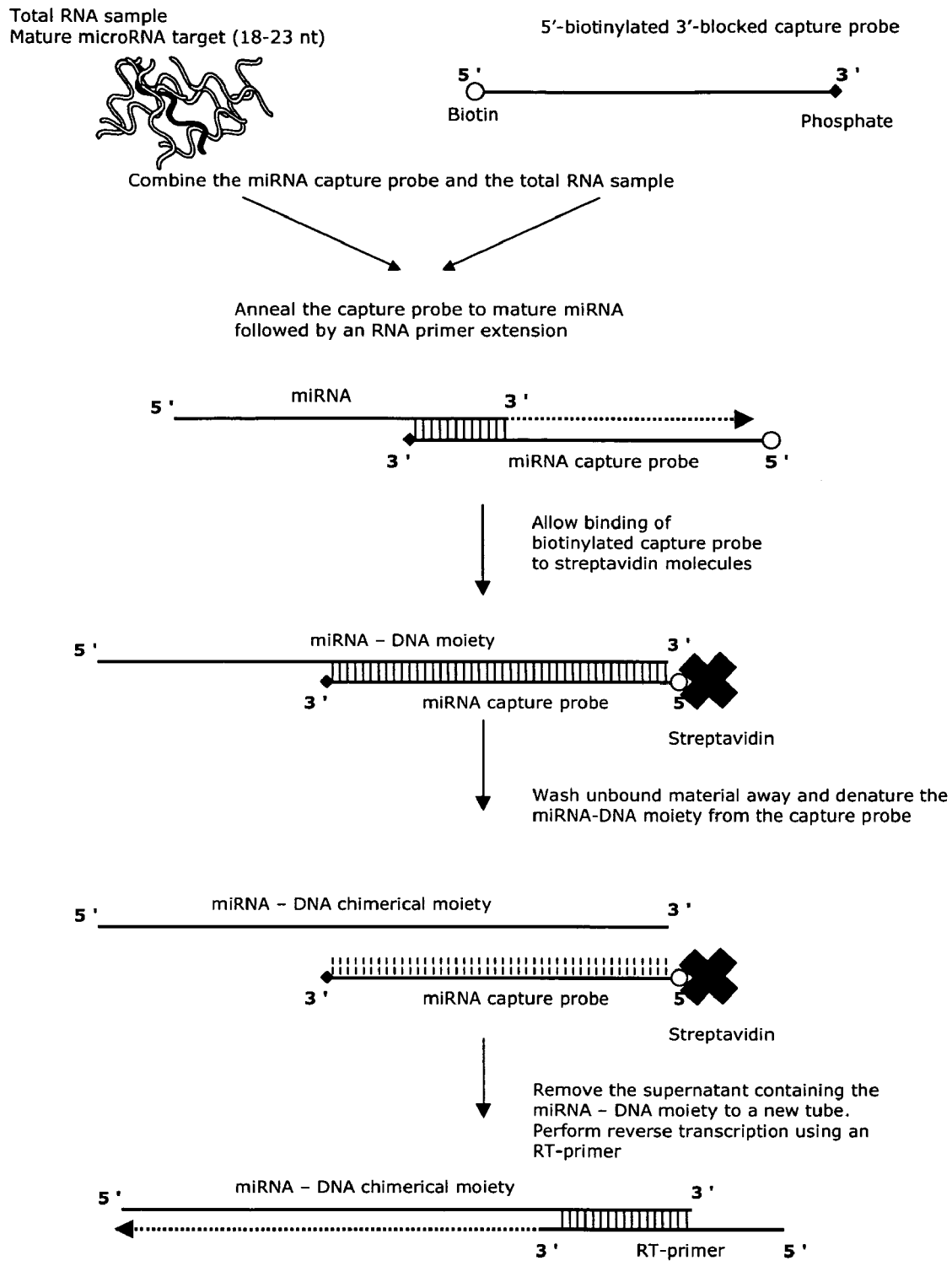
FIG. 27 is a schematic presentation of one method of the invention for quantification of microRNAs by sequence-specific real-time quantitative RT-PCR.

In a further preferred embodiment of the invention detection and quantification comprises the steps shown in FIG. 27:
a) contacting the target ribonucleic acid sequence with a oligonucleotide capture probe, wherein the recognition nucleotide sequence is complementary to a sequence in the target sequence;
b) synthesis of a complementary strand to the anchor nucleotide sequence in the capture probe using a DNA polymerase enzyme and the target ribonucleic acid sequence as primer,
c) immobilization of the formed duplex on to a solid support and an enrichment of the target sample follow by a release of the target sequence from the solid support;
d) synthesis of a complementary DNA strand to the target ribonucleic acid by reverse transcription using a reverse transcriptase enzyme and the anchor nucleotide sequence in the tagging probe as primer binding site
e) replacing of the ribonucleic acid sequence in the heteroduplex by synthesis of a second strand using a DNA polymerase and a second tagging probe as primer, wherein said second tagging probe consists of an anchor nucleotide sequence and a recognition nucleotide sequence, wherein said recognition nucleotide sequence is complementary to a sequence in the reverse transcriptase-extended nucleic acid sequence
f) quantifying the resulting nucleic acids by real-time PCR using primers corresponding to the anchor nucleotide sequences attached to the oligonucleotide tagging probes and a labelled detection probe comprising a target recognition sequence and a detection moiety.

Figure 28:
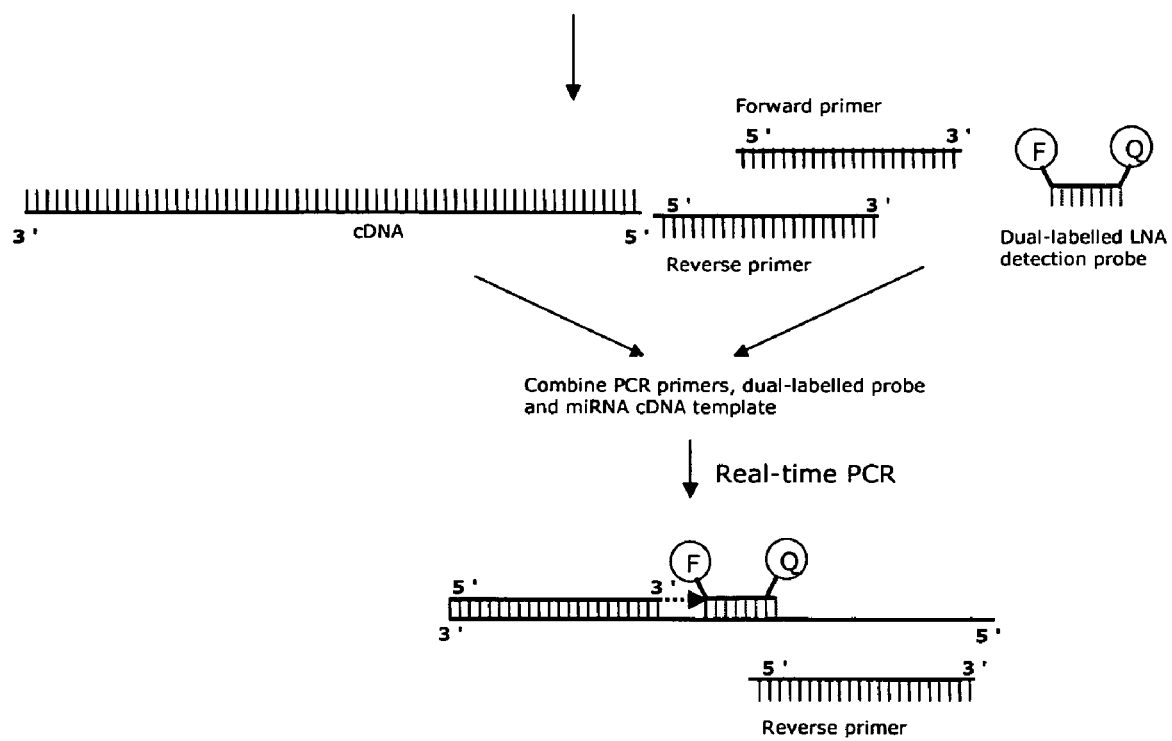
FIG. 28 is a schematic presentation of one method of the invention for quantification of microRNAs by sequence-specific real-time quantitative RT-PCR.

In a further preferred embodiment of the invention detection and quantification comprises the steps shown in FIG. 28:
a) contacting the target ribonucleic acid sequence with a oligonucleotide capture probe, wherein the recognition nucleotide sequence is complementary to a sequence in the target sequence;

b) synthesis of a complementary strand to the anchor nucleotide sequence in the capture probe using a DNA polymerase enzyme and the target ribonucleic acid sequence as primer,
c) immobilization of the formed duplex on to a solid support and an enrichment of the target sample,
d) synthesis of a complementary DNA strand to the target ribonucleic acid by reverse transcription using a reverse transcriptase enzyme and the capture probe as primer
e) replacing of the ribonucleic acid sequence in the heteroduplex by synthesis of a second strand using a DNA polymerase and a second tagging probe as primer, and wherein said second tagging probe consists of an anchor nucleotide sequence and a recognition nucleotide sequence, wherein said recognition nucleotide sequence is complementary to a sequence in the reverse transcriptase-extended nucleic acid sequence
f) following target sequence-templated PCR amplification using a DNA polymerase and a pair of primers,
e) quantifying the resulting nucleic acids by real-time PCR using primers corresponding to the anchor nucleotide sequences attached to the oligonucleotide tagging probes and a labelled detection probe comprising a target recognition sequence and a detection moiety.

One advantage for the immobilized capture probe methods is that initial enrichment of the total RNA sample for non-protein-coding RNAs, such as small nucleolar RNAs, siRNAs, microRNAs and antisense RNAs, is not necessary. Preferably, the capture probe will hybridize to the specific target in solution. Secondly, when the capture probe is immobilized on the solid support, unbound material can be removed and thereby enrichment for the specific target has been performed.

In another further preferred embodiment the invention comprises the following steps as shown in FIG. 11:

1) Two tagging probes, the RT tagging probe and the $2^{nd}$ strand tagging probe are designed and synthesized so that each consist of a nucleotide recognition sequence corresponding to 6-12 nt of the target ribonucleic acid sequence, e.g. a mature miRNA, and an anchor sequence without any complementarity to the target sequence or each other. The recognition sequence of the RT tagging probe or both the RT and $2^{nd}$ strand probes are modified by high-affinity nucleotide analogues, e.g. LNA. The recognition sequence in the RT tagging probe is complementary to a sequence in the target ribonucleic acid sequence, e.g. to the 3'-end of the mature microRNA or siRNA or to a sequence located 3' to a RNA-edited nucleotide, splice junction, single nucleotide polymorphism or point mutation in the target ribonucleic acid sequence. The RT tagging probe is hybridized to the target RNA sequence in a complex nucleic acid sample under stringent hybridization conditions and used as an anchored primer in a reverse transcription reaction to generate an anchored primer extension product, complementary to the target RNA sequence using a reverse transcriptase enzyme.
2) The $2^{nd}$ strand tagging probe comprises a recognition sequence, which is complementary to the reverse transcriptase-extended nucleotide sequence corresponding to the 5'-end of the mature microRNA or siRNA or located 5' to the RNA edited nucleotide, splice junction, single nucleotide polymorphism or point mutation in the initial ribonucleic acid target sequence. The $2^{nd}$ strand tagging probe is hybridized to the RT reaction products under stringent hybridization conditions and subsequently used as an anchored primer to generate the second strand by a DNA polymerase, e.g. a thermostable DNA polymerase, which is complementary to the primer extension product. The specificity of the reaction is based on the sequential use of the anchored RT and $2^{nd}$ strand tagging probes with non-overlapping recognition sequences, hybridising to complementary 3'-end and 5'-end regions of the target RNA and complementary DNA sequences, respectively. The anchor sequences attached to the tagging probes are designed so that they do not cross-hybridize to any target nucleic acid in a given transcriptome or to each other under the hybridization conditions used in the method of invention. The anchor sequences function as priming sites for the PCR primers in subsequent real-time quantitative PCR or as tags for capture assays. The reverse transcription reaction as well as the second strand reaction can be carried out at elevated temperatures due to the use of high-affinity nucleotide analogues in the recognition sequences, which is a novel component of the invention, using thermostable reverse transcriptases and thermostable DNA polymerases, thus increasing the specificity in the generation of the template molecules for subsequent amplification by PCR. Another novel component of the invention is the finding that the said high-affinity recognition sequences, modified by e.g. LNA, can be used as primers by a reverse transcriptase or a DNA polymerase, and furthermore that such said high-affinity recognition sequences can be used as a template to synthesize a complementary strand by a DNA polymerase.
3) Following the target RNA sequence-specific reverse transcription and $2^{nd}$ strand synthesis reactions, the double-stranded molecules are used as templates for quantitative real-time PCR, using a short detection probe with sufficient duplex stability to allow binding to the amplicon, and employing any of a variety of detection principles used in homogeneous assays.

The detection of binding is either direct by a measurable change in the properties of one or more of the labels following binding to the target (e.g. a molecular beacon type assay with or without stem structure) or indirect by a subsequent reaction following binding, e.g. cleavage by the 5' nuclease activity of the DNA polymerase in 5' nuclease assays. The detection probe is yet another novel component of the present invention. It comprises a short oligonucleotide moiety which sequence has been selected to enable specific detection of the short amplified DNA molecules corresponding to the target sequence in the core segment and the anchored sequences used as annealing sites for the PCR primers.

The novel, short detection probes designed to detect target sequences, for example different mature miRNA target molecules, are enabled by the discovery that very short 8-12-mer LNA-DNA chimeric, mix-mer probes are compatible with real-time PCR based assays. In one aspect of the present invention modified or nucleobase analogues, nucleosidic bases or nucleotides are incorporated in the tagging probes as well as the detection probe, possibly together with minor groove binders and other modifications, that all aim to stabilize the duplex formed between the probes and the target molecule so that the shortest possible probe sequences can be used to hybridized and detect the target molecules. In a preferred aspect of the invention the modifications are incorporation of LNA residues to reduce the length of the detection probe to 8 or 9 or 10 or 11 or 12 to 14 nucleotides while maintaining sufficient stability of the formed duplex to be detectable under standard real-time PCR assay conditions. In another preferred aspect of the invention, the target recognition sequences in one or both tagging probes for the ligation reaction or the recognition sequence in the RT tagging probe or the recognition sequences in both the RT tagging probe and the $2^{nd}$ strand tagging probe for the RT-PCR reaction, are substituted with LNA monomers at every second, every third or every fourth nucleotide position with at least one DNA nucleotide at the 3'-ends of both probes, respectively, allowing highly specific and sensitive hybridization even at elevated temperatures due to the increased duplex stability of LNA modified oligonucleotide probes to their complementary target molecules, particularly target RNA molecules.

In a further preferred embodiment of the invention detection and quantification comprises the steps shown in FIG. 22:
a) contacting the target ribonucleic acid sequence with an oligonucleotide tagging probe of claim 1 to 3, wherein the recognition nucleotide sequence is complementary to a sequence in the target sequence;
b) synthesis of a complementary strand to the anchor nucleotide sequence in the tagging probe using a DNA polymerase enzyme and the target ribonucleic acid sequence as primer,
c) synthesis of a complementary DNA strand to the target ribonucleic acid by reverse transcription using a reverse transcriptase enzyme and the anchor nucleotide sequence in the tagging probe as primer binding site
d) replacing of the ribonucleic acid sequence in the heteroduplex by synthesis of a second strand using a DNA polymerase and a second tagging probe as primer, wherein said second tagging probe consists of an anchor nucleotide sequence and a recognition nucleotide sequence, wherein said recognition nucleotide sequence is complementary to a sequence in the reverse transcriptase-extended nucleic acid sequence
e) quantifying the resulting nucleic acids by real-time PCR using primers corresponding to the anchor nucleotide sequences attached to the oligonucleotide tagging probes and a labelled detection probe comprising a target recognition sequence and a detection moiety.

Figure 29:
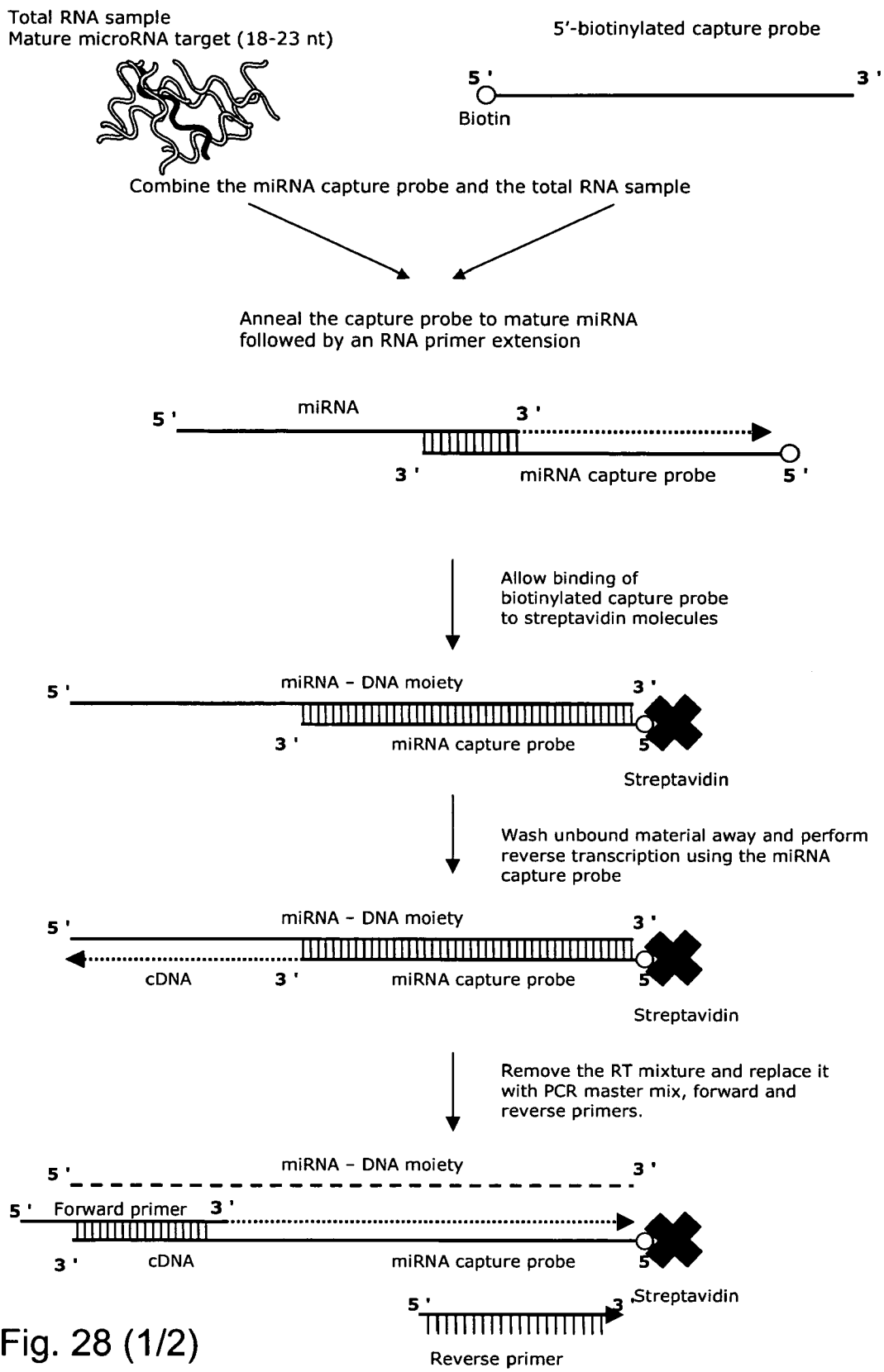
FIG. 29 shows part of the Hsa miR-15a precursor sequence, the mature Hsa miR-15a sequence and a schematic presentation of one method of the invention for quantification of microRNAs by sequence-specific real-time quantitative RT-PCR.

In a further preferred embodiment the invention comprises the steps as shown in FIG. 29.

Figure 30:
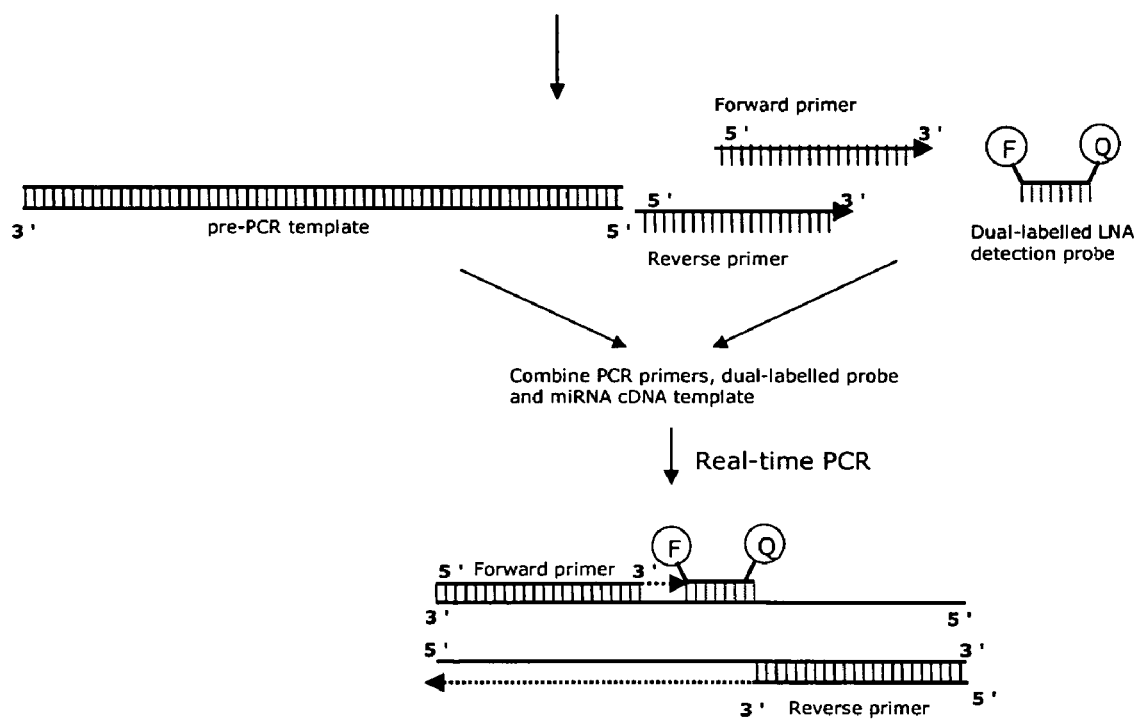
FIG. 30 shows part of the Hsa miR-143 precursor sequence, the mature Hsa miR-143 sequence and a schematic presentation of one method of the invention for quantification of microRNAs by sequence-specific real-time quantitative RT-PCR.

In a further preferred embodiment the invention comprises the steps as shown in FIG. 30.

Figure 33:
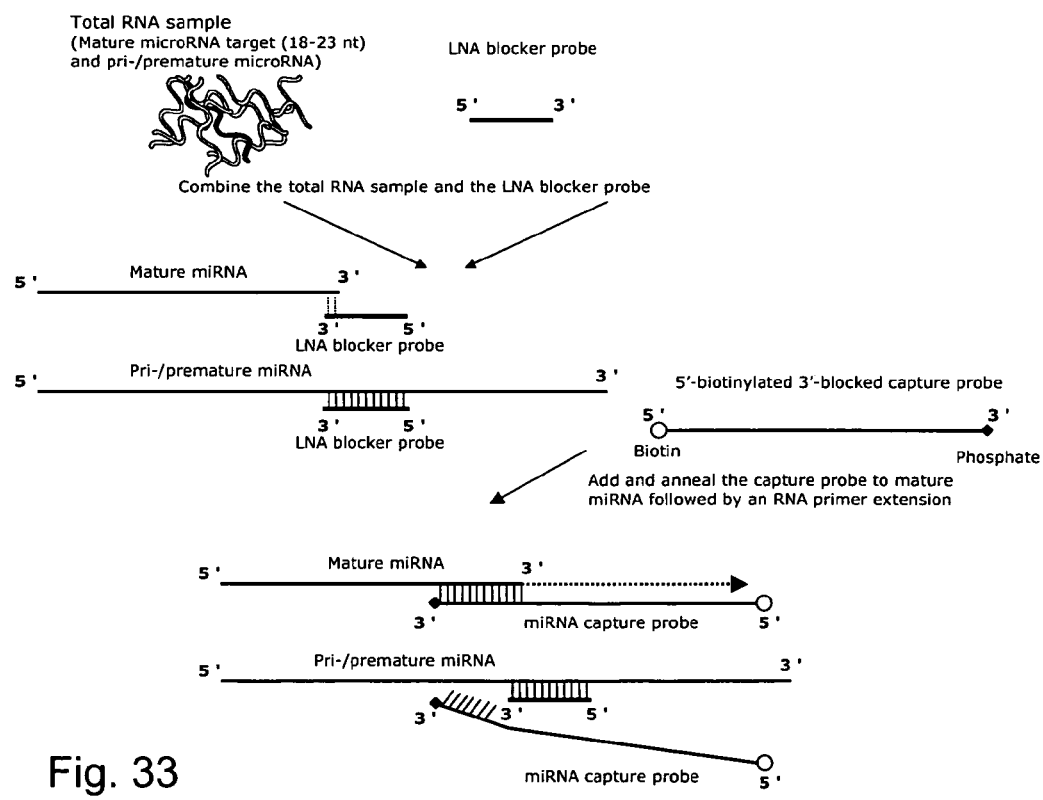
FIG. 33 shows a schematic presentation of one method of the invention for quantification of microRNAs by sequence-specific real-time quantitative RT-PCR

A further embodiment comprises the use of a LNA containing "blocker probe" to prevent binding of the RT-primer to templates exceeding the length of the mature miRNA transcript. The blocker probe is designed to bind sequences complementary to the non-mature miRNA regions within the pri-/precursor miRNA sequence flanking the 3' region of the mature miRNA sequence. The blocker probe is further designed to partly overlap the mature sequence, hence preventing binding of the RT-primer (as described in Example 12-16, and as depicted in FIG. 11, step 1) to the pri-/precursor sequence and allowing the RT tagging probe to anneal to the mature miRNA sequences only. The reaction steps are depicted in FIG. 33, step I and in FIG. 22.2-22.4.

In another embodiment employing a mature miRNA sequence (similar to the Hsa miR-15a sequence, FIG. 29) is detected utilizing an RT-primer designed to inhibit binding to templates exceeding a certain length i.e. such as the length of pri- and premature miRNA. The blocking is obtained by e.g. incorporating a large molecular structure into the RT-primer, or by annealing a short LNA-containing probe (blocker probe) to the primer to introduce a duplex structure, positioned to prevent binding of the primer to templates exceeding the length of the mature miRNA. The blocked primer design allow a mature miRNA sequence to anneal only, whereas longer templates does'nt anneal. The reaction steps are depicted in FIG. 29.

In another embodiment, the RT-primer from the previous embodiment also comprises one of the PCR primers in the reaction. Optionally the other PCR primer may also be designed to inhibit binding to templates exceeding a certain length. The reaction steps are depicted in FIG. 29*b*.

Figure 31:
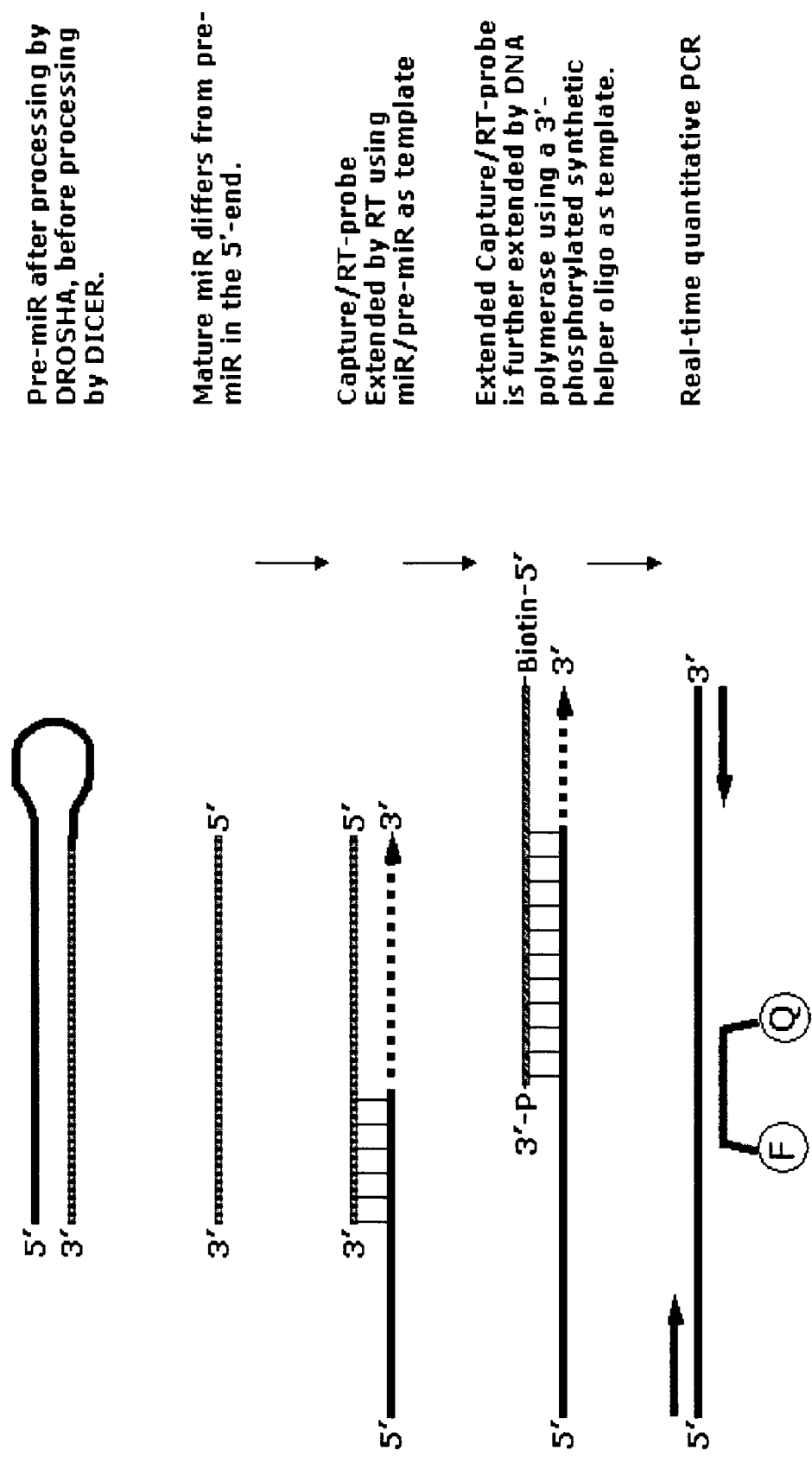
FIG. 31 is a schematic presentation of one method of the invention for quantification of microRNAs by sequence-specific real-time quantitative RT-PCR.

Another embodiment employs the addition of an artificial oligonucleotide template to the reaction. In cases where the miRNA is expressed from the far 3'-end of the precursor molecule (similar to the Hsa miR-143 sequence FIG. 30), the mature as well as the precursor miRNA template contain a 3'-end suitable for extension by a polymerase, e.g. the Klenow fragment. By employing a RT-primer as depicted in FIG. 31, which is subsequently extended by an RNA-directed DNA polymerase (e.g. reverse transcriptase), the resulting template will differ in length depending on whether the mature or precursor miRNA transcript serve as template. The $2^{nd}$ strand tagging probe described in Example 12-16, and as depicted in FIG. 11 step 2 has been exchanged by a 3'-blocked artificial oligonucleotide template depicted in FIG. 31 to allow the extension of the RT transcript originating from the mature miRNA, only. The 3'-blocked artificial oligonucleotide is subsequently used as a template to generate the primer site for subsequent amplification by PCR.

In another embodiment where the miRNA is expressed from the far 3'-end of the precursor molecule (similar to the Hsa miR-143 sequence, FIG. 30) the mature miRNA is detected utilizing a PCR primer hybridizing to the 3'-end of the reverse transcribed miRNA (the original 5'-end of the mature miRNA), and designed to inhibit binding to templates exceeding a certain length i.e. such as the length of the reverse transcribed pri-/precursor miRNA. This blocking is obtained by e.g. incorporating a large molecular structure into this PCR primer—e.g. being a looped primer—keeping an anchor sequence and forming an intramolecular hairpin structure, mediated by complementary sequences at the 5'- and the 3'-end of the oligonucleotide, at the chosen assay temperature, or by annealing a short LNA-containing probe (blocker probe) to the primer to introduce a duplex structure, positioned to prevent binding of the primer to templates exceeding the length of the mature miRNA. The primer is specifically designed to allow a mature processed miRNA sequence to anneal only, whereas longer templates don't anneal. The reaction steps are depicted in FIG. 34.

In cells, microRNA molecules occur both as longer (over 70 nucleotides) pricursor and precursor molecules as well as in the active form of mature miRNAs (17-25 nucleotides). One challenge in the detection of microRNA molecules is to detect the mature form of the molecule only, which is a 17-25 bp long single strand RNA molecule.

In a preferred embodiment of the present invention, the mature miRNA functions as a primer, i.e. the miRNA is hybridized to a template and extended by an enzyme capable of RNA-primed DNA-directed DNA synthesis. Secondly the detection relies on the occurence of this extension and furthermore the occurence of extension relies on having an —OH termination at the 3'end of the miRNA available at the expected distance from the annealing site to the template, which is used to ensure detection of processed mature miRNA molecules only. The principle of using the target (in this case miRNAs) as a primer in the detection reaction can be applied to other detection formats using other targets (both DNA and RNA).

General Aspect of the Invention

Many non-coding RNA molecules, such as microRNA molecules are very short and do not accommodate placement of primers for both reverse transcriptase, PCR amplification and optionally a labelled detection probe for amplification and detection by PCR. One solution for accommodating this is, according to the present invention, to append additional sequence to the microRNA, preferably by a method that enables the design of mature-specific assays.

As described (cf. the Examples), such sequence(s) may be appended by means of providing (by sequence specific hybridisation) a template for a polymerase-reaction to the microRNA, and providing a polymerase (e.g. a Klenow polymerase) and nucleotides to allow extension, leading to the appending to the mature microRNA of a sequence similar in part to that of the provided template. Such appended sequences may accommodate in part primers for reverse transcriptase, for PCR amplification or for a labelled detection probe, alone or in combination with the nucleic acid sequence of the microRNA.

Another means of appending additional sequence may be that of a ligation reaction. In such a reaction, an adaptor nucleic acid sequence may be attached to either the 3'-end, the 5'-end or both ends of the microRNA molecule by means of a ligation reaction. Such ligation reaction may be assisted by providing a "bridging" nucleic acid sequence comprising a nucleotide sequence specific for a terminal part of a mature target RNA sequence and a nucleotide sequence specific for terminal part of said adapter molecule such that the mature RNA target and said adaptor molecule are place in close vicinity to each other upon sequence specific hybridisation. Such sequence appended by ligation may accommodate in part primers for reverse transcriptase, for PCR amplification or for a labelled detection probe, alone or in combination with the nucleic acid sequence of the microRNA.

Yet another means of appending additional sequence to a target small RNA molecule may be that of a template-independent polymerase reaction. In one such an embodiment a sample of small target RNA molecules are subjected to a polymerase reaction, providing a polyA tail to all microRNAs present in the sample. This could for example be performed by using a polyA polymerase. In another such embodiment a sample of small target RNA molecules are subjected to a terminal transferase enzyme reaction, capable of providing an A, C, G or T polynucleotide tail to all microRNAs present in the sample when respective dATP, dCTP, dGTP or dTTPs are added. Such a microRNA sample provided with a nucleotide tail of similar nucleotides may be converted to cDNA by using a primer comprising the complementary similar nucleotides in a reverse transcriptase reaction, hence providing a cDNA sample of microRNAs with an appended polynucleotide tail of similar nucleotides. By overlapping part of the micro RNA sequence the RT-primer may also be specific for a specific microRNA or a group or family of microRNAs. Such a cDNA sample may subsequently serve a template for a PCR amplification reaction using primers specific for specific microRNA sequences, encompassed within the mature microRNA sequence or partly overlapping the sequence appended by means of a template independent polymerase reaction.

One such example is described in FIG. 37, where a total RNA sample or an RNA sample fraction containing only RNAs of a size below 200 nucleotides, is subjected to a polyA polymerase to append to all microRNA target molecules a polyA nucleotide tail. Subsequently, a poly T primer is used a primer in a reverse transcriptase reaction to convert the RNA sample into cDNA. Said RT reaction may further be rendered sequence specific by allowing the RT-primer seqrunce to partly overlap the microRNA sequence spec fic for a specific microRNA or group or family of microRNAs. Subsequently, said cDNA sample is subjected to a PCR amplification using PCR primers specific for a specific microRNA target and optionally a labelled detection probe. Such PCR primers may partly in total or partly overlap the appended sequence.

A broad aspect of the invention thus relates to a method for quantitative determination of a short-length RNA (which can be any of the small RNA types described herein), which has a length of at most 100 nucleotides, comprising
a) preparing, from a sample comprising said short-length RNA, a template polynucleotide which consists of 1) a single stranded target sequence consisting of the sequence of said short-length RNA, its correponding DNA sequence or a nucleotide sequence complementary to the sequence of said short-length RNA and 2) a 5' and/or a 3' adjacent nucleotide sequence,
b) using said template polynucleotide in a reverse transcription or a nucleotide polymerization to obtain a strand of cDNA, and
c) performing a quantitative real-time PCR (qPCR) including as template(s) said cDNA and optionally the template polynucleotide.

This aspect of the invention reflects the underlying concept of the invention, namely that specific detection of short-length RNA can be accomplished by ensuring a relatively high degree of specificity in all of steps a to c and that the specificity in each step adds to the general specificity of the method. One main characteristic is the provision of the template polynucleotide in step a, where said template includes appended sequences which can serve as "handles" for primers in the subsequent steps, thus providing space for all primers necessary and for the detection probes used. As will appear from the description herein, these "handles" can be both specific and non-specific for the short-length RNA one desires to quantify—in the case of specific sequences, these are appended in a reaction that preferentially or specifically will add the sequences to the short-length RNA but not to sequences which include the short-length RNA.

When using the term "corresponding to" is in the present context meant that a nucleotide sequence that corresponds to a reference nucleotide sequence is either identical to the reference sequence or constitutes a sequence that is hybridizes stringently to a sequence complementary to the reference nucleotide sequence. Typically, this means that an RNA sequence can correspond to a DNA sequence if the complementary sequence to the DNA sequence can be transcribed to the RNA sequence in question.

The term "cDNA" in this context means a DNA fragment which is obtained by means of either reverse transcription of the template polynucleotide or by means of nucleotide polymerization (such a DNA polymerization) based on the template nucleotide.

The short-length RNA is as mentioned at most 100 nucleotides, but much shorter RNA can be determined by means of the method. RNA having lengths of at most 90, at most 80, at most 70, at most 60, at most 50, at most 40, at most 30, and at most 25 nucleotide residues can conveniently be determined by means of the present methods and kits, but even shorter RNAs such as those having 10, 11, 12, 13, 14, 15, 16, 17, 18, 19, 20, 21, 22, 23, 24, and 25 nucleotide residues. Preferably, the short-length RNAs have lengths between 16 and 25 nucleotide residues.

The primers used for the qPCR in step c are in one embodiment selected from
at least 2 oligonucleotides, wherein at least one of said oligonucleotides corresponds to or is complementary to a sequence in the 5' or 3' adjacent nucleotide sequence—an embodiment which, especially if both primers relate to the adjacent sequences, benefits from the existence in steps a and b of sequence specific (for the short-length RNA or a sequence derived therefrom) appending of the 5' and/or 3' sequences and/or that step b has utilised an approach specific for the short-length RNA;

at least 2 oligonucleotides, wherein at least one of said oligonucleotides corresponds to or is complementary to a contiguous sequence in the template polynucleotide constituted by part of the single stranded target sequence and part of the adjacent 5' or 3' nucleotide sequence—an embodiment, where a relatively high degree of specificity is present in step c due to the specific recognition of part of the short-length RNA (or a sequence derived therefrom) and where it may be advantageous that the 5' or 3' nucleotide sequence has been appended based on a sequence specific approach and/or that step b has utilised an approach specific for the short-length RNA; and at least 2 oligonucleotides, wherein one corresponds to a first nucleotide sequence in the single stranded target sequence and the other is complementary to a second nucleotide sequence in the single stranded target sequence—an embodiment, where a high degree of specificity is present in step c due to the specific recognition of the short-length RNA (or a sequence derived therefrom).

Said primers used for the qPCR may each independently include a detectable label.

In another embodiment, the reaction in step (b) utilises a reverse transcription primer or a DNA poymerization primer which corresponds to or is complementary to the single stranded target sequence or which corresponds to or is complementary to a contiguous sequence in the template polynucleotide constituted by part of the single stranded target sequence and part of the adjacent 5' or 3' nucleotide sequence. It is preferred that the reverse transcription primer or nucleotide polymerization primer is specific for at least one short-length RNA; this reflects the fact that a number of short-length RNAs falls in certain families having a high degree of sequence identity.

The appended 5' and/or a 3' adjacent nucleotide sequence is in some embodiments a polynucleotide consisting of identical nucleotides (an effect which can be attained by utilising terminal transferase enzymes for appending the sequence or, alternatively by utilising a polymerase which adds identical nucleotide residues).

At any rate, the single stranded target sequence and the 5' and/or a 3' adjacent nucleotide sequence(s) may be covalently joined but also non-covalently joined—the important issue is whether the template sequence can be subjected to reverse transcription or nucleotide polemerization in step b.

The 5' and/or a 3' adjacent nucleotide sequence in some embodiments include(s) a detectable label, thus facilitating subsequent detection.

In most embodiments the 5' and/or 3' adjacent nucleotide sequence is joined to the single stranded target sequence by an enzymatic reaction, but also non-enzymatic reactions are envisaged.

Useful enzymes for adding identical nucleotides include, using the IUBMB Enzyme Nomenclature are provided in the following:

Transferases: EC 2.7.7.19 (polynucleotide adenylyltransferase), EC 2.7.7.52 (RNA uridylyltransferase), and EC 2.7.7.31 (DNA nucleotidylexotransferase).

Ligases: EC 6.5.1.1 (DNA ligase (ATP)), EC 6.5.1.2 (DNA ligase (NAD+)), and EC 6.5.1.3 (RNA ligase (ATP)).

In certain embodiments, the 5' and/or 3' adjacent nucleotide sequence does not occur naturally in the organism from where the sample RNA is derived. This is believed to reduce the risk of detecting irrelevant sequences in the sample. It is preferred that the 5' and/or 3' adjacent nucleotide sequence is non-mammalian.

In other embodiments, step (a) comprises preparation of the template polynucleotide by ligation of the 5' and/or 3' adjacent nucleotide sequence to the short-length RNA, or step (a) comprises preparation of the template polynucleotide by joining the 5' and/or 3' adjacent nucleotide sequence to the short-length RNA in a terminal transferase reaction, preferably in a poly-A transferase reaction. The ligation can be both sequence specific (e.g. overhang ligation) and blunt-end ligation, but it is preferred to utilise overhang ligation. In a preferred version of overhang ligation, the method involves annealing, to the short-length RNA, an oligonucleotide in part complementary to the ligase-reactive end of the 5' or 3' adjacent nucleotide sequence and in part complementary to the ligase-reative end of the short-length RNA molecule so as to position the ligase-reactive end of the 5' or 3' adjacent nucleotide sequence directly adjacent to the ligase-reative end of the small RNA molecule to allow overhang ligation.

One main advantage of using ligation or terminal transferases is that all RNA in the sample can be rendered useful for the subsequent steps (which then, on the other hand, should be highly specific). This enables creation of e.g. a non-specific cDNA library which can later be used for the more specific steps in b and c.

Typically, ligation or the terminal transferase reaction is only performed at the 3' end of the target sequence, but ligation to the 5' end of the target sequence can be performed by phosphorylating the 5' end of the target sequence prior to the ligation reaction. At any rate, in order to avoid "self-ligation" of the adjacent nucleotide sequences, it is preferred to block one of the termini (since ligases require 3'-hydroxyl and 5'-phosphate in the molecules to be ligated, this is a fairly easy task for the skilled person). Hence, the 5' adjacent nucleotide sequence is blocked at its 5' terminus and the 3' adjacent nucleotide sequence is blocked at its 3' terminus prior to ligation, and since these two nucleotide sequences are normally added in separate steps, it is avoided that they self-ligate.

The 5' and/or 3' adjacent nucleotide sequence(s) is/are preferentially or exclusively joined to a defined processing state of said short-length RNA in step (a). This is to mean that the means for appending the adjacent nucleotide sequence utilises a sequence coupling step which depends on the presence of a free 3' or 5' end in the short-length RNA (whereby discrimination is introduced over e.g. a pre-mature RNA that includes the same sequence but not in its relevant terminus). It is preferred that the defined processing state of said RNA is the mature state.

Step (b) in many embodiments comprises reverse transcription of the template polynucleotide to obtain the cDNA, (cf. e.g. FIG. 27). However, as mentioned above, step b may also comprise nucleotide polymerisation in step b to obtain the cDNA (cf. e.g. the embodiment of FIG. 31).

Instead of utilising ligation or terminal transferases, step (a) may comprise a step of nucleotide polymerization to attach the adjacent nucleotide sequences. The polymerase used for this purpose can be both a template-independent and a template-dependent polymerase. Typically employed polymerases are DNA polymerases.

Even though preferred embodiments utilise polymerization which is template specific, the polymerization may also consist in addition of a poly-A, poly-G, poly-T or a poly-C tail to the 3' end of the target sequence.

However, as mentioned, the currently preferred embodiments entail use of template specific approaches. In the cases of detection of microRNA, it is one object of the invention to be able to discriminate between mature and pre-mature microRNA, and in this context it is important to look at two different situations: the situation where the microRNA is situated in the 3' terminus of its premature precursor and the situation where the microRNA is situated in the 5' terminus of the premature precursor. To discriminate the mature forms from each of thes precursors, different approaches have to be used.

The following embodiments addresses various ways of achieving this discrimination, but is not in any way limited to the quantification of microRNA, since the embodiments are useful when quantifying or detecting any short-length RNA:

One embodiment (cf. FIG. 27) entails that step (a) comprises preparation of the template polynucleotide by the steps of
- annealing the 3' end of the short-length RNA to an oligonucleotide capture probe (the 5' end of which is complementary to the 3' end of the short-length RNA), and
- extending the short-length RNA by nucleotide polymerization using the oligonucleotide capture probe as template so as to obtain an extended short-length RNA molecule which constitutes the template polynucleotide. Typically the nucleotide polymerisation comprises a DNA polymerisation to so as to obtain an RNA-DNA hybrid which constitutes the template polynucleotide.

In this embodiment, step (b) preferably comprises that the RNA-DNA hybrid strand is reverse transcribed to obtain the cDNA, optionally after removal of material not annealing to the oligonucleotide capture probe (can be obtained if the capture probe includes a tag, that enables immobilisation). In the reverse transcription, the primer used can be the oligonucleotide capture probe itself or, alternatively, a separate reverse transcription primer (often the case, when the capture probe can be immobilised—in that case, the duplex is denatured and the template is transferred to another vessel where the new primer and other reagents are added).

Another embodiment (cf. FIG. 31) entails that step (a) comprises preparation of the template polynucleotide by the steps of
- annealing the 5' end of the short-length RNA to an oligonucleotide capture probe the 3' end of which is complementary to the 5' of the short-length RNA and the 5' end of which comprises the 5' adjacent nucleotide sequence, and
- extending the capture probe by reverse transcription using the short-length RNA as template to obtain an extended capture probe constituting the template polynucleotide. In this case the template polynucleotide does not include any of the original short-length RNA.

This embodiment may further entail that step (b) comprises that the short-length RNA is removed from the extended capture probe (by e.g. elevating the temperature), the capture probe is allowed to anneal at its 3' end to a helper oligonucleotide comprising a nucleotide sequence complementary to the 3' adjacent nucleotide sequence, and the capture probe is further elongated in the 5'→3' direction to obtain the cDNA by means of DNA polymerization using the helper oligonucleotide as template. Hence, in this embodiment, there is addition of both a 5' and 3' adjacent nucleotide sequence which are both added by means of a target sequence specific approach. As mentioned, both of these embodiments can benefit if the capture oligonucleotide contains a moiety that enables immobilisation onto a solid support. In such cases the capture probe is typically immobilised after annealing so as to allow removal of non-annealing material.

All the embodiments described herein may be optimised by enriching the sample in step (a) for RNA of short lengths—this can be done by various separation methods known to the skilled person (size exclusion chromatography, electrophoresis etc). This reduces the risk of obtaining false positive hits in the determination step derived from sequences in mRNA and other long RNA fragments.

In accordance with the principles of the present invention, step c can entail any of the detection methods described herein. It is, however, preferred that step (c) comprises use of a detection probe which comprises modified nucleotides (such as LNA nucleotides). In most of these embodiments, the detection probe corresponds to or is complementary to a sequence in the short-length RNA, but if the earlier steps a and b are sufficiently specific, this is not a necessity—in those cases the detection probe could be specific for other parts of the reaction product from step b.

Also the various primers (and/or capture probes and/or helper oligonucleotides) used in reverse transcription or in DNA polymerization or in general in steps a-c, may comprise modified nucleotides. The main advantage is that the total length of primers and other oligonucleotides can be reduced because e.g. LNA exhibits a high degree of hybridization with DNA, so sequence specific binding can be obtained using shorter oligonucleotides.

It is also possible to utilise, as a primer in the detection in step c, the same primer used in step b, i.e. a primer constituted by a primer used in the reverse transcription or nucleotide polymerization of step (b). Again, if the degree of specificity in the steps as a whole is sufficiently high to allow a "noise-free" detection of the short-length RNA, then the use of such a "recycled" primer in step c will not affect the method significantly.

In accordance with the description of this general aspect of the invention, the present invention also relates to a kit useful in the quantitative determination of mature short-length RNA having a length of at most 100 nucleotides, said kit comprising
- the minimum number of reverse transcription primers and/or nucleotide polymerization primers and/or primers for qPCR and/or oligonucleotide capture probes and/or helper oligonucleotides and/or oligonucleotide probes, which are used in a method described herein, wherein the reverse transcription primers, nucleotide polymerization primers, primers for qPCR, oligonucleotide capture probes, helper oligonucleotides, and oligonucleotide probes share the features described above; and
- instructions for quantitative determination of the mature short-length RNA using the the reverse transcription primers and/or nucleotide polymerization primers and/or primers for qPCR and/or oligonucleotide capture probes and/or helper oligonucleotides and/or oligonucleotide probes. All disclosures relating to the provision of kits apply mutatis mutandis do this kit.

The kit may further comprise one or more enzymes and other reagents as described herein.

As an example os such a "minimal kit", the following is provided for exercising the method set forth in FIG. 27 (the reference primers and probes are optional):
The miR-specific Assay
  Biotinyleret LNA capture probe
  miR-specific reverse primer
  miR-specific forward and reverse primers
  miR-specific dual-labeled probe
  RNA control oligonucleotide
  DNA control oligonucleotide
The Reference U6 snoRNA Assay
  Reference U6 snoRNA RT primer/random hexamer primer
  Reference U6 snoRNA primers and dual-labeled probe

| Oligonucleotide | amount: 1 assay | 10 assays | concentration | volume |
|---|---|---|---|---|
| Biotinylated LNA capture probe | 0.5 pmol | 5 pmol | 0.5 µM | 1 µL |
| miR-specific reverse primer | 0.1 pmol | 1 pmol | 0.1 µM | 1 µL |
| miR-specific forward primer | 2.025 pmol | 20.25 pmol | 0.9 µM | 2.25 µL |
| miR-specific reverse primer | 2.025 pmol | 20.25 pmol | 0.9 µM | 2.25 µL |
| miR-specific dual-labeled probe | 0.3125 pmol | 3.125 pmol | 0.25 µM | 1.25 µL |
| RNA control oligonucleotide | 0.01 pmol | 0.1 pmol | 0.01 µM | 1 µL |
| DNA control oligonucleotide | 0.01 pmol | 0.1 pmol | 0.01 µM | 1 µL |
| Reference U6 snoRNA RT primer/ random hexamer primer | 2 pmol | 20 pmol | 2 µM | 1 µL |
| Reference U6 snoRNA forward primer | 2.025 pmol | 20.25 pmol | 0.9 µM | 2.25 µL |
| Reference U6 snoRNA reverse primer | 2.025 pmol | 20.25 pmol | 0.9 µM | 2.25 µL |
| Reference U6 snoRNA dual-labeled probe | 0.3125 pmol | 3.125 pmol | 0.25 µM | 1.25 µL |

Further Aspects of the Invention

Once the appropriate target sequences have been selected, LNA substituted tagging probes and detection probes are preferably chemically synthesized using commercially available methods and equipment as described in the art (*Tetrahedron* 54: 3607-30, 1998). For example, the solid phase phosphoramidite method can be used to produce short LNA probes (Caruthers, et al., *Cold Spring Harbor Symp. Quant. Biol.* 47:411-418, 1982, Adams, et al., *J. Am. Chem. Soc.* 105: 661 (1983).

LNA-containing-probes are typically labelled during synthesis. The flexibility of the phosphoramidite synthesis approach furthermore facilitates the easy production of LNAs carrying all commercially available linkers, fluorophores and labelling-molecules available for this standard chemistry. LNA may also be labelled by enzymatic reactions e.g. by kinasing.

Detection probes according to the invention can comprise single labels or a plurality of labels. In one aspect, the plurality of labels comprise a pair of labels which interact with each other either to produce a signal or to produce a change in a signal when hybridization of the detection probe to a target sequence occurs.

In another aspect, the detection probe comprises a fluorophore moiety and a quencher moiety, positioned in such a way that the hybridized state of the probe can be distinguished from the unhybridized state of the probe by an increase in the fluorescent signal from the nucleotide. In one aspect, the detection probe comprises, in addition to the recognition element, first and second complementary sequences, which specifically hybridize to each other, when the probe is not hybridized to a recognition sequence in a target molecule, bringing the quencher molecule in sufficient proximity to said reporter molecule to quench fluorescence of the reporter molecule. Hybridization of the target molecule distances the quencher from the reporter molecule and results in a signal, which is proportional to the amount of hybridization.

In another aspect polymerization of strands of nucleic acids can be detected using a polymerase with 5' nuclease activity. Fluorophore and quencher molecules are incorporated into the probe in sufficient proximity such that the quencher quenches the signal of the fluorophore molecule when the probe is hybridized to its recognition sequence. Cleavage of the probe by the polymerase with 5' nuclease activity results in separation of the quencher and fluorophore molecule, and the presence in increasing amounts of signal as nucleic acid sequences Suitable samples of target nucleic acid molecules may comprise a wide range of eukaryotic and prokaryotic cells, including protoplasts; or other biological materials, which may harbour target nucleic acids. The methods are thus applicable to tissue culture animal cells, animal cells (e.g., blood, serum, plasma, reticulocytes, lymphocytes, urine, bone marrow tissue, cerebrospinal fluid or any product prepared from blood or lymph) or any type of tissue biopsy (e.g. a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a mammae biopsy, a uterus biopsy, a testicular biopsy, an eye biopsy or a brain biopsy, e.g., homogenized in lysis buffer), archival tissue nucleic acids, plant cells or other cells sensitive to osmotic shock and cells of bacteria, yeasts, viruses, mycoplasmas, protozoa, rickettsia, fungi and other small microbial cells and the like.

Various amplifying reactions are well known to one of ordinary skill in the art and include, but are not limited to PCR, RT-PCR, LCR, in vitro transcription, rolling circle PCR, OLA and the like. Multiple primers can also be used in multiplex PCR for detecting a set of specific target molecules.

Preferably, the tagging probes as well as the detection probes of the invention are modified in order to increase the binding affinity of the probes for the target sequence by at least two-fold compared to probes of the same sequence without the modification, under the same conditions for hybridization or stringent hybridization conditions. The preferred modifications include, but are not limited to, inclusion of nucleobases, nucleosidic bases or nucleotides that have been modified by a chemical moiety or replaced by an analogue to increase the binding affinity. The preferred modifications may also include attachment of duplex-stabilizing agents e.g., such as minor-groove-binders (MGB) or intercalating nucleic acids (INA). Additionally, the preferred modifications may also include addition of non-discriminatory bases e.g., such as 5-nitroindole, which are capable of stabilizing duplex formation regardless of the nucleobase at the opposing position on the target strand. Finally, multi-probes composed of a non-sugar-phosphate backbone, e.g. such as PNA, that are capable of binding sequence specifically to a target sequence are also considered as a modification. All the different binding affinity-increasing modifications mentioned above will in the following be referred to as "the stabilizing modification(s)", and the tagging probes and the detection probes will in the following also be referred to as "modified oligonucleotide". More preferably the binding affinity of the modified oligonucleotide is at least about 3-fold, 4-fold, 5-fold, or 20-fold higher than the binding of a probe of the same sequence but without the stabilizing modification(s).

Most preferably, the stabilizing modification(s) is inclusion of one or more LNA nucleotide analogs. Probes from 6 to 30 nucleotides according to the invention may comprise from 1 to 8 stabilizing nucleotides, such as LNA nucleotides. When at least two LNA nucleotides are included, these may be consecutive or separated by one or more non-LNA nucleotides. In one aspect, LNA nucleotides are alpha and/or xylo LNA nucleotides.

The invention also provides a probe library comprising tagging probes and detection probes with stabilizing modifications as defined above. Preferably, the detection probes are less than about 20 nucleotides in length and more preferably less than 15 nucleotides, and most preferably about 7 or 8 or 9 or 10 or 11 nucleotides. Also, preferably, the tagging probes are less than about 40 nucleotides in length and more preferably less than 35 nucleotides, and most preferably about 20 or 30 nucleotides. Also, preferably, the tagging probes ligation reaction and the RT tagging probe and the $2^{nd}$ strand tagging probe for the RT-PCR reaction are composed of a high-affinity tagging recognition sequence of less than about 15 nucleotides in length and more preferably less than 14 nucleotides, and most preferably between 6 and 13 nucleotides, and furthermore of an anchored sequence as a primer site for PCR primers of less than about 30 nucleotides in length and more preferably less than 25 nucleotides, and most preferably between 15 to 20 nucleotides. The probe libraries containing labelled detection probes may be used in a variety of applications depending on the type of detection element attached to the recognition element. These applications include, but are not limited to, dual or single labelled assays such as 5' nuclease assay, molecular beacon applications (see, e.g., Tyagi and Kramer Nat. Biotechnol. 14: 303-308, 1996) and other FRET-based assays.

The problems with existing quantification assays for microRNAs, siRNAs, RNA-edited transcripts, alternative splice variants and antisense non-coding RNAs as outlined above are addressed by the use of the probes of the invention in combination with any of the methods of the invention consisting of a set of RNA tagging probes and detection probes or sets of RNA RT tagging probes combined with $2^{nd}$ strand tagging probes and detection probes, selected so as to recognize or detect a majority of all discovered and detected miRNAs, RNA-edited transcripts, siRNAs, alternative splice variants and antisense non-coding RNAs in a given cell type from a given organism. In one aspect, the probe library comprises probes that tag and detect mammalian mature miRNAs, e.g., such as mouse, rat, rabbit, monkey, or human miRNAs. By providing a cost-efficient useful method for quantitative real-time and end-point PCR assays for mature miRNAs, RNA-edited transcripts, siRNAs, alternative splice variants and antisense non-coding RNAs, the present invention overcomes the limitations discussed above especially for conventional miRNA assays and siRNA assays. The detection element of the detection probes according to the invention may be single or double labelled (e.g. by comprising a label at each end of the probe, or an internal position). Thus, probes according to the invention can be adapted for use in 5' nuclease assays, molecular beacon assays, FRET assays, and other similar assays. In one aspect, the detection probe comprises two labels capable of interacting with each other to produce a signal or to modify a signal, such that a signal or a change in a signal may be detected when the probe hybridizes to a target sequence. A particular aspect is when the two labels comprise a quencher and a reporter molecule.

In another aspect, the probe comprises a target-specific recognition segment capable of specifically hybridizing to a target molecule comprising the complementary recognition sequence. A particular detection aspect of the invention referred to as a "molecular beacon with a stem region" is when the recognition segment is flanked by first and second complementary hairpin-forming sequences which may anneal to form a hairpin. A reporter label is attached to the end of one complementary sequence and a quenching moiety is attached to the end of the other complementary sequence. The stem formed when the first and second complementary sequences are hybridized (i.e., when the probe recognition segment is not hybridized to its target) keeps these two labels in close proximity to each other, causing a signal produced by the reporter to be quenched by fluorescence resonance energy transfer (FRET). The proximity of the two labels is reduced when the probe is hybridized to a target sequence and the change in proximity produces a change in the interaction between the labels. Hybridization of the probe thus results in a signal (e.g. fluorescence) being produced by the reporter molecule, which can be detected and/or quantified.

In yet another aspect, the target detection probe comprises a reporter and a quencher molecule at opposing ends of the short target recognition sequence, so that these moieties are in sufficient proximity to each other, that the quencher substantially reduces the signal produced by the reporter molecule. This is the case both when the probe is free in solution as well as when it is bound to the target nucleic acid. A particular detection aspect of the invention referred to as a "5' nuclease assay" is when the detection probe may be susceptible to cleavage by the 5' nuclease activity of the DNA polymerase. This reaction may possibly result in separation of the quencher molecule from the reporter molecule and the production of a detectable signal. Thus, such probes can be used in amplification-based assays to detect and/or quantify the amplification process for a target nucleic acid.

The invention also provides a method, system and computer program embedded in a computer readable medium ("a computer program product") for designing tagging probes and detection probes comprising at least one stabilizing nucleobase. The method comprises querying a database of target sequences (e.g., such as the miRNA registry at http://www.sanger.ac.uk/Software/Rfam/mirna/index.shtml) and designing probes which: i) have sufficient binding stability to bind their respective target sequence under stringent hybridization conditions, ii) have limited propensity to form duplex structures with itself, and iii) are capable of binding to and detecting/quantifying at least about 60%, at least about 70%, at least about 80%, at least about 90% or at least about 95% of all the target sequences in the given database of.

Capture Probe Design Program.

The invention also provides a method, system and computer program embedded in a computer readable medium ("a computer program product") for designing the sequence of nucleotides to implement the capture probe.

The method consists of the following steps:
a) Initial guess of one or mores sequence(s) of nucleotides to implement the capture probe(s).
b) Iterative improvement of the initial guesses based on the fulfillment of conditions and aims.
c) Stopping the algorithm when there is a sufficient fulfillment of the conditions and aims also including the computing time used on the current method.

The melting temperature is designated "Tm".

Detailed description of the three steps:
A) The initial guess is based on the miRNA sequence to match a list of suitable reverse primers found by using a primer finding software (primer3). Random sequences are generated to fill up not initialized parts of the capture probe. The random generation is guided by the use of di-nucleotide Tm tables to ensure sequences with Tm in the neighborhood of the aimed Tm value.
B) The iterative improvement will be directed by a scoring function based on the aims and conditions and of di-nucleotide Tm tables. Random changes are made to avoid suboptimal iteration.
C) The algorithm stops when a scoring function based on the aims, conditions and computation time is fulfilled.

The aims to obtain the primer and probe conditions listed below:
1. The Melting Temperature Condition for the Hybridization of the Capture Probe Towards the miRNA The melting temperature of the duplex formed by the capture probe and the miRNA is extended to be suitable for a DNA polymerase extension reaction. The oligonucleotide length within this duplex ought to satisfy the Tm condition for a DNA polymerase extension reaction mentioned above. The miRNA hybridized to the 3'-end of the capture probe.
2. The Melting Temperature Condition for the Duplex Formed by the Capture Probe and the DNA Polymerase-extended miRNA The Tm of the duplex formed by the capture probe and the DNA polymerase-extended miRNA target is not allowed to exceed the temperature by means of which the heteroduplex can be denatured without destroying the RNA-DNA target.
3. The Relationship Between the Capture Probe and the Reverse Transcription (RT) Primer The RT primer is sequence identical to the 5' end of the capture probe and hybridizes to the 3'-end of the DNA polymerase-extended miRNA. The Tm for this duplex formed by RT primer and DNA polymerase-extended miRNA has to be suitable for a first strand synthesis using a reverse transcriptase.
4. The Differentiation Between the Mature and Precursor miRNA.

The 3'-end of the precursor miRNA is not allowed to hybridize with a significant amount of oligonucleotides to the capture probe under the given hybridization conditions for the capture reaction. Likewise the preceding monomers after the mature miRNA sequence motive within the precursor miRNA sequence are not allowed to hybridize to the non-miRNA-related capture probe sequence.

A general condition for every designed probe and primers is the requirement of low self-annealing and low self-hybridization.

Dual-labeled Probe Design Program.

The invention also provides a method, system and computer program embedded in a computer readable medium ("a computer program product") for designing nucleotide sequences to implement into the dual-labeled probe. The dual-labeled probe is used for detection of a particular miRNA or a particular family of miRNA's with maximal specificity.

The dual-labeled probe must fulfill the following conditions:
a) A requirement of low self-annealing and low self-hybridization.
b) Must anneal to the target by having a suitable Tm to function in the PCR reaction.
c) Must not anneal to the primers in the PCR reaction.

The method consist of the following steps:
A) A design of probes with maximal specificity toward miRNA or a family of miRNA's. The preferred probes that fulfil the conditions, called dual-labeled probe matches, are investigated by the ability of the dual-labeled probes to bind to other miRNA's. A dual-labeled probe match is then assigned a specificity score according to a scoring function. A sequence match, length of the sequence, and the use of LNA-modified nucleotides in the sequence determine a dual-labeled probe match.
B) Dual-labeled probe matches are scored by how well they fulfil the conditions above. The dual-labeled probes are scored by how well they fulfil the conditions above according to the scoring functions. The specificity score and the scores from the conditions are then used to deside the best nucleotide sequence of dual-labeled probe.

The quencher is preferably selected from dark quencher as disclosed in EP Application No. 2004078170.0, in particular compounds selected from 1,4-bis-(3-hydroxy-propylamino)-anthraquinone, 1-(3-(4,4'-dimethoxy-trityloxy)propylamino)-4-(3-hydroxypropylamino)-anthraquinone, 1-(3-(2-cyanoethoxy(diisopropylamino)phosphinoxy) propylamino)-4-(3-(4,4'-dimethoxy-trityloxy) propylamino)-anthraquinone (#Q1), 1,5-bis-(3-hydroxy-propylamino)-anthraquinone, 1-(3-hydroxypropylamino)-5-(3-(4,4'-dimethoxy-trityloxy)propylamino)-anthraquinone, 1-(3-(cyanoethoxy(diisopropylamino)phosphinoxy)propylamino)-5-(3-(4,4'-dimethoxy-trityloxy)propylamino)-anthraquinone (#Q2), 1,4-bis-(4-(2-hydroxyethyl)phenylamino)-anthraquinone, 1-(4-(2-(4,4'-dimethoxy-trityloxy)ethyl)phenylamino)-4-(4-(2-hydroethyl)phenylamino)-anthraquinone, 1-(4-(2-(2-cyanoethoxy(diisopropylamino)phosphinoxy)ethyl)phenylamino)-4-(4-(2-(4,4'-dimethoxy-trityloxy)ethyl)phenylamino)-anthraquinone, and 1,8-bis-(3-hydroxy-propylamino)-anthraquinone; or alternatively selected from 6-methyl-Quinizarin, 1,4-bis(3-hydroxypropylamino)-6-methyl-anthraquinone, 1-(3-(4,4'-dimethoxy-trityloxy)propylamino)-4-(3-hydroxypropylamino)-6(7)-methyl-anthraquinone, 1-(3-(2-cyanoethoxy(diisopropylamino) phosphinoxy)propylamino)-4-(3-(4,4'-dimethoxy-trityloxy) propylamino)-6(7)-methyl-anthraquinone, 1,4-bis(4-(2-hydroethyl)phenylamino)-6-methyl-anthraquinone, 1,4-Dihydroxy-2,3-dihydro-6-carboxy-anthraquinone, 1,4-bis (4-methyl-phenylamino)-6-carboxy-anthraquinone, 1,4-bis (4-methyl-phenylamino)-6-(N-(6,7-dihydroxy-4-oxo-heptane-1-yl))carboxamido-anthraquinone, 1,4-bis(4-methyl-phenylamino)-6-(N-(7-dimethoxytrityloxy-6-hydroxy-4-oxo-heptane-1-yl))carboxamido-anthraquinone, 1,4-Bis(4-methyl-phenylamino)-6-(N-(7-(2-cyanoethoxy (diisopropylamino)phosphinoxy)-6-hydroxy-4-oxo-heptane-1-yl))carboxamido-anthraquinone, 1,4-bis(propylamino)-6-carboxy-anthraquinone, 1,4-bis(propylamino)-6-(N-(6,7-dihydroxy-4-oxo-heptane-1-yl))carboxamido-anthraquinone, 1,4-bis(propylamino)-6-(N-(7-dimethoxytrityloxy-6-hydroxy-4-oxo-heptane-1-yl)) carboxamido-anthraquinone, 1,5-bis(4-(2-hydroethyl) phenylamino)-anthraquinone, 1-(4-(2-hydroethyl) phenylamino)-5-(4-(2-(4,4'-dimethoxy-trityloxy)ethyl) phenylamino)-anthraquinone, 1-(4-(2-(cyanoethoxy (diisopropylamino)phosphinoxy)ethyl)phenylamino)-5-(4-(2-(4,4'-dimethoxy-trityloxy)ethyl)phenylamino)-anthraquinone, 1,8-bis(3-hydroxypropylamino)-anthraquinone, 1-(3-hydroxypropylamino)-8-(3-(4,4'- dimethoxy-trityloxy)propylamino)-anthraquinone, 1,8-bis (4-(2-hydroethyl)phenylamino)-anthraquinone, and 1-(4-(2-hydroethyl)phenylamino)-8-(4-(2-(4,4'-dimethoxy-trityloxy)ethyl)phenylamino)-anthraquinone.

One preferred method for covalent coupling of oligonucleotides on different solid supports is photochemical immobilization using a photochemically active anthraquinone attached to the 5'- or 3'-end of the oligonucleotide as described in WO 96/31557 or in WO 99/14226.

In another preferred embodiment the high affinity and specificity of LNA modified oligonucleotides is exploited in the sequence specific capture and purification of natural or synthetic nucleic acids. In one aspect, the natural or synthetic nucleic acids are contacted with the LNA modified oligonucleotide immobilised on a solid surface. In this case hybridisation and capture occurs simultaneously. The captured nucleic acids may be, for instance, detected, characterised, quantified or amplified directly on the surface by a variety of methods well known in the art or it may be released from the surface, before such characterisation or amplification occurs, by subjecting the immobilised, modified oligonucleotide and captured nucleic acid to dehybridising conditions, such as for example heat or by using buffers of low ionic strength.

In another aspect the LNA modified oligonucleotide carries a ligand covalently attached to either the 5' or 3' end. In this case the LNA modified oligonucleotide is contacted with the natural or synthetic nucleic acids in solution whereafter the hybrids formed are captured onto a solid support carrying molecules that can specifically bind the ligand.

In one preferred aspect, the target sequence database comprises nucleic acid sequences corresponding to human, mouse, rat, *Drosophila melanogaster*, *C. elegans*, *Arabidopsis thaliana*, maize, fugu, zebrafish, Gallus, vira or rice miRNAs.

In another aspect, the method further comprises calculating stability based on the assumption that the recognition sequence comprises at least one stabilizing nucleotide, such as an LNA molecule. In one preferred aspect the calculated stability is used to eliminate probes with inadequate stability from the database of virtual candidate probes prior to the initial query against the database of target sequence to initiate the identification of optimal probe recognition sequences.

In another aspect, the method further comprises calculating the capability for a given probe sequence to form a duplex structure with itself based on the assumption that the sequence comprises at least one stabilizing nucleotide, such as an LNA molecule. In one preferred aspect the calculated propensity is used to eliminate probe sequences that are likely to form probe duplexes from the database of virtual candidate probes.

A preferred embodiment of the invention are kits for the detection or quantification of target miRNAs, siRNAs, RNA-edited transcripts, non-coding antisense transcripts or alternative splice variants comprising libraries of tagging probes and target detection probes. In one aspect, the kit comprises in silico protocols for their use. In another aspect, the kit comprises information relating to suggestions for obtaining inexpensive DNA primers. The probes contained within these kits may have any or all of the characteristics described above. In one preferred aspect, a plurality of probes comprises at least one stabilizing nucleotide, such as an LNA nucleotide. In another aspect, the plurality of probes comprises a nucleotide coupled to or stably associated with at least one chemical moiety for increasing the stability of binding of the probe. The kits according to the invention allow a user to quickly and efficiently develop an assay for different miRNA targets, siRNA targets, RNA-edited transcripts, non-coding antisense transcripts or alternative splice variants.

In general, the invention features the design of high affinity oligonucleotide probes that have duplex stabilizing properties and methods highly useful for a variety of target nucleic acid detection, amplification, and quantification methods (e.g., monitoring expression of microRNAs or siRNAs by real-time quantitative PCR). Some of these oligonucleotide probes contain novel nucleotides created by combining specialized synthetic nucleobases with an LNA backbone, thus creating high affinity oligonucleotides with specialized properties such as reduced sequence discrimination for the complementary strand or reduced ability to form intramolecular double stranded structures. The invention also provides improved methods for detecting and quantifying nucleic acids in a complex nucleic acid sample. Other desirable modified bases have decreased ability to self-anneal or to form duplexes with oligonucleotide probes containing one or more modified bases.

EXAMPLES

The invention will now be further illustrated with reference to the following examples. It will be appreciated that what follows is by way of example only and that modifications to detail may be made while still falling within the scope of the invention.

In the following Examples probe reference numbers designate the LNA-oligonucleotide sequences shown in the synthesis examples below.

Assessment of sensitivity and specificity of the real-time quantitative PCR assays for the human miR-15a microRNA target sequence.

Materials and Methods

1. Design and Synthesis of the Oligonucleotide Tagging Probes and Detection Probes for Microrna Detection and Quantification.

The RNA oligonucleotides (EQ15885 and EQ15886) were purchased at DNA Technology (Aarhus, Denmark) and purified by reverse phase chromatography (RP-HPLC). The RNA oligonucleotides were dissolved in Diethyl pyrocarbonate-(DEPC) treated $H_2O$ and the concentrations were determined on a NanoDrop ND-1000 (NanoDrop technologies, USA). Otherwise, the oligonucleotides were synthesised or standard DNA oligonucleotides were purchased at DNA technology.

TABLE I

The design of the microRNA tagging probes, synthetic transcription templates and detection probes.

| EQ No | Name | 5'-end Sequence$^a$ | 3'-end |
|---|---|---|---|
| 7396 | M13 for | gtaaaacgacggccagt | |
| 7655 | pTRIampl8 M13 rev | gaaacagctatgacatg | |
| 15848 | hsa-miR-15a micROLA probe 1 | aTgtGctGcTaactggccgtcgttttac | |
| 15849 | hsa-miR-15a micROLA probe 2 | gaaacagctatgacatgcacAaamCcaTt | |

TABLE I-continued

The design of the microRNA tagging probes, synthetic transcription templates and detection probes.

| EQ No | Name | 5'-end Sequence[a] | 3'-end |
|---|---|---|---|
| 15852 | hsa-miR-15a DNA phos | tagcagcacataatggtttgtg | P |
| 15853 | hsa-miR-16 DNA phos | tagcagcacgtaaatattggcg | P |
| 15866 | hsa-miR-15 A_02 | 6-Fitc aATGGTTTG#Q1z | P |
| 15867 | hsa-miR-15 A_03 | 6-Fitc tGTGmCTGmCT#Q1z | P |
| 15885 | hsa-miR-15a RNA | *uagcagcacauaaugguuugug* | |
| 15886 | hsa-miR-16 RNA | *uagcagcacguaaauauuggcg* | |
| 15887 | hsa miR-15a M13 for ex | cgtaaaacgacggccagt | |
| 15888 | hsa miR-15a M13 rev ex | caagtcttgaaacagctatgacatg | |

[a]LNA (upper cases), DNA (lower cases), RNA (italic and lower cases), 5-methyl C (mC); Fluorescein (6-FITC (Glenn Research, Prod.Id.No. 10-1964)), #Q1 (Prepared as described in Example 8a), z (5-nitroindole (Glenn Research, Prod.Id.No. 10-1044)), and Phosphate (P).

The human miR-15a microRNA tagging probe with the 3'-end recognition sequence was enzymatically 5'-phosphorylated in a 50 µL reaction using 10 U T4 polynucleotide kinase (New England Biolabs (NEB) USA), 400 pmol hsa-miR-15a microRNA probe 1 (EQ15848), and 1×T4 DNA ligase buffer (NEB, USA). The reaction was incubated 30 min at 37° C. and heat inactivated 10 min at 70° C. The kinase was removed by adding 50 µL DECP-treated $H_2O$ and filtering the reaction through an YM-30 Microcon spin column (Millipore, USA) 3 min 14000×g. The concentration of the phosphorylated tagging probe was determined on a NanoDrop ND-1000 (Nano-Drop technologies, USA).

2. MicroRNA-templated Ligation Reactions

The ligation reaction was performed in 20 µL consisting of 120 nM miR-15a RNA template (EQ15885), 120 nM of each microRNA tagging probe (phosphylated EQ15848 (see above) and EQ15849), 10 mM Tris-HCl pH 7.0 (Ambion, USA), 10 mM $MgCl_2$ (PE Biosystems, USA), 0.05×T4 DNA ligase buffer [2.5 mM TRIS-HCl, 0.5 mM $MgCl_2$, 0.5 mM DTT, 50 µM ATP, 1.25 µg/mL BSA, pH 7.5 @ 25° C.; (NEB, USA)]. The reactions were pre-incubated for 15 min at 37° C. and 800 U T4 DNA ligase was added and incubated for additional 2 hours at 37° C. Finally the reactions were heat-inactivated 20 min at 65° C. The ligation reaction was repeated using miR-15a DNA (EQ15852), miR-16RNA (EQ15886) as target or no template instead of the miR-15a RNA target. In addition to the 1:1 molar ratio of the target:microRNA tagging probes the ratios 5:1 and 1:5 were used in separate ligation reactions.

The ligation reaction performed using the Quick ligation kit (NEB, USA) was carried out according to the supplier's instructions. In brief, the oligonucleotides were the same as described above, In a 20 µL reaction mixture, the oligonucleotides and 1×quick ligation buffer (NEB, USA) were incubated 15 min at 25° C. and 1 µL Quick T4 DNA ligase (NEB, USA) was added and the incubation was prolonged for additional 30 min. The enzyme was heat-inactivated for 20 min at 65° C.

3. Real-time Polymerase Chain Reaction (PCR) Assays
3.1. MicroRNA Real-time PCR Assays Using SYBR Green Detection The reaction comprised (50 µL) 1×SYBR® Green PCR Master Mix (Applied Biosystems, USA) 200 nM of M13 forward primer (EQ7396), 200 nM M13 reverse primer (EQ7655) and 2.5 µL ligation reaction (described above). Cycling procedure: 10 min 95° C., 50 cycles of 15 sec 95° C., 1 min 45° C., 1 min 60° C., and finally dissociation 20 min from 60° C. to 95° C. in an ABI Prism® 7000 Sequence Detection System.

3.2. MicroRNA Real-time PCR Assays Using LNA-modified Detection Probes

The reaction (50 µL) was 1×QuantiTect Probe PCR master mix (Qiagen, Germany) 200 nM hsa miR-15a M13 forward primer (EQ15887), 200 nM hsa miR-15a M13 reverse primer (EQ15888), 100 nM LNA sequence-specific probe (EQ15866 or EQ15867), 2.5 µL ligation reaction (described above). Cycling procedure: 15 min 95° C., 50 cycles of 20 sec 95° C., 1 min 60° C. in an ABI Prism® 7000 Sequence Detection System.

In the following, dUTP means 2'-deoxyuridine-5'-triphosphate

Example 1

Real-time Quantitative PCR Assay for the Human miR-15a MicroRNA Target Sequence.

Figure 2B:
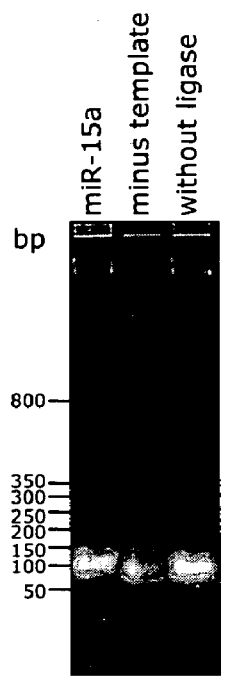
FIG. 2B shows the end-point analysis of the real-time PCR reactions on a 2% agarose gel electrophoresis stained with Gelstar (dilution 1:10000, Cambrex Bio Science, USA). The ligated miR-15a tagging probes template shows a PCR fragment in lane 1 (~65 bp). The negative control experiments (minus template (lane 2) and minus ligase (lane 3)) showed shorter fragments with a lower molecular weight than for the ligated mir-15a tagging probes template. The No template control (NTC) in the real-time PCR reaction was without any fragments on the agarose gel electrophoresis (not shown).

The sequence-specific LNA-modified microRNA tagging probes were annealed and ligated. The ligated templates were subsequently detected using real-time PCR, anchor PCR primers and an LNA-modified dual-labelled detection probe for the miR-15a microRNA using a minus template as a negative control. The specificity of the reaction was tested using a reaction without ligase. The threshold cycle (Ct), which represents the PCR cycle at which an increase in reporter fluorescence above a baseline signal can first be detected, for the ligated microRNA probes, using the miR-15a microRNA template was 35.0 (FIG. 2A), whereas no Ct values were detectable for the negative control experiments (minus template and minus ligase, respectively). The normalized reporter signal (Rn) is measured over the PCR reaction, which represents the fluorescence signal of the reporter dye divided by the fluorescence signal of the passive reference dye. During PCR, Rn increases as amplicon copy number increases, until the reaction approaches a plateau. The baseline corrected Rn (ΔRn) represents the Rn minus the baseline signal that was established in the first few cycles of PCR. For end-point analysis (FIG. 2B) the real-time PCR samples (4 µL) were applied on a 2% agarose gel stained with 1:10000

Gelstar and electrophoresis in 1×TBE buffer (90 mM Tris-borate, 2 mM EDTA, pH 8.3) for 2 hours at 8 V/cm. Lane 1 shows the ligated miR-15a tagging probes as template in the real-time PCR. The negative controls were Lane 2: minus template, and Lane 3: without ligase.

Example 2

Real-time Quantitative PCR Assay for the Human miR-15a MicroRNA Target Sequence and the Corresponding DNA 3′-blocked Target.

Figure 3:
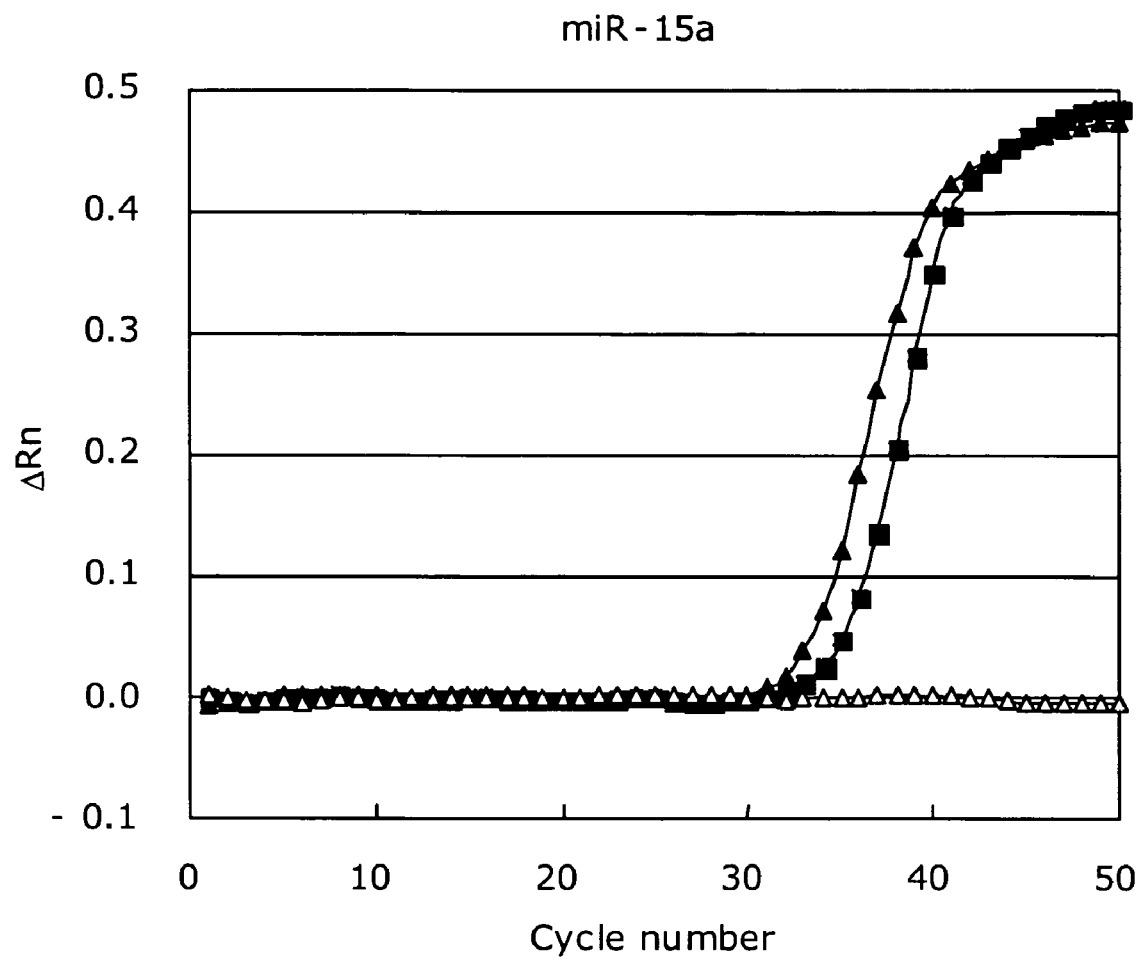
FIG. 3 shows the real-time quantitative PCR amplification plot for the human miR-15a microRNA target sequence and the corresponding DNA 3'-blocked target. The RNA template (solid squares) was replaced by a DNA template chemically blocked with a phosphate at the 3'-end (solid triangles). Without ligase (open triangles) the blocked DNA template could not be detected in the LNA sequence-specific real-time PCR assay. The Ct values for the RNA template and the DNA template were 35.0 and 33.3, respectively.

The RNA template was replaced by a DNA template, which was chemically blocked with a phosphate at the 3′-end. Without addition of ligase in the ligation reaction, the blocked DNA template could not be detected in the LNA sequence-specific real-time PCR assay. The Ct values for the RNA template and the DNA template were 35.0 and 33.3, respectively (FIG. 3).

Example 3

Specificity of the Real-time Quantitative PCR Assays for the Human miR-15a and Human miR-16 MicroRNA Target Sequences.

Sequence-specific microRNA target sequence recognition of the method of invention was assessed by using the miR-15a microRNA target in comparison with the human miR-16 target that has 72% sequence identity with the miR-15a target sequence. Neither the minus template control nor the no template control (NTC) in the real-time PCR reaction were shown to give any signals. Using the hybridization conditions for the annealing of the LNA-modified miR-15a target sequence-specific tagging probes as described above towards the miR-15a target resulted in a Ct value of 36.2, whereas the use of the same tagging probes for the highly homologous miR-16 resulted in a Ct value of 39.9, corresponding to a 13-fold discriminative difference (FIG. 4).

Example 4

Real-time Quantitative PCR Assays for the Human miR-15a MicroRNA Target Sequence Using Two Different LNA-modified, Dual-labeled Detection Probes.

Figure 5:
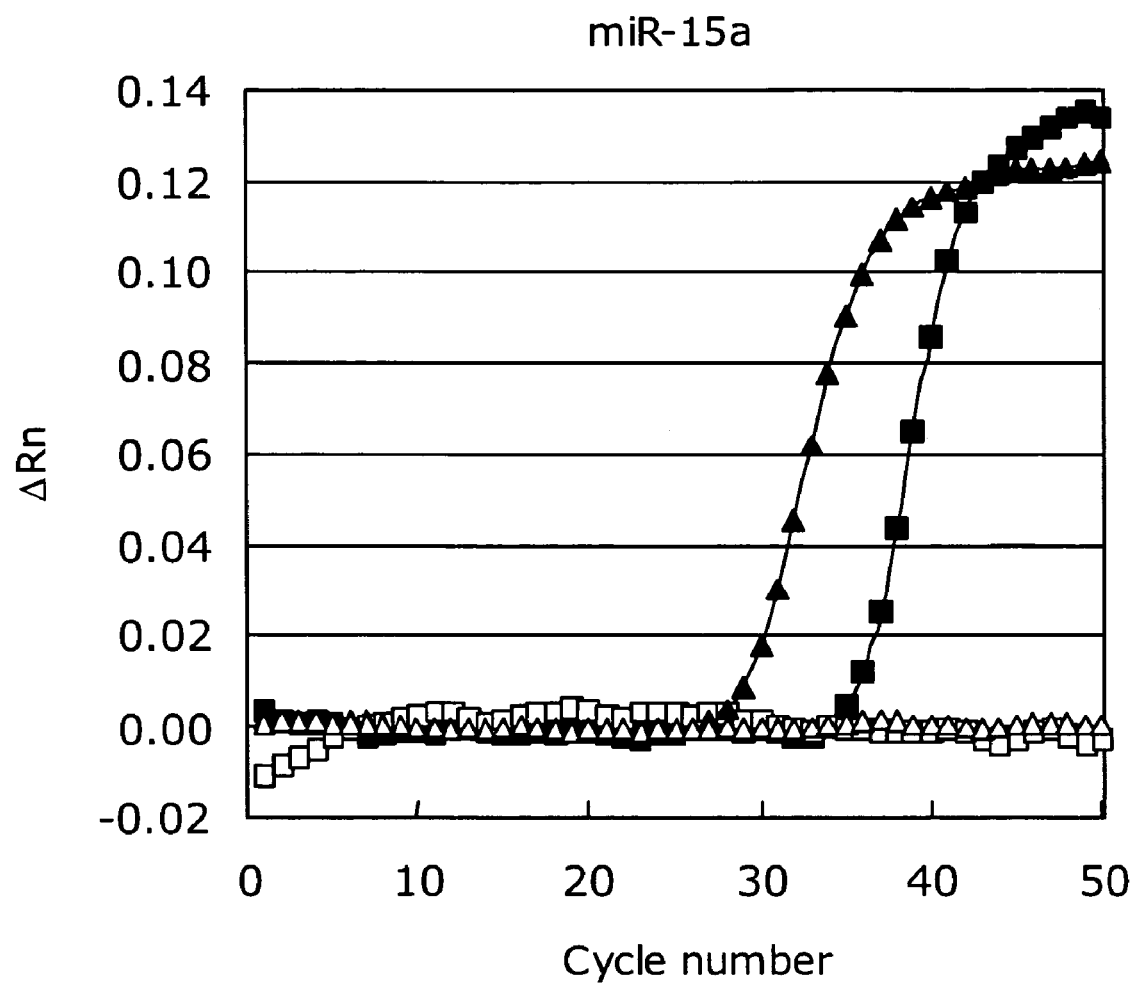
FIG. 5 shows the real-time quantitative PCR amplification plots for the human miR-15a microRNA target sequence using two different LNA-modified, dual-labelled detection probes. Two different LNA-modified real-time PCR detection probes were designed for the human miR-15a microRNA target sequence using the same LNA-modified tagging probes ligated by the Quick T4 DNA ligation kit. The use of the LNA-modified detection probes EQ15866 (solid squares) and EQ15867 (solid triangles) in the real-time PCR assays resulted in Ct values of 38.2 and 32.2, respectively. No signals where detected from both the minus ligase controls (EQ15866 open squares; EQ15867 open triangles).

Two different LNA-modified real-time PCR detection probes were designed for the human miR-15a microRNA target sequence using the same LNA-modified tagging probes ligated by the Quick T4 DNA ligation kit. The use of the LNA-modified detection probes EQ15866 and EQ15867 in the real-time PCR assays resulted in Ct values of 38.2 and 32.2, respectively (FIG. 5). No signals where detected from both the minus ligase controls (EQ15866 open squares; EQ15867 open triangles).

Example 5

Real-time Quantitative PCR Assays for the Human miR-15a Target Sequence Using Different Molar Ratios Between the Target and the miR-15a Tagging Probes.

Figure 6:
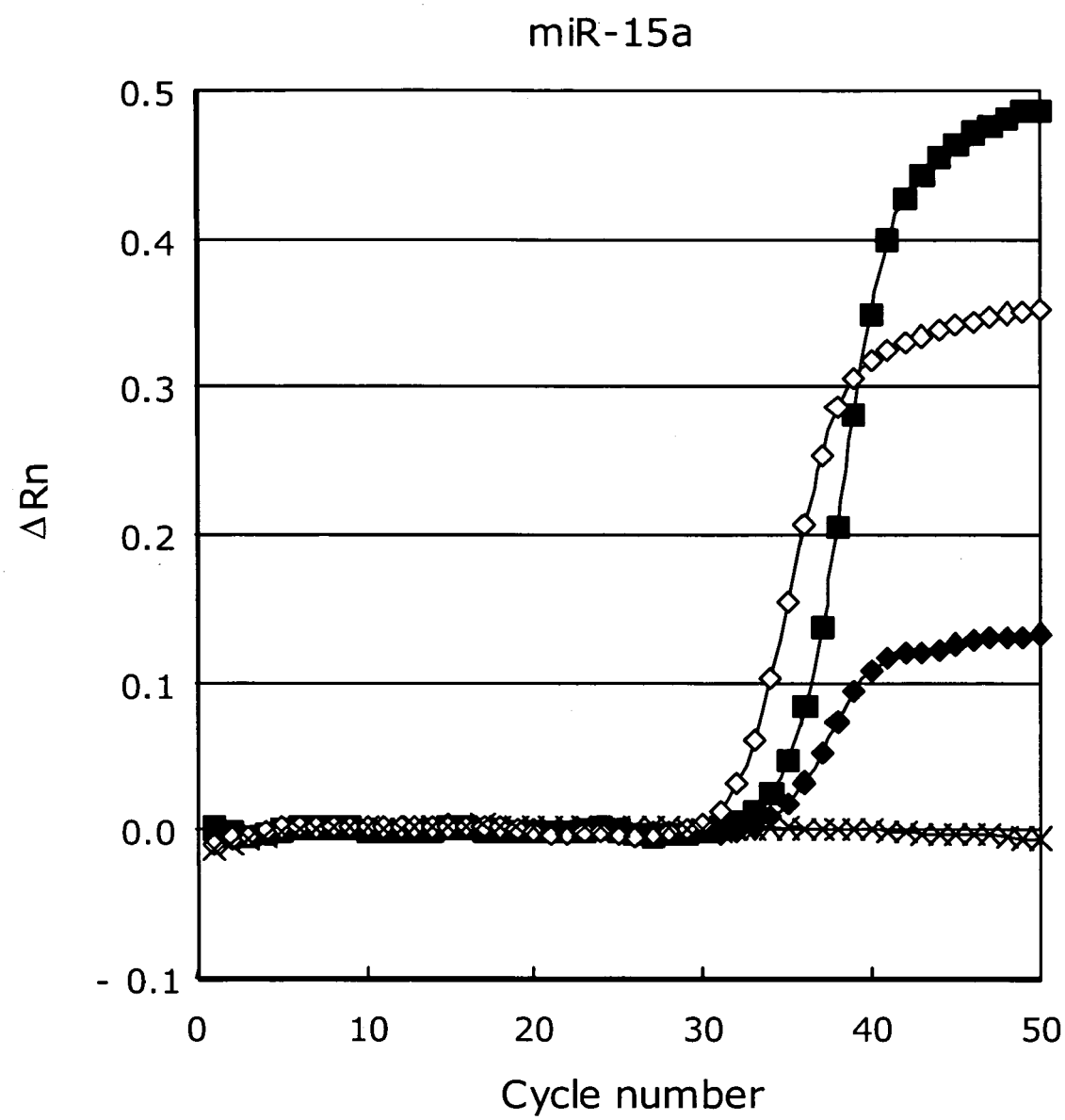
FIG. 6 shows the real-time quantitative PCR amplification plots for the human miR-15a target sequence using different molar ratios between the target and the miR-15a tagging probes. The molar ratios between target and tagging probes were 1:1 (solid square) resulted in the highest end-point fluorescence signal (ΔRn value), while the 1:5 molar ratios (open diamonds) resulted in the lowest end-point signal (ΔRn value). A molar excess of the miR-15a tagging probes (1:5 molar ratio (solid diamonds)) also resulted in a specific end-point signal, whereas no fluorescence signal was detected from NTC in the PCR reaction.

The molar ratios between target and tagging probes were 1:1 resulted in the highest end-point fluorescence signal (FIG. 6) (ΔRn value), while the 1:5 molar ratios resulted in the lowest end-point signal (ΔRn value). A molar excess of the miR-15a tagging probes (1:5 molar ratio) also resulted in a specific end-point signal (FIG. 6), whereas the No template control (NTC) in the PCR reaction did not show any significant fluorescence signal.

Example 6

Real-time Quantitative PCR Assays for the Human miR-15a Target Sequence Spiked into a Complex Background of *Torulla* Yeast RNA Using the miR-15a Tagging Probes and the Best-mode LNA-modified Detection Probe.

Figure 7:
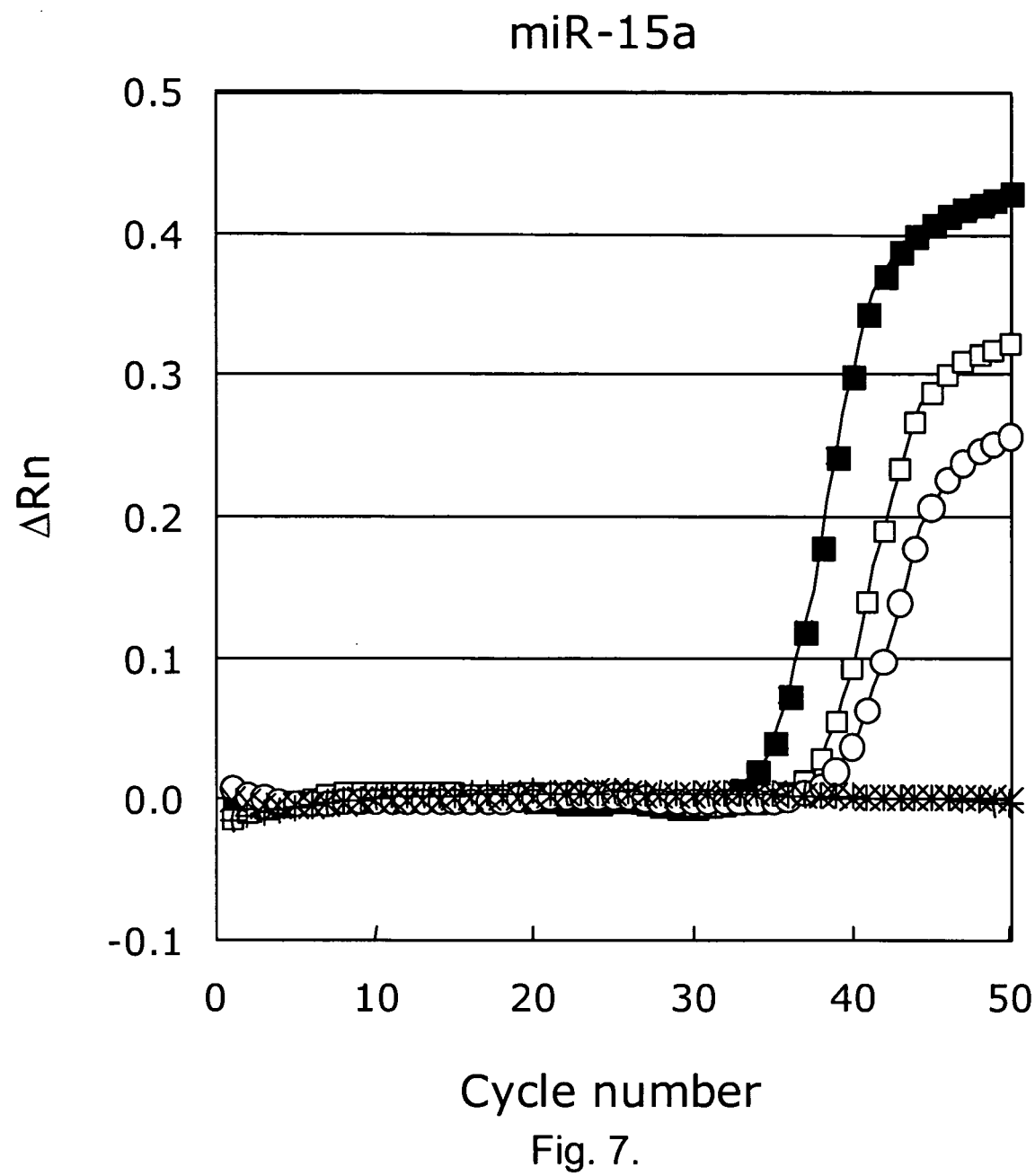
FIG. 7 shows the real-time quantitative PCR amplification plots for the human miR-15a target sequence spiked into a complex background of *Torulla* yeast total RNA using the miR-15a tagging probes and the best-mode LNA-modified detection probe. The miR-15a microRNA was spiked into 10 μg of yeast total RNA at 2.4 μM (open squares) and 1 μM (open circles) concentrations, annealed with the miR-15a tagging probes at equimolar concentrations, respectively, followed by ligation and miR-15a detection by quantitative real-time PCR. The highest fluorescence signal was observed from the miR-15a target sequence control (without the complex yeast total RNA background (solid squares), while no fluorescence signals were detected from the yeast total RNA sample (vertical line). No contamination of the real-time PCR assays was observed, as demonstrated with the NTC (crosses).

The miR-15a microRNA was spiked into 10 μg of *Torulla* yeast RNA at 2.4 μM and 1 μM concentrations, annealed with the miR-15a tagging probes at equimolar concentrations, respectively, followed by ligation and miR-15a detection by quantitative real-time PCR. The highest fluorescence signal was observed from the miR-15a target sequence control (without the complex yeast total RNA background), while no fluorescence signals were detected from the yeast total RNA sample (FIG. 7). No contamination of the real-time PCR assays were observed, as demonstrated with the minus template control.

Example 7

Real-time Quantitative PCR Assay for the Human miR-15a MicroRNA Target Sequence Using SYBR Detection.

Figure 8:
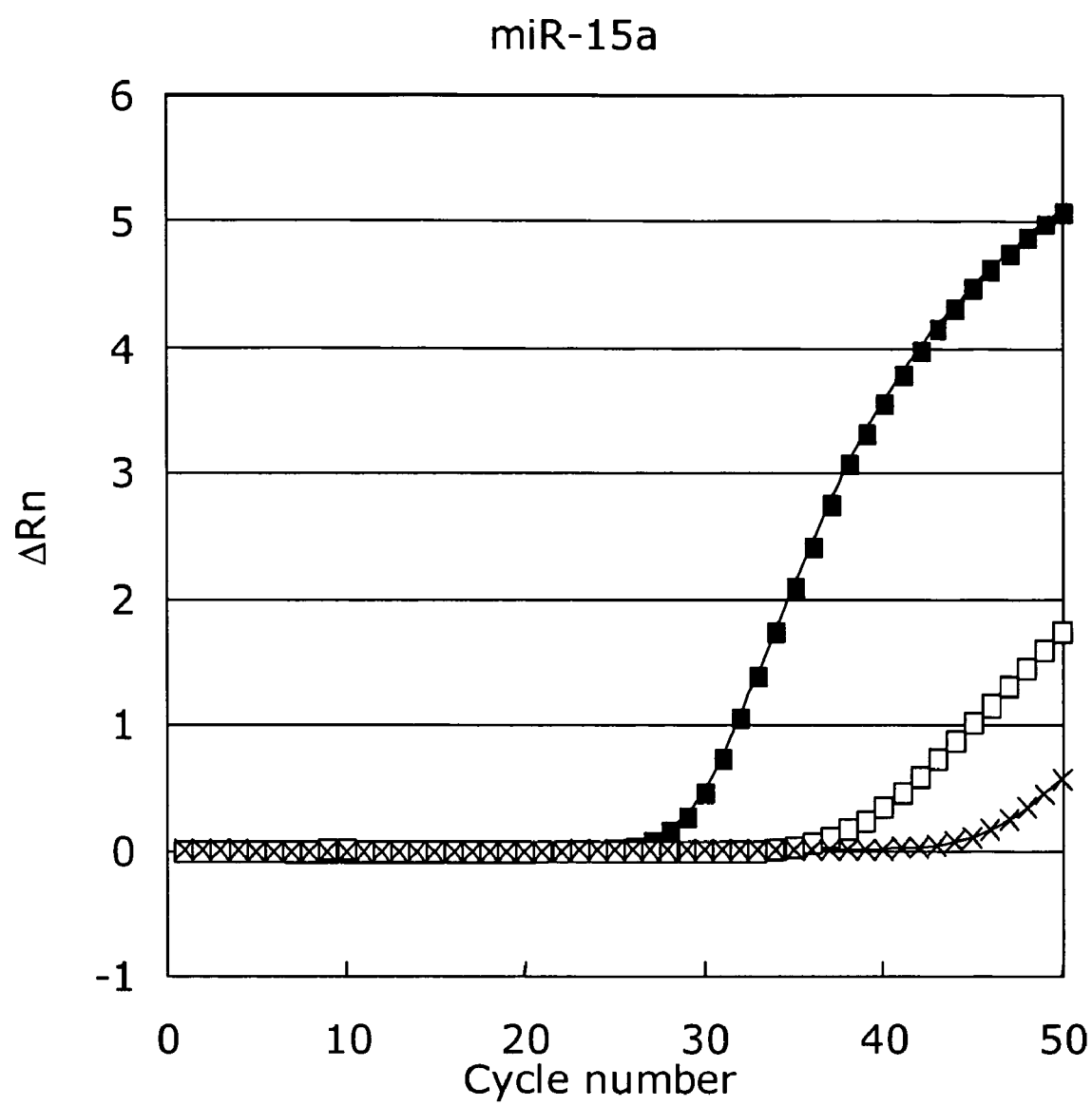
FIG. 8 shows the real-time quantitative PCR amplification plot for the human miR-15a microRNA target sequence. The sequence-specific LNA-modified microRNA tagging probes were annealed, ligated and the ligated templates were subsequently detected using real-time PCR, the anchor PCR primers and SYBR green detection (solid squares) using a minus template as a negative control (crosses). The specificity of the reaction was tested using a reaction without ligase (open diamonds).
Figure 10:
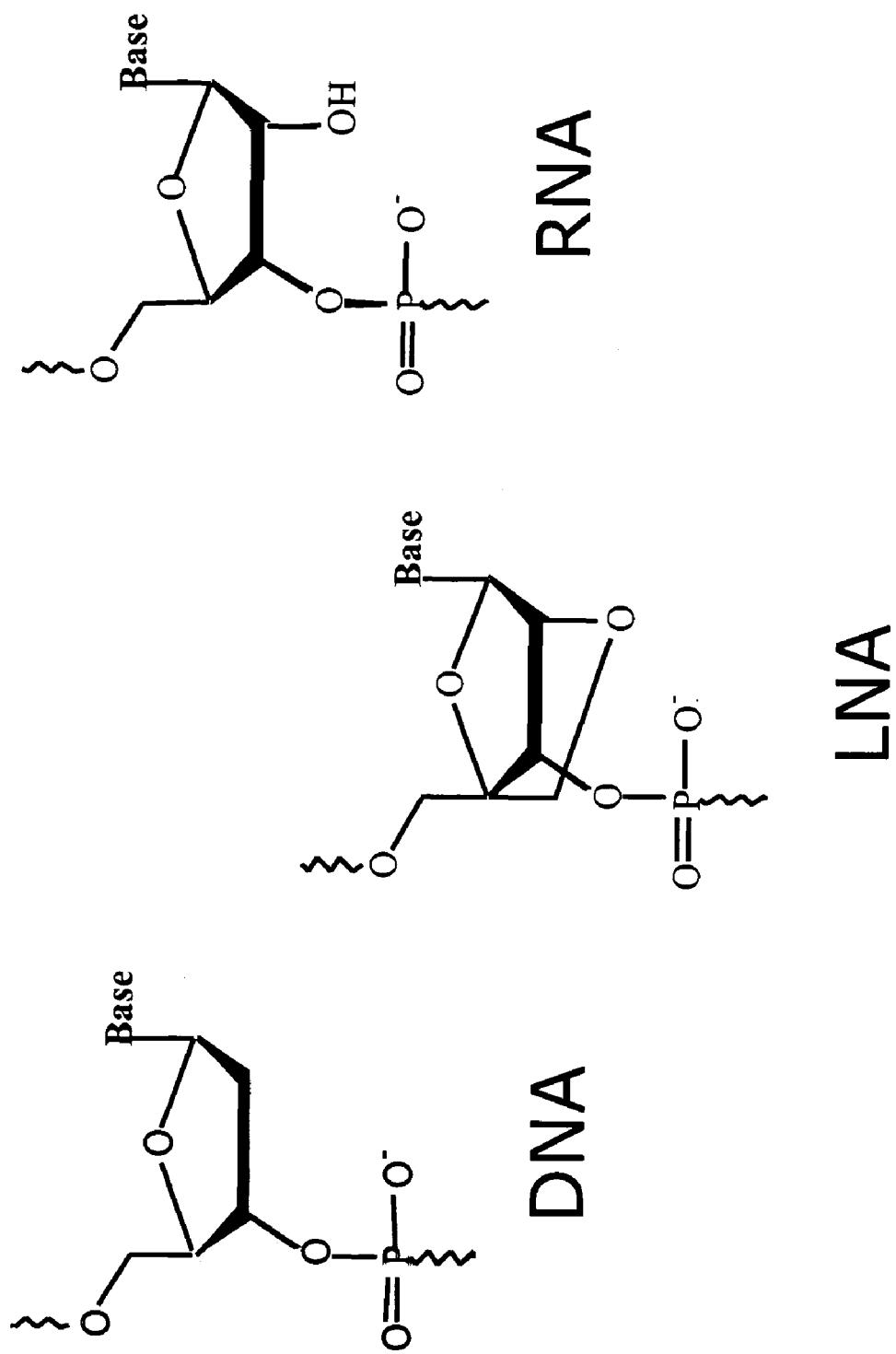
FIG. 10 shows the structures of DNA, LNA and RNA nucleosides.

The sequence-specific LNA-modified microRNA tagging probes were annealed and ligated. The ligated templates were readily detected using real-time PCR, the anchor PCR primers and SYBR green detection (FIG. 8), whereas no signals were detected from the minus template or minus ligase controls.

Example 8a

Preparation of 1-(3-(2-cyanoethoxy(diisopropylamino)phosphinoxy)pro-pylamino)-4-(3-(4,4′-dimethoxy-trityloxy)propylamino)-anthraquinone (3) Quencher "Q1"

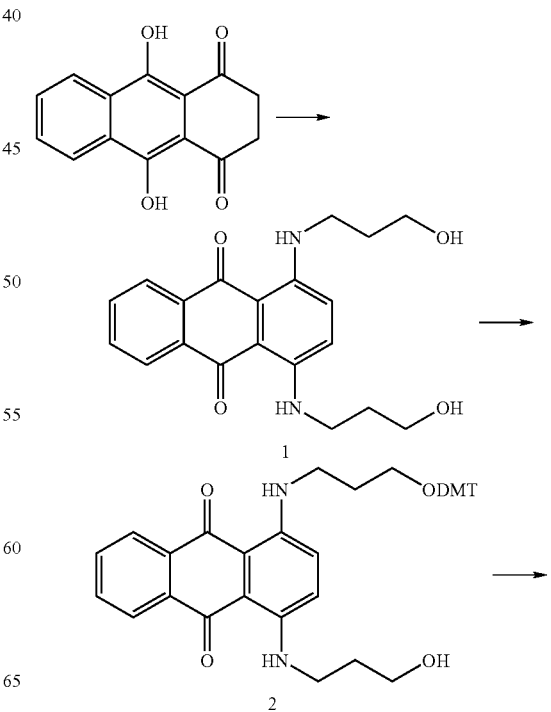

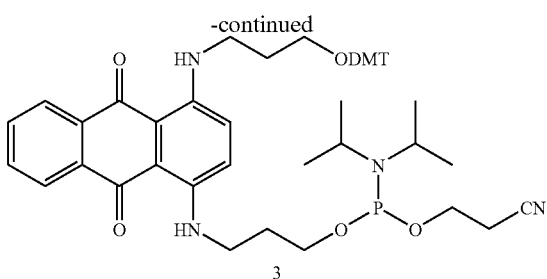

1,4-Bis(3-hydroxypropylamino)-anthraquinone (1)

Leucoquinizarin (9.9 g; 0.04 mol) is mixed with 3-amino-1-propanol (10 mL) and Ethanol (200 mL) and heated to reflux for 6 hours. The mixture is cooled to room temperature and stirred overnight under atmospheric conditions. The mixture is poured into water (500 mL) and the precipitate is filtered off washed with water (200 mL) and dried. The solid is boiled in ethylacetate (300 mL), cooled to room temperature and the solid is collected by filtration.

Yield: 8.2 g (56%)

1-(3-(4,4'-dimethoxy-trityloxy)propylamino)-4-(3-hydroxypropylamino)-anthraquinone (2)

1,4-Bis(3-hydroxypropylamino)-anthraquinone (7.08 g; 0.02 mol) is dissolved in a mixture of dry N,N-dimethylformamide (150 mL) and dry pyridine (50 mL). Dimethoxytritylchloride (3.4 g; 0.01 mol) is added and the mixture is stirred for 2 hours. Additional dimethoxytritylchloride (3.4 g; 0.01 mol) is added and the mixture is stirred for 3 hours. The mixture is concentrated under vacuum and the residue is redissolved in dichloromethane (400 mL) washed with water (2×200 ml) and dried ($Na_2SO_4$). The solution is filtered through a silica gel pad (φ 10 cm; h 10 cm) and eluted with dichloromethane until mono-DMT-anthraquinone product begins to elute where after the solvent is the changed to 2% methanol in dichloromethane. The pure fractions are combined and concentrated resulting in a blue foam.

Yield: 7.1 g (54%)

$^1$H-NMR(CDCl$_3$): 10.8 (2H, 2xt, J=5.3 Hz, NH), 8.31 (2H, m, AqH), 7.67 (2H, dt, J=3.8 and 9.4, AqH), 7.4-7.1 (9H, m, ArH+AqH), 6.76 (4H, m, ArH) 3.86 (2H, q, J=5.5 Hz, CH$_2$OH), 3.71 (6H, s, CH$_3$), 3.54 (4H, m, NCH$_2$), 3.26 (2H, t, J=5.7 Hz, CH$_2$ODMT), 2.05 (4H, m, CCH$_2$C), 1.74 (1H, t, J=5 Hz, OH).

1-(3-(2-cyanoethoxy(diisopropylamino)phosphinoxy)propylamino)-4-(3-(4,4'-dimethoxy-trityloxy)propylamino)-anthraquinone (3)

1-(3-(4,4'-dimethoxy-trityloxy)propylamino)-4-(3-hydroxypropylamino)-anthraquinone (0.66 g; 1.0 mmol) is dissolved in dry dichloromethane (100 mL) and added 3 Å molecular sieves. The mixture is stirred for 3 hours and then added 2-cyanoethyl-N,N,N',N'-tetraisopropylphosphordiamidite (335 mg; 1.1 mmol) and 4,5-dicyanoimidazole (105 mg; 0.9 mmol). The mixture is stirred for 5 hours and then added sat. NaHCO$_3$ (50 mL) and stirred for 10 minutes. The phases are separated and the organic phase is washed with sat. NaHCO$_3$ (50 mL), brine (50 mL) and dried (Na$_2$SO$_4$). After concentration the phosphoramidite is obtained as a blue foam and is used in oligonucleotide synthesis without further purification.

Yield: 705 mg (82%)

$^{31}$P-NMR (CDCl$_3$): 150.0

$^1$H-NMR(CDCl$_3$): 10.8 (2H, 2xt, J=5.3 Hz, NH), 8.32 (2H, m, AqH), 7.67 (2H, m, AqH), 7.5-7.1 (9H, m, ArH+AqH), 6.77 (4H, m, ArH) 3.9-3.75 (4H, m), 3.71 (6H, s, OCH$_3$), 3.64-3.52 (3.54 (6H, m), 3.26 (2H, t, J=5.8 Hz, CH$_2$ODMT), 2.63 (2H, t, J=6.4 Hz, CH$_2$CN) 2.05 (4H, m, CCH$_2$C), 1.18 (12H, dd, J=3.1 Hz, CCH$_3$).

Example 8b

Preparation of 1-(3-(cyanoethoxy(diisopropylamino)phosphinoxy)propylamino)-5-(3-(4,4'-dimethoxy-trityloxy)propylamino)-anthraquinone (6) Quencher "Q2"

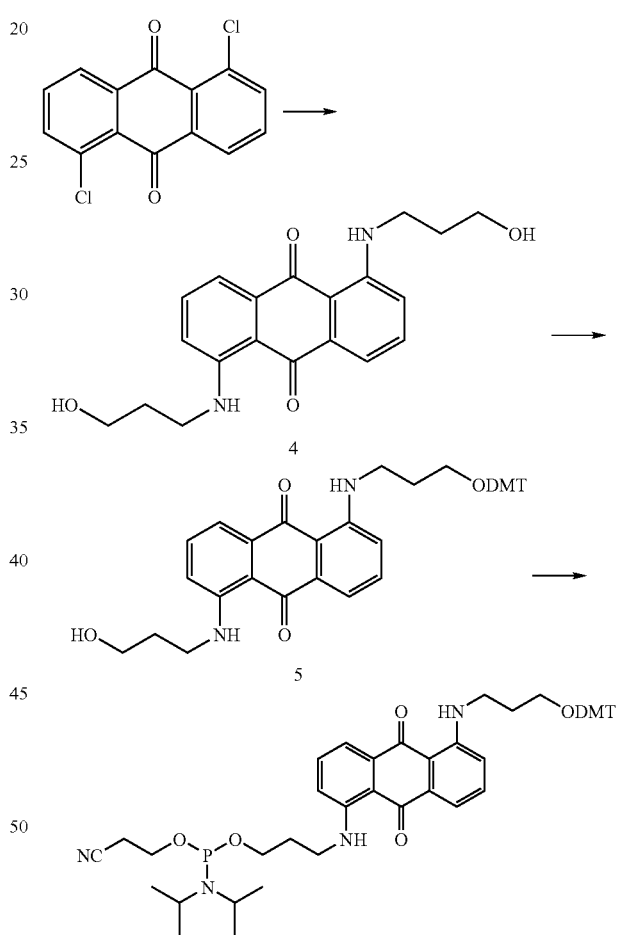

1,5-Bis(3-hydroxypropylamino)-anthraquinone (4)

1,5-Dichloroanthraquinone (2.8 g; 10 mmol) is mixed with 3-amino-1-propanol (10 mL) in DMSO (50 mL) and heated to 130° C. for 4 hours. The mixture is cooled to ~80° and added water (150 mL). When the mixture has reached RT the formed precipitate is isolated by filtration, washed with water (2×50 mL), boiled in toluene (200 mL) and the un-dissolved product is isolated by filtration and dried. Yield: 3.2 g (90%).

1-(3-hydroxypropylamino)-5-(3-(4,4'-dimethoxy-trityloxy)propylamino)-anthraquinone 5

1,5-Bis(3-hydroxypropylamino)-anthraquinone (1.4 g; 4 mmol) is co-evapourated with pyridine (50 mL) and then resuspended in pyridine (50 mL) added dimethoxytrityl-chloride (1.4 g; 4.1 mmol) and stirred overnight. The mixture is concentrated and the residue redissolved in dichloromethane (150 mL), washed with sat. $NaHCO_3$ (2×50 mL), brine (50 mL), dried ($Na_2SO_4$) and concentrated. Purify on silica gel column (MeOH/dichloromethane 2/98). After concentration of the appropriate fractions the mono-DMT compound is obtained as a red foam. Yield: 0.9 g (34%). $^1$H-NMR($CDCl_3$): 9.7 (2H, 2xt, NH), 7.6-6.7 (19H, m, ArH), 3.86 (2H, q, J=5.5 Hz, $CH_2$), 3.74 (6H, s, $CH_3$), 3.48 (4H, m, $NCH_2$), 3.26 (2H, t, J=5.9 Hz), 2.05 (4H, m, $CH_2$), 1.45 (1H, t, J=5 Hz).

1-(3-(cyanoethoxy(diisopropylamino)phosphinoxy)propylamino)-5-(3-(4,4'-dimethoxy-trityloxy)propylamino)-anthraquinone (6)

1-(3-hydroxypropylamino)-5-(3-(4,4'-dimethoxy-trityloxy)propylamino)-anthraquinone (0.4 g; 0.61 mmol) is dissolved in dry dichloromethane (50 mL) and added 3 Å molecular sieves. The mixture is stirred for 3 hours and then added 2-cyanoethyl-N,N,N',N'-tetraisopropylphosphordiamidite (200 mg; 0.66 mmol) and 4,5-dicyanoimidazole (71 mg; 0.6 mmol). The mixture is stirred for 2 hours and then added sat. $NaHCO_3$ (50 mL) and stirred for 10 minutes. The phases are separated and the organic phase is washed with sat. $NaHCO_3$ (50 mL), brine (50 mL) and dried ($Na_2SO_4$). After concentration the phosphoramidite is obtained as a red foam and is used in oligonucleotide synthesis without further purification. Yield: 490 mg (93%). $^{31}$P-NMR ($CDCl_3$): 148.3.

Materials and Methods Used in Examples 9 to 11

1. MicroRNA-templated Ligation Reaction Using Trehalose

The ligation reaction was performed in 20 µL consisting of 50 nM miR-15a RNA template (EQ15885, Table I), 500 nM of each of the microRNA tagging probe, 10 mM Tris-HCl pH 7.0 (Ambion, USA), 10 mM $MgCl_2$ (Ambion, USA), 0.05× T4 DNA ligase buffer [2.5 mM Tris-HCl, 0.5 mM $MgCl_2$, 0.5 mM DTT, 50 µM ATP, 1.25 µg/mL BSA, pH 7.5 at 25° C.; (NEB, USA)], 24 g/100 mL trehalose (Sigma-Aldrich, USA), 0.05 µg/µL *Torulla* yeast RNA (Ambion, USA). The reactions were pre-incubated for 15 min at 42° C. and 800 U T4 DNA ligase (NEB, USA) were added and incubated for 1 hours at 42° C. in a thermocycler DYAD™ (MJ Research DNA engine, USA). Finally the reactions were heat-inactivated for 20 min at 95° C. The ligation reaction was repeated without template instead of the miR-15a RNA target.

2. MicroRNA Real-time PCR Assays Using LNA-modified Detection Probe

The reaction (50 µL) was 1×PCR buffer [contains Tris-HCl, KCl, $(NH_4)_2SO_4$, 1.5 mM $MgCl_2$; pH 8.7 (20° C.)] (Qiagen, Germany), $MgCl_2$ to a final concentration of 4 mM, 200 nM of each dATP, dCTP, dGTP and 600 nM dUTP (Applied Biosystems, USA)"); 200 nM hsa-miR-15a forward primer 2 (EQ16444, Table II), 200 nM hsa-miR-15a reverse primer 2 (EQ16445, Table II), 250 nM LNA sequence-specific miR-15a detection probe (EQ15866, Table I), 0.1×ROX Reference Dye (Invitrogen, USA), 5 µL ligation reaction (as described above) and 2.5 U HotStarTaq DNA polymerase (Qiagen, Germany). Cycling procedure: 10 min 95° C., 50 cycles of 20 sec 95° C., 1 min 60° C. in an Applied Biosystems 7500 Real Time PCR System.

TABLE II

The design of different microRNA tagging probes, detection probes and real-time PCR primers used in examples 9 to 16.

| Oligo id (EQ No) | Oligonucleotide name | 5'-end | Sequence (5'-3')$^a$ | 3'-end |
|---|---|---|---|---|
| 16444 | hsa-miR-15a Forward primer 2 | | gtaaaacgacggccagttag | |
| 16445 | hsa-miR-15a Reverse primer 2 | | ccgaaacagctatgacatgc | |
| 16307 | hsa-miR-15a micROLA probe 1.1 DNA | P | atgtgctgctaactggccgtcgttttac | |
| 16311 | hsa-miR-15a micROLA probe 2.1 DNA | | gaaacagctatgacatgcacaaaccatt | |
| 16314 | hsa-miR-15a micROLA probe 2.4 | | gaaacagctatgacatgmCamCaaAccAtt | |
| 16447 | hsa-miR-15a micROLA probe 3.4 | | gaaacagctatgacatgCacAaaCcatt | |
| 16452 | hsa-miR-15a micROLA probe 3.9 | P | aTgtgmCtgcTaactggccgtcgttttac | |
| 16453 | hsa-miR-15a micROLA probe 3.10 | | gaaacagctatgacatgcAcaaAccaTt | |
| 16580 | axkOL140 | | 6-Fitc aGmCAmCATAAT#Q1z | P |
| 16581 | axkOL142 | | 6-Fitc aGmCAmCXTAAT#Q1z | P |
| 16582 | axkOL143 | | 6-Fitc aGmCXmCXTAAT#Q1z | P |
| 16583 | axkOL144 | | 6-Fitc aGmCXmCXTXAT#Q1z | P |
| 16589 | hsa-miR-15a FP 3 LNA_3 2 DNA | | gtaaaacgacggccagttaGcaGcamCat | |
| 16591 | hsa-miR-15a FP 3 DNA | | gtaaaacgacggccagttagcagcacat | |
| 16618 | hsa-miR-15a RT 4.1 DNA | | gaaacagctatgacatgcacaaacc | |

TABLE II-continued

The design of different microRNA tagging probes, detection probes
and real-time PCR primers used in examples 9 to 16.

| Oligo id (EQ No) | Oligonucleotide name | 5'-end | Sequence (5'-3')[a] | 3'-end |
|---|---|---|---|---|
| 16620 | hsa-miR-15a RT 4.3 LNA | | gaaacagctatgacatgmCacAaamCc | |
| 16623 | hsa-miR-15a FP 4.6 DNA | | gtaaaacgacggccagttagcagcaca | |
| 16624 | hsa-miR-15a FP 4.7 LNA | | gtaaaacgacggccagtTagmCagmCaca | |
| 16679 | axkOL150 | 6-Fitc | aGmCXmCXZAX#Q1z | P |

[a]LNA (uppercase), DNA (lowercase), 5-methyl C (mC); Fluorescein (6-FITC (Glenn Research, Prod.Id.No. 10-1964)), #Q1 (Prepared as described in Example 8a), z (5-nitroindole (Glenn Research, Prod.Id.No. 10-1044)), Phosphate (P), X denotes LNA-2,6-diaminopurine, and Z denotes LNA-2-thiothymidine.

Example 9

Real-time Quantitative PCR for the Human miR-15a MicroRNA Using MicroRNA-templated Ligation with Three Different Sets of miR-15a Tagging Probe Pairs.

Figure 13:
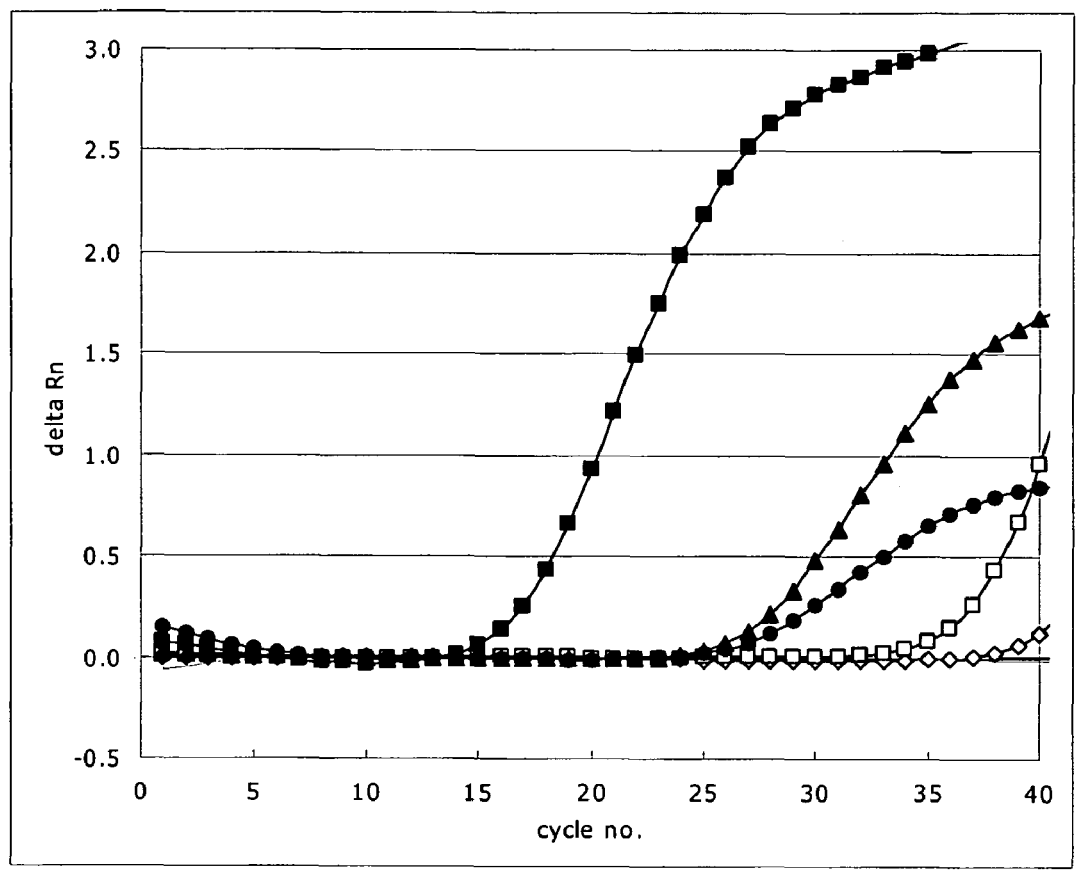
FIG. 13. Shows the real-time quantitative PCR amplification plots for the human miR-15a microRNA using microRNA-templated ligation with three different pairs of miR-15a tagging probes (I; EQ16311/EQ16452, II; EQ16453/EQ16307, and III; EQ16447/EQ16307)). Pair I: miR-15a template (solid squares) no template (open squares) and no T4 DNA ligase (open diamonds), pair II: miR-15a template (solid triangles), no template (open triangles) and no T4 DNA ligase (dotted line), pair III: miR-15a template (solid circles), no template (open circles) and no T4 DNA ligase (black line).

The sequence-specific LNA-modified microRNA tagging probes were annealed and ligated. Three different pairs of human miR-15a microRNA tagging probes were chosen (Table II): Pair I. EQ16311/EQ16452, II. EQ16453/EQ16307, and III. EQ16447/EQ16307) and the ligation reactions were performed as described above. The ligated templates were subsequently detected using real-time PCR as described above, by the anchor PCR primers and an LNA-modified dual-labelled detection probe for the miR-15a microRNA using a minus template as a negative control. The specificity of the ligation reaction was tested using a reaction without addition of the T4 DNA ligase. The threshold cycles (Ct), which represent the PCR cycles at which an increase in reporter fluorescence above a baseline signal can first be detected, for the miR-15a microRNA template were 17.2, 30.5 and 28.7 for the microRNA tagging probes pairs I, II, and III, respectively (FIG. 13). While no Ct values were detectable for the negative control experiments performed with pairs II and III (minus template and minus ligase, respectively), the Ct values from the negative controls performed with pair I were detectable after cycle no. 37 and 39, respectively, which is still acceptable when compared to the corresponding Ct value of 17.2 (FIG. 13). The normalized reporter signal (Rn) was measured over the entire PCR cycling program, which represents the fluorescence signal of the reporter dye divided by the fluorescence signal of the passive reference dye. During PCR, Rn increases as amplicon copy number increases, until the reaction approaches a plateau. The baseline corrected Rn (ΔRn) represents the Rn minus the baseline signal that was established in the first few cycles of PCR.

Example 10

Improved Real-time Quantitative PCR for the Human miR-15a MicroRNA Using MicroRNA-templated ligation and LNA 2,6-diaminopurine-enhanced Detection Probes.

Figure 14:
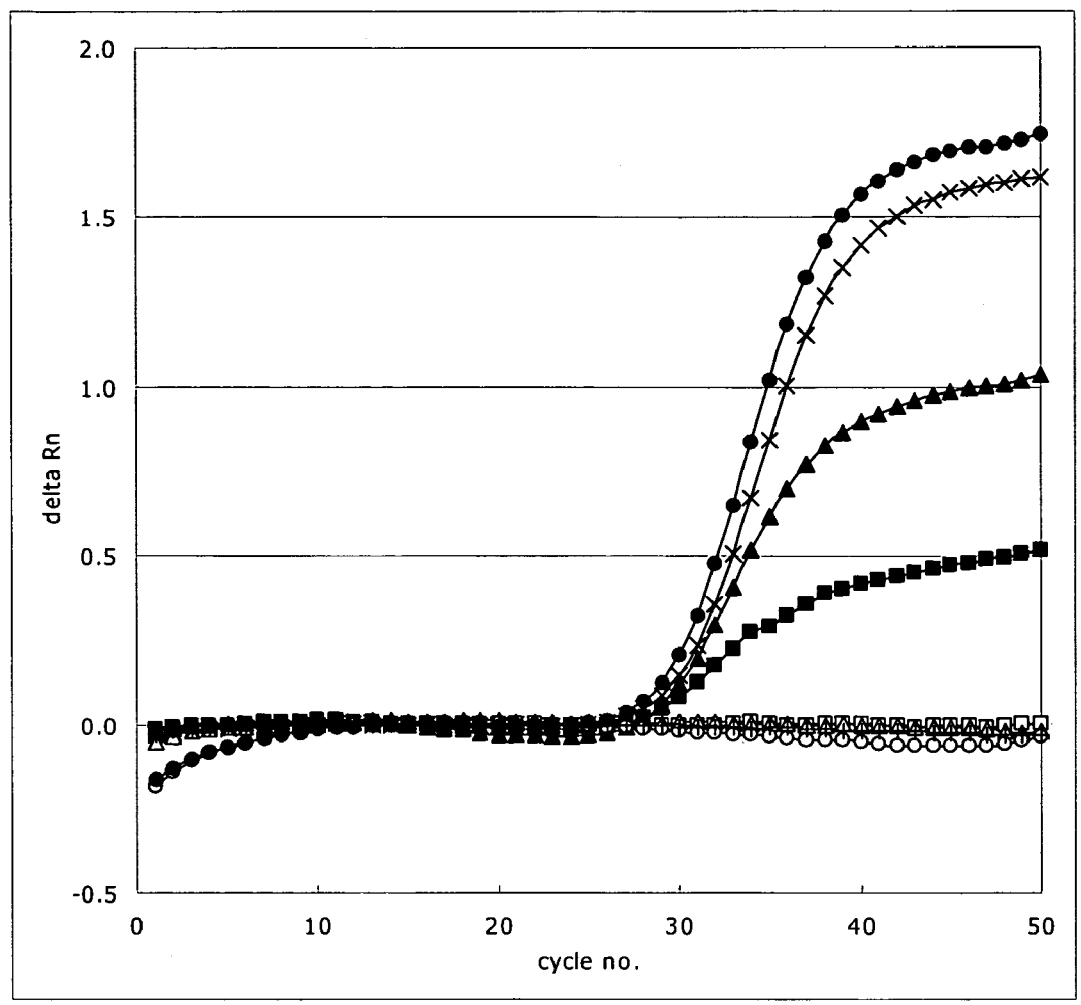
FIG. 14. Shows the real-time quantitative PCR amplification plots demonstrating improved detection for the human miR-15a microRNA by microRNA-templated ligation and LNA 2,6-diaminopurine-enhanced miR-15a detection probes. The detection probe EQ16580 solid squares, EQ16581 solid triangles, EQ16582 solid circles and EQ16583 crosses, and corresponding no template controls; EQ16580 open squares, EQ16581 open triangles, EQ16582 open circles and EQ16583 black line.

The real-time PCR reactions were repeated using the LNA-modified sequence-specific microRNA tagging probes EQ16311/EQ16452 (pair I in Example 9) in human miR-15a-templated ligation reaction as described above. The ligated templates were subsequently detected using real-time quantitative PCR as described above, by anchor PCR primers and LNA-modified dual-labelled detection probes (EQ16580, EQ16581, EQ16582 or EQ16583, Table II) for the miR-15a microRNA using a minus template as a negative control. The specificity of the ligation reaction was tested using a reaction without addition of T4 DNA ligase. The Ct values using the human miR-15a microRNA template spiked into a complex background of *Torulla* yeast RNA were highly comparable, i.e. 30.4, 30.0, 29.9 and 30.6 for LNA-modified dual-labelled detection probes EQ16580, EQ16581, EQ16582 and EQ16583, respectively (FIG. 14, Table II). In contrast, no Ct values were detectable for the negative control experiments (minus template and minus ligase, FIG. 14). By substituting one to two of the LNA A nucleotides with the LNA 2,6-diaminopurine monomers significantly enhanced the baseline corrected fluorescence signal, ΔRn, detected in the microRNA assay, whereas substitution with a third LNA 2,6-diaminopurine monomer (EQ 16583, Table II) did not enhance the fluorescence signal further, showing comparable results with the double LNA 2,6-diaminopurine-substituted miR-15a detection probe (EQ 16582, Table II, FIG. 14).

Example 11

Real-time Quantitative PCR Standard Curve Generated for the Human miR-15a MicroRNA Using the MicroRNA-templated Ligation Reaction as Template.

Figure 15:
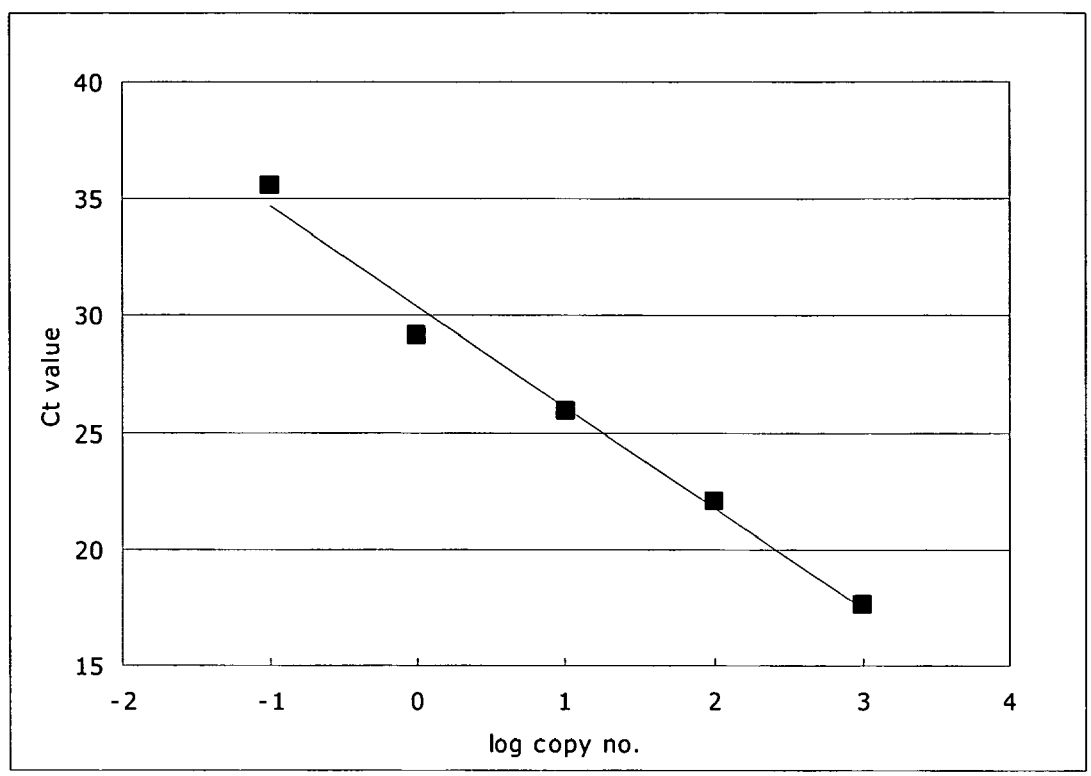
FIG. 15. Standard curve for the human miR-15a real-time quantitative PCR assay. The LNA-modified human miR-15a microRNA tagging probes EQ16311/EQ16452 (pair I) was used in miR-15a-templated ligation reactions, where the human miR-15a template concentration was 50, 5, 0.5, 0.05, or 0.005 nM, respectively. The ligated templates were subsequently detected using real-time PCR by the anchor PCR primers and the LNA-modified dual-labelled detection probe EQ15866 for the miR-15a microRNA using a minus template as a negative control. Plotting of the cycle threshold values versus log of template copy number was used to generate the standard curve.

The LNA-modified human miR-15a microRNA tagging probe pair EQ16311/EQ16452 (pair I in Example 9) was used in miR-15a-templated ligation reactions as described above, where the human miR-15a template concentration was 50, 5, 0.5, 0.05, or 0.005 nM, respectively. The ligated templates were subsequently detected using real-time quantitative PCR as described above, by the anchor PCR primers and the LNA-modified dual-labelled detection probe (EQ15866, Table I) for the miR-15a microRNA using a minus template as a negative control. The specificity of the ligation reaction was tested using a reaction without ligase. The Ct value using the miR-15a microRNA template were 17.6, 22.0, 25.9, 29.6, and 35.6 for the 50, 5, 0.5, 0.05, and 0.005 nM concentrations of the miR-15a microRNA, respectively, whereas no Ct values were detectable for the negative control experiments (minus template and minus ligase). The Ct value is inversely proportional to the logarithm of the initial template copy number. Therefore, a standard curve is generated by plotting the Ct values against the logarithm of the copy number as depicted in FIG. 15. By linear regression analysis the slope and the intercept were determined. The slope of the titration curve was −4.31 and the intercept 30.9.

Example 12

Real-time Quantitative PCR for the Human miR-15a MicroRNA Using MicroRNA-templated RT-PCR Reactions with LNA-modified Tagging Probes and an LNA-modified Dual-labelled Detection Probe 1. MicroRNA Reverse Transcription and Second Strand Reaction with LNA-modified Tagging Probes.

The reverse transcription and PCR (RT-PCR) reaction was performed in 50 μL consisting of 2 nM miR-15a RNA template (EQ15885, Table I), 600 nM of each microRNA tagging probe, 1×OneStep RT-PCR buffer [contains Tris-HCl, KCl, $(NH_4)_2SO_4$, 1.5 mM $MgCl_2$, DTT, pH 8.7 (20° C.)] (Qiagen, Germany), 400 μM of each dNTP (Qiagen, Germany), 20 U SUPERase-In (Ambion, USA), 0.05 μg/μL *Torulla* yeast RNA, and 2 μL Qiagen OneStep RT-PCR Enzyme mix (Qiagen, Germany). The thermocycler DYAD™ (MJ Research DNA engine, USA) was pre-heated to the start temperature. Temperature profile was 30 min 50° C., 15 min 95° C., 1 min 50° C., 3 min 72° C., and cooled down to 4° C., finally. The RT-PCR reaction was repeated without template as negative control.

2. MicroRNA Real-time Quantitative PCR Assays Using LNA-Modified Detection Probes The PCR reaction (50 μL) in 1×PCR buffer [contains Tris-HCl, KCl, $(NH_4)_2SO_4$, pH 8.7 (20° C.)] (Qiagen, Germany), $MgCl_2$ to a final concentration of 4 mM, 200 nM of each of dATP, dCTP, dGTP and 600 nM dUTP (Applied Biosystems, USA)"); 200 nM hsa-miR-15a forward primer 2 (EQ16444, Table II), 200 nM hsa-miR-15a reverse primer 2 (EQ16445, Table II), 250 nM LNA sequence-specific detection probe (EQ15866, Table I), 0.1×ROX reference dye (Invitrogen, USA), 5 μL of the RT-PCR reaction as template (described above) and 2.5 U HotStarTaq DNA polymerase (Qiagen, Germany). Cycling procedure: 10 min 95° C., 50 cycles of 20 sec 95° C., 1 min 60° C. in an Applied Biosystems 7500 Real Time PCR System (Applied Biosystems, USA).

Figure 16:
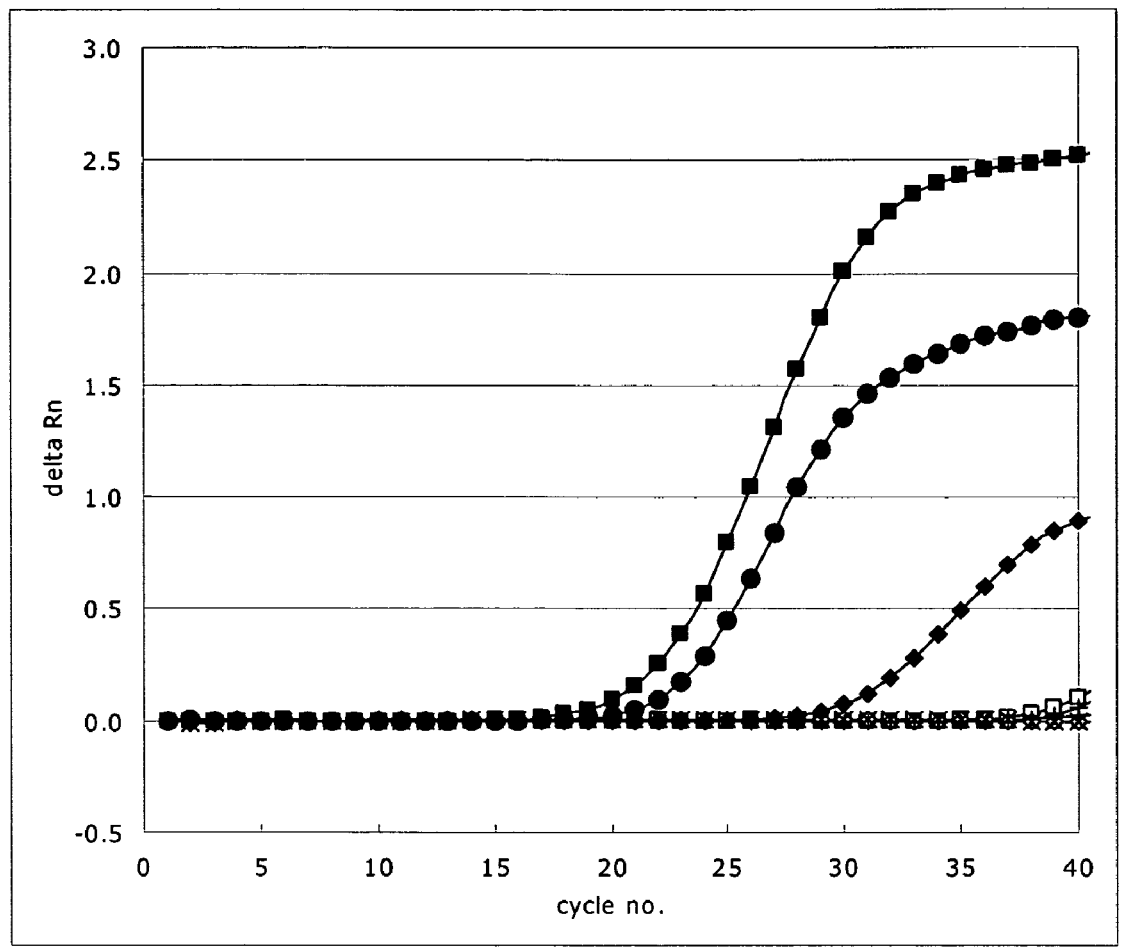
FIG. 16. Shows the real-time quantitative PCR amplification plots demonstrating detection for the human mir-15a microRNA using miR-15a microRNA-templated RT-PCR reaction and different LNA-modified anchored tagging probes and an LNA-modified dual-labelled detection probe. Three different pairs of microRNA RT-PCR tagging probes were chosen pair IV: EQ16591/EQ16311, miR-15 template (solid squares), no template (black mark); pair V: EQ16591/EQ16314 miR-15 template (solid diamonds), no template (open triangle); and pair VI: EQ16589/EQ16314 miR-15 template (solid circles), no template (black line). Open circles depict the no RT-PCR enzyme mix control.

The LNA-modified microRNA tagging probes for human miR-15a were annealed and extended as a reverse transcription primer (RT tagging probe) and $2^{nd}$ strand tagging probe. Three different pairs of microRNA tagging probes were chosen (Table II): Pair IV. EQ16591/EQ16311, V. EQ16591/EQ16314, and VI. EQ16589/EQ16314. The miR-15a RT-PCR reactions were performed as described above. The templates were subsequently detected using real-time PCR as described above, using anchor PCR primers and an LNA-modified dual-labelled detection probe (EQ15866, Table I) for the miR-15a microRNA with a minus template as a negative control. The specificity of the microRNA RT-PCR assay was assessed using a reaction without addition of OneStep RT-PCR Enzyme mix. The Ct value, which represents the PCR cycle at which an increase in reporter fluorescence above a baseline signal can first be detected, for the microRNA probes, using the miR-15a microRNA template were 19.2, 28.2 and 22.0 for pair IV, V, and VI, respectively (FIG. 16). Whereas no Ct values were detectable for the negative control experiments performed with pairs V and VI (minus template and minus ligase, respectively), the corresponding Ct values from the negative controls with the pair V were 39.0 and 39.9 for the no template and no RT-PCR enzyme mix, respectively, which is still acceptable values. The Rn signal was measured over the entire real-time PCR program, which represents the fluorescence signal of the reporter dye divided by the fluorescence signal of the passive reference dye. During PCR, Rn increased as amplicon copy number increased, until the reaction approaches a plateau. The ΔRn represents the Rn minus the baseline signal that was established in the first few cycles of PCR.

Example 13

Improved Real-time Quantitative PCR for the Human miR-15a MicroRNA Using MicroRNA-templated RT-PCR Reactions with LNA-modified Tagging Probes and LNA 2,6-diaminopurine-enhanced Detection Probes.

1. MicroRNA Reverse Transcription and Second Strand Reaction with LNA-modified Tagging Probes.

The RT-PCR reaction was performed in 25 μL consisting of 2 nM miR-15a RNA template (EQ15885, Table I), 60 nM of each microRNA tagging probe, 1×OneStep RT-PCR buffer [contains Tris-HCl, KCl, $(NH_4)_2SO_4$, 1.5 mM $MgCl_2$, DTT, pH 8.7 (20° C.)] (Qiagen, Germany), 400 μM of each of dNTP (Qiagen, Germany), 10 U SUPERase-In (Ambion, USA), 0.05 μg/μL *Torulla* yeast RNA, and 1 μL Qiagen OneStep RT-PCR Enzyme mix (Qiagen, Germany). The thermocycler DYAD™ (MJ Research DNA engine, USA) was heated to the reaction start temperature. Temperature profile was 30 min 50° C., 15 min 95° C., 1 min 50° C., 3 min 72° C., and cooled down to 4° C., finally. The RT-PCR reaction was repeated without template as negative control instead of the miR-15a RNA target.

2. MicroRNA Real-time Quantitative PCR Assays Using LNA-modified Detection Probes.

The reaction (25 μL) was 1×PCR buffer [contains Tris-HCl, KCl, $(NH_4)_2SO_4$, pH 8.7 (20° C.)] (Qiagen, Germany), $MgCl_2$ to a final concentration of 4 mM, 200 nM of each of dATP, dCTP, dGTP and 600 nM dUTP (Applied Biosystems, USA); 200 nM hsa-miR-15a forward primer 2 (EQ16444, Table II), 200 nM hsa-miR-15a reverse primer 2 (EQ16445, Table II), 250 nM LNA detection probe (EQ15866, Table I), 0.1×ROX reference dye (Invitrogen, USA), 5 μL of the RT-PCR reaction (described above) and 1.25 U HotStarTaq DNA polymerase (Qiagen, Germany). Cycling procedure: 10 min 95° C., 50 cycles of 20 sec 95° C., 1 min 60° C. in an Applied Biosystems 7500 Real Time PCR System (Applied Biosystems, USA).

Figure 17:
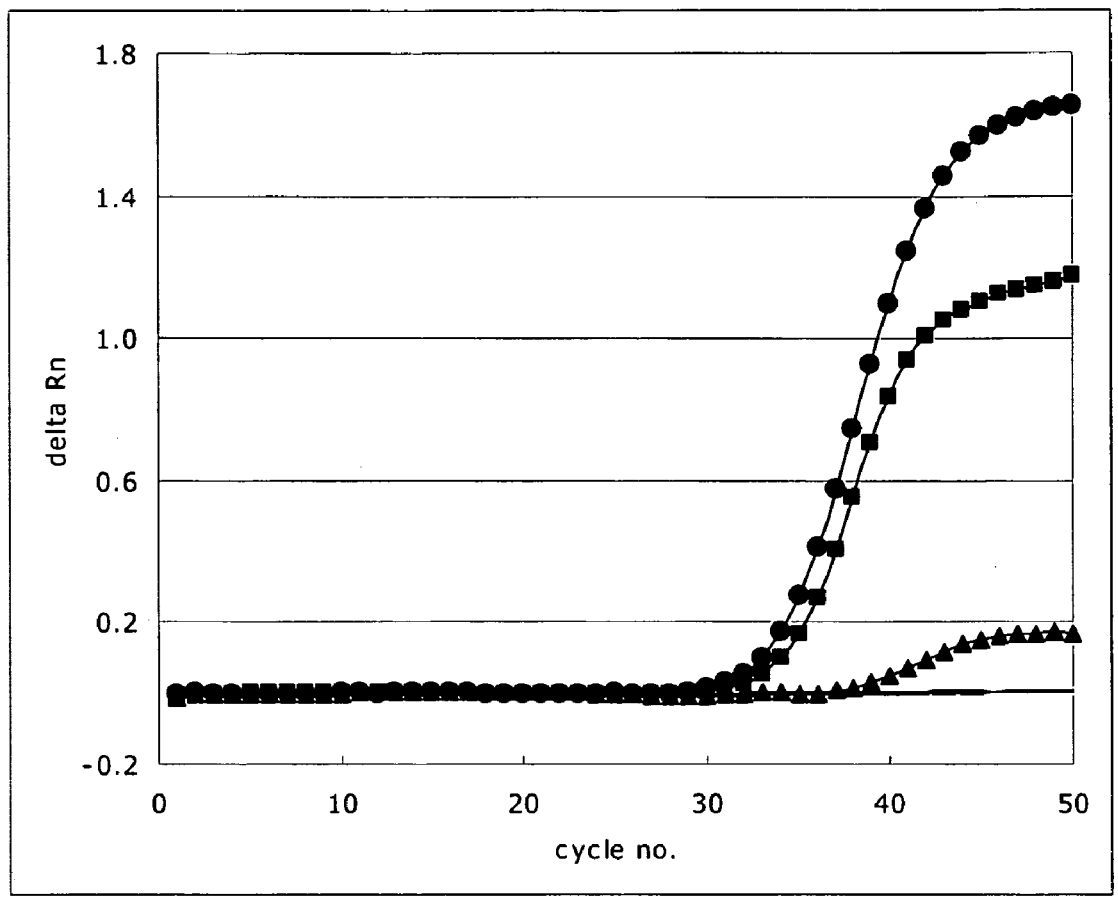
FIG. 17. Shows the real-time quantitative PCR amplification plots demonstrating improved detection of the human miR-15a by microRNA-templated RT-PCR reaction using LNA 2,6-diaminopurine-enhanced miR-15a detection probes. The different dual-labelled detection probes are shown as follows: EQ16580 (solid triangles), EQ16581 (solid squares), EQ16582 (solid squares) detection probes and no template negative control (solid line)

The LNA-modified microRNA tagging probes EQ16591/EQ16314 (pair V in Example 12) for human miR-15a microRNA were annealed and extended as a reverse transcription primer (RT tagging probe) and $2^{nd}$ strand tagging probe as described above. The miR-15 RT-PCR reactions were subsequently detected using real-time PCR as described above, the anchor PCR primers and LNA-modified dual-labelled detection probes (EQ16580, EQ16581, and EQ16582, Table II) for the miR-15a microRNA using a minus template as a negative control. The Ct values using the miR-15a microRNA template were 33.0, 33.2, and 33.7 for LNA-modified dual-labelled detection probes EQ16580, EQ16581, and EQ16582, respectively (FIG. 17), whereas no Ct values were detectable for the negative control experiments (minus template and minus OneStep RT-PCR Enzyme mix). By substituting one to two of the LNA A nucleotides with the LNA 2,6-diaminopurine monomers significantly enhanced the baseline corrected fluorescence signal, ΔRn, detected in the microRNA assay (FIG. 17).

Example 14

Real-time Quantitative PCR Standard Curve Generated for the Human miR-15a MicroRNA Using MicroRNA-templated RT-PCR Reactions as Template.

Figure 18:
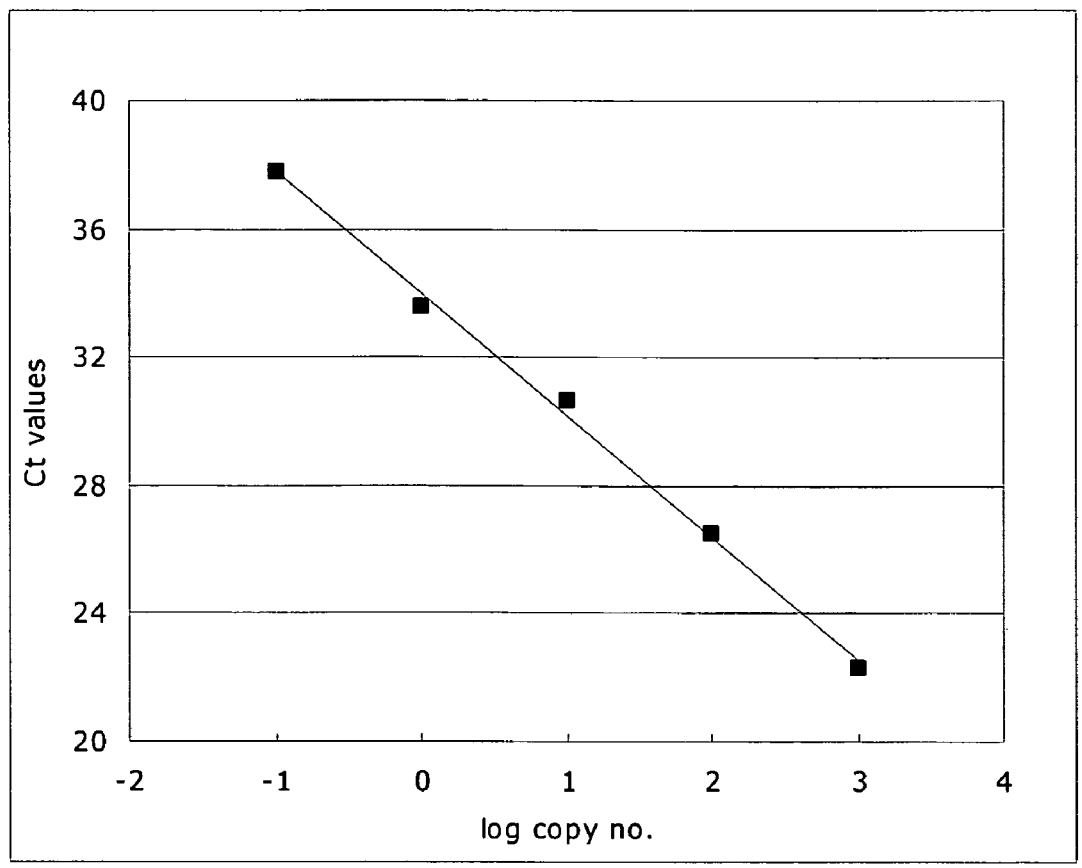
FIG. 18. Standard curve for the human miR-15a real-time quantitative PCR assay. The LNA-modified microRNA tagging probes EQ16624/EQ16620 (pair VII) for human miR-15a were used as a reverse transcription primer (RT tagging probe) and $2^{nd}$ strand tagging probe. The RT-PCR reactions were performed with varying miR-15a template concentration of 50, 5, 0.5, 0.05, or 0.005 nM, respectively. The miR-15a was subsequently detected using real-time PCR by using the anchor PCR primers and an LNA-modified dual-labelled detection probe (EQ16582) for the miR-15a microRNA. Plotting of the cycle threshold values versus log of template copy number was used to generate the standard curve.

The LNA-modified microRNA tagging probes EQ16624/EQ16620 (pair VII) for human miR-15a microRNA were annealed and extended as a reverse transcription primer (RT tagging probe) and $2^{nd}$ strand tagging probe. The RT-PCR reactions were performed as described above, where the human miR-15a microRNA template concentration was 50, 5, 0.5, 0.05, or 0.005 nM, respectively. The miR-15a RT-PCR reactions were subsequently detected using real-time quantitative PCR as described above, by using the anchor PCR primers and an LNA-modified dual-labelled detection probes (EQ16582) for the miR-15a microRNA using a minus template as a negative control. The specificity of the microRNA RT-PCR reaction was assessed using a reaction without addition of the OneStep RT-PCR Enzyme mix. The Ct values using the miR-15a microRNA template were 22.2, 26.5, 30.6, 33.6, and 37.8 for the 50, 5, 0.5, 0.05, and 0.005 nM concentrations of the miR-15a microRNA, respectively, whereas no Ct values were detectable for the negative control experiments (minus template and minus OneStep RT-PCR Enzyme mix). The Ct value is inversely proportional to the logarithm of the initial template copy number. Therefore, a standard curve is generated by plotting the Ct values against the logarithm of the copy number as depicted in FIG. 18. By linear regression analysis the slope and the intercept is determined. The slope of the titration curve was −3.81 and the intercept 34.0.

Example 15

Real-time Quantitative PCR for the Human miR-15a MicroRNA Using MicroRNA-templated RT-PCR Reactions as Template and Elevated Annealing Temperatures.

Figure 19:
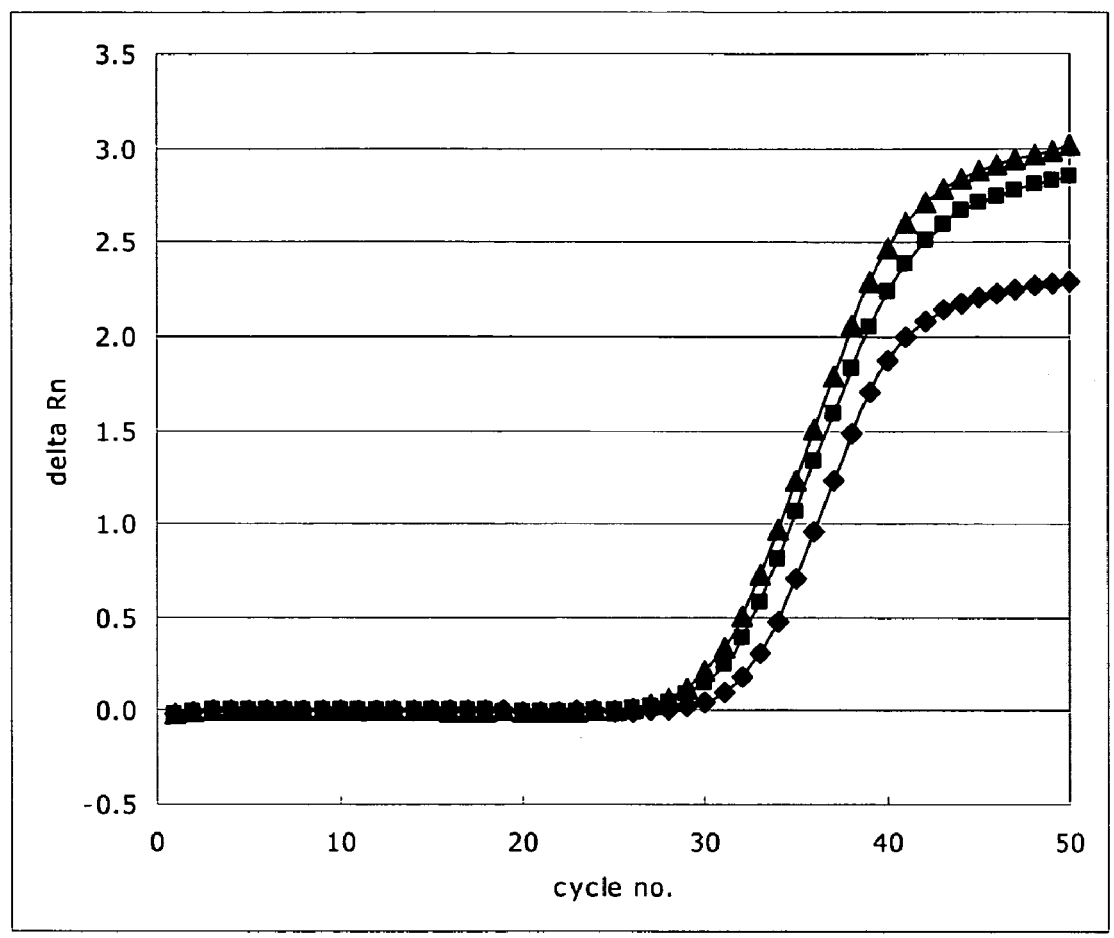
FIG. 19 Shows the real-time quantitative PCR amplification plots demonstrating detection of the human miR-15a by microRNA-templated RT-PCR reaction using varied annealing temperatures 60° C. (solid triangles), 55° C. (solid squares) and 50° C. (solid diamonds). No signals were detected for the no RT-PCR enzyme mix control and the no template negative control.

The LNA-modified microRNA tagging probes EQ16624/EQ16620 (pair VII) for human miR-15a microRNA were annealed and extended as a reverse transcription primer (RT tagging probe) and $2^{nd}$ strand tagging probe. The annealing temperature profile was changed from 50° C. to either 55° C. or 60° C. for both the reverse transcription primer and $2^{nd}$ strand tagging probe. The RT-PCR reactions were performed as described above. The miR-15a RT-PCR reactions were subsequently detected using real-time quantitative PCR as described above, by using the anchor PCR primers and an LNA-modified dual-labelled detection probes (EQ16582) for the miR-15a microRNA using a minus template as a negative control. The specificity of the microRNA RT-PCR reaction was assessed using a reaction without addition of the OneStep RT-PCR Enzyme mix; The Ct values using the miR-15a microRNA template were 28.6, 29.3, and 31.0 for the 50, 55 and 60° C. annealing temperature, respectively (FIG. 19), whereas no Ct values were detectable for the negative control experiments (minus template and minus OneStep RT-PCR Enzyme mix).

Example 16

Improved Real-time Quantitative PCR for the Human miR-15a MicroRNA Using MicroRNA-templated RT-PCR Reactions with LNA-modified Tagging Probes and LNA 2,6-diaminopurine/LNA 2-thiothymidine-enhanced Detection Probes.

1. MicroRNA Reverse Transcription and Second Strand Reaction with LNA-modified Tagging Probes.

The RT-PCR reaction was performed in 50 µL consisting of 2 nM miR-15a RNA template (EQ15885, Table I), 60 nM of each microRNA tagging probe, 1×OneStep RT-PCR buffer [contains Tris-HCl, KCl, $(NH_4)_2SO_4$, 1.5 mM $MgCl_2$, DTT, pH 8.7 (20° C.)] (Qiagen, Germany), 400 µM of each dNTP (Qiagen, Germany), 20 U SUPERase-In (Ambion, USA), 0.05 µg/µL *Torulla* yeast RNA (Ambion, USA), and 2 µL Qiagen OneStep RT-PCR Enzyme mix (Qiagen, Germany). The thermocycler DYAD™ (MJ Research DNA engine, USA) was heated to the reaction start temperature. Temperature profile was 30 min 50° C., 15 min 95° C., 1 min 50° C., 3 min 72° C., and cooled down to 4° C., finally. The RT-PCR reaction was repeated without template as negative control instead of the miR-15a RNA target.

2. MicroRNA Real-time Quantitative PCR Assays Using LNA-Modified Detection Probes.

The reaction (25 µL) was 1×PCR buffer [contains Tris-HCl, KCl, $(NH_4)_2SO_4$, pH 8.7 (20° C.)] (Qiagen, Germany), $MgCl_2$ to a final concentration of 4 mM, 200 nM of each of dATP, dCTP, dGTP and 600 nM dUTP (Applied Biosystems)"); 200 nM hsa-miR-15a forward primer 2 (EQ16444, Table II), 200 nM hsa-miR-15a reverse primer 2 (EQ16445, Table II), 250 nM LNA detection probe (EQ15866, Table I), 0.1×ROX reference dye (Invitrogen, USA), 5 µL of the RT-PCR reaction (described above) and 1.25 U HotStarTaq DNA polymerase (Qiagen, Germany). Cycling procedure: 10 min 95° C., 50 cycles of 20 sec 95° C., 1 min 60° C. in an Applied Biosystems 7500 Real Time PCR System (Applied Biosystems, USA).

Figure 20:
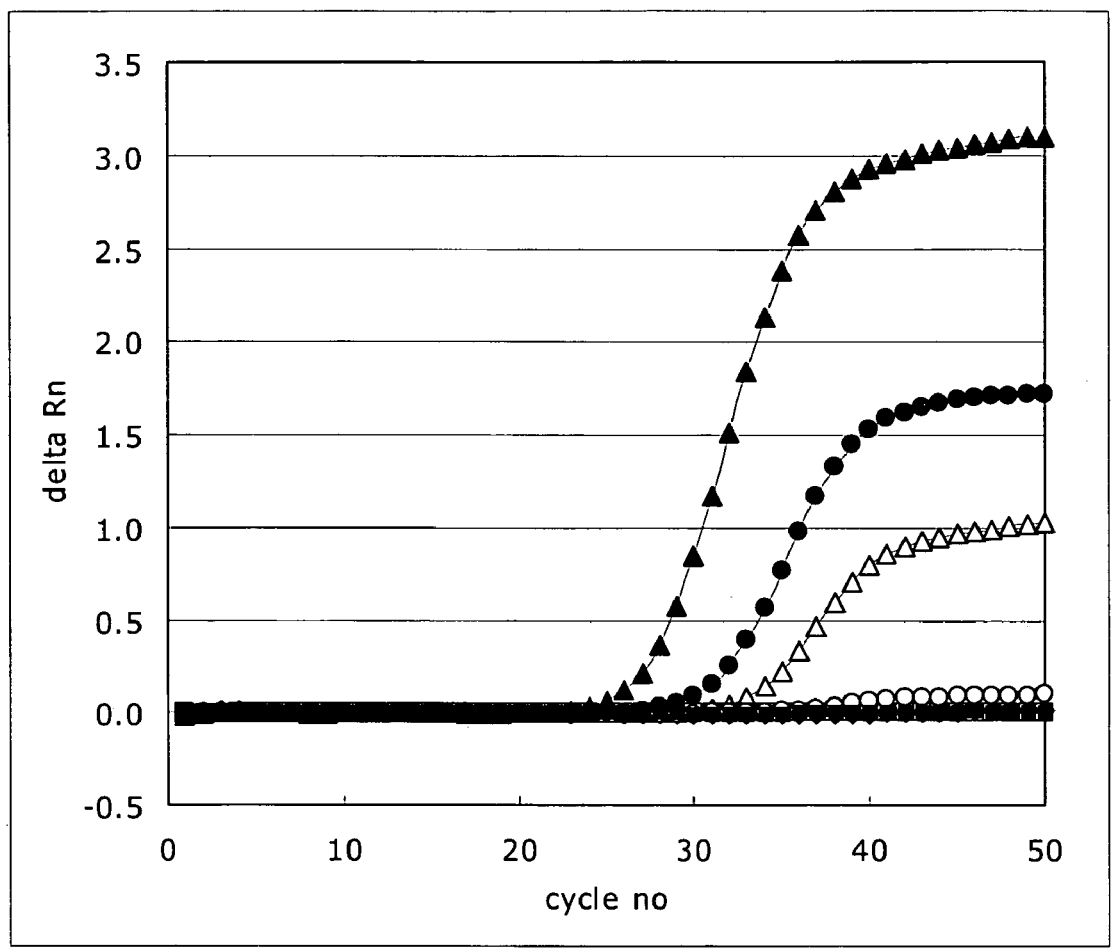
FIG. 20. Shows the real-time quantitative PCR amplification plots demonstrating detection for the human mir-15a microRNA using miR-15a microRNA-templated RT-PCR reaction and different LNA-modified dual-labelled detection probes. The different dual-labelled detection probes are shown as follows: miR-15a-templated real-time PCR and detection probe EQ16582 (solid triangles), scrambled miR-16-templated real-time PCR and detection probe EQ16582 (open triangles), miR-15a-templated real-time PCR and detection probe EQ16679 (solid circles), scrambled miR-16-templated real-time PCR and detection probe EQ16679 (open circles), and no signals were detected for the no RT-PCR enzyme mix controls and the no template negative controls.

The microRNA tagging probes EQ16623/EQ16618 (pair VIII) for human miR-15a microRNA were annealed and extended as a reverse transcription primer (RT tagging probe) and $2^{nd}$ strand tagging probe as described above. The miR-15 RT-PCR reactions were subsequently detected using real-time PCR as described above, the anchor PCR primers and LNA-modified dual-labelled detection probes (EQ16852 and EQ16679, Table II) for the miR-15a microRNA using a scramble control miR-16 microRNA (EQ15886, Table I) and a minus template as a negative controls. The Ct values using the miR-15a microRNA template were 25.6 and 30.1 for LNA-modified dual-labelled detection probes EQ16582 and EQ16679, respectively (FIG. 19), The Ct values for the scrambled miR-16 microRNA control were 33.3 and undetectable for LNA-modified dual-labelled detection probes EQ16582 and EQ16679, respectively, whereas no Ct values were detectable for the negative control experiments (minus template and minus OneStep RT-PCR Enzyme mix). By substituting the LNA A and LNA T nucleotides with the LNA 2,6-diaminopurine and LNA 2-thiothymidine monomers significantly enhanced discrimination between the perfectly matched and the scrambled microRNA templates detected in the microRNA assay (FIG. 20).

TABLE III

The design of blocked microRNA tagging probe used in Example 17

| Oligo id (EQ No) | Oligonucleotide name | 3'-end | Sequence (5'-3')[a] |
|---|---|---|---|
| 16695 | hsa-miR-15a RT 4.3 LNA | P | gaaacagctatgacatgmCacAaamCc | aLNA (uppercase), DNA (lowercase), 5-methyl C (mC); and Phosphate (P).

Example 17

Real-time Quantitative PCR for the Human miR-15a MicroRNA Using MicroRNA-templated RT-PCR Reactions with a 3'-blocked LNA-modified Tagging Probe and a LNA Modified Detection Probe.

1. MicroRNA 1. Strand transcription reaction with a blocked LNA-modified tagging probe.

The reverse transcription (RT) reaction was performed in 20 µL consisting of 25 nM miR-15a RNA template (EQ15885, Table I), 50 nM microRNA blocked tagging probe (EQ16695), 200 nM hsa-miR-15a reverse primer 2 (EQ16445, Table 1), 1×First strand buffer (50 mM Tris-HCl, 75 mM KCl, 3 mM MgCl$_2$, pH 8.3 20° C.) (Invitrogen, USA), 5 mM DTT (Invitrogen, USA), 500 µM of each of dNTP (Applied Biosystems, USA), 10 U SUPERase-In (Ambion, USA), 0.05 µg/µL *Torulla* yeast RNA, and 1 U Superscript III reverse transcriptase (Invitrogen, USA). The mir-15a template, the microRNA blocked tagging probe and the reverse primer were mix and heated 10 min at 70° C. and quenched on ice. The thermocycler DYAD™ (MJ Research DNA engine, USA) was heated to the reaction start temperature. Temperature profile was 60 min 55° C., 15 min 70° C. and cooled down to 4° C., finally. The first strand synthesis was repeated without template or Superscript III as negative control instead of the miR-15a RNA target. The first strand reaction was also repeated using miR-16 RNA (EQ15886) as target instead of the miR-15a RNA target.

2. MicroRNA Second Strand Time Release PCR Amplification with an LNA-modified Tagging Probe.

The reaction (50 µL) was 1×AmpliTaq Gold buffer (Applied Biosystems, USA) 1.5 mM MgCl$_2$, 200 nM second strand LNA tagging probe (EQ16624, Table II, 20 µL of the RT reaction (described above) and 1.25 U AmpliTaq Gold® DNA Polymerase (Applied Biosystems, USA). Cycling procedure: 10 cycles of 1 min 95° C. and 1 min 55° C. in a DYAD™ thermocycler (MJ Research DNA engine, USA)

3. MicroRNA Real-time Quantitative PCR Assays Using an LNA-modified Detection Probe.

The reaction (25 µL) was 1×PCR buffer [contains Tris-HCl, KCl, (NH4)2SO4, pH 8.7 (20° C.)] (Qiagen, Germany), MgCl$_2$ to a final concentration of 4 mM, 200 nM of each of dATP, dCTP, dGTP and 600.nM dUTP (Applied Biosystems, USA); 200 nM hsa-miR-15a forward primer 2 (EQ16444, Table II), The hsa-miR-15a reverse primer 2 (EQ16445, Table II) to a final concentration of 200 nM, 250 nM LNA detection probe (EQ15866, Table I), 0.1×ROX reference dye (Invitrogen, USA), 5 µL of the $1^{st}$ and $2^{nd}$ strand reaction (described above) and 1.25 U HotStarTaq DNA polymerase (Qiagen, Germany). Cycling procedure: 10 min 95° C.,45 cycles of 20 sec 95° C., 1 min 60° C. in an Applied Biosystems 7500 Real Time PCR System (Applied Biosystems, USA).

Figure 21:
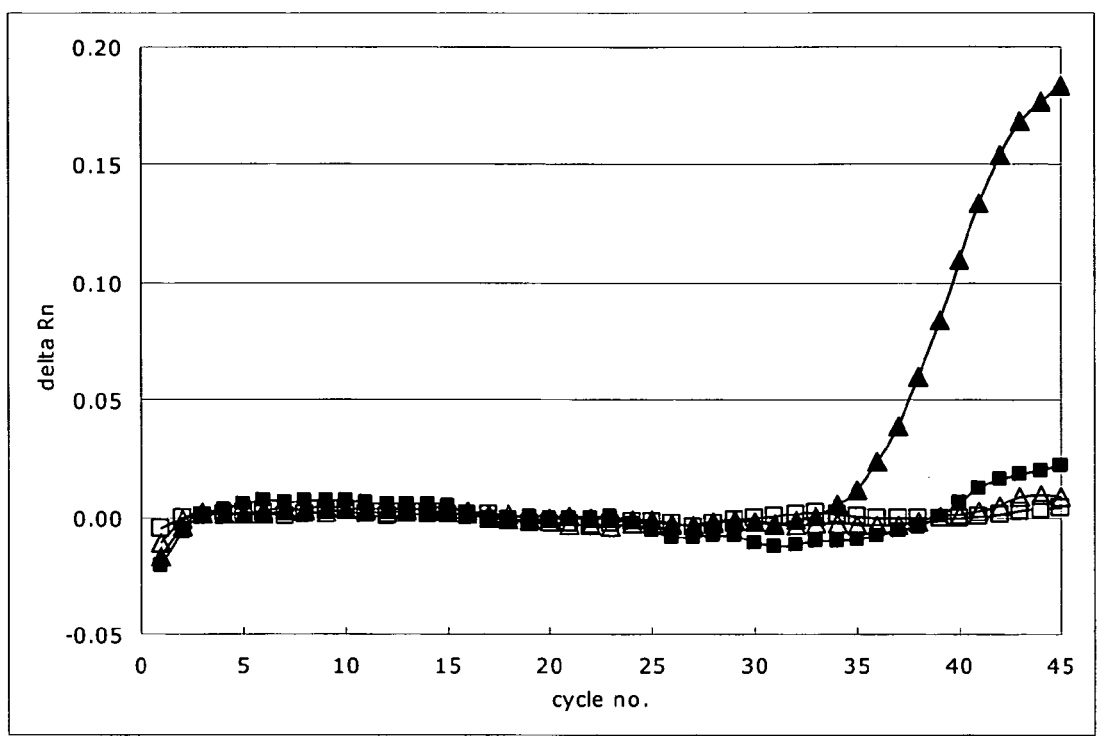
FIG. 21. Shows the real-time quantitative PCR amplification plots demonstrating detection for the human mir-15a microRNA using miR-15a microRNA-templated RT and PCR reaction and LNA-modified anchored tagging probes and an LNA-modified dual-labelled detection probe. The samples are shown as follows: miR-15a-templated real-time PCR (solid triangles), scrambled miR-16-templated real-time PCR (solid squares), the no Superscript III negative control (open squares), and the no template negative control (open triangles).

The LNA-modified microRNA tagging probe EQ16695 (RT tagging probe) for human miR-15a microRNA and the hsa-miR-15a reverse primer were annealed and extended as a reverse transcription primers. The first strand reaction was followed by the $2^{nd}$ strand tagging probe was annealed and extended as described above. The miR-15 RT and PCR reactions were subsequently detected using real-time PCR as described above, the anchor PCR primers and LNA-modified dual-labelled detection probes (EQ16582, Table II) for the miR-15a microRNA using a minus template as a negative control. The Ct values using the miR-15a microRNA template were 37.1 for LNA-modified dual-labelled detection probes EQ16582, (FIG. 21), whereas no Ct values were detectable for the miR-16 microRNA template and the negative control experiments (minus template and minus Superscript III)

Example 18

Real-time Quantitative PCR for the Mature Human miR-15a MicroRNA Using miRNA-templated RT-PCR with a 3'-blocked LNA-modified Tagging Probe and an LNA Modified Detection Probe.

1. MicroRNA Primer Extension with a Blocked LNA-modified miRNA Tagging Probe Using an Enzyme Capable of RNA-primed DNA-directed DNA-synthesis.

The miRNA primer extension reaction was performed in 20 µL. First 500 nmol miR-15a RNA template (EQ15885, Table I), 1 µg *Torulla* yeast RNA (Ambion, USA) and 25 nM microRNA blocked tagging probe (EQ16695, Table II) were mixed, heated 10 min at 70° C. and quenched on ice. 1×Eco-Pol buffer (NEB, USA), 500 µM of each dNTP (Applied Biosystems, USA), 10 U SUPERase-In (Ambion, USA) 5 U Klenow Fragment (3'→5' exo-) enzyme (NEB, USA) and DEPC-treated H$_2$O to total volume of 20 µL were added. The thermocycler DYAD™ (MJ Research DNA engine, USA) was heated to 37° C. and cycled using the following profile; 30 min 37° C., 20 min 75° C. followed by cooling down to 4° C.

2. Amplification of Mature miRNA by RT-PCR Using an LNA-Modified Tagging Probe and an Enzyme Capable of DNA-primed RNA/DNA-directed DNA Synthesis.

The primer extension reaction from step nr 1 was diluted to 50 µL reaction mixture containing the following; 60 nM second strand LNA tagging probe (EQ16624, Table II), 200 nM hsa-miR-15a reverse primer 2 (EQ16445, Table I), 400 µM of each of dNTP, 1×Qiagen OneStep RT-PCR buffer (Qiagen, USA), 2 µL Qiagen OneStep RT-PCR Enzyme mix (contains Omniscript™ Reverse Transcriptase, SensiScript™ Reverse Transcriptase and HotStarTaq® DNA polymerase; the dNTPs, buffer and enzymes were purchased from Qiagen, USA) and DEPC-treated H$_2$O up to a final volume of 50 µL. The thermocycler DYAD™ (MJ Research DNA engine, USA) was heated to 50° C. And cycled using the following temperature profile; 30 min 50° C., 15 min 95° C. and 10 cycles of 1 min 95° C., 1 min 55° C., 2 min 72° C., followed by cooling down to 4° C.

The reaction was also repeated using miR-16 RNA (EQ15886, Table I) as target instead of the miR-15a RNA target. As negative controls either the microRNA blocked tagging probe, second strand LNA tagging probe, hsa-miR-15a reverse primer 2, Klenow Fragment (3'→5' exo-) enzyme or Qiagen OneStep RT-PCR Enzyme were omitted in the respective reaction mixtures.

3. miRNA Real-time Quantitative PCR Using an LNA-modified Detection Probe.

The real-time PCR reaction mixture (25 µL) contained 1×PCR buffer [contains Tris-HCl, KCl, (NH4)$_2$SO$_4$, pH 8.7 (20° C.)] (Qiagen, Germany), MgCl$_2$ to a final concentration of 4 mM, 200 nM of each of dATP, dCTP, dGTP and 600 nM dUTP (Applied Biosystems, USA); 200 nM hsa-miR-15a forward primer 2 (EQ16444, Table II), the hsa-miR-15a reverse primer 2 (EQ16445, Table II) to a final concentration of 300 nM, 250 nM LNA detection probe (EQ15866, Table I), 0.1×ROX reference dye (Invitrogen, USA), 5 µL of the $1^{st}$ and $2^{nd}$ strand reaction (described above) and 1.25 U Hot-StarTaq DNA polymerase (Qiagen, Germany). Cycling procedure: 10 min 95° C., 40 cycles of 20 sec 95° C., 1 min 60° C. in an Applied Biosystems 7500 Real-Time PCR System (Applied Biosystems, USA).

Figure 23:
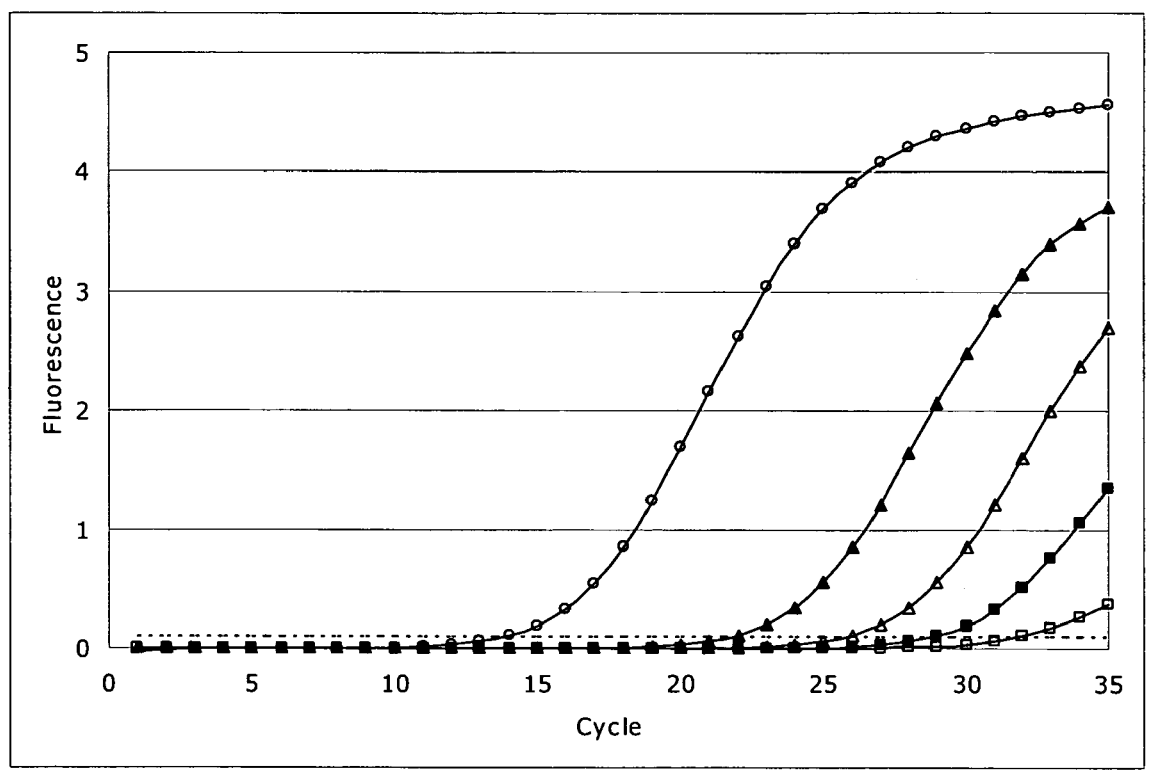
FIG. 23. Shows the real-time quantitative PCR amplification plots demonstrating improved detection of the human miR-15a by microRNA-templated RT-PCR reaction using LNA 2,6-diaminopurine-enhanced miR-15a detection probes. The graphs depict the miR-15a microRNA target (open circles) in comparison with the miR-16 target (solid triangles) that has 72% sequence identity with the miR-15a target sequence. The negative controls were no microRNA blocked tagging probe (open triangles), no second strand LNA tagging probe (solid squares), and no Klenow Fragment (3'→5' exo-) enzyme (open squares), whereas no Ct values were detectable for the no hsa-miR-15a reverse primer 2 control (line) or no Qiagen OneStep RT-PCR Enzyme mix control (line) in the real-time PCR reaction.

The LNA-modified microRNA tagging probe EQ16695 (1st strand tagging probe) for human miR-15a which is blocked at its 3' end was used to tag the mature miR-15a and extended by using the miR-15 as primer employing a RNA-primed DNA-directed DNA polymerase. The reverse transcription reaction was performed by annealing an RT-primer and extended by a RNA/DNA-directed DNA polymerase reaction. Finally the 2nd strand tagging probe was annealed and extended by a DNA-directed DNA polymerase reaction. The tagged human miRNA template generated by miR-15a primer extension reaction, reverse transcription and PCR respectively, was subsequently detected using real-time PCR as described above, the anchor PCR primers and LNA-modified dual-labelled detection probe (EQ16582, Table II) for the miR-15a microRNA using a no template as a negative control. The Ct value using the miR-15a microRNA template was 14.9 for LNA-modified dual-labelled detection probes EQ16582, (FIG. 23), whereas the Ct values for the miR-16 microRNA template was 23.4 while the Ct values for the negative control experiments were 32.3, 27.7, and 29.9 for the no microRNA blocked tagging probe, no second strand LNA tagging probe, and no Klenow Fragment (3'→5' exo-) enzyme reactions, respectively. No detectable Ct values were obtained for the negative control experiments (no hsa-miR-15a reverse primer 2 or no Qiagen OneStep RT-PCR Enzyme mix.)

Example 19

Real-time Quantitative PCR Standard Curve Generated for the Mature Human miR-15a MicroRNA Using miRNA-templated RT-PCR with a 3'-Blocked LNA-modified Tagging Probe.

Figure 24:
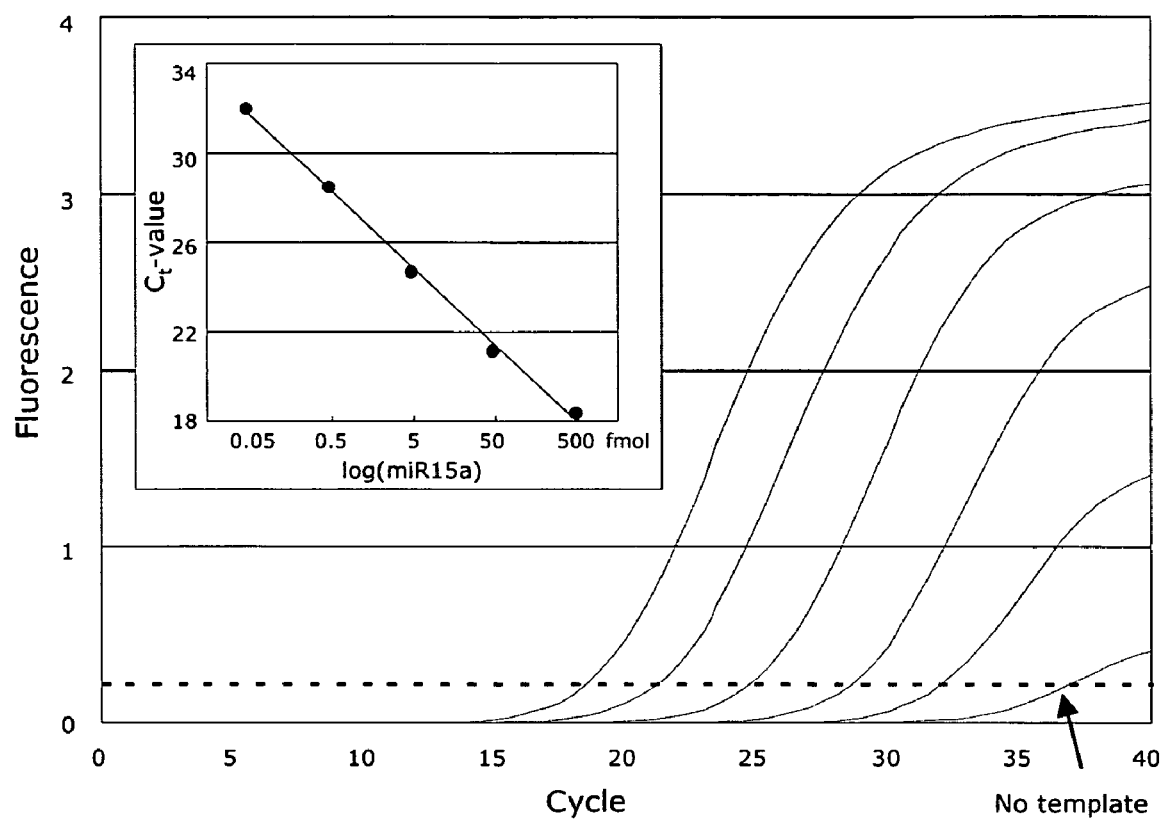
FIG. 24. The amplification plots and the standard curve (small graph) for the human miR-15a real-time quantitative PCR assay. The LNA-modified human miR-15a microRNA tagging probes EQ1695 and EQ16624 (pair IX) were used in miR-15a-templated RT-PCR reactions with a 3'-blocked LNA-modified tagging probe as capture, where the mature human miR-15a template was 500, 50, 5, 0.5, or 0.05 fmol, respectively, in the individual reactions The templates were subsequently detected using real-time PCR by the anchor PCR primers and the LNA-modified dual-labelled detection probe EQ15866 for the miR-15a microRNA using a minus template as a negative control. Plotting of the cycle threshold values versus log of template copy number was used to generate the standard curve.

The LNA-modified human miR-15a microRNA tagging probe pair EQ1695/EQ16624 (pair IX in Example 18) was used in miR-15a-templated RT-PCR with a 3'-blocked LNA-modified tagging probe as described above (Example 18), where the human miR-15a template concentration was 500, 50, 5, 0.5, or 0.05 fmol respectively. The miRNA-15a template was subsequently detected using real-time quantitative PCR as described above, by the anchor PCR primers and the LNA-modified dual-labelled detection probe (EQ15866, Table I) for the miR-15a microRNA using a minus template as a negative control. The Ct values were 18.4, 21.1, 24.7, 28.5, and 32.0, respectively, for 500, 50, 5, 0.5, and 0.05 fmol of the miR-15a microRNA template, respectively, whereas the Ct value was 36.8 for the negative control experiment without template. The Ct value is inversely proportional to the logarithm of the initial template copy number. Therefore, a standard curve was generated by plotting the Ct values against the logarithm of the copy number as depicted in FIG. 24. By linear regression analysis the slope and the intercept were determined. The slope of the titration curve was −3.45 and the intercept 27.4.

TABLE IV

The design of the microRNA 3'-blocked tagging probes.

| EQ No. | Name | 5'-end Sequences | 3'-end |
|---|---|---|---|
| 16858 | P-hsa-miR-15a rt 5.1 LNA | gaaacagctatgacatgmCacAaamC | P |
| 16859 | P-hsa-miR-15a rt 5.2 LNA | gaaacagctatgacatgmCacAaAmC | P |
| 16860 | P-hsa-miR-15a rt 5.3 LNA | gaaacagctatgacatgmCacAAamC | P |
| 16861 | P-hsa-miR-15a rt 5.4 LNA | gaaacagctatgacatgmCacAAAmC | P |
| 16862 | hsa-miR-15a rt 5.5 LNA | gaaacagctatgacatgmCacAaamCc | |
| 16863 | hsa-miR-15a rt 5.6 LNA | gaaacagctatgacatgmCacAaamC | |
| 16864 | hsa-miR-15a rt 5.7 LNA | gaaacagctatgacatgmCacAaAmC | |
| 16865 | hsa-miR-15a rt 5.8 LNA | gaaacagctatgacatgmCacAAamC | |
| 16866 | hsa-miR-15a rt 5.9 LNA | gaaacagctatgacatgmCacAAAmC | |
| 16867 | hsa-miR-15a rt 5.10 LNA | gaaacagctatgacatgmCACAAAmC | |
| 16868 | hsa-miR-15a rt 5.11 LNA | gaaacagctatgacatgmCAmCAAA | |
| 16869 | hsa-miR-15a rt 5.12 LNA | gaaacagctatgacatgmCAmCAA | |
| 16882 | hsa-miR-15a rt 6.1 LNA | gaaacagctatgacatgmCAmCAAAmCmCATT | |
| 16883 | hsa-miR-15a rt 6.2 LNA | gaaacagctatgacatgmCAmCAAAmCmCAT | |

TABLE IV-continued

The design of the microRNA 3'-blocked tagging probes.

| EQ No. | Name | 5'-end | Sequences | 3'-end |
|---|---|---|---|---|
| 16884 | hsa-miR-15a rt 6.3 LNA | | gaaacagctatgacatgmCAmCAAAmCmCA | |
| 16885 | hsa-miR-15a rt 6.4 LNA | | gaaacagctatgacatgmCAmCAAAmCmC | |

[a] LNA (upper cases), DNA (lower cases), 5-methyl C (mC), and Phosphate (P).

TABLE V

The design of U6 snRNA detection probe and real-time PCR primers used in Example 20.

| Oligo id (EQ No) | Oligonucleotide name | 5'-end | Sequence (5'-3')[a] | 3'-end |
|---|---|---|---|---|
| 17159 | U6 snRNA RT primer | | tatggaacgcttcacgaatttgcg | |
| 17160 | U6 snRNA forward rimer | | cgcttcggcagcacatatac | |
| 17167 | U6 snRNA detection robe | 6-Fitc | CAGGgGcmC#Q1z | P |

[a] LNA (uppercase), DNA (lowercase), 5-methyl C (mC); Fluorescein (6-FITC (Glenn Research, Prod.Id.No. 10-1964)), #Q1 (Prepared as described in Example 8a), z (5-nitroindole (Glenn Research, Prod.Id.No. 10-1044)), Phosphate (P).

Example 20

Real-time PCR for the *Homo Sapiens* U6 snRNA.

1. U6 snRNA Reverse Transcription

The reverse transcription (RT) reaction was performed in 20 µL containing 1 µg Quantitative PCR Human Reference Total RNA template (Stratagene, USA), 5 µg pd(N)$_6$ random hexamer (Amersham Biosciences, Sweden), 1×First strand buffer (50 mM Tris-HCl, 75 mM KCl, 3 mM MgCl$_2$, pH 8.3 at 20° C.) (Invitrogen, USA), 10 mM DTT (Invitrogen, USA), 1 mM of each of dNTP (Applied Biosystems, USA), 10 U SUPERase-In (Ambion, USA), and 200 U Superscript II reverse transcriptase (Invitrogen, USA). The Reference Total RNA template and the random hexamer were mixed and heated 5 min at 70° C. and quenched on ice. The temperature profile on the thermocycler DYAD™ (MJ Research DNA engine, USA) was 30 min at 37° C., 90 min at 42° C. and then on hold at 4° C. The first strand synthesis was purified on a Microcon YM-30 Centrifugal Filter Unit (Millipore, USA) according to the manufacture's instructions. The sample recovered after centrifugation was diluted to five times the original RT starting volume (100 µL in total).

2. U6 snRNA Real-time PCR Assay Using a LNA-modified Detection Probe.

The reaction (50 µL) was 1×PCR buffer [Tris-HCl, KCl, (NH$_4$)$_2$SO$_4$, pH 8.7 at 20° C.] (Qiagen, Germany), MgCl$_2$ to a final concentration of 4 mM, 200 nM of each of dATP, dCTP, dGTP and 600 nM dUTP (Applied Biosystems, USA); 900 nM U6 snRNA forward primer (EQ17160, Table V), 900 nM U6 snRNA RT primer (EQ17159, Table V), 250 nM LNA detection probe (EQ17167, Table V), 0.1×ROX reference dye (Invitrogen, USA), 1 or 5 µL of the first strand synthesis (RT) reaction (described above) and 2.5 U HotStarTaq DNA polymerase (Qiagen, Germany). Cycling procedure: 10 min at 95° C., 40 cycles of 15 sec. at 95° C., 1 min at 60° C. in an Applied Biosystems 7500 Real Time PCR System (Applied Biosystems, USA).

Figure 25:
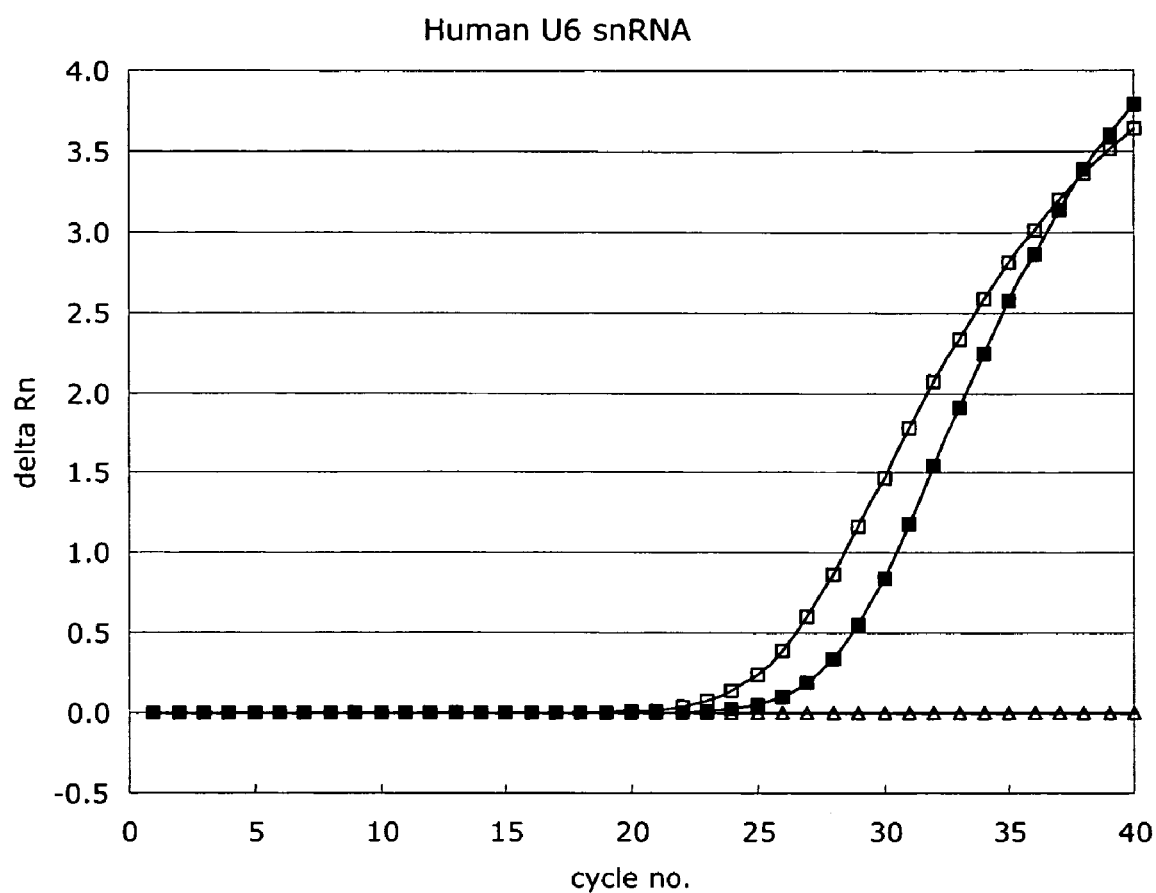
FIG. 25. Shows the real-time quantitative PCR amplification plots demonstrating detection of the human U6 snRNA-templated RT-PCR reaction using LNA detection probe 1 μL cDNA template (solid squares), 5 μL cDNA template (open squares), and no template negative control (open triangles)

The U6 snRNA (acc. no. X59362, GenBank) RT reactions were subsequently detected using real-time PCR as described above, PCR primers and LNA-modified dual-labelled detection probe for the human U6 snRNA using a minus template as a negative control. The Ct values using 1 or 5 µL U6 snRNA cDNA template were 28.0 and 25.6 for the LNA-modified dual-labelled detection probe (EQ17167, Table V), respectively (FIG. 25), whereas no Ct value was obtained for the negative control experiment (no template).

Example 21

Real-time RT-PCR for the Human miR-15a Using; MicroRNA-primed Extension Reaction on a 3'- blocked and 5'-biotin-labelled LNA-modified Capture Probe, Immobilization of Extension Product in a Streptavidin Tube, Reverse Transcriptase Reaction in Solution, and Real-time PCR Using a LNA-modified Detection Probe.

1. The MicroRNA-primed Extension Reaction on a 3'-blocked, 5'-biotin Labelled LNA-modified Capture Probe.

Hsa miR-15a RNA (1 fmol; EQ15885, Table I) was mixed with 1 µg *Torulla* yeast RNA (Ambion, USA) and 100 fmol miR-15a capture probe (EQ16879, Table VI) in a total volume of 6 µL, heated for 5 min at 65° C. and quenched on ice, 1 µL 10×NE-Buffer 2 (New England Biolabs, USA), 1 µL dNTP mix (1 mM of each dNTP; Applied Biosystems, USA), 20 U SUPERase-In (Ambion, USA) and 5 U Klenow exo- (New England Biolabs, USA) were added. Incubations were continued for 30 min at 37° C.

2. The Immobilization in a Streptavidin Tube

One volume of 2×binding buffer (200 mM Tris-HCl pH 7.5 at 20° C., 800 mM LiCl, 40 mM EDTA) was added to the Klenow exo- reaction and the supernatant was transferred to a streptavidin coated PCR tube (Roche, Germany). Incubation for 3 min at 37° C. allowed the biotin-streptavidin binding to be formed. Unbound material was removed by washing three times in five volumes of washing buffer (10 mM Tris- HCl pH 7.5 at 20° C., 20 mM LiCl,) at room temperature. "Proceed immediately with the RT reaction".

3. The RT Reaction in Solution

The RT-primer (100 fmol, EQ16994, Table VI) and 10 nmoles of each of dNTP (Applied Biosystems, USA) were mixed in 12 μL total volume and added to the streptavidin PCR tube containing the immobilized capture probe and the chimerical RNA-DNA strand. The tube was heated 5 min at 70° C. and the supernatant was removed to a new tube on ice. 5×First strand buffer a (50 mM Tris-HCl pH 8.3 at 20° C., 75 mM KCl, 3 mM $MgCl_2$; Invitrogen, USA), 10×DTT (1×=10 mM, Invitrogen, USA), 20 U SUPERase-In (Ambion, USA), and 200 U Superscript II reverse transcriptase (Invitrogen, USA) were added (in a volume of 8 μL) and the incubation was continued for 1 h at 42° C. Heating for 15 min at 70° C. terminated the reaction.

4. The Real-time PCR Using a LNA-modified Detection Probe

The reaction (50 μL) was 1×PCR buffer (Qiagen, Germany), $MgCl_2$ to a final concentration of 4 mM, 0.2 mM of each of dATP, dCTP, dGTP and 0.6 mM dUTP (Applied Biosystems, USA), 900 nM miR-15a forward primer (EQ16990, Table VI), 900 nM miR reverse primer (EQ16989, Table VI), 250 nM miR-15a LNA detection probe (EQ16992, Table VI), 0.1×ROX reference dye (Invitrogen, USA), 1 μL of the first strand synthesis (RT) reaction (described above), 0.5 U Uracil DNA Glycosylase (Invitrogen, USA) and 2.5 U HotStarTaq DNA polymerase (Qiagen, Germany). The temperature cycling program was; 10 min at 37° C., 10 min at 95° C., 1 min at 45° C., 1 min at 60° C., followed by 40 cycles of 20 s at 95° C. and 1 min at 60° C. The real-time RT-PCR analysis was run on an ABI 7500 Real Time PCR System (Applied Biosystems, USA).

The result for the described reaction was a Ct value of 33.1. A reaction without *Torulla* yeast RNA gave a Ct of 33.3 whereas a reaction without SUPERase-In in step 1 gave a Ct of 32.1. Negative control experiments without hsa miR-15a RNA (EQ15885, Table I), or without miR-15a capture probe (EQ16879, Table VI), or without Klenow exo- all gave no Ct values. Also a no template control (NTC) qPCR gave no Ct value. End-point analysis by running samples of the real-time RT-PCR reaction on an agarose gel confirmed the results, i.e., no Ct values correspond to the absence of the PCR amplicon on the gel.

Probe, Immobilization of Extension Product in a Streptavidin Tube, Reverse Transcriptase (RT) Reaction in Solution, and Real-time PCR Using a LNA-modified Detection Probe.

1. The MicroRNA-primed Extension Reaction on a 3'-blocked, 5'-biotin-labelled LNA-modified Capture Probe Hsa miR-15a RNA (100 fmol, 10 fmol, 1 fmol, 100 amol, or 10 amol; EQ15885, Table I) was mixed with 1 μg *Torulla* yeast RNA (Ambion, USA) and 100 fmol miR-15a capture probe (EQ16879, Table VI) in a total volume of 7 μL, heated for 5 min at 65° C. and cooled on ice. 1 μL 10×NEBuffer 2 (New England Biolabs, USA), 1 μL dNTP mix (1 mM of each dNTP; Applied Biosystems, USA), and 5 U Klenow exo- (New England Biolabs, USA) were added. The incubation was continued for 30 min at 37° C.

2. The Immobilization in a Streptavidin Tube

One volume of 2×binding buffer (200 mM Tris-HCl pH 7.5 at 20° C., 800 mM LiCl, 40 mM EDTA) was added to the Klenow exo- reaction and the supernatant was transferred to a streptavidin coated PCR tube (Roche, Germany). Incubation for 3 min at 37° C. allowed the biotin-streptavidin binding to be formed. Unbound material was removed by washing three times in five volumes of washing buffer (10 mM Tris-HCl pH 7.5 at 20° C., 20 mM LiCl,) at room temperature.

3. The RT Reaction in Solution

The RT-primer (100 fmol, EQ16994, Table VI) and 10 nmol of each of dNTP (Applied Biosystems, USA) were mixed in 12 μL total volume and added to the streptavidin PCR tube containing the immobilized capture probe and the chimerical RNA-DNA strand. The tube was heated 5 min at 70° C. and the supernatant was transferred to a new tube on ice. 5×First strand buffer a (50 mM Tris-HCl pH 8.3 at 20° C., 75 mM KCl, 3 mM $MgCl_2$; Invitrogen, USA), 10×DTT (1×=10 mM, Invitrogen, USA), 20 U SUPERase-In (Ambion, USA), and 200 U Superscript II reverse transcriptase (Invitrogen, USA) was added (in a volume of 8 μL) and the incubation was continued for 1 h at 42° C. Heating for 15 min at 70° C. terminated the reaction.

4. The Real-time PCR Using an LNA-modified Detection Probe

The reaction (50 μL) was 1×PCR buffer (Qiagen, Germany), $MgCl_2$ to a final concentration of 4 mM, 0.2 mM of each of dATP, dCTP, dGTP and 0.6 mM dUTP (Applied Biosystems, USA), 900 nM miR-15a forward primer (EQ16990, Table VI), 900 nM miR reverse primer (EQ16989,

TABLE VI

Oligonucleotides used in Example 21 to 23

| EQ No: | Oligo Name: | 5' | Linker: | Sequence (5'-3')[a] | 3' |
|---|---|---|---|---|---|
| 16879 | Hsa miR-15a capture probe | Bio | HEG2 | tactgagtaatcgatatcmCacAaamCca | P |
| 16989 | miR rev PCR primer | | | Caatttcacacaggatactgagt | |
| 16990 | Hsa miR-15a PCR primer | | | Agcggataactagcagcacata | |
| 16992 | miR-15a qPCR probe | 6-Fitc | | TTGTGGATAT#Q1z | P |
| 16994 | miR RT primer | | | caatttcacacaggatactgagtaatcg | |

[a]LNA (uppercase), DNA (lowercase), Fluorescein (6-FITC (Glenn Research, Prod.Id.No. 10-1964)), biotin (Bio (Glenn Research)), two moieties of hexaethylene-glycol (HEG2 (Glenn Research)), #Q1 (Prepared as described in Example 8a), z (5-nitroindole (Glenn Research, Prod.Id.No. 10-1044)), Phosphate (P).

Example 22

Real-time RT-PCR for a Dilution Series of the Human miR-15a Using; MicroRNA-primed Extension Reaction on a 3'-blocked and 5'-biotin-labelled LNA-modified Capture Table VI), 250 nM miR-15a LNA detection probe (EQ16992, Table VI), 0.1×ROX reference dye (Invitrogen, USA), 1 μL of the first strand synthesis (RT) reaction (described above), 0.5 U Uracil DNA Glycosylase (Invitrogen, USA) and 2.5 U HotStarTaq DNA polymerase (Qiagen, Germany). The temperature cycling program was 10 min at 37° C., 10 min at 95° C., 1 min at 45° C., 1 min at 60° C., followed by 40 cycles of 20 s at 95° C. and 1 min at 60° C. The real-time RT-PCR analysis was run on an ABI 7500 Real Time PCR System (Applied Biosystems, USA).

The result for the described reaction was Ct values of 24.0, 27.6, 31.1, 34.8, and 37.0 for 100 fmol, 10 fmol, 1 fmol, 100 amol, and 10 amol hsa miR-15a RNA (EQ15885, Table I) input, respectively. A negative control experiment without hsa miR-15a RNA (EQ15885, Table I) gave no Ct value. Also a no template control (NTC) qPCR gave no Ct value. The input of 10 amol hsa miR-15a RNA (EQ15885, Table I) corresponded to a concentration of 10 fM or less in the 50 µL real-time RT-PCR mixture. End-point analysis by running samples of the real-time RT-PCR reaction on an agarose gel confirmed the results, i.e., no Ct values correspond to absence of PCR amplicons on the gel.

Example 23

Real-time RT-PCR for the Human miR-15a Using MicroRNA-primed Extension Reaction on a 3'-blocked and 5'-biotin-labelled LNA-modified Capture Probe, Immobilization of Extension Product on Streptavidin Beads, Reverse Transcriptase (RT) Reaction in Solution, and Real-time PCR Using an LNA-modified Detection Probe.
1. The MicroRNA-primed Extension Reactions on a 3'-blocked, 5'-biotin-labelled LNA-modified Capture Probe Hsa miR-15a RNA (1 fmol; EQ15885, Table I) was mixed with 1 µg *Torulla* yeast RNA (Ambion, USA) and 100 fmol miR-15a capture probe (EQ16879, Table VI) in a total volume of 7 µL, heated for 5 min at 65° C. and cooled on ice. 1 µL 10×NEBuffer 2 (New England Biolabs, USA), 1 µL dNTP mix (1 mM of each; Applied Biosystems, USA), and 5 U Klenow exo- (New England Biolabs, USA) were added. The incubation was continued for 30 min at 37° C.
2. The Immobilization onto Streptavidin Beads One volume (10 µL) of 2×binding buffer (10 mM Tris-HCl pH 7.5 at 20° C., 2 M NaCl, 1 mM EDTA) containing 10 µg Dynabeads M-270 Streptavidin; (Dynal Biotech, Norway) was added to the Klenow exo-reaction and incubated for 10 min at 20° C. with rotation to allow the biotin-streptavidin binding to be formed. The tube was placed in the magnetic particle concentrator (Dynal MPC-9600; Dynal Biotech, Norway). The supernatant was removed and the beads were washed three times in 100 µL wash buffer (10 mM Tris-HCl pH 7.5 at 20° C., 20 mM NaCl). "Proceed immediately with the RT reaction".
3. The RT Reaction in Solution The RT-primer (100 fmol, EQ16994, Table VI) and 10 nmol of each of dNTP (Applied Biosystems, USA) were mixed in 12 µL total volume and added to the tubes containing the immobilized capture probe and the chimerical RNA-DNA strand. The tube was heated 5 min at 70° C.; transferred to the magnetic particle concentrator and the supernatant was transferred to a new tube on ice. 5×First strand buffer a (50 mM Tris-HCl pH 8.3 at 20° C., 75 mM KCl, 3 mM MgCl$_2$; Invitrogen, USA), 10×DTT (1×=10 mM, Invitrogen, USA), 20 U SUPERase-In (Ambion, USA), and 200 U Superscript II reverse transcriptase (Invitrogen, USA) were added (in a volume of 8 µL) and the incubation was continued for 1 h at 42° C. Heating for 15 min at 70° C. terminated the reaction.
4. Real-time PCR Using a LNA-modified Detection Probe The reaction (50 µL) was 1×PCR buffer (Qiagen, Germany), MgCl$_2$ to a final concentration of 4 mM, 0.2 mM of each of dATP, dCTP, dGTP and 0.6 mM dUTP (Applied Biosystems, USA), 900 nM miR-15a forward primer (EQ16990, Table VI), 900 nM miR reverse primer (EQ16989, Table VI), 250 nM miR-15a LNA detection probe (EQ16992, Table VI), 0.1×ROX reference dye (Invitrogen, USA), 5 µL of the first strand synthesis (RT) reaction (described above), 0.5 U Uracil DNA Glycosylase (Invitrogen, USA) and 2.5 U HotStarTaq DNA polymerase (Qiagen, Germany). The temperature cycling program was; 10 min at 37° C., 10 min at 95° C., 1 min at 45° C., 1 min at 60° C., followed by 40 cycles of 20 s at 95° C. and 1 min at 60° C. The real-time RT-PCR analysis was run on an ABI 7500 Real Time PCR System (Applied Biosystems, USA).

The result for the described reaction was a Ct value of 28.0. A no template control (NTC) qPCR gave no Ct value.

Example 24

Real-time Quantitative PCR for the Human miR-7a Using Reverse Transcription on Solid Support Primed by a LNA-modified Capture Probe Containing a 5'-biotin Followed by Real-time PCR Using a LNA-modified Detection Probe.
1. The microRNA-primed Extension Reaction on a 5'-biotin Labelled LNA-modified Capture Probe In a total volume of 10 µL the following was mixed: Hsa miR-7a RNA (10 fmol; EQ16898, Table VII), 1 µg *Torulla* yeast RNA (Ambion, USA) and 100 fmol miR-7a capture probe (EQ 17367, Table VII), 1 µL 10×NEBuffer 2 (New England Biolabs, USA), 1 µL dNTP mix (1 mM of each dNTP; Applied Biosystems, USA), and 5 U Klenow exo- (New England Biolabs, USA). The mixture was incubated for 30 min at 37° C.
2. The Immobilization in a Streptavidin Tube 2.5 µL 5×binding buffer (500 mM Tris-HCl pH 7.5 at 20° C., 2 M LiCl, 100 mM EDTA) was added to the Klenow exo-reaction and the supernatant was transferred to a streptavidin coated PCR tube (Roche, Germany). Incubation for 3 min at 37° C. allowed the biotin-streptavidin binding to be formed. Unbound material was removed by washing five times in 100 µL of washing buffer (10 mM Tris-HCl pH 7.5 at 20° C., 20 mM LiCl,) at room temperature.
3. The RT Reaction 20 µL of the following RT reaction mixture was added to the streptavidin coated PCR tube containing the immobilized capture probe and the chimerical RNA-DNA strand: 1×First strand buffer (50 mM Tris-HCl pH 8.3 at 20° C., 75 mM KCl, 3 mM MgCl$_2$; Invitrogen, USA), 10 mM DTT (Invitrogen, USA), 1.25 mM of each dNTP (Applied Biosystems, USA), 20 U SUPERase-In (Ambion, USA), and 200 U Superscript II reverse transcriptase (Invitrogen, USA) was incubated for 1 h at 42° C.
4. The Pre-PCR The RT-mixture was removed and replaced with 20 µL of the PCR master mixture containing 1×Quantitect Probe PCR Master Mix (Qiagen, USA) forward and reverse primer (EQ17372 & EQ17374, Table VII) each at 0.4 µM, 1 U Uracil-DNA Glycosylase (UNG, Roche, Germany). The Pre-PCR was subjected to the flowing PCR conditions: 95° C. for 15 min, 30° C. for 1 min, 40° C. for 1 min, 60° C. for 1 min, and 10 cycles of 94° C. for 20 s and 60° C .for 1 min. The reaction was kept at 4° C. until performance of real-time PCR. Afterwards 80 µL of DEPC-H$_2$O was added to the pre-PCR reaction before use in the real-time PCR.
5. The Real-time PCR Using a LNA-modified Detection Probe The 50 µL real-time PCR mix contained 1×Quantitect Probe PCR Master Mix (Qiagen) forward and reverse primer (EQ17372 & EQ17374, Table VII) each at 0.4 µM, 0.2 µM miR-7a LNA detection probe (EQ17377, Table VII), 1 U UNG (Roche, Germany), and 5 μL of the diluted first strand synthesis (RT)-pre-PCR reaction (described above). The temperature cycling program was; 95° C. for 15 min, and 40 cycles of 94° C. for 20 s & 60° C. for 1 min. The real-time PCR was performed on an Opticon real-time PCR instrument (MJ Research, USA).

Results.

Figure 26:
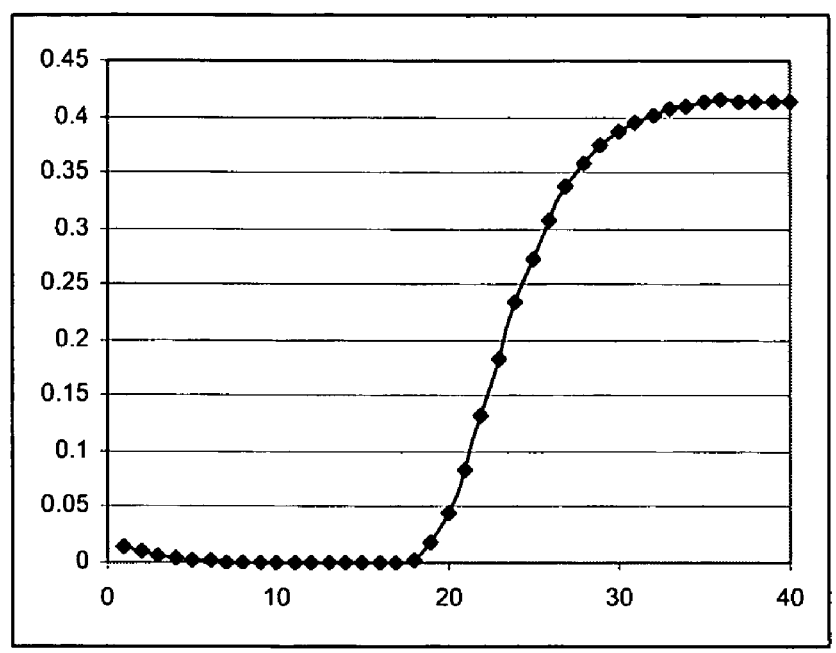
FIG. 26 shows the real-time quantitative PCR amplification plots demonstrating detection of the hsa miR-7a templated RT-PCR produced a sigmoid amplification plot with ample amount of signal and a Ct value of 18.5.

The real-time PCR produced a sigmoid amplification plot with ample amount of signal (FIG. 26) and a Ct value of 18.5. The obtained Ct value is realistic for the amount of Hsa-miR-7a used in the current experiment and indicates full functionality of the assay.

Example 26

Real-time Rt-PCR for the Human hsa-Let-7a Using; MicroRNA-primed Extension Reaction on a 3'-blocked and 5'-biotin-labelled LNA-modified Capture Probe, Immobilization of Extension Product in a Streptavidin Tube, Reverse Transcriptase Reaction in Solution, and Real-time PCR Using a LNA-modified Detection Probe with the Quencher Q2.

1. The MicroRNA-primed Extension Reaction on a 3'-blocked, 5'-biotin Labelled LNA-modified Capture Probe.

TABLE VII

Oligonucleotides used in Example 24

| EQ No: | Oligo Name: | 5' | Sequence (5'-3')[a] | 3' |
|---|---|---|---|---|
| 16898 | hsa-let-7a | | ugagguaguagguuguauaguu | |
| 16899 | hsa-let-7f | | ugagguaguagauuguauaguu | |
| 16917 | hsa-let-7g | | ugagguaguaguuuguacagu | |
| 17367 | cP5_hsa-let-7a capture probe | Bio | gttgaggatggatggtaggatgagtaactAtAmCaA | |
| 17372 | hsa-let-7a_qPcR-F-primer3 | | agaatggatggatctgaggtagt | |
| 17374 | hsa-let-7a_qPcR-R-primer1 | | aggatggatggtaggatgagt | |
| 17375 | hsa-let-7a_qPcR-R-primer2 | | gttgaggatggatggtaggat | |
| 17377 | hsa-let-7a_qPcR-Probe2 | 6-Fitc | AcTATAmCAAmCmCT#Q1z | P |
| 18089 | hsa-let-7a_qPcR-Probe2_Q2 | 6-Fitc | acTATAmCAAmCmCT#Q2z | P |

[a]LNA (uppercase), DNA (lowercase), RNA (italic and lower cases), 5-methyl C (mC); Fluorescein (6-FITC (Glenn Research, Prod.Id.No. 10-1964)), biotin (Bio Glenn Research)), #Q1 (Prepared as described in Example 8a), #Q2 (Prepared as described in Example 8b), z (5-nitroindole (Glenn Research, Prod.Id.No. 10-1044)), Phosphate (P).

Example 25

Synthesis, Deprotection and Purification of Dual Labelled Oligonucleotide Probes The dual labelled oligonucleotide probes of Table I, II and V to VII, i.e. EQ15866, EQ15867, EQ16580-16583, EQ16679, EQ17167, EQ16879, EQ16992, EQ17367 and EQ17377 were prepared on an automated DNA synthesizer (Expedite 8909 DNA synthesizer, PerSeptive Biosystems, 0.2 μmol scale) using the phosphoramidite approach (Beaucage and Caruthers, *Tetrahedron Lett.* 22: 1859-1862, 1981) with 2-cyanoethyl protected LNA and DNA phosphoramidites, (Sinha, et al., *Tetrahedron Lett.* 24: 5843-5846, 1983).

The synthesis cycle was modified for LNA phosphoramidites (250s coupling time) compared to DNA phosphoramidites. 1H-tetrazole or 4,5-dicyanoimidazole (Proligo, Hamburg, Germany) was used as activator in the coupling step.

The oligonucleotides were deprotected using 32% aqueous ammonia (1 h at room temperature, then 2 hours at 60° C.) and purified by HPLC (Shimadzu-SpectraChrom series; Xterra™ RP18 column, 10 μm 7.8×150 mm (Waters). Buffers: A: 0.05M Triethylammonium acetate pH 7.4. B. 50% acetonitrile in water. Eluent: 0-25 min: 10-80% B; 25-30 min: 80% B). The composition and purity of the oligonucleotides were verified by MALDI-MS (PerSeptive Biosystem, Voyager DE-PRO) analysis Hsa Let-7a RNA (10 fmol; EQ16898, Table VII) was mixed with 1 μg *Torulla* yeast RNA (Ambion, USA), 100 fmol cP5_hsa-let-7a capture probe (EQ17367, Table VII), 1 μL 10×NEBuffer 2 (New England Biolabs, USA), 1 μL dNTP mix (1 mM of each dNTP; Applied Biosystems, USA), and 5 U Klenow exo- (New England Biolabs, USA) in a total volume of 10 μL. Incubation was performed for 30 min at 37° C.

2. The Immobilization in a Streptavidin Tube

A volume of 2.5 μL 5×binding buffer (500 mM Tris-HCl pH 7.5 at 20° C., 2 M LiCl, 100 mM EDTA) was added to the Klenow exo-reaction and the mixture was transferred to the bottom of a streptavidin coated PCR tube (Roche, Germany). Incubation was performed for 3 min at 37° C. to allow the biotin-streptavidin binding to occur. Unbound material was removed by washing five times in 100 μL of washing buffer (10 mM Tris-HCl pH 7.5 at 20° C., 20 mM LiCl,) at room temperature. The washed tube was immediately subjected to the reverse transcription reaction.

3. The RT Reaction in Solution

The RT-primer (1 μL 100 fmol/μl, EQ17374, Table VII) and 2.5 dNTP (10 mM of each dNTP, Applied Biosystems, USA) were mixed in 12 μL total volume and added to the streptavidin PCR tube containing the immobilized capture probe and the chimerical RNA-DNA strand. The tube was heated 5 min at 70° C. and the supernatant was removed to a new tube on ice. 4 μl 5×first strand buffer (250 mM Tris-HCl pH 8.3 at 20° C., 375 mM KCl, 15 mM MgCl$_2$; Invitrogen, USA), 2 μl 100 mM DTT (Invitrogen, USA), 1 μl 20 U/μl SUPERase-In (Ambion, USA), and 1 μl 200 U/μl Superscript II reverse transcriptase (Invitrogen, USA) were added and the incubation was continued for 1 h at 42° C. Heating for 15 min at 70° C. terminated the reaction. The total volume was adjusted to 100 μL by adding 80 μL of DEPC H$_2$O.

4. The Real-time PCR Using a LNA-modified Detection Probe

The reaction (50 μL) was 1×QuantiTect Probe PCR Master Mix (Qiagen, Germany), 400 nM hsa-let-7a_qPcR-F-primer3 (EQ17372, Table VII), 400 nM hsa-let-7a qPcR-R-primer2 (EQ17375, Table VII), 200 nM hsa-let-7a_qPcR-Probe2_Q2 detection probe (EQ18089, Table VII), 5 μL of the first strand synthesis (RT) reaction (described above), and 0.5 U Uracil DNA Glycosylase (Invitrogen, USA). The temperature cycling program was; 10 min at 37° C., 15 min at 95° C., 1 min at 30° C., 1 min at 40° C., 1 min at 60° C., followed by 40 cycles of 20 s at 94° C. and 1 min at 60° C. The real-time RT-PCR analysis was performed on the Opticon real-time PCR instrument (MJ Research, USA).

5. Results.

The experiment was performed with a replica of 3, and the average Ct value obtained was 19.0 with a CV of 0.01. Three replicas of a reaction without addition of hsa Let-7a miRNA did not produce signal and no Ct value was obtained Example 27

Preparation of Precursor Pre-miRNA hsa Let-7a
1. In Vitro Transcription
a. The T7 promoter/leader oligo (EQ18219, see Table VIII) was mixed with the hsa-let-7a-1 precursor longmer DNA oligonucleotide (EQ18213, see Table VIII) in a final concentration of 20 μM of each oligonucleotide.
b. The sample was heated 5 minutes at 95° C. and the solution was allowed to cool to room temperature on the bench.
c. 8 μL of the above solution was used as template in an ordinary 20-μL MegaScript reaction (Ambion, USA) containing ATP, GTP, CTP, UTP, Reaction buffer, and enzyme mix.
d. The reaction was incubated over night at 37° C.
e. 1 μL DNase was added and the reaction was incubated 15 min at 37° C.
f. The in vitro transcribed precursor pre=miRNA was purified on RNeasy MinElute Cleanup spin columns using a modified protocol for miRNA cleanup.

6. Add 1.4 volumes of 100% ethanol (980 μl), and mix thoroughly by vortexing. Do not centrifuge. Proceed immediately to step 7.
7. Pipet 700 μl of the sample into an RNeasy MinElute spin column placed in a 2 ml collection tube. Close the lid gently, and centrifuge for 15 s at 8000×g. Discard the flow-through. Repeat step 7 until the whole sample has been pipetted into the spin column. Discard the flow-through each time.
8. Pipet 500 μl Buffer RPE into the RNeasy MinElute spin column. Close the lid gently, and centrifuge for 15 s at 8000×g. Discard the flow-through.
9. Pipet 500 μl of 80% ethanol into the RNeasy MinElute spin column. Close the lid gently, and centrifuge for 15 s at 8000×g. Discard the flow-through and the collection tube.
10. Place the RNeasy MinElute spin column into a new 2 ml collection tube. Open the lid, and centrifuge for 1 min at 8000×g.
11. Place the RNeasy MinElute spin column into a 1.5 ml collection tube, and pipet 14 μl RNase-free water onto the spin column membrane. Close the lid gently, and centrifuge for 1 min at 8000×g to elute the miRNA.

The concentration of the miRNA eluate was measured at OD$_{260}$ followed by dilution in DEPC H$_2$O to a final concentration of 10 nM (10 fmol per μL).

Example 28

Real-time RT-PCR for Selective Detection of Mature Versus Precursor of the Human hsa-Let-7a Using; MicroRNA-primed Extension Reaction on a 3'-blocked and 5'-biotin-labelled LNA-modified Capture Probe, Immobilization of Extension Product in a Streptavidin Tube, Reverse Transcriptase Reaction in Solution, and Real-time PCR Using a LNA-modified Detection Probe with Quencher Q2.

1. The MicroRNA-primed Extension Reaction on a 3'-blocked, 5'-biotin Labelled LNA-modified Capture Probe.
miRNA hsa Let-7a (10 fmol; EQ16898, Table VII) and/or precursor pre-miRNA hsa Let-7a ((10 fmol; produced as outlined in Example 27 ) was mixed with 1 μg *Torulla* Yeast RNA (Ambion, USA), 100 fmol cP5_hsa-let-7a capture probe (EQ17367, Table VII), 1 μL 10×NEBuffer 2 (New England

TABLE VIII

Oligonucleotides used in Example 27

| EQ No: Oligo Name: | 5' Sequence (5'-3') | 3' |
|---|---|---|
| 18213 hsa-let 7a-1 precursor longmer | aagacagtagattgtatagttatctcccagtgg tgggtgtgaccctaaaactatacaacctactac ctcatctccctatagtgagtcgtattaaatt | |
| 18219 T7 promotor/leader sequence | aatttaatacgactcactataggaga | |

2: Modified Protocol for Precursor miRNA Cleanup
1 Add 350 μl Buffer RLT to the sample, and mix thoroughly by vortexing.
2. Add 1 volume of 80% ethanol (350 μl), and mix thoroughly by vortexing. Do not centrifuge. Proceed immediately to step 3.
3. Pipet the sample, including any precipitate that may have formed, into an RNeasy Mini spin column placed in a 2 ml collection tube. Close the lid gently, and centrifuge for 15 s at 8000×g.
4. Discard the RNeasy Mini spin column
5. Pipet the flow-through from step 3 (which contains miRNA) into a 2 ml reaction tube Biolabs, USA), 1 μL dNTP mix (1 mM of each dNTP; Applied Biosystems, USA), and 5 U Klenow exo- (New England Biolabs, USA) in a total volume of 10 μL. Incubation was performed for 30 min at 37° C.

2. The Immobilization in a Streptavidin Tube
A volume of 2.5 μL 5×binding buffer (500 mM Tris-HCl pH 7.5 at 20° C., 2 M LiCl, 100 mM EDTA) was added to the Klenow exo-reaction and the mixture was transferred to the bottom of a streptavidin coated PCR tube (Roche, Germany). Incubation was performed for 3 min at 37° C. to allow the biotin-streptavidin binding to occur. Unbound material was removed by washing five times in 100 μL of washing buffer (10 mM Tris-HCl pH 7.5 at 20° C., 20 mM LiCl,) at room temperature. The washed tube was immediately subjected to the reverse transcription reaction.

3. The RT Reaction in Solution

The RT-primer (1 µl 100 fmol/µl, EQ17374, Table VII) and 2.5 µl dNTP (10 mM of each dNTP, Applied Biosystems, USA) were mixed in 12 µL total volume and added to the streptavidin PCR tube containing the immobilized capture probe and the chimerical RNA-DNA strand. The tube was heated 5 min at 70° C. and the supernatant was removed to a new tube on ice. 4 µl 5×first strand buffer (250 mM Tris-HCl pH 8.3 at 20° C., 375 mM KCl, 15 mM $MgCl_2$; Invitrogen, USA), 2 µl 100 mM DTT (Invitrogen, USA), 1 µl 20 U/µl SUPERase-In (Ambion, USA), and 1 µl 200 U/µl Superscript II reverse transcriptase (Invitrogen, USA) were added and the incubation was continued for 1 h at 42° C. Heating for 15 min at 70° C. terminated the reaction. The total volume was adjusted to 100 µL by adding 80 µL of DEPC $H_2O$.

4. The Real-time PCR Using a LNA-modified Detection Probe

The reaction (50 µL) was 1×QuantiTect Probe PCR Master Mix (Qiagen, Germany), 400 nM hsa-let-7a_qPcR-F-primer3 (EQ17372, Table VII), 400 nM hsa-let-7a qPcR-R-primer2 (EQ17375, Table VII), 200 nM hsa-let-7a_qPcR-Probe2_Q2 detection probe (EQ18089, Table VII), 5 µL of the first strand synthesis (RT) reaction (described above), and 0.5 U Uracil DNA Glycosylase (Invitrogen, USA). The temperature cycling program was; 10 min at 37° C., 15 min at 95° C., 1 min at 30° C., 1 min at 40° C., 1 min at 60° C., followed by 40 cycles of 20 s at 94° C. and 1 min at 60° C. The real-time RT-PCR analysis was performed on the Opticon real-time PCR instrument (MJ Research, USA).

5. Results.

The following Ct values was obtained (Table IX) by performing the assay outlined above on the mature miRNA hsa Let-7a and/or pre-miRNA hsa Let-7a:

TABLE IX

| Input RNA | Amount of input RNA | Ct value |
| --- | --- | --- |
| miRNA hsa Let-7a | 10 fmol | 17.0 |
| pre-miRNA hsa Let-7a | 10 fmol | 28.9 |
| miRNA hsa Let-7a & pre-miRNA hsa Let-7a | 10 fmol each | 17.7 |
| No miRNA or pre-miRNA | — | none |

There is a difference in Ct values of 11.8 (ΔCt) between the mature and the precursor hsa-let-7a miRNA. A ΔCt of 11.8 corresponds to a 1000-10,000 fold higher sensitivity of the assay for the mature hsa-let-7a miRNA over the precursor, which demonstrates the ability of the assay to discriminate between the two miRNA species. Accordingly, very similar Ct values are obtained when assaying the mature hsa-let-7a miRNA alone or the mature plus precursor hsa-let-7a miRNA present in equimolar concentrations. No signal and Ct value is obtained when the assay is performed without addition of miRNA. Little or no signal was obtained in the qPCR when no RT reaction was added or when the template consisted of the oligo-template used for in vitro transcription of precursor hsa-let-7a miRNA (result not shown). Likewise little or no signal was obtained when the template added to the qPCR consisted of RT performed as outlined above but using the precursor hsa-let-7a miRNA as template i.e. omitting the microRNA-primed extension reaction step (result not shown).

Example 29

Real-time RT-PCR for Selective Detection of the hsa-let-7a Versus Closely Related miRNAs hsa-Let-7f and hsa-Let-7g Using; MicroRNA-primed Extension Reaction on a 3'-blocked and 5'-biotin-labelled LNA-modified Capture Probe, Immobilization of Extension Product in a Streptavidin Tube, Reverse Transcriptase Reaction in Solution, and Real-time PCR Using a LNA-modified Detection Probe with Quencher Q2.

1. The MicroRNA-primed Extension Reaction on a 3'-blocked, 5'-biotin Labelled LNA-modified Capture Probe.

10 fmol hsa Let-7a miRNA, hsa Let-7f miRNA, or hsa Let-7g miRNA (EQ16898, EQ16899 and EQ16917, respectively—Table VII) was mixed with 1 µg Torulla yeast RNA (Ambion, USA), 100 fmol cP5_hsa-let-7a capture probe (EQ17367, Table VII), 1 µL 10×NEBuffer 2 (New England Biolabs, USA), 1 µL dNTP mix (1 mM of each dNTP; Applied Biosystems, USA), and 5 U Klenow exo- (New England Biolabs, USA) in a total volume of 10 µL. Incubation was performed for 30 min at 37° C.

2. The Immobilization in a Streptavidin Tube

A volume of 2.5 µL 5×binding buffer (500 mM Tris-HCl pH 7.5 at 20° C., 2 M LiCl, 100 mM EDTA) was added to the Klenow exo- reaction and the mixture was transferred to the bottom of a streptavidin coated PCR tube (Roche, Germany). Incubation was performed for 3 min at 37° C. to allow the biotin-streptavidin binding to occur. Unbound material was removed by washing five times in 100 µL of washing buffer (10 mM Tris-HCl pH 7.5 at 20° C., 20 mM LiCl,) at room temperature. The washed tube was immediately subjected to the reverse transcription reaction.

3. The RT Reaction in Solution

The RT-primer (1 µl 100 fmol/µl, EQ17374, Table VII) and 2.5 µl dNTP (10 mM of each dNTP, Applied Biosystems, USA) were mixed in 12 µL total volume and added to the streptavidin PCR tube containing the immobilized capture probe and the chimerical RNA-DNA strand. The tube was heated 5 min at 70° C. and the supernatant was removed to a new tube on ice. 4 µl 5×first strand buffer (250. mM Tris-HCl pH 8.3 at 20° C., 375 mM KCl, 15 mM $MgCl_2$; Invitrogen, USA), 2 µl 100 mM DTT (Invitrogen, USA), 1 µl 20 U/µl SUPERase-In (Ambion, USA), and 1 µl 200 U/µl Superscript II reverse transcriptase (Invitrogen, USA) were added and the incubation was continued for 1 h at 42° C. Heating for 15 min at 70° C. terminated the reaction. The total volume was adjusted to 100 µL by adding 80 µL of DEPC $H_2O$.

4. The Real-time PCR Using a LNA-modified Detection Probe

The reaction (50 µL) was 1×QuantiTect Probe PCR Master Mix (Qiagen, Germany), 400 nM hsa-let-7a_qPcR-F-primer3 (EQ17372, Table VII), 400 nM hsa-let-7a qPcR-R-primer2 (EQ17375, Table VII), 200 nM hsa-let-7a_qPcR-Probe2_Q2 detection probe (EQ18089, Table VII), 5 µL of the first strand synthesis (RT) reaction (described above), and 0.5 U Uracil DNA Glycosylase (Invitrogen, USA). The temperature cycling program was; 10 min at 37° C., 15 min at 95° C., 1 min at 30° C., 1 min at 40° C., 1 min at 60° C., followed by 40 cycles of 20 s at 94° C. and 1 min at 60° C. The real-time RT-PCR analysis was performed on the Opticon real-time PCR instrument (MJ Research, USA).

5. Results.

A Ct value of 20.4 was obtained in the hsa Let-7a miRNA assay using the hsa Let-7a miRNA as template. No signal was generated and no Ct value was obtained in the assays where hsa Let-7f miRNA and hsa Let-7g miRNA was used as template. Likewise no signal and no Ct value was obtained from assays where no miRNA was added or from qPCRs where no RT was added as template. This indicate that the assay is discriminatively detecting the hsa-let-7a miRNA and not the close miRNA homologues hsa Let-7f miRNA and hsa Let-7g miRNA where the only difference between let-7a and hsa Let-7f miRNAs is a single nucleotide change from G to A.

Example 30

Real-time RT-PCR Quantification of hsa-mir-143 Using Two Step Extension of a Capture/RT-probe Using as First Template the Investigated MicroRNA and As Second Template an Artificial Helper Oligonucleotide Followed by Real-time PCR Quantification by Amplification of the Fully Extended Capture/RT-probe Using a LNA Modified Dual-labelled Detection Probe.

When the miRNA is located on the lower strand of the stem-loop molecule, processing by the Dicer enzyme results in a unique 5'-end of the mature miR, whereas the 3'-end is identical for the pre-miR and the mature miR.

The example follows the assay layout in FIG. 31.

The two capture/RT-probe extension reactions take place in the same reaction mixture using a "One Step RT/PCR mix". The reaction mixture thus contains micro-RNA, capture/RT-probe, reverse transcriptase, 3'-phosphorylated and 5'-biotinylated artificial helper template, and Taq-polymerase.

Subsequent to the 2-step capture/RT-probe extension an aliquot of this reaction mixture is then used as input in a real-time PCR quantification reaction.

1. The 2-step Capture/RT Extension Reaction Mixture.

In a reaction mixture with a total volume of 25 µL the following was mixed: hsa-mir -143 microRNA (1 fmol; EQ16900, Table X), 1 µg Torulla yeast RNA (Ambion, USA), hsa-Rim-143_CP5_NoBio (125 fmol; EQ18080, Table X), has -Rim-143_AT_Bio (6.25 pmol; EQ18079, Table X), dNTP mix (0.2 mM final conc. of each dNTP; Applied Biosystems, USA),1×Qiagen OneStep RT-PCR buffer (Qiagen, Germany), 1×Qiagen OneStep RT-PCR Enzyme Mix and DEPC treated water (Ambion, USA).

A "No-miR" control was performed in which the microRNA (hsa-mir-143, Table X) was omitted.

The reaction mixtures were subjected to the following temperature cycling program using a DNA Engine Dyad thermocycler (MJ Research, USA):
Reverse Transcription: 60° C. for 30 min
Activation of Taq: 95° C. for 15 min
Capture probe extension: 10 cycles of (95° C. for 20 sec+60° C. for 30 sec)
Cooling: 4° C.

The reaction mixtures were diluted with 75 µL DEPC treated water (Ambion, USA) immediately prior to further processing.

2. Removal of Artificial Helper Oligonucleotide From the Reaction Mixture by Binding to Streptavidin.

An aliquot of 20 µL of each of the reaction mixtures from step 1 above was mixed with 1 µL ImmunoPure® Immobilized Streptavidin (Pierce), vortexed and incubated at 37° C. for 5 min and spun through a spin-column (Harvard Apparatus).

3. Real-time PCR Quantification Using a LNA Modified Dual-labelled Detection Probe.

In a reaction mixture with a total volume of 25 µL the following was mixed: hsa-Rim143_Primer2 (0.5 µM final conc., EQ17724, Table X), hsa-miR-143_Primer143_C2 (0.5 µM final conc., EQ17574, Table X), hsa-Rim-143_P4 (0.25 µM final conc., EQ18057, Table X),1×TaqMan® Universal PCR Master Mix (Applied Biosystems, USA), 2.5 µL of the diluted reaction mixture from step 1 or step 2 above and DEPC treated water.

The reaction mixtures were subjected to the following temperature cycling program using an ABI 7500 Real Time PCR System (Applied Biosystems, USA):
Activation of Taq: 95° C. for 15 min
PCR amplification: 40 cycles of (95° C. for 20 sec+60° C. for 30 sec)

Figure 32:
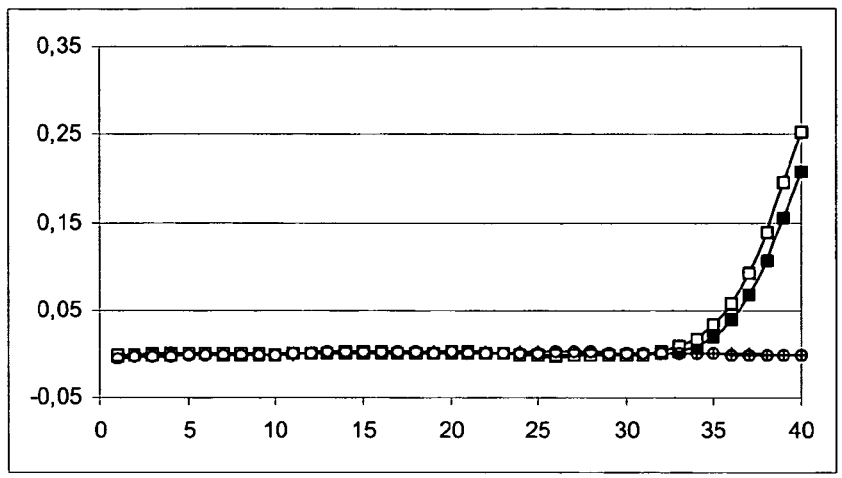
FIG. 32 shows the real-time quantitative PCR amplification plot for the human miR 143 microRNA target sequence. The assay was performed according to the schematic representation in FIG. 31 and as described in Example 30. Open squares represent reaction with purification in step 2 of Example 30, closed squares represent reaction without purification in step 2 of Example 30. The curves that do not rise from the baseline represent the corresponding "No miR"-controls.

The results for the described reactions was a Ct-value of 37 for the microRNA containing sample without purification in step 2 and a Ct-value of 36 for the corresponding sample including purification in step 2. Neither of the two corresponding "No miR"-controls gave any Ct-value within the 40 cycles. See FIG. 32.

TABLE X

Oligonucleotides used in Example Rim

| EQ No: | Oligo Name: | 5' | Sequence (5'-3')[a] | 3' |
|---|---|---|---|---|
| 16900 | hsa-mir-143 | | ugagaugaagcacuguagcuca | |
| 18080 | hsa-Rim-143_CP5_NoBio | | ctgatagagctttgcgtccactgattGagmCtamCagt | |
| 18079 | hsa-Rim-143_AT_Bio | Bio | tgaatccgaatctaacgttgcctaggctgagatgaagcact | P |
| 17724 | hsa-Rim-143_Primer2 | | tgaatccgaatctaacgttgc | |
| 17574 | hsa-miR-143_Primer143_C2 | | ctgatagagctttgcgtcca | |
| 18057 | hsa-Rim-143_P4 | | 6-FITC aGmCTAmCAGT#Q2z | P |

[a]LNA (uppercase), DNA (lowercase), Fluorescein (6-FITC (Glenn Research, Prod.Id.No. 10-1964)), biotin (Bio (Glenn Research)), two moieties of hexaethyleneglycol (HEG2 (Glenn Research)), #Q2 (Prepared as described in Example 8b), z (5-nitroindole (Glenn Research, Prod.Id.No. 10-1044)), Phosphate (P).

Example 31

Real-time RT-PCR for Selective Detection of the hsa-let-7a Versus the Closely Related hsa-Let-7g Using; LIGATION of an RNA Adaptor to Mature MicroRNA Followed by Reverse Transcription, and Real-time PCR Using a LNA-modified Detection Probe With Quencher Q2.

Figure 36:
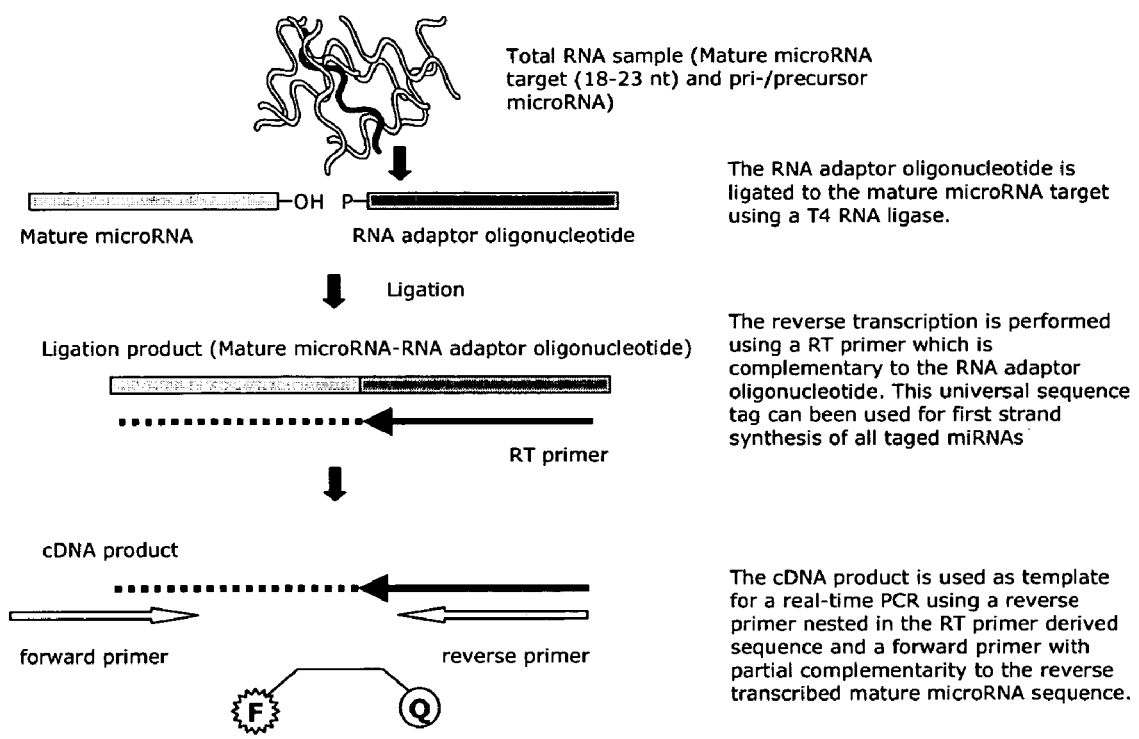
FIG. 36 shows a schematic presentation of one method of the invention for quantification of microRNAs by sequence-specific real-time quantitative RT-PCR.

The method employed in this example is generally depicted in FIG. 36.

1. The Ligation of an RNA Adaptor to the Mature MicroRNA.

Ten fmol hsa Let-7a miRNA or hsa Let-7g miRNA (EQ16898 and EQ16917, respectively—Table VII) was mixed with 20 fmol RNA Adaptor (EQ18557-Table XI) and 40 U of T4 RNA Ligase (New England Biolabs, USA) in a total volume of 20 µL consisting of 1×T4 RNA Ligase Buffer (50 mM Tris-HCl pH 7.8 at 25° C., 10 mM MgCl$_2$, 1 mM ATP, and 10 mM dithiothreitol). Ligation was performed by incubation for 15 min at 37° C. Heating for 15 min at 65° C. terminated the reaction.

2. The RT Reaction

The reverse transcription reaction was performed in 50 μL consisting of 2 μM RT-primer (EQ17374, Table VII) and 500 μM of each dNTP (Applied Biosystems, USA), 1×First strand buffer (50 mM Tris-HCl pH 8.3 at 20° C., 75 mM KCl, 3 mM MgCl$_2$; Invitrogen, USA), 10 mM DTT (Invitrogen, USA), 60 U SUPERase-In (Ambion, USA), 500 U Superscript II reverse transcriptase (Invitrogen, USA), and 20 μL of the Ligation mixture described above The reverse transcription reaction was performed for 1 h at 42° C. Heating for 15 min at 70° C. terminated the reaction.

4. The Real-time PCR Using a LNA-modified Detection Probe

The reaction (50 μL) was 1×PCR buffer (Qiagen, Germany), MgCl$_2$ to a final concentration of 4 mM, 0.2 mM of each of dATP, dCTP, dGTP and 0.6 mM dUTP (Applied Biosystems, USA), 900 nM hsa-let-7a_qPcR-F-primer3 (EQ17372, Table VII), 900 nM hsa-let-7a qPcR-R-primer2 (EQ17375, Table VII), 250 nM hsa-let-7a_qPcR-Probe2_Q2 detection probe (EQ18089, Table VII), 0.1×ROX reference dye (Invitrogen, USA), 2.5 μL of the first strand synthesis (RT) reaction (described above), 0.5 U Uracil DNA Glycosylase (Invitrogen, USA) and 2.5 U HotStarTaq DNA polymerase (Qiagen, Germany). The temperature cy-cling program was; 10 min at 37° C., 10 min at 95° C., followed by 40 cycles of 20 s at 95° C. and 1 min at 60° C. The real-time RT-PCR analysis was run on an ABI 7500 Real Time PCR System (Applied Biosystems, USA).

5. Results.

Figure 35:
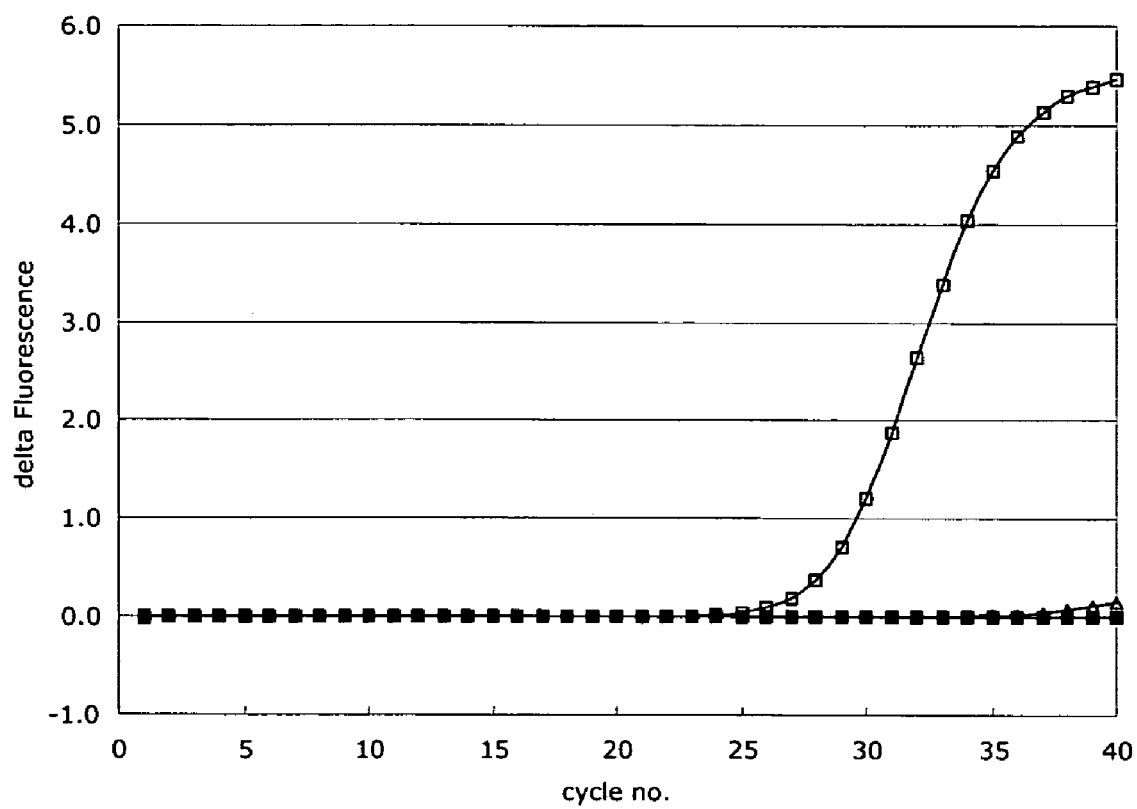
FIG. 35 Shows the real-time quantitative PCR amplification plots demonstrating Ligation of an RNA adaptor to mature microRNA followed by reverse transcription, and real-time PCR using an LNA-modified detection probe with quencher Q2. The hsa-let-7a open squares, the hsa-let-7g solid squares, no miRNA open triangles, and no PCR template control solid triangles.

A Ct value of 27.1 was obtained in the hsa Let-7a miRNA assay using the hsa Let-7a miRNA as template (FIG. 35). No signal was generated and no Ct value was obtained in the assays where the hsa Let-7g miRNA was used as template. Likewise no signal and no Ct value was obtained from assays where no miRNA was added or from qPCRs where no RT was added as template. Indicating that the assay is discriminatively detecting the hsa-let-7a miRNA and not the close miRNA homologue hsa Let-7g.

TABLE XI

Oligonucleotide used in Ligation.

| EQ No: | Oligo Name: | 5' | Sequence (5'-3')$^a$ | 3' |
|---|---|---|---|---|
| 18557 | RNA Adaptor | P | acucauccuaccauccauccu | P |

RNA (italic and lowercase) and Phosphate (P).

1. The Ligation of RNA Ligation Oligo to the Mature MicroRNA.

Mix 10 fmol hsa Let-7a miRNA or hsa Let-7g miRNA (EQ16898 and EQ16917, respectively-Table VII) with, 100 fmol Ligation Oligo and 100 fmol Ligation Helper Oligo (EQ18557 and EQ18565, respectively-Table XII) and 400 U of T4 DNA Ligase (New England Biolabs, USA) in a total volume of 20 μL consisting of 1× T4 DNA Ligase Reaction Buffer (50 mM Tris-HCl pH 7.5 at 25° C., 10 mM MgCl$_2$, 1 mM ATP, 10 mM dithiothreitol, 25 μg/ml BSA). Perform ligation by incubation for 30 min at room temperature. Heat for 10 min at 65° C. to terminate the reaction.

2. The RT Reaction

Add 1 μL RT-primer (100 fmol/μL, EQ17374, Table VII) and 2 μL dNTP (10 mM of each of dNTP-Applied Biosystems, USA) together with 1 μL 5× First strand buffer (250 mM Tris-HCl pH 8.3 at 20° C., 375 mM KCl, 15 mM MgCl$_2$; Invitrogen, USA), 1 μL 20 U/μL SUPERase-In (Ambion, USA), and 1 μL 200 U/μL Superscript II reverse transcriptase (Invitrogen, USA). Perform the reverse transcription reaction for 1 h at 42° C. Heat for 15 min at 70° C. to terminate the reaction. Adjust the total volume to 100 μL by adding 74 μL of DEPC H$_2$O.

3. The Real-time PCR Using a LNA-modified Detection Probe

Set up a real time PCR reaction (50 μL) with 1×QuantiTect Probe PCR Master Mix (Qiagen, Germany), 400 nM hsa-let-7a_qPcR-F-primer3 (EQ17372, Table VII), 400 nM hsa-let-7a qPcR-R-primer2 (EQ17375, Table VII), 200 nM hsa-let-7a_qPcR-Probe2_Q2 detection probe (EQ18089, Table VII), 5 μL of the first strand synthesis (RT) reaction (described above), and 0.5 U Uracil DNA Glycosylase (Invitrogen, USA). Use the following temperature cycling program: 10 min at 37° C., 15 min at 95° C., 1 min at 30° C., 1 min at 40° C., 1 min at 60° C., followed by 40 cycles of 20 s at 94° C. and 1 min at 60° C. The real-time RT-PCR analysis may be performed on the Opticon real-time PCR instrument (MJ Research, USA).

TABLE XII

Oligonucleotides used in Ligation.

| EQ No: | Oligo Name: | 5' Sequence (5'-3')$^a$ | 3' |
|---|---|---|---|
| 18557 | hsa-let-7 Ligation Oligo | P acucauccuaccauccauccu | P |
| 18565 | hsa-let-7a Ligation-Helper | ggatgagtaactatac | P |

Example 32

Real-time RT-PCR for Selective Detection of the hsa-let-7a Versus the Closely Related miRNA hsa-Let-7g Using; Ligation of RNA Oligo to Mature MicroRNA Using a "Bridging" Nucleic Acid Sequence (Ligation Helper Oligo) Followed by Reverse Transcription, and Real-time PCR Using a LNA-modified Detection Probe with Quencher Q2.

The following is an example of how the Ligation-Helper-Oligo assisted ligation and subsequent reverse transcription and qPCR may be performed to detect the mature microRNA hsa-let-7a.

Embodiments

The invention can also be defined by means of the following embodiments, wherein the term "item" refers to a preceding item with the specified number.

1. A method of quantifying a target nucleotide sequence in a nucleic acid sample comprising:
   a) contacting the target nucleotide sequence with two oligonucleotide tagging probes each consisting of an anchor nucleotide sequence and a recognition nucleotide sequence, wherein said recognition nucleotide sequence is complementary to the target sequence, and wherein the recognition sequence of the first tagging probe hybridizes to a first region of the target sequence and the second recognition sequence of the second tagging probe hybridizes to a second region of the target sequence adjacent to the first region of the target sequence;
b) joining the two adjacent recognition sequences of the hybridized tagging probes covalently by ligation to form a contiguous nucleotide sequence, comprising a sequence complementary to the target nucleotide sequence and the two anchor nucleotide sequences, and
c) quantifying the ligated oligonucleotide molecules by real-time PCR using primers corresponding to the anchor nucleotide sequences and a labelled detection probe comprising a target recognition sequence and a detection moiety.
2. A method of item 1, wherein the recognition nucleotide sequences in the tagging probes and the detection probe are modified with high-affinity nucleotide analogues.
3. A method of item 1 to 2, wherein the high-affinity nucleotide analogue is LNA.
4. A method of item 1 to 3, wherein the recognition nucleotide sequence in the 5'-phosphorylated tagging probe is modified with an LNA at every second, third or fourth position starting with an LNA at the nucleotide position next to the 5' nucleotide position, and wherein the recognition nucleotide sequence in the second tagging probe is modified with an LNA at every second, third or fourth position ending at the nucleotide position prior to the 3' nucleotide position.
5. A method of item 4, wherein the recognition nucleotide sequence in the 5'-phosphorylated tagging probe is modified with an LNA at every third position starting with an LNA at the nucleotide position next to the 5' nucleotide position, and wherein the recognition nucleotide sequence in the second tagging probe is modified with an LNA at every third position ending at the nucleotide position prior to the 3' nucleotide position.
6. A method of item 1 to 5, wherein the anchor nucleotide sequences in the tagging probes are DNA sequences.
7. A method of item 1 to 5, wherein the anchor nucleotide sequences in the tagging probes are modified with high-affinity nucleotide analogues.
8. A method of item 7, wherein the anchor nucleotide sequences in the tagging probes are modified with LNA.
9. A method of item 1 to 8, wherein the recognition nucleotide sequences in the tagging probes are less than about 20 nucleotides in length and more preferably less than 15 nucleotides, and most preferably between 10 and 14 nucleotides.
10. A method of item 1 to 9, wherein the anchor nucleotide sequences in the tagging probes are less than about 30 nucleotides in length and more preferably less than 27 nucleotides, and most preferably between 15 and 25 nucleotides.
11. A method of item 1 to 10, wherein the recognition sequence in the detection probe is modified with high-affinity nucleotide analogues.
12. A method of item 11, wherein .the high-affinity nucleotide analogue is LNA.
13. A method of item 12, wherein the length of the detection probe is less than about 20 nucleotides and more preferably less than 15 nucleotides, and most preferably between 8 and 12 nucleotides.
14. A method of item 13, wherein the detection probe comprises an LNA sequence containing a DNA nucleotide at the 5'-end and a phosphate group at the 3'-end.
15. A method of item 14, wherein the detection probe is substituted with at least one chemical moiety.
16. A method of item 15, wherein the detection probe contains a fluorophore-quencher pair.
17. A method of item 1 to 16, wherein the detection probe is detected using a dual label by the 5' nuclease assay principle.
18. A method of item 1 to 16, wherein the detection probe is detected by the molecular beacon principle.
19. A method of anyone of items 1 to 18, wherein the tagging probes are ligated using a T4 DNA ligase.
20. A method of anyone of items 1 to 18, wherein the tagging probes are ligated using a thermostable DNA ligase.
21. A method of anyone of items 1 to 18, wherein the tagging probes are ligated using a RNA ligase.
22. A method of anyone of items 1 to 18, wherein the tagging probes are ligated using a thermostable RNA ligase.
23. A method of item 20 or 22, wherein the ligation reaction is a repeated cycle between denaturation and tagging probe annealing and joining, producing a plurality of ligated oligonucleotide molecules.
24. A method of anyone of items 1 to 23, wherein one of the tagging probes is labelled with a ligand.
25. A method of item 24, wherein the ligated molecules are purified utilizing a ligand-capture molecule interaction.
26. A method of item 24 to 25, wherein the ligand is biotin, and wherein the ligand-capture molecule interaction is biotin-avidin or biotin-streptavidin.
27. A method of anyone of items 1 to 26, wherein the target nucleotide sequence is a RNA sequence.
28. A method of anyone of items 1 to 26, wherein the-target nucleotide sequence is a microRNA sequence.
29. A method of item 28, wherein the target nucleotide sequence is a mature microRNA sequence.
30. A method of anyone of items 1 to 26, wherein the target nucleotide sequence is a siRNA or a RNA-edited sequence.
31. A method of anyone of items 1 to 26, wherein the target nucleotide sequence is an alternative splice variant sequence.
32. A method of anyone of items 1 to 26, wherein the target nucleotide sequence is a non-coding or an antisense RNA sequence or a RNA sequence containing a single nucleotide polymorphism or a point mutation.
33. A method of anyone of items 1 to 26, wherein the target nucleotide sequence is a DNA sequence.
34. A method of anyone of items 1 to 26, wherein the target nucleotide sequence is a DNA sequence containing a single nucleotide polymorphism or a point mutation.
35. A method of items 1 to 34, wherein the target nucleotide sequence is a human sequence.
36. A method of item 35, wherein the target nucleotide sequence is involved in a disease or useful for the diagnosis of a disease, e.g. cancer.
37. A library of tagging probes and detection probes of anyone of items 1 to 36 for detection or quantification of microRNAs.
38. A library of probes of item 37 for detection and quantification of plant or mammalian microRNAs.
39. A library of probes of item 37 for detection and quantification of human or animal microRNAs.
40. A library of tagging probes and detection probes of anyone of items 1 to 36 for detection or quantification of antisense RNAs, non-coding RNAs or siRNAs.
41. A library of tagging probes and detection probes of anyone of items 1 to 36 for detection or quantification of RNA-edited transcripts.
42. A library of tagging probes and detection probes of anyone of items 1 to 36 for detection or quantification of alternative splice variants.

43. A kit of anyone of items 37 to 42.

44. A method of quantifying a target ribonucleic acid sequence in a nucleic acid sample comprising:
   a) contacting the target ribonucleic acid sequence with an oligonucleotide tagging probe, consisting of an anchor nucleotide sequence and a recognition nucleotide sequence, wherein said recognition nucleotide sequence is complementary to a sequence in the target ribonucleic acid sequence;
   b) synthesis of a complementary strand to the target ribonucleic acid by reverse transcription using a reverse transcriptase enzyme and the oligonucleotide tagging probe as primer,
   c) replacing of the ribonucleic acid sequence in the heteroduplex by synthesis of a second strand using a DNA polymerase and a second tagging probe as primer, wherein said second tagging probe consists of an anchor nucleotide sequence and a recognition nucleotide sequence, wherein said recognition nucleotide sequence is complementary to a sequence in the reverse transcriptase-extended nucleic acid sequence
   d) quantifying the resulting nucleic acids by real-time PCR using primers corresponding to the anchor nucleotide sequences attached to the oligonucleotide tagging probes and a labelled detection probe comprising a target recognition sequence and a detection moiety.

45. A method of item 44, wherein the recognition nucleotide sequences in the tagging probes and the detection probe are modified with high-affinity nucleotide analogues.

46. A method of item 44, wherein the recognition nucleotide sequence complementary to a sequence in the target ribonucleic acid in the first tagging probe and the detection probe are modified with high-affinity nucleotide analoques, and the recognition sequence in the second tagging probe is unmodified.

47. A method of item 44, wherein the recognition sequences in the tagging probes are unmodified and the detection probe is modified with high-affinity nucleotide analogues.

48. A method of item 44 to 47, wherein the high-affinity nucleotide analogue is LNA.

48. A method of item 44 to 48, wherein the recognition sequences in the tagging probes are modified with an LNA at every second, third or fourth position with at least one DNA nucleotide in the 3' end of the recognition sequence.

49. A method of item 48, wherein the recognition sequences in the tagging probes are modified with an LNA at every third position starting ending with at least one DNA nucleotide in the 3' end of the recognition sequence.

50. A method of item 44 to 49, wherein the anchor nucleotide sequences in the tagging probes are DNA sequences.

51. A method of item 44 to 50, wherein the anchor nucleotide sequences in the tagging probes are modified with high-affinity nucleotide analogues.

52. A method of item 51, wherein the anchor nucleotide sequences in the tagging probes are modified with LNA.

53. A method of item 44 to 52, wherein the recognition sequences in the tagging probes are less than about 20 nucleotides in length and more preferably less than 15 nucleotides, and most preferably between 6 and 14 nucleotides.

54. A method of item 44 to 53, wherein the anchor nucleotide sequences in the tagging probes are less than about 30 nucleotides in length and more preferably less than 27 nucleotides, and most preferably between 15 and 25 nucleotides.

55. A method of item 44 to 54, wherein the recognition sequence in the detection probe is modified with high-affinity nucleotide analogues.

56. A method of item 55, wherein the high-affinity nucleotide analogue is LNA.

57. A method of item 56, wherein the LNA is optionally modified with SBC nucleobases, 2'-O-methyl, 2,6-diaminopurine, 2-thiouracil, 2-thiothymidine, 5-nitroindole, universal or degenerate bases, intercalating nucleic acids or minor-groove-binders.

58. A method of item 57, wherein at least one of the LNA adenosine monomers in the recognition sequence is substituted with LNA 2,6-diaminopurine.

59. A method of item 58, wherein at least one of the LNA monomers are substituted with LNA 2-thiothymidine.

60. A method of item 59, wherein the length of the detection probe is less than about 20 nucleotides and more preferably less than 15 nucleotides, and most preferably between 7 and 12 nucleotides.

61. A method of item 59, wherein the detection probe comprises an LNA sequence containing a DNA nucleotide at the 5'-end and a phosphate group at the 3'-end.

62. A method of item 61, wherein the detection probe is substituted with at least one chemical moiety.

63. A method of item 62, wherein the detection probe contains a fluorophore-quencher pair.

64. A method of item 44 to 63, wherein the detection probe is detected using a dual label by the 5' nuclease assay principle.

65. A method of item 44 to 63, wherein the detection probe is detected by the molecular beacon principle.

66. A method of anyone of items 44 to 65, wherein the complementary strand to the target ribonucleic acid is synthesized using a thermostable reverse transcriptase 67. A method of anyone of items 44 to 66, wherein the second strand replacing the target ribonucleic acid sequence in the heteroduplex is synthesized using a thermostable DNA polymerase 68. A method of anyone of items 44 to 67, wherein the second strand tagging probe is labelled with a ligand.

69. A method of item 68, wherein the second strand molecules are purified utilizing a ligand-capture molecule interaction.

70. A method of item 68 to 69, wherein the ligand is biotin, and wherein the ligand-capture molecule interaction is biotin-avidin or biotin-streptavidin.

71. A method of anyone of items 44 to 70, wherein the target ribonucleic acid sequence is a microRNA sequence.

72. A method of item 71, wherein the target ribonucleic acid sequence is a mature microRNA sequence.

73. A method of item 72, wherein the recognition sequence of the first tagging probe is complementary to the 3'-end of the mature microRNA and the recognition sequence of the second tagging probe is complementary to the 3'-end of the reverse transcriptase-extended nucleotide sequence corresponding to the 5'-end of the mature microRNA 74. A method of anyone of items 44 to 70, wherein the target ribonucleic acid sequence is a siRNA or a RNA-edited sequence.

75. A method of anyone of items 44 to 70, wherein the target ribonucleic acid sequence is an alternative splice variant sequence.

76. A method of anyone of items 44 to 70, wherein the target ribonucleic acid sequence is a non-coding or an antisense RNA sequence or a RNA sequence containing a single nucleotide polymorphism or a point mutation.

77. A method of anyone of items 74 to 76, wherein the recognition sequence of the first tagging probe is complementary to the 3'-end of the mature siRNA or to a sequence located 3' to the RNA edited nucleotide, splice junction, single nucleotide polymorphism or point mutation, and the recognition sequence of the second tagging probe is complementary to the reverse transcriptase-extended nucleotide sequence corresponding to the 5'-end of the siRNA or located 5' to the RNA edited nucleotide, splice junction, single nucleotide polymorphism or point mutation in the ribonucleic acid target sequence 78. A method of items 44 to 77, wherein the target ribonucleic acid sequence is a human sequence.

79. A method of item 78, wherein the target ribonucleic acid sequence is involved in a disease or useful for the diagnosis of a disease, e.g. cancer.

80. A library of tagging probes and detection probes of anyone of items 44 to 79 for detection or quantification of microRNAs.

81. A library of probes of item 80 for detection and quantification of plant or mammalian microRNAs.

82. A library of probes of item 80 for detection and quantification of human or animal microRNAs.

83. A library of tagging probes and detection probes of anyone of items 44 to 79 for detection or quantification of antisense RNAs, non-coding RNAs, siRNAs, RNA-edited transcripts or alternative splice variants.

84. A kit of anyone of items 80 to 83.

The invention claimed is:

1. A method for quantitative determination of a target non-protein coding RNA, comprising the steps of:
   a) adding a nucleotide sequence to the 3'-end of the target RNA by nucleotide polymerization;
   b) hybridizing a single-stranded reverse transcription (RT) tagging probe to the target RNA, wherein said probe comprises a sequence complementary to the 3'-end of the target RNA and a sequence for subsequent amplification of the nucleic acid by polymerase chain reaction (PCR) in real-time quantitative PCR (qPCR);
   c) performing reverse transcription to obtain a strand of cDNA;
   d) hybridizing a primer comprising a sequence corresponding to the 5'-end of the target RNA to the cDNA of step (c) and generating a double-stranded target sequence;
   e) performing qPCR including as template said double-stranded target sequence of step (d), wherein said primer comprises a nucleotide analog.

2. The method according to claim 1, wherein at least one primer used for the qPCR in step (e) is selected from: (i) an oligonucleotide comprising a sequence corresponding to the sequence for subsequent amplification in the RT tagging probe of step (b) or (ii) an oligonucleotide comprising a contiguous sequence complementary to the 3'-end of the target RNA and corresponding to a part of the sequence for subsequent amplification in the RT tagging probe.

3. The method according to claim 2, wherein at least one primer used in the qPCR in step (e) is constituted by a primer corresponding to the sequence of the primer of step (d).

4. The method according to claim 2, wherein a primer used for qPCR includes a label.

5. The method according to claim 4, wherein said label is a fluorescent group.

6. The method according to claim 5, wherein said fluorescent group is fluorescein.

7. The method according to claim 4, wherein said label is a radioactive label.

8. The method according to claim 1, wherein said RT tagging probe in step (b) is specific for at least one target RNA.

9. The method according to claim 1, wherein the target RNA is present in a sample enriched for RNA of short length.

10. The method according to claim 1, wherein said nucleotide analog is a LNA nucleotide.

11. The method according to claim 10, wherein the LNA nucleotide is selected from the group consisting of an oxy-LNA, a LNA diaminopurine, and a LNA 2-thio-T analog.

12. The method according to claim 1, wherein said target RNA is a small nucleolar RNA, a small interfering RNA (siRNA), a microRNA, or an antisense RNA.

13. The method according to claim 12, wherein said target RNA is microRNA.

14. The method according to claim 13, wherein said microRNA is a mature microRNA.

15. The method according to claim 12, wherein said microRNA or said siRNA is 21-25 nucleotides in length.

16. The method according to claim 1, wherein said RT tagging probe in step (b) is 6-30 nucleotides in length.

17. The method according to claim 1, wherein said RT tagging probe binds to the target RNA under stringent conditions.

18. The method according to claim 1 or claim 17, wherein said primer in step (d) binds to the cDNA in step (c) under stringent conditions.

19. The method according to claim 1, wherein said primer in step (d) is specific for at least one target RNA.

20. The method according to claim 19, wherein the RT tagging probe in step (b) and the primer in step (d) are both specific for the same target RNA.

21. The method according to claim 1, wherein said primer in step (d) further comprises a sequence for subsequent amplification by PCR, and wherein at least one primer used for the qPCR in step (e) is selected from: (i) an oligonucleotide comprising a sequence corresponding to the sequence for subsequent amplification in the primer of step (d) or (ii) an oligonucleotide comprising a contiguous sequence corresponding to the 5'-end of the target RNA and corresponding to a part of the sequence for subsequent amplification in the primer of step (d).

22. The method according to claim 1, wherein said primer in step (d) is single-stranded.

23. The method according to claim 1, wherein said RT tagging probe further comprises a nucleotide analog.

24. The method according to claim 23, wherein said RT tagging probe in step (b) contains 1-8 LNA nucleotides.

25. The method according to claim 23, wherein said nucleotide analog in the RT tagging probe is a LNA nucleotide.

26. The method according to claim 25, wherein the LNA nucleotide in the RT tagging probe is selected from the group consisting of an oxy-LNA, a LNA diaminopurine, and a LNA 2-thio-T analog.

27. The method according to claim 1, wherein the nucleotide sequence added to the 3'-end of the target RNA is a poly-A tail.

28. A method for quantitative determination of a target non-protein coding RNA, comprising the steps of:
  a) hybridizing a single-stranded reverse transcription (RT) tagging probe to the target RNA, wherein said probe comprises a sequence complementary to the 3'-end of the target RNA and a sequence for subsequent amplification of the nucleic acid by polymerase chain reaction (PCR) in real-time quantitative PCR (qPCR);
  b) performing reverse transcription to obtain a strand of cDNA;
  c) hybridizing a primer comprising a sequence corresponding to the 5'-end of the target RNA to the cDNA of step (b) and generating a double-stranded target sequence, wherein said primer comprises a nucleotide analog;
  d) performing qPCR including as template said double-stranded target sequence of step (c), wherein primers used for the qPCR in step (d) are (i) an oligonucleotide comprising a sequence corresponding to the 5'-end of the target RNA, and (ii) an oligonucleotide comprising a sequence corresponding to the sequence for subsequent amplification in the RT tagging probe of step (a) or an oligonucleotide comprising a contiguous sequence complementary to the 3'-end of the target RNA and corresponding to a part of the sequence for subsequent amplification in the RT tagging probe; and wherein one of the primers used for qPCR includes a label, wherein said label is a radioactive label.

* * * * *